US012351646B2

(12) United States Patent
Bamdad

(10) Patent No.: US 12,351,646 B2
(45) Date of Patent: Jul. 8, 2025

(54) **DIAGNOSTIC METHODS USING ANTI-MUC1* ANTIBODIES**

(71) Applicant: Minerva Biotechnologies Corporation, Waltham, MA (US)

(72) Inventor: Cynthia Bamdad, Boston, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

(21) Appl. No.: 18/612,767

(22) Filed: Mar. 21, 2024

(65) Prior Publication Data

US 2024/0352149 A1 Oct. 24, 2024

Related U.S. Application Data

(63) Continuation of application No. 16/975,625, filed as application No. PCT/US2019/019566 on Feb. 26, 2019, now Pat. No. 11,976,132, which is a continuation-in-part of application No. PCT/US2018/062569, filed on Nov. 27, 2018.

(60) Provisional application No. 62/791,661, filed on Jan. 11, 2019, provisional application No. 62/640,697, filed on Mar. 9, 2018, provisional application No. 62/635,378, filed on Feb. 26, 2018.

(51) Int. Cl.

| | |
|---|---|
| ***C07K 16/30*** | (2006.01) |
| ***A61K 35/17*** | (2025.01) |
| ***A61K 40/11*** | (2025.01) |
| ***A61K 40/31*** | (2025.01) |
| ***A61K 40/42*** | (2025.01) |
| ***A61K 47/68*** | (2017.01) |
| ***G01N 33/574*** | (2006.01) |

(52) U.S. Cl.

CPC .......... *C07K 16/3092* (2013.01); *A61K 35/17* (2013.01); *A61K 40/11* (2025.01); *A61K 40/31* (2025.01); *A61K 40/4257* (2025.01); *A61K 47/6851* (2017.08); *G01N 33/57492* (2013.01); *C07K 2317/34* (2013.01)

(58) Field of Classification Search

None

See application file for complete search history.

(56) References Cited

U.S. PATENT DOCUMENTS

| | | | |
|---|---|---|---|
| 10,239,950 | B2 | 3/2019 | Nishimura et al. |
| 11,976,132 | B2 | 5/2024 | Bamdad |
| 2014/0356359 | A1 | 12/2014 | Siebel et al. |

FOREIGN PATENT DOCUMENTS

| | | | |
|---|---|---|---|
| CN | 1455680 | A | 11/2003 |
| CN | 106661110 | A | 5/2017 |
| WO | WO-0222685 | A2 | 3/2002 |
| WO | WO-2008058127 | A2 | 5/2008 |
| WO | WO-2016130726 | A1 | 8/2016 |
| WO | WO-2019165421 | A1 | 8/2019 |

OTHER PUBLICATIONS

Bamdad et al. Abstract 3330: MUC1* targeting CAR T. Cancer Research 77(13):3330 (2017).
Gong et al. Expression of matrix metalloproteinases and the tissue inhibitors of metalloproteinases and their local invasiveness and metastasis in Chinese human pancreatic cancer. J Surg Oncol 73:95-99 (2000).
Ig Heavy Chain Precursor V Region (mAb H8)—Mouse (Fragment). PIR: PC1213. 1999; downloaded from the internet https://www.ncbi.nlm.nih.gov/protein/PC1213 ?report=genbank&logS=protalign&blast_rank=I&RID=D6FNSFA6015 on May 8, 2019.
Immunoglobulin, Kappa Chain, Variable Region, Partial [Mus musculus]. GenBank CAA10057.1. Jul. 26, 2016; downloaded from the internet https://www.ncbi.nlm.nih.gov/protein/CAA10057.1?report=genbank&log$=protalign&blast_rank=I&RIO=D6E6TDK9014 on May 8, 2019.
Mehner et al. Tumor cell-produced matrix metalloproteinase 9 (MMP-9) drives malignant progression and metastasis of basal-like triple negative breast cancer. Oncotarget 5(9):2736-2749 (2014).
PCT/US2019/019566 International Search Report and Written Opinion dated Jun. 27, 2019.
Radisky et al. Matrix metalloproteinases as breast cancer drivers and therapeutic targets. Front Biosci (Landmark Ed). 20:1144-1163 (2015).
Schevchenko et al. Mass spectrometric sequencing of proteins silver-stained polyacrylamide gels. Anal. Chem. 68:850-858 (1996).
Sillanpaa et al. Prognostic significance of matrix metalloproteinase-9 (MMP-9) in epithelial ovarian cancer. Gynecologic Oncology 104:296-303 (2007).
Sorensen et al. Chemoenzymatically synthesized multimeric Tn/STn MUC1 glycopeptides elicit cancer-specific anti-MUC1 antibody responses and override tolerance. Glycobiology 16(2):96-107 (2006).
Tadic-Latinovic et al. The prognostic value of MMP-9 expression in lung adenocarcinoma. Arch Oncol 21(3-4):109-14 (2013).
Yousef et al. MMP-9 expression varies according to molecular subtypes of breast cancer. BMC Cancer 14:609 (2014).

*Primary Examiner* — Peter J Reddig
*Assistant Examiner* — Sarah A Alsomairy
(74) *Attorney, Agent, or Firm* — WILSON SONSINI GOODRICH & ROSATI

(57) ABSTRACT

The present application discloses a method of determining suitability of treating a patient suffering from cancer or metastasis of cancer characterized by aberrant expression of MUC1, with a MUC1* targeting therapeutic.

16 Claims, 76 Drawing Sheets

Specification includes a Sequence Listing.

Serial sections of breast cancer arrays stained with anti-MUC1-full-length, VU4H5 or anti-MUC1*, MNC2

Figure 2A ~ 2B

Fig. 3A
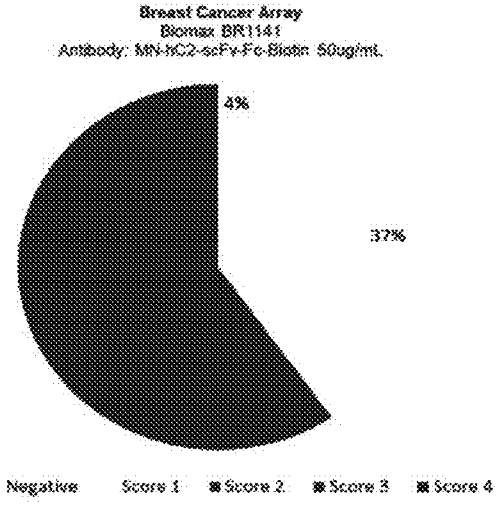
Fig. 3B
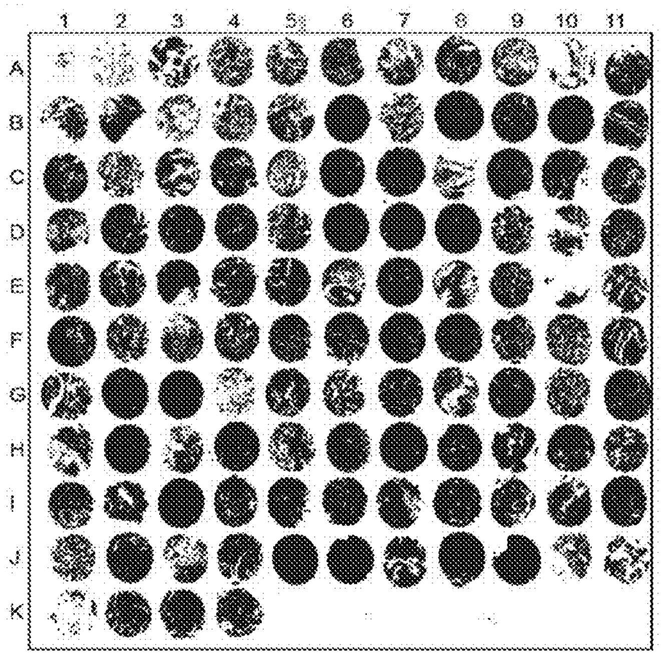
Breast cancer array BR1141
huMNC2-scFv-Fc-biotin
Figure 3A – 3B Fig. 4A
Array BC1141
Position: A7
Cell Type: Invasive Ductal Carcinoma
Tumor Grade: 2
TNM: T2N1M0
Pathologist Score: Negative
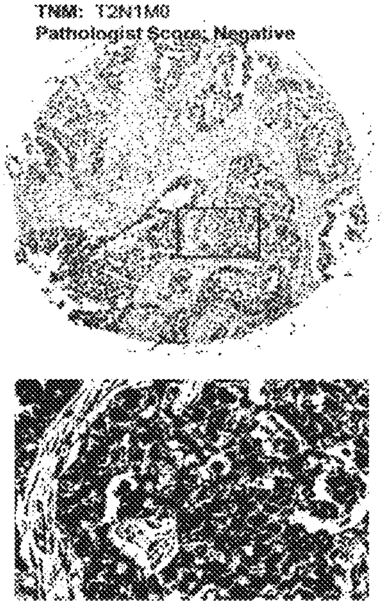
Fig. 4B
Array BC1141
Position: A9
Cell Type: Invasive Ductal Carcinoma
Tumor Grade: 2
TNM: T3N1M0
Pathologist Score: 1+
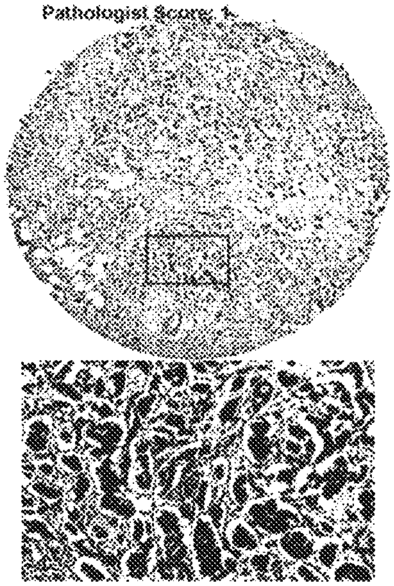
Fig. 4C
Array BC1141
Position: B10
Cell Type: Invasive Ductal Carcinoma
Tumor Grade: 2
TNM: T3N1M0
Patholo
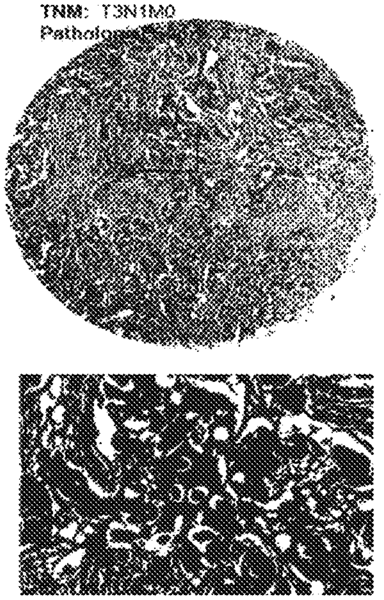
Figure 4A – 4C Fig. 5A
Array BC1141
Position: D7
Cell Type: Invasive Ductal Carcinoma
Tumor Grade: 2
TNM: T2N0M0
Pathologist Score: 3
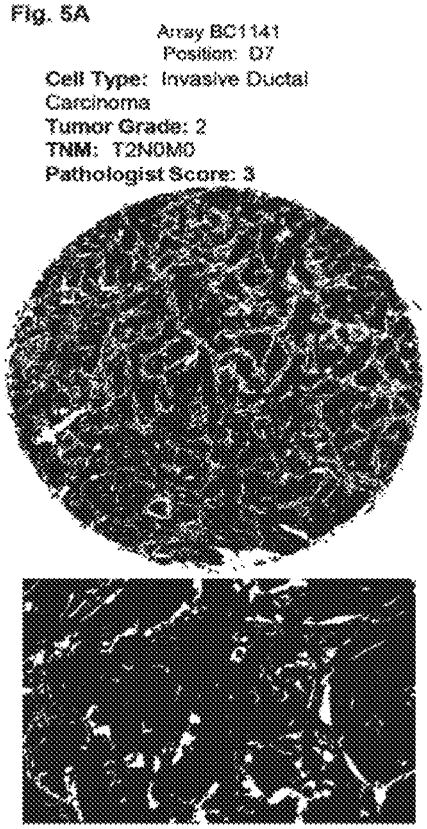
Fig. 5B
Array BC1141
Position: F8
Cell Type: Invasive Ductal Carcinoma
Tumor Grade: 2
TNM: T2N1M0
Pathologist Score: 4
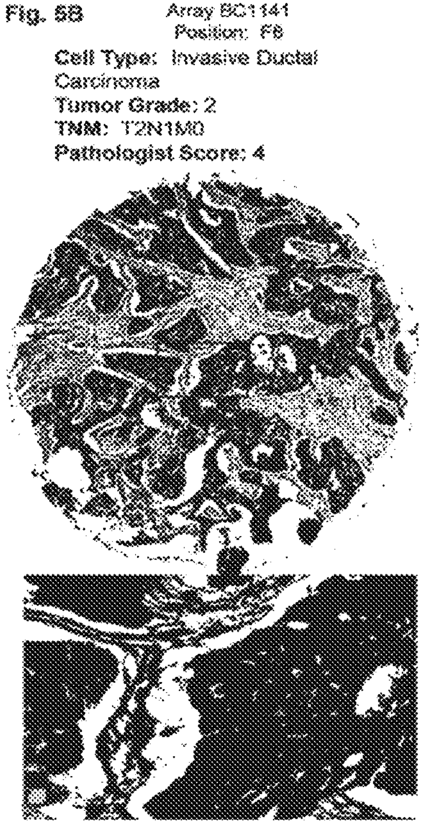
Figure 5A – 5B Fig. 6A
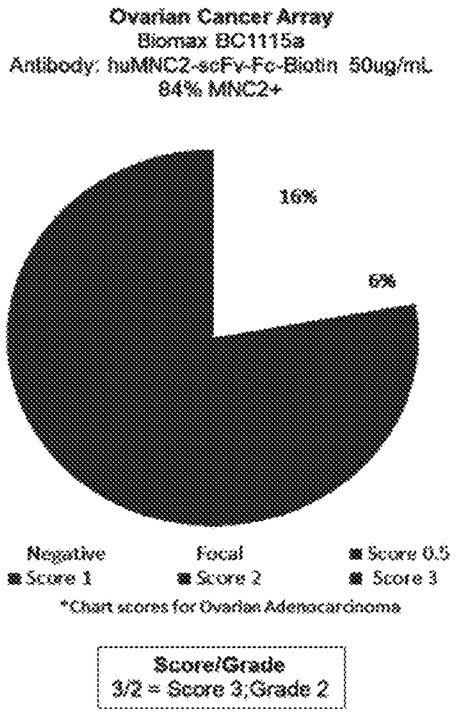
Fig. 6B
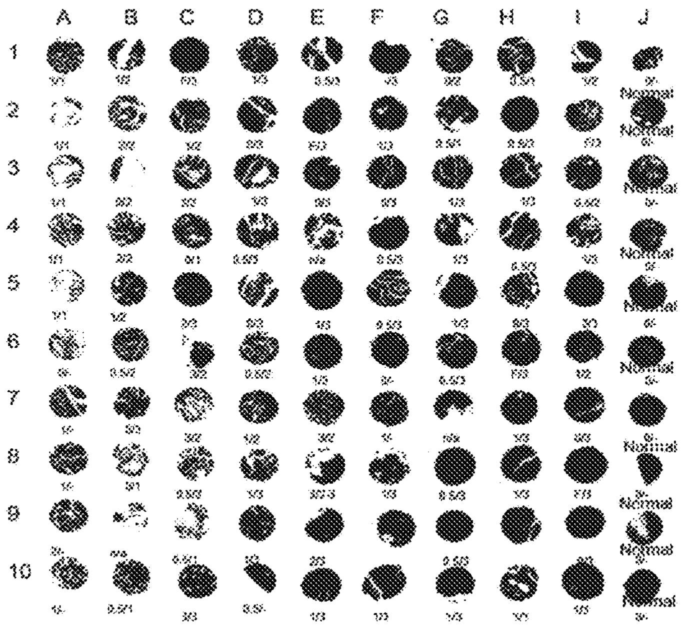
Figure 6A-6B hu C2-scFv-Fc labeling of Normal Tissues

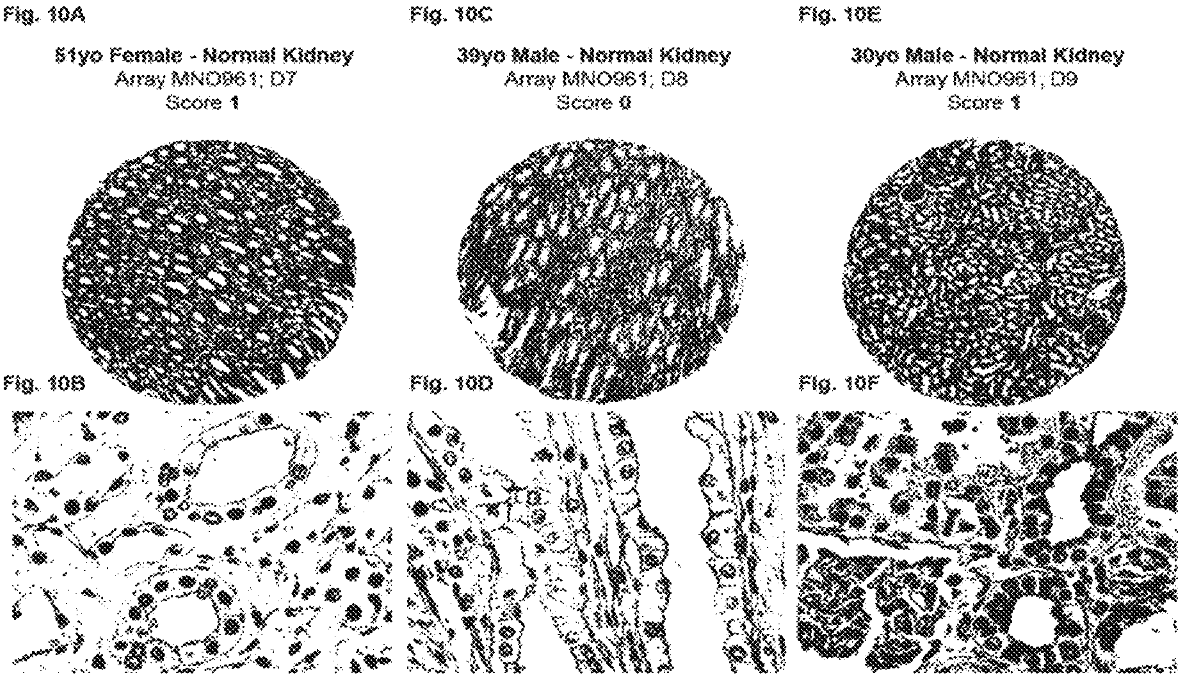
Figure 10A-10F huMNC2-scFv-Fc-Biotin – Normal Human Kidney

Fig. 11A
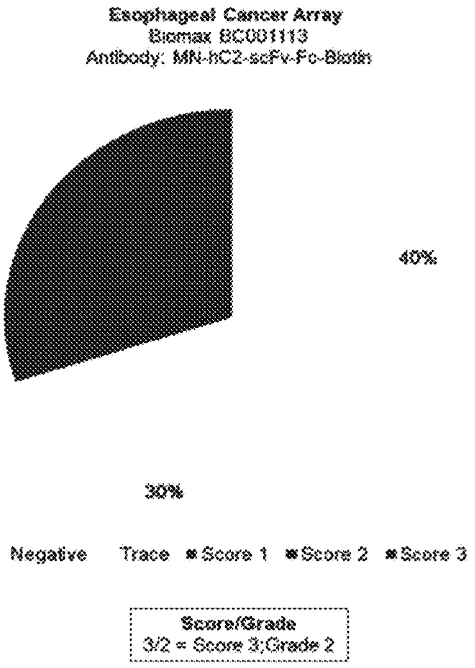
Fig. 11B
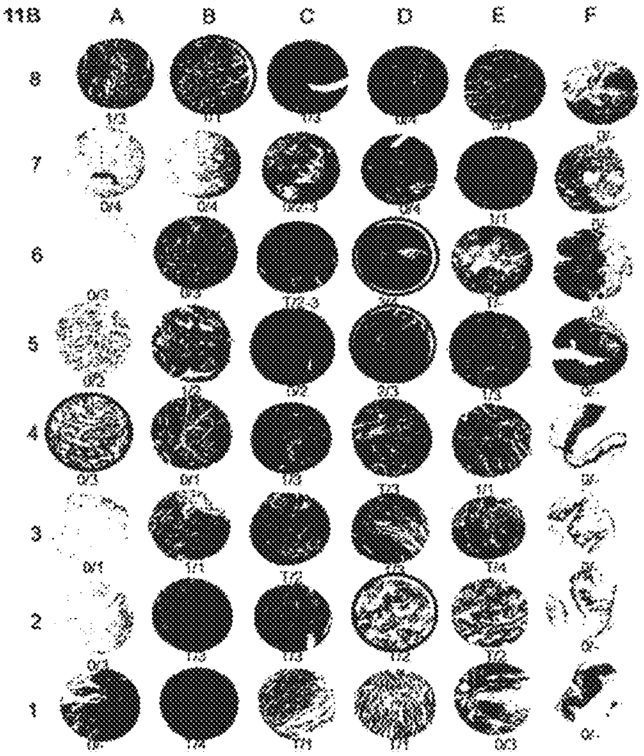
Figure 11A-11B

Fig. 12A
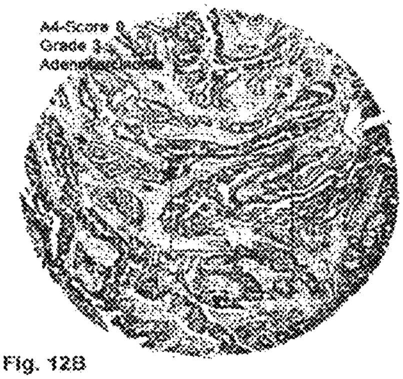
Fig. 12C
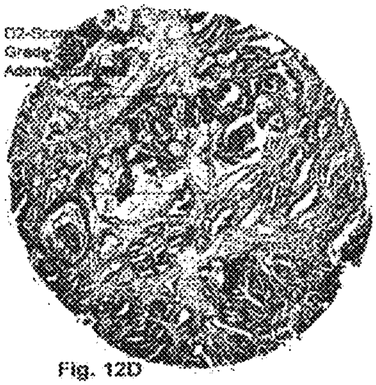
Fig. 12E
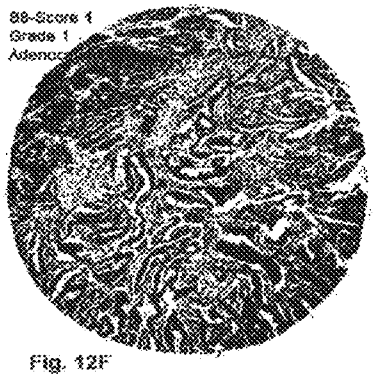
Fig. 12B
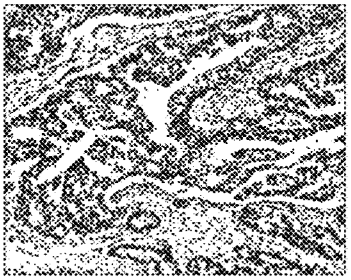
Fig. 12D
Fig. 12F
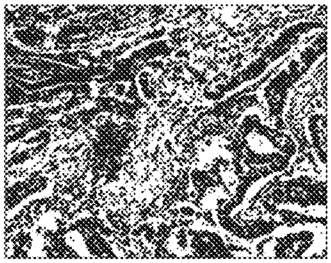
Figure 12A-12F
Esophageal Cancer Array; MN-hC2-scFv-Fc-biotin

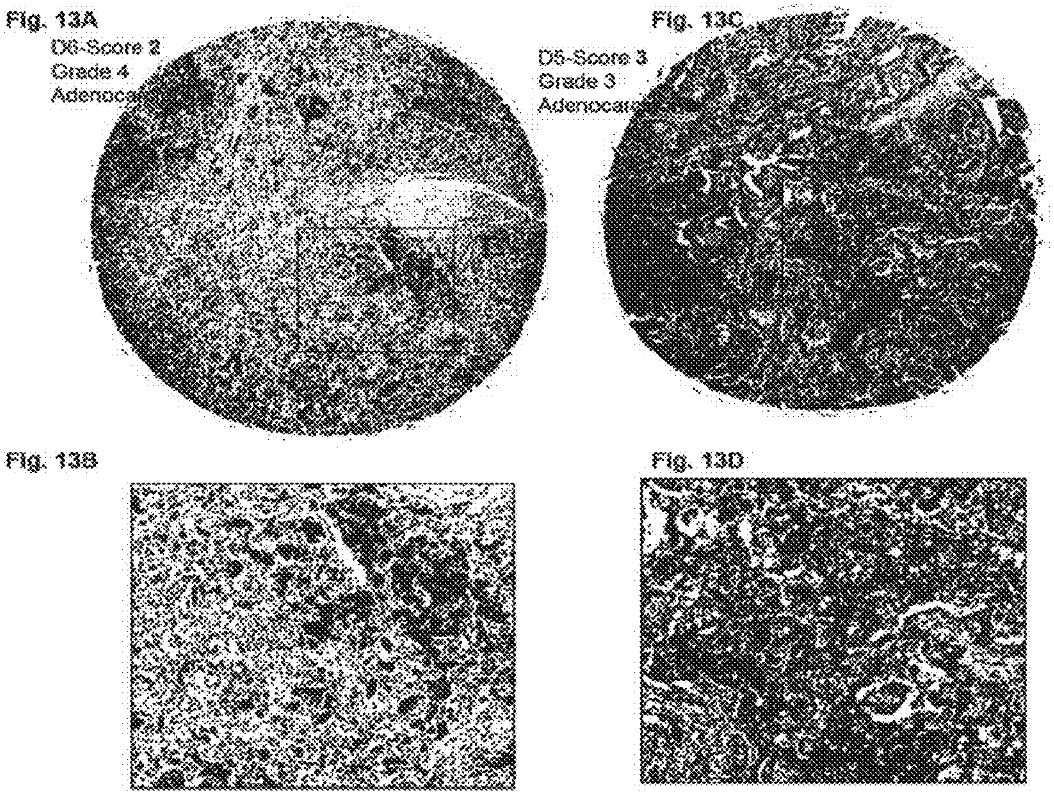
Figure 13A-13D Esophageal Cancer Array; huMNC2-scFv-Fc-Biotin

Fig. 14A
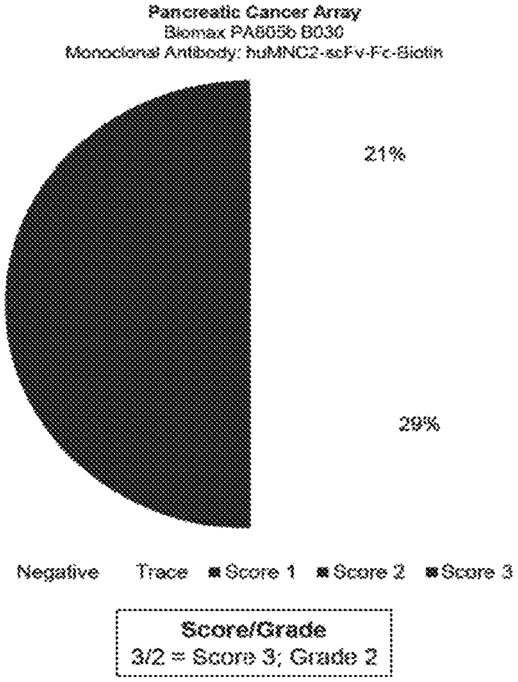
Fig. 14B
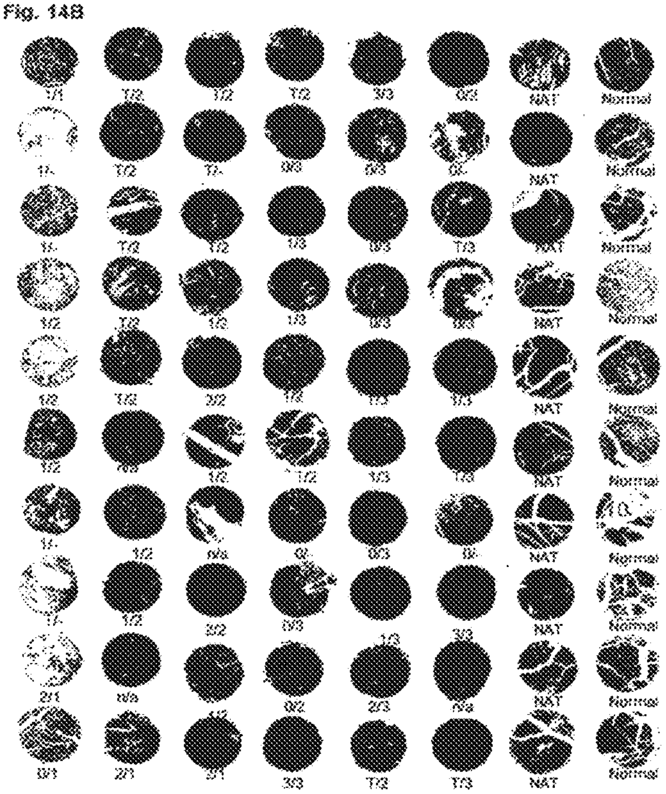
Figure 14A – 14B

Figure 15A-15D Pancreatic Cancer Array Antibody: huMNC2-scFv-Fc-Biotin

Fig. 16A
Fig. 16C
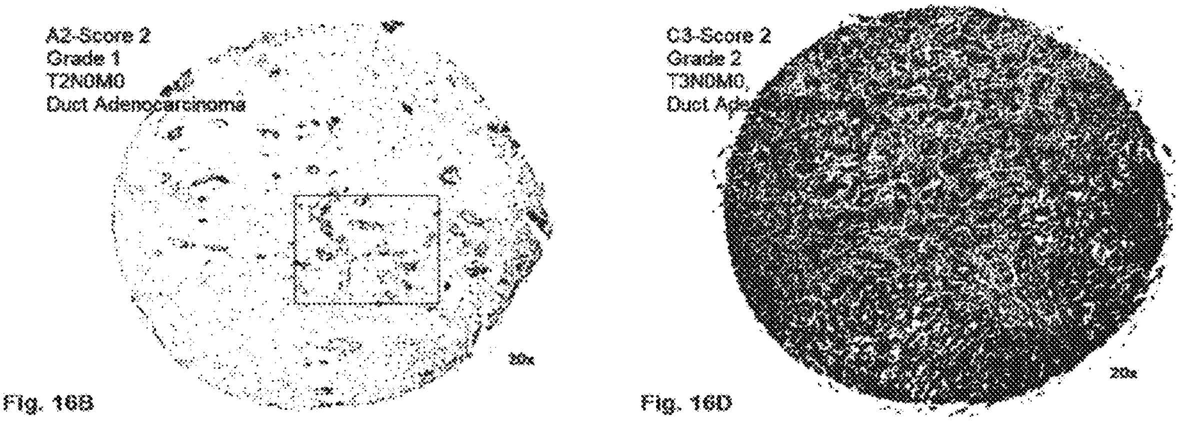
Fig. 16B
Fig. 16D
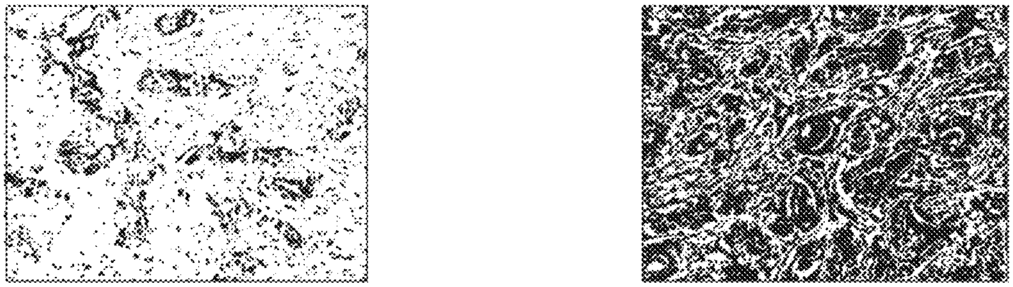
Pancreatic Cancer Array Antibody: huMNC2-scFv-Fc-Biotin
Figure 16A-16D Fig. 17A
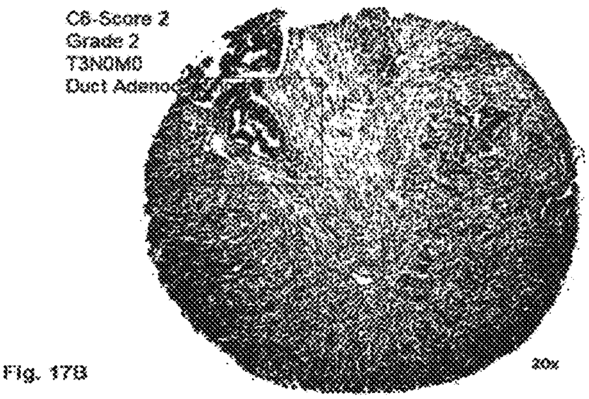
Fig. 17C
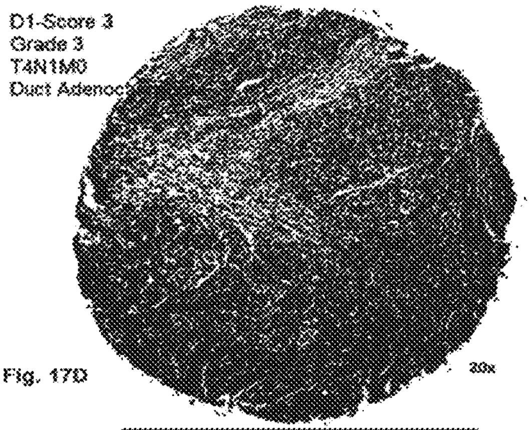
Fig. 17B
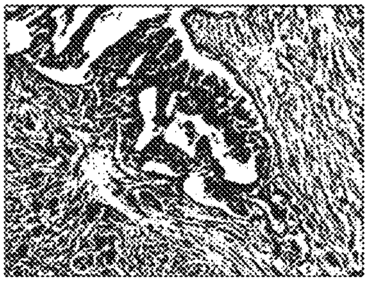
Fig. 17D
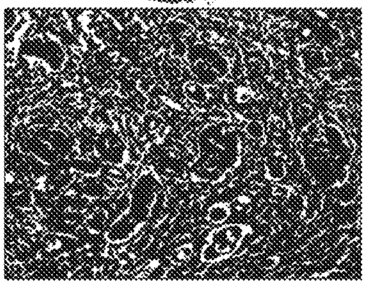
Figure 17A-17D
Pancreatic Cancer Array Antibody: huMNC2-scFv-Fc-Biotin Figure 18A-18D Pancreatic Cancer Array Antibody: huMNC2-scFv-Fc-Biotin Pancreatic Cancer Array
No Primary Antibody
Biomax - PA805b Pancreatic Cancer Array
D5-Score Trace
Grade 2
T2N0M0
Duct Adenocarcinoma Pancreatic Cancer Array
F1-Score Trace
Grade 3
T3N0M0
Duct Adenocarcinoma

Pancreatic Cancer Array
F3-Score 3
Grade 3
T2N1M0
Duct Adenocarcinoma
Fig. 27A
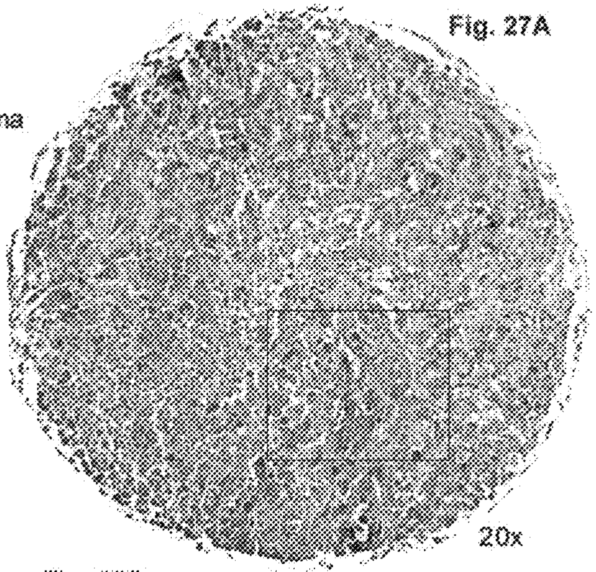
20x
Fig. 27C
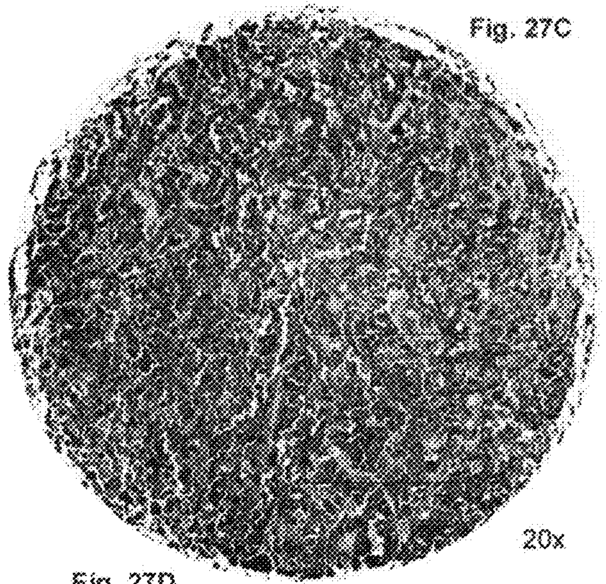
20x
Fig. 27B
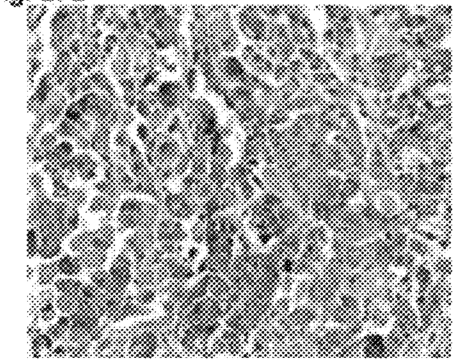
huMNC2-scFv-Fc
Monoclonal
Fig. 27D
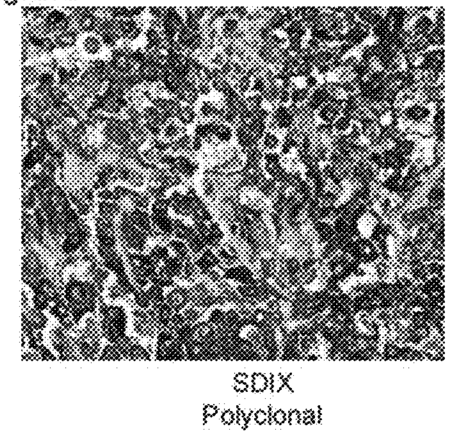
SDIX
Polyclonal
Figure 27A-27D

Pancreatic Cancer Array

F4-Score 0
Grade 3
T3N0M0
Duct Adenocarcinoma

Pancreatic Cancer Array
F9-Score 0
Grade -
T2N0M0
Acini cell carcinoma

Pancreatic Cancer Array
F10-Score 0
Grade 2
T3N0M0
Squamous cell carcinoma
Fig. 31A
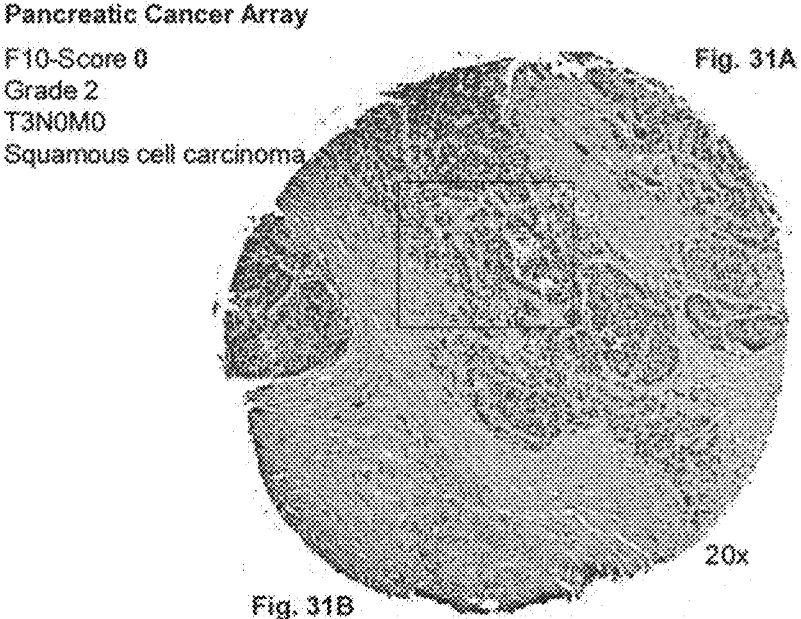
Fig. 31C
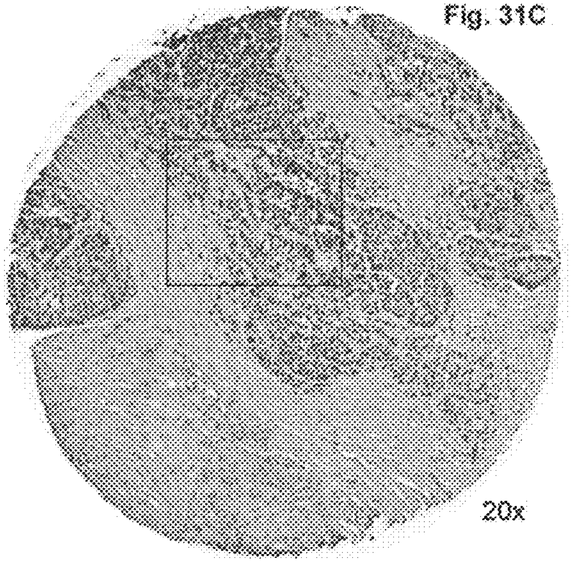
Fig. 31B
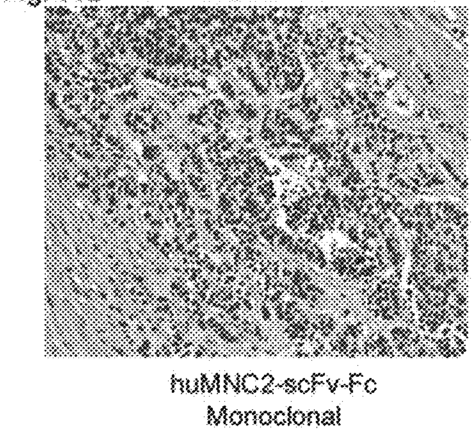
huMNC2-scFv-Fc
Monoclonal
Fig. 31D
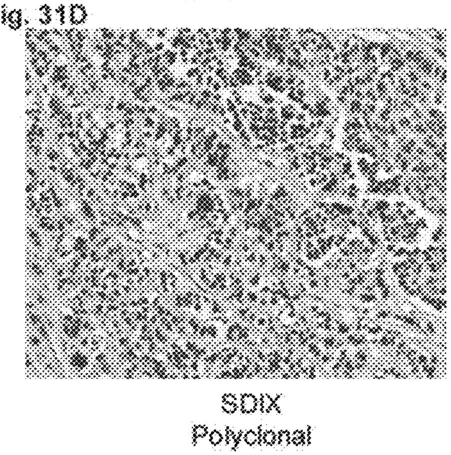
SDIX
Polyclonal
Figure 31A-31D G9
Normal adjacent pancreas tissue huMNC2-scFv-Fc
Monoclonal SDIX
Polyclonal The conformation as well as length of MUC1* extra cellular domain varies according to which cleavage enzyme cleaves MUC1; monoclonal antibodies are identified that are cleavage enzyme dependent, cancer sub-type dependent, patient dependent or tissue/cell type dependent.
Fig. 35A
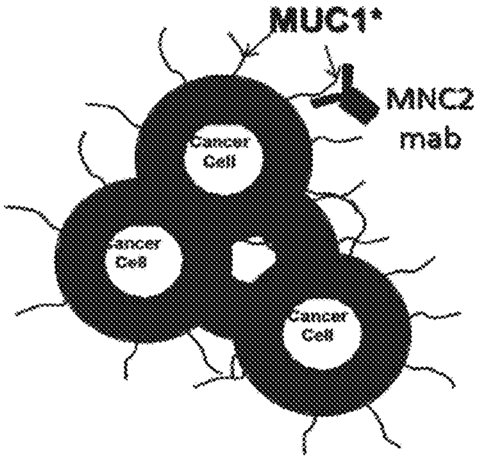
Fig. 35B
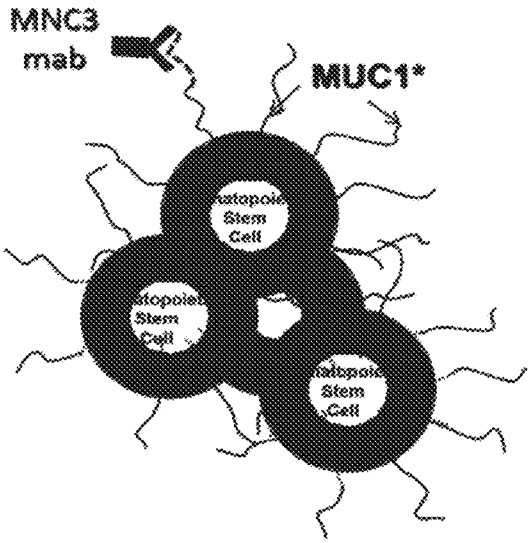
Figure 35A-35B Fig. 36A
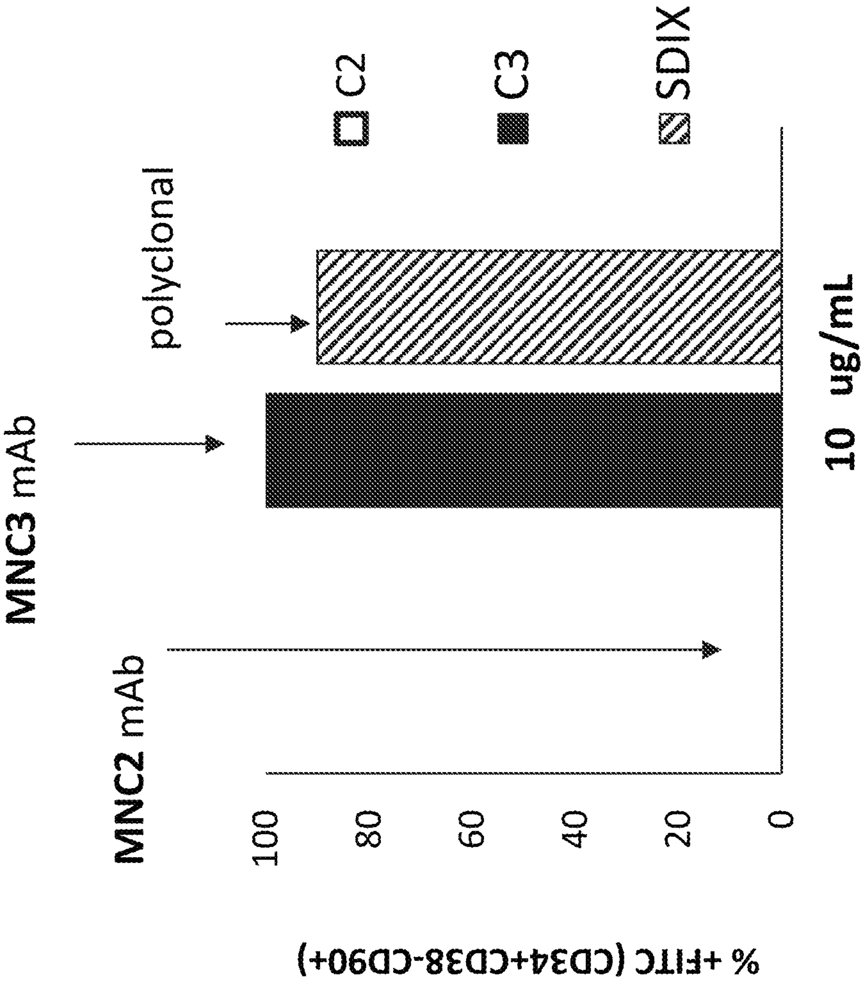
Fig. 36B
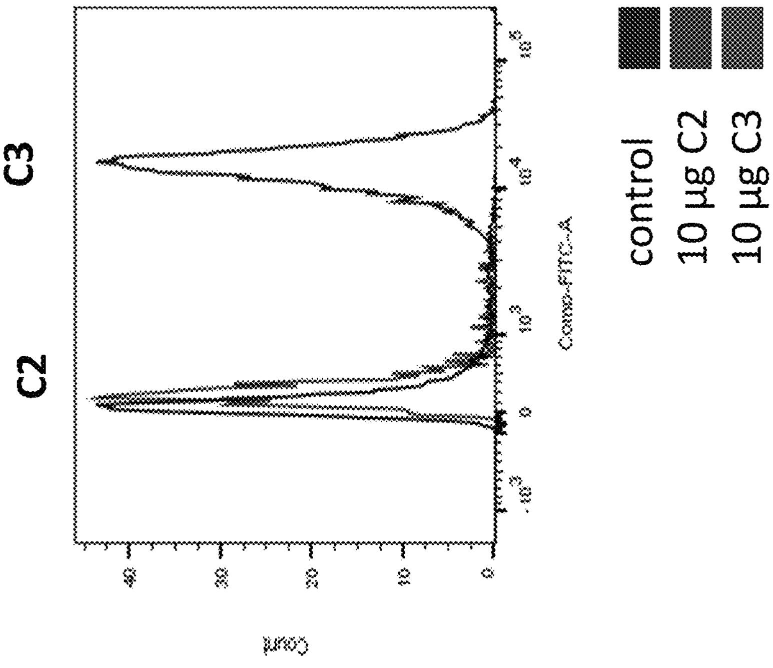
Figure 36A-36B

Fig. 38A

| PSMGFR clones | [] ug/mL |
|---|---|
| 18B4-1 | 17.3 |
| 18B4-2 | 6.8 |
| 18G12-1 | 2.6 |
| 18G12-2 | 5.9 |
| 20A10-1 | 18.3 |
| 20A10-2 | 16.2 |
| 25E6-1 | 3.4 |
| 25E6-2 | 2.1 |
| 28F9-1 | 3.9 |
| 28F9-2 | 8.2 |

Fig. 38B

| N+20/C-27 | [] ug/mL |
|---|---|
| 1E4-1 | 13.8 |
| 1E4-2 | 6.3 |
| 29H1-1 | 12.3 |
| 29H1-2 | 11.6 |
| 31A1-1 | 4.3 |
| 31A1-2 | 5.9 |
| 32C1-1 | 3.3 |
| 32C1-2 | 1.8 |
| 45C11-1 | 2.2 |
| 45C11-2 | 1.7 |

Fig. 38C

| N+9/C-9 | [] ug/mL |
|---|---|
| 3C5-1 | 2.4 |
| 3C5-2 | 5.5 |
| 8A9-1 | 1.0 |
| 8A9-2 | 1.1 |
| 17H6-1 | 4.2 |
| 17H6-2 | 2.4 |
| 39H5-1 | 1.6 |
| 39H5-2 | 2.6 |

Figure 38A – 38C

N+20/C-27 SNIKFRPGSVVVQLTLAFREGTINVHDVETQFNQYKTE

N+9/C-9 VQLTLAFREGTINVHDVETQFNQYKTEAASRYNLTISDVSVSDVP

PSMGFR GTINVHDVETQFNQYKTEAASRYNLTISDVSVSDVPFPFSAQSGA

N-10 QFNQYKTEAASRYNLTISDVSVSDVPFPFSAQSGA

C-10 GTINVHDVETQFNQYKTEAASRYNLTISDVSVSDV

ELISA: Anti-N+20 monoclonal antibodies binding to various peptides derived from MUC1* extra cellular domain sequence

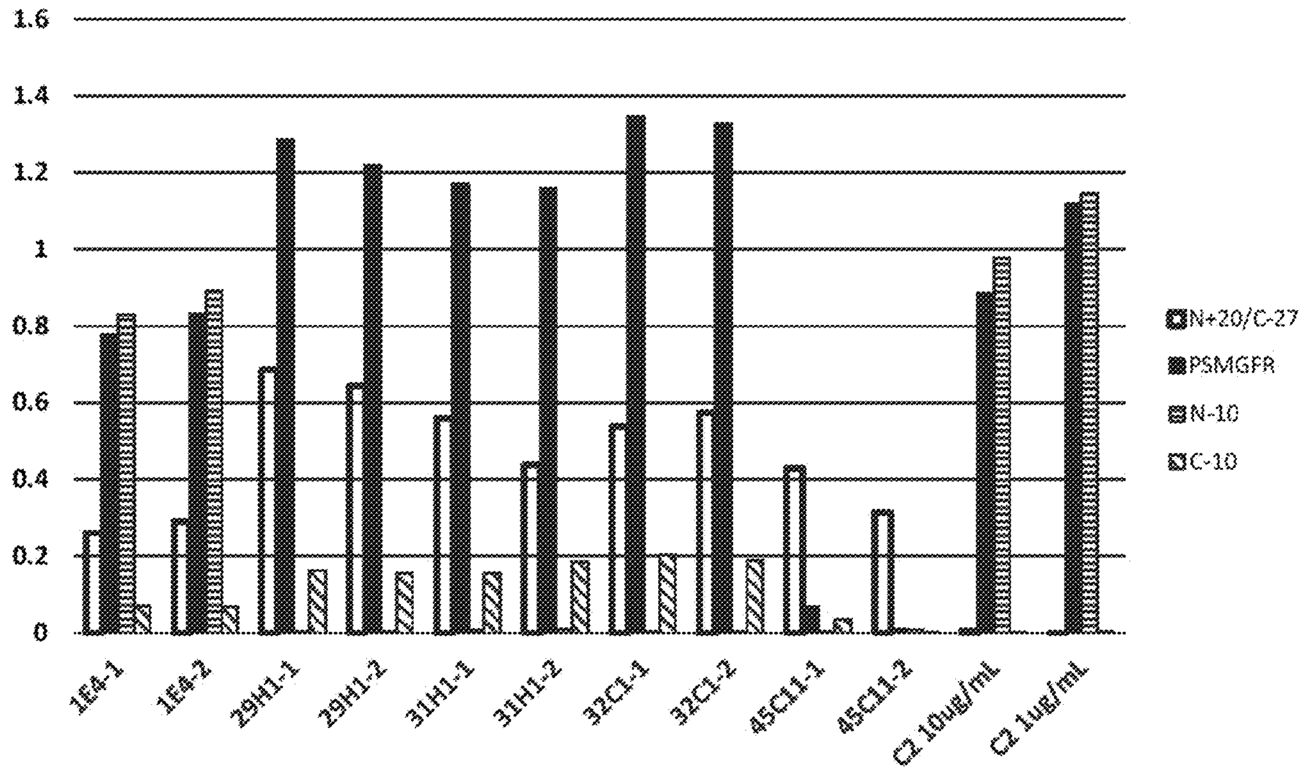

N+20/C-27 SNIKFRPGSVVVQLTLAFREGTINVHDVETQFNQYKTE

N+9/C-9 VQLTLAFREGTINVHDVETQFNQYKTEAASRYNLTISDVSVSDVP

PSMGFR GTINVHDVETQFNQYKTEAASRYNLTISDVSVSDVPFPFSAQSGA

N-10 QFNQYKTEAASRYNLTISDVSVSDVPFPFSAQSGA

C-10 GTINVHDVETQFNQYKTEAASRYNLTISDVSVSDV

Figure 41

FACS: Binding of anti-N+20 monoclonal antibodies to T47D breast cancer cells

ELISA: Anti-9+C-9 monoclonal antibodies binding to various peptides derived from MUC1* extra cellular domain sequence

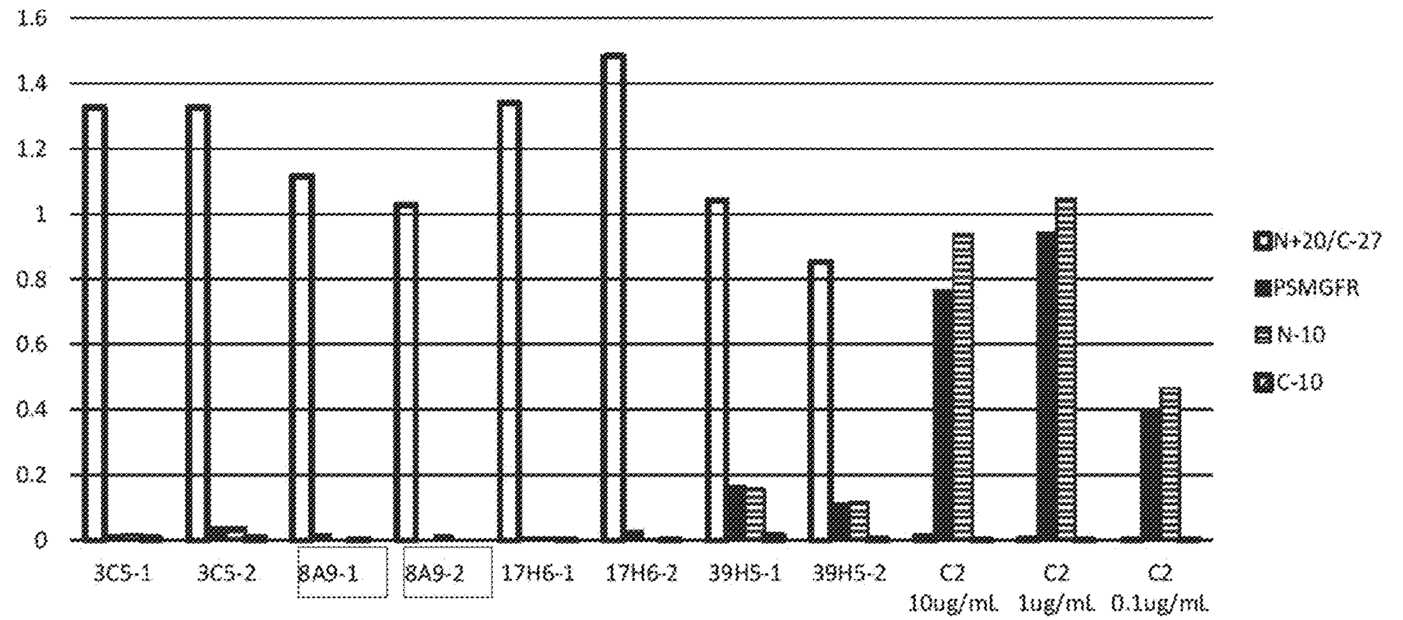

N+20/C-27 SNIKFRPGSVVVQLTLAFREGTINVHDVETQFNQYKTE

N+9/C-9 VQLTLAFREGTINVHDVETQFNQYKTEAASRYNLTISDVSVSDVP

PSMGFR GTINVHDVETQFNQYKTEAASRYNLTISDVSVSDVPFPFSAQSGA

N-10 QFNQYKTEAASRYNLTISDVSVSDVPFPFSAQSGA

C-10 GTINVHDVETQFNQYKTEAASRYNLTISDVSVSDV

Figure 43

FACS: Binding of 9+C-9 monoclonal antibodies to T47D breast cancer cells
Fig. 44A
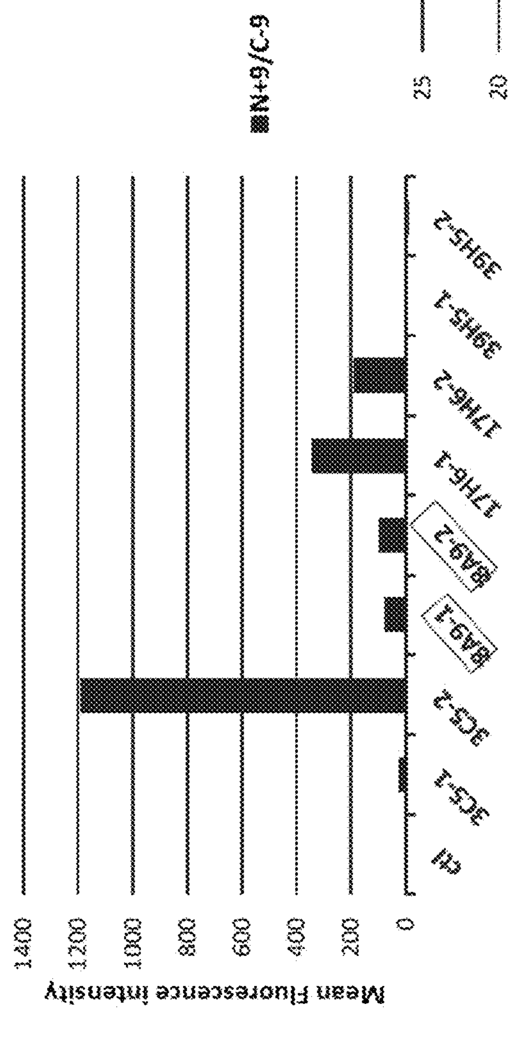
Fig. 44B
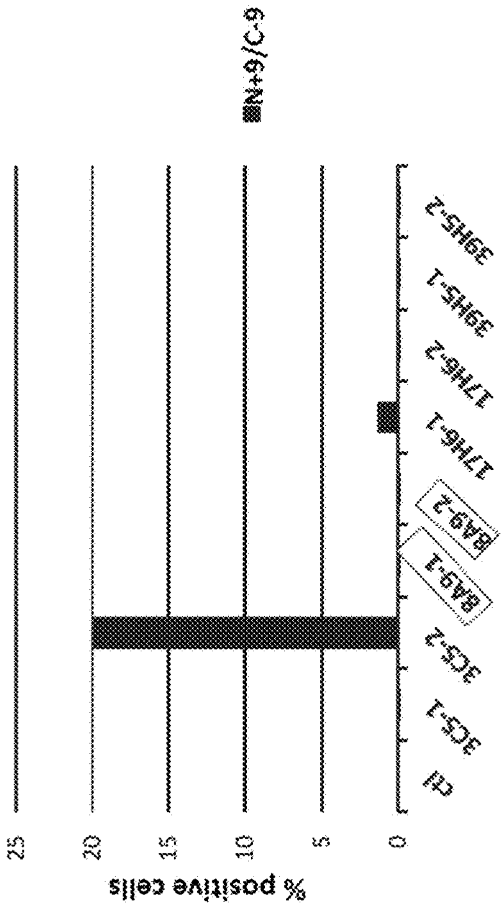
Figure 44A-44B

SDIX (α-PSMGFR)

18B4 (α-PSMGFR)

1E4 (α-N+20/C-27)

Pancreatic Cancer Array PA1003

SDIX (α-PSMGFR)
Fig. 47A
Fig. 47B
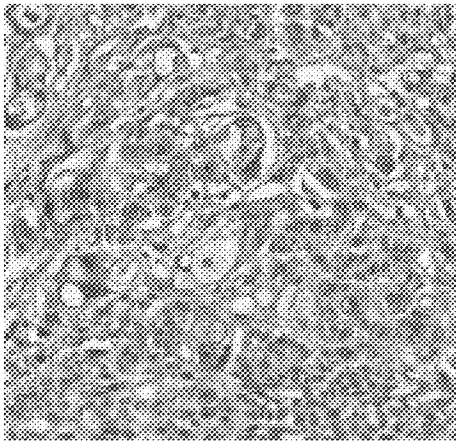
18B4 (α-PSMGFR)
Fig. 47C
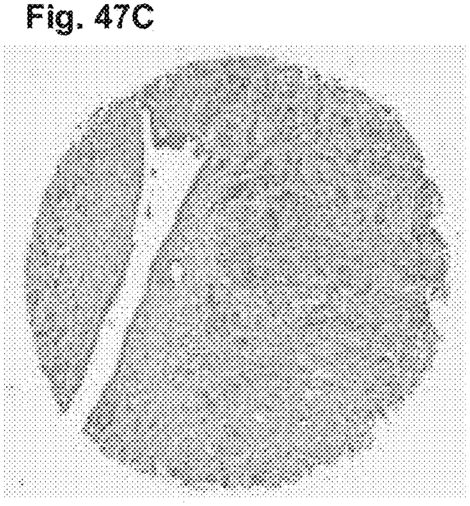
Fig. 47D
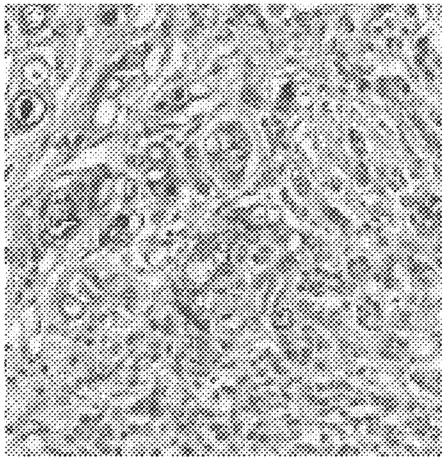
Figs. 47A-47D
Pancreatic Cancer Array PA1003

SDIX (α-PSMGFR)
18B4 (α-PSMGFR)
Fig. 48A
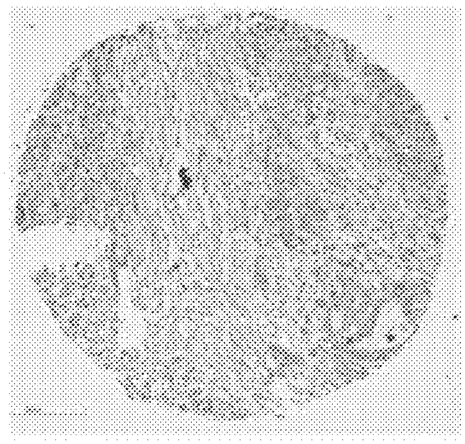
Fig. 48C
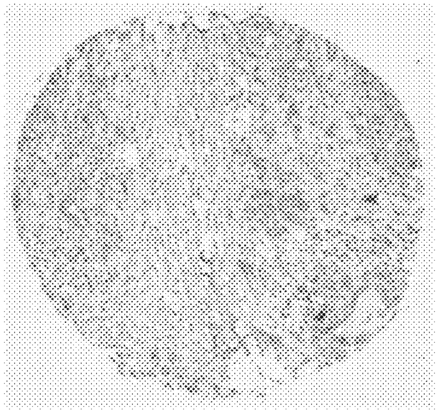
Fig. 48B
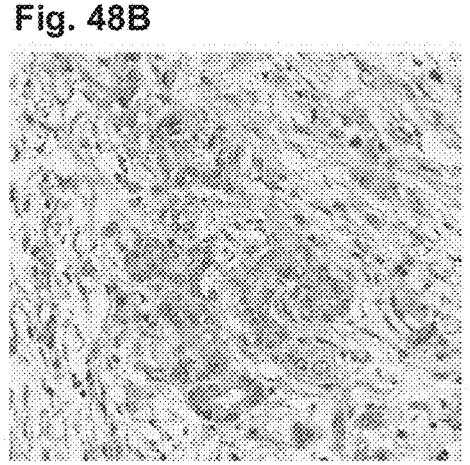
Fig. 48D
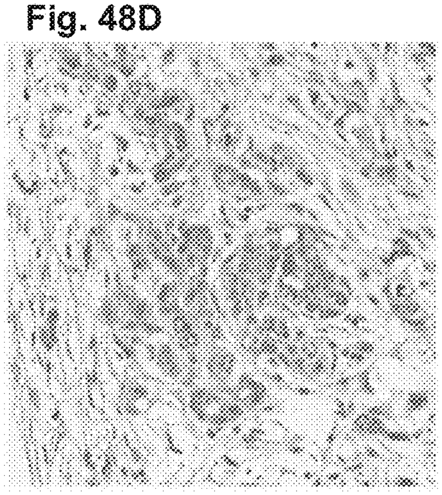
Figs. 48A-48D
Pancreatic Cancer Array PA1003

SDIX (α-PSMGFR)
Fig. 49A
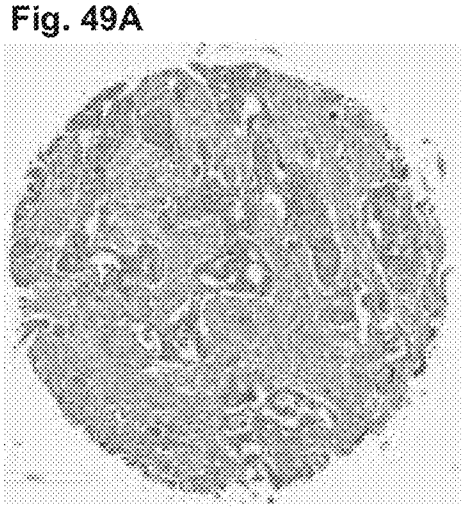
1E4 (α-N+20/C-27)
Fig. 49C
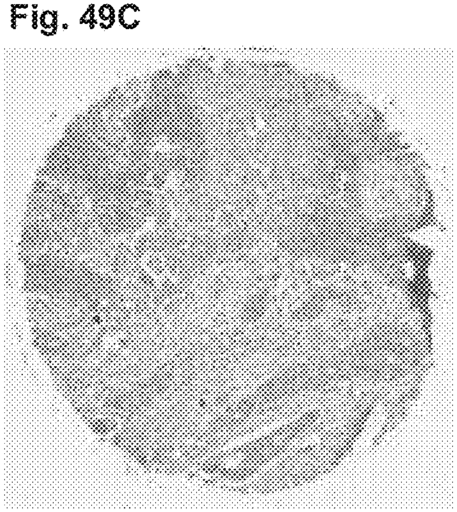
Fig. 49B
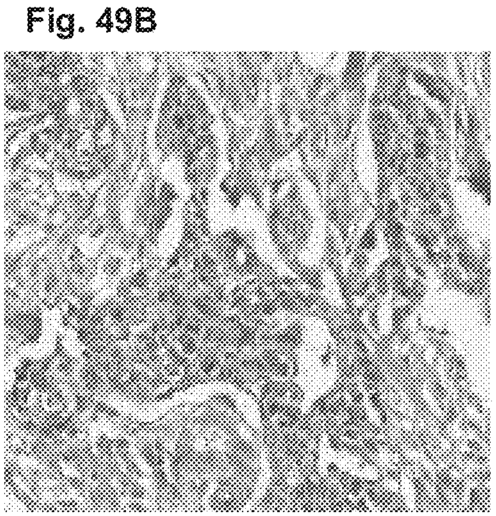
Fig. 49D
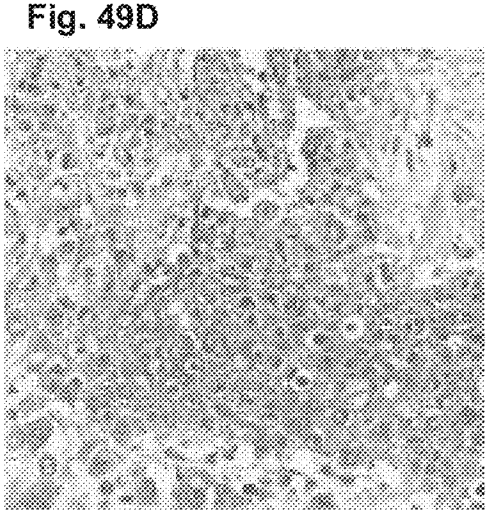
Figs. 49A-49D
Pancreatic Cancer Array PA1003

SDIX (α-PSMGFR)
Fig. 50A
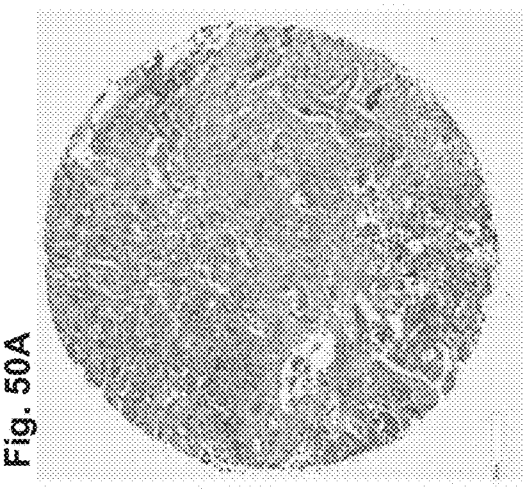
1E4 (α-N+20/C-27)
Fig. 50C
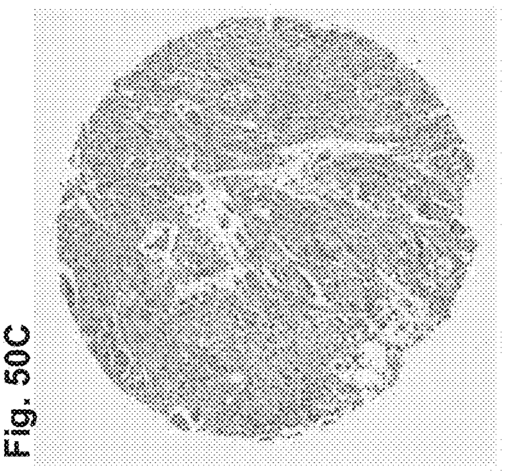
Fig. 50B
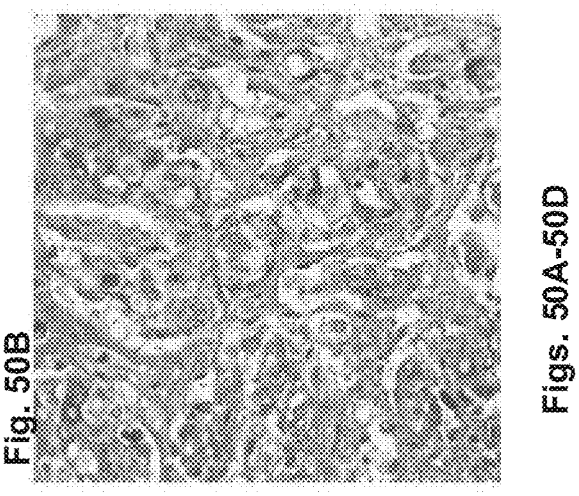
Fig. 50D
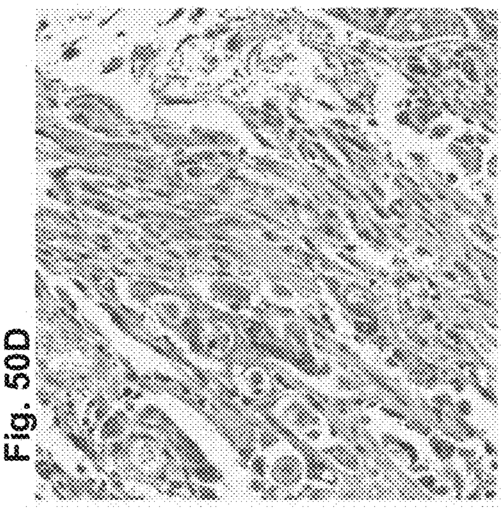
Figs. 50A-50D
Pancreatic Cancer Array PA1003

29H1-1 (α-N+20/C-27)

20A10 (α-PSMGFR)

SDIX (α-PSMGFR)

Pancreatic Cancer Array PA1003

Pancreatic Cancer Array PA1003

Fig. 54A
SDIX (α-PSMGFR)
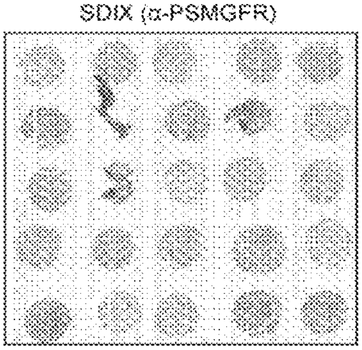
Fig. 54B
20A10 (α-PSMGFR)
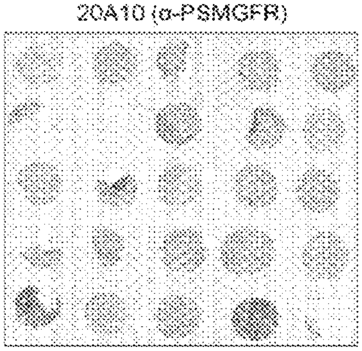
Fig. 54C
29H1 (α-N+20/C-27)
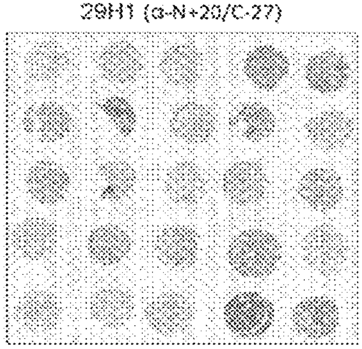
Fig. 54D
31A1 (α-N+20/C-27)
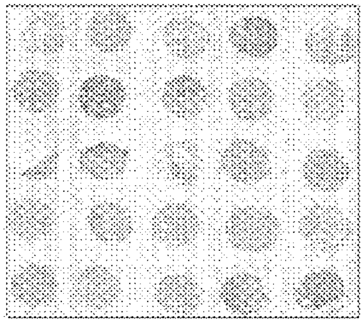
Figure 54A-54D
Esophageal Cancer Array ES1001

SDIX (α-PSMGFR)

17H6 (α- N+9/C-9)

MNC2 (α-PSMGFR)

45C11 (α-N+20/C-27)

Esophageal Cancer Array ES1001

Fig. 56A
5E5
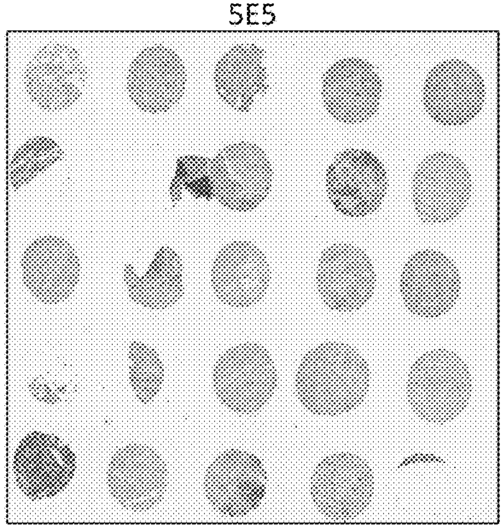
Fig. 56C
29H1-1 (α-N+20/C-27)
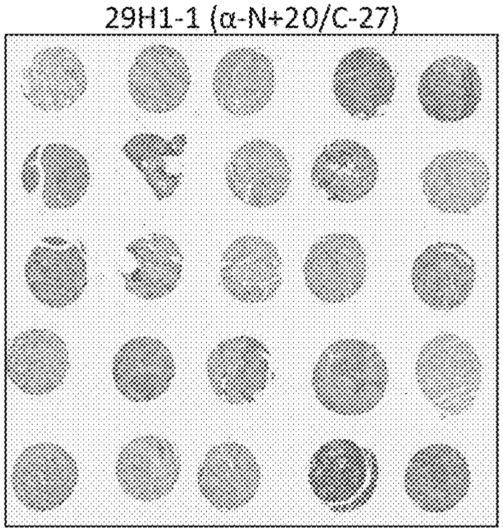
Fig. 56E
VU4H5
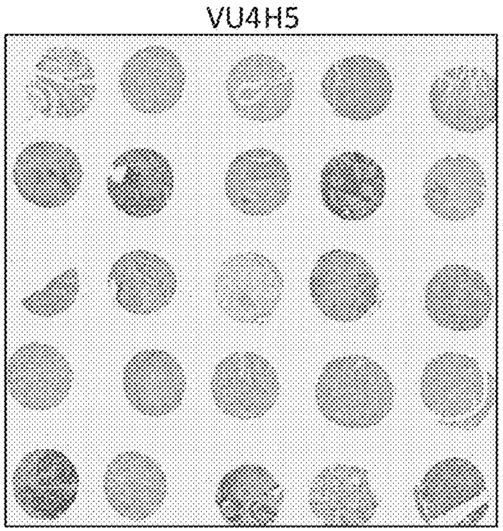
Fig. 56B
| 5E5 | | α-MUC1-FL-G |
|---|---|---|
| | 1 | 2 | 3 | 4 | 5 |
|---|---|---|---|---|---|
| A | 1 | 0.5 | 0 | 0 | 0.5 |
| B | 0 | 0 | 0 | 4 | 0 |
| C | 0 | 0 | 0 | 1 | 0 |
| D | 0 | 0 | 0.5 | 0.5 | 0 |
| E | 4 | 1 | 4 | 3 | n/a |
Fig. 56D
| 29H1-1 | | αN+20/C-27 |
|---|---|---|
| | 1 | 2 | 3 | 4 | 5 |
|---|---|---|---|---|---|
| A | 2 | 2 | 2 | 3 | 3 |
| B | 2 | 1 | 2 | 2 | 0.5 |
| C | 3 | 3 | 1 | 0.5 | 2 |
| D | 2 | 3 | 3 | 2 | 0 |
| E | 0.5 | 3 | 2 | 4 | 3 |
Fig. 56F
| VU4H5 | | α-MUC1-FL |
|---|---|---|
| | 1 | 2 | 3 | 4 | 5 |
|---|---|---|---|---|---|
| A | 2 | 1 | 1 | 0.5 | 0 |
| B | 0.5 | 4 | 1 | 4 | 2 |
| C | 0.5 | 0 | 0 | 3 | 1 |
| D | 0 | 0 | 0.5 | 0 | 0 |
| E | 4 | 2 | 4 | 4 | 3 |
Esophageal Cancer Array ES1001
Figs. 56A-56F Esophageal Cancer Array ES1001

Esophageal Cancer Array ES1001
Fig. 57E
5E5
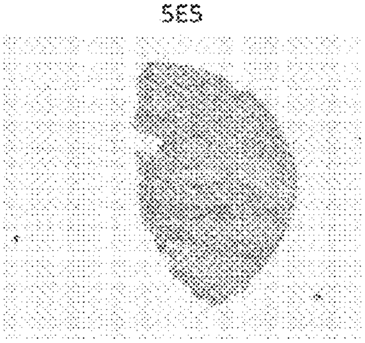
Fig. 57F
VU4H5
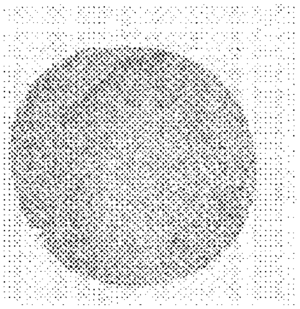
Fig. 57G
29H1 (α-N+20/C-27)
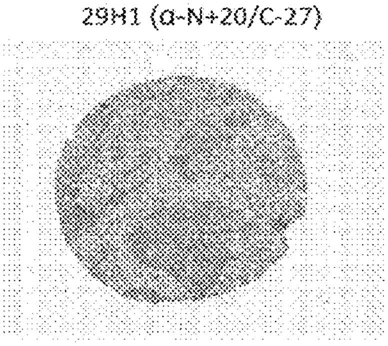
Figure 57E-57G

SDIX (α-PSMGFR)

20A10 (α-PSMGFR)

29H1 (α-N+20/C-27)

Figure 58A-58C Prostate Cancer Array PR1001

Prostate Cancer Array PR1001

Fig. 60A
5E5
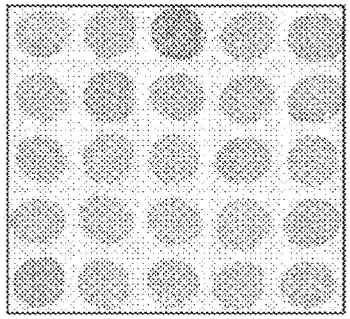
Fig. 60C
29H1-1 (α-N+20/C-27)
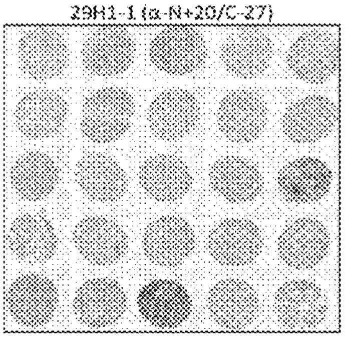
Fig. 60E
VU4H5
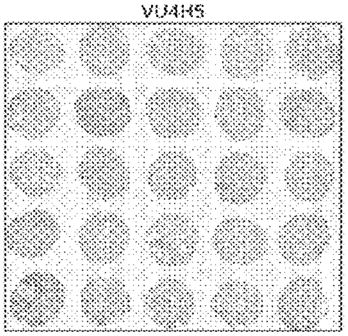
Fig. 60B
| SES | | α-MUC1-FL-B |
|---|---|---|
| | 1 | 2 | 3 | 4 | 5 |
|---|---|---|---|---|---|
| A | 0 | 0 | 0 | 0 | 0 |
| B | 0 | 0 | 0 | 0 | 0 |
| C | 0 | 0 | 0 | 0 | 1 |
| D | 0 | 0 | 0 | 0 | 0 |
| E | 2 | 0 | 0 | 0 | 0 |
Fig. 60D
| 29H1-1 | | α-(N+20/C-27) |
|---|---|---|
| | 1 | 2 | 3 | 4 | 5 |
|---|---|---|---|---|---|
| A | 0.5 | 2 | 0 | 0.5 | 0.5 |
| B | 0 | 0.5 | 0 | 0.5 | 1 |
| C | 2 | 0 | 0 | 1 | [illegible] |
| D | 1 | 0 | 2 | 1 | 0.5 |
| E | 2 | 3 | [illegible] | 2 | 1 |
Fig. 60F
| VU4H5 | | α-MUC1-FL |
|---|---|---|
| | 1 | 2 | 3 | 4 | 5 |
|---|---|---|---|---|---|
| A | 0 | 0 | 0 | 0 | 0 |
| B | 0 | 0 | 0 | 0 | 0 |
| C | 0 | 0 | 0 | 0 | 1 |
| D | 0 | 0 | 0 | 0 | 0 |
| E | [illegible] | 0 | 0 | 0 | 0 |
Figure 60A-60F
Prostate Cancer Array PR1001

No primary antibody control

Prostate Cancer Array PR1001

Fig. 61E
5E5
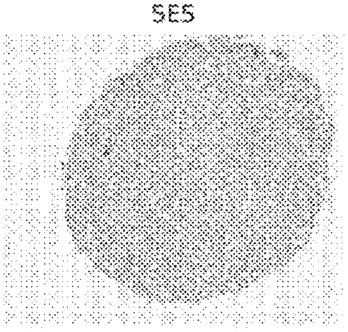
Fig. 61F
29H1 (α-N+20/C-27)
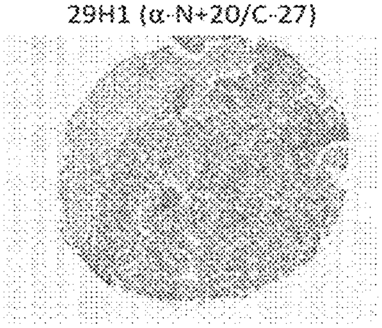
Fig. 61G
VU4H5
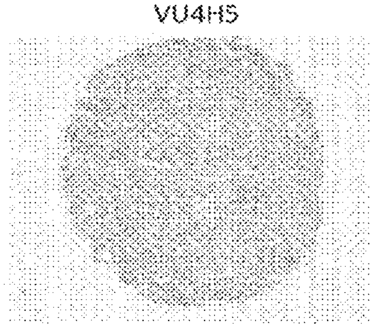
Figure 61E-61G
Prostate Cancer Array PR1001

Figure 62A-62B Breast Cancer Array BR1141

Fig. 63A
MNC2 (α-PSMGFR)
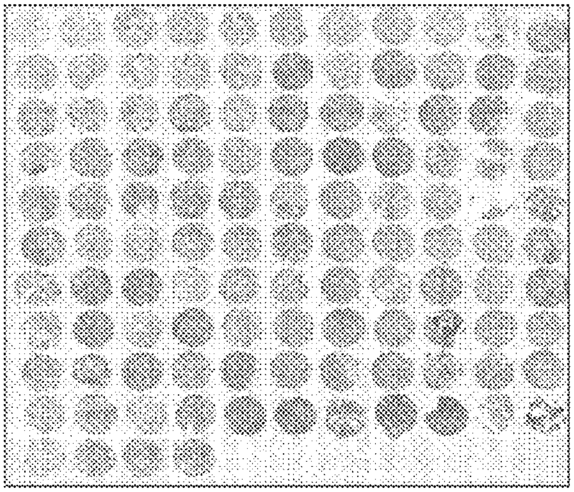
Fig. 63B
25E6 (α-PSMGFR)
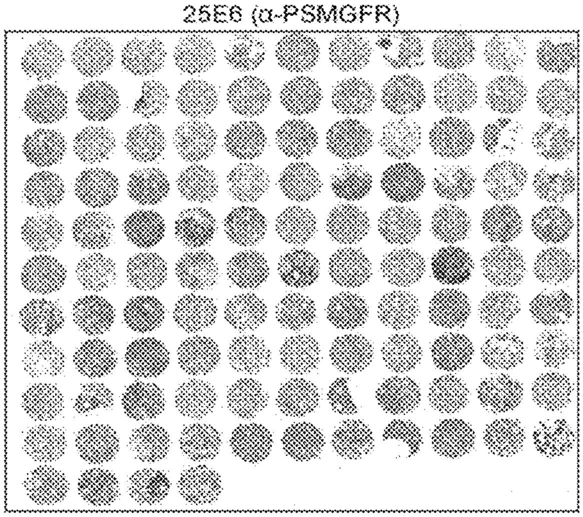
Figure 63A-63B
Breast Cancer Array BR1141

MNC2 (α-PSMGFR)

18B4 (α-PSMGFR)

Figure 64A-64B Breast Cancer Array BR1141

MNC2 (α-PSMGFR)

18G12 (α-PSMGFR)

Figure 65A-65B Breast Cancer Array BR1141

MNC2 (α-PSMGFR)

8A9 (α-N+9/C-9)

Figure 66A-66B Breast Cancer Array BR1141

Fig. 67A
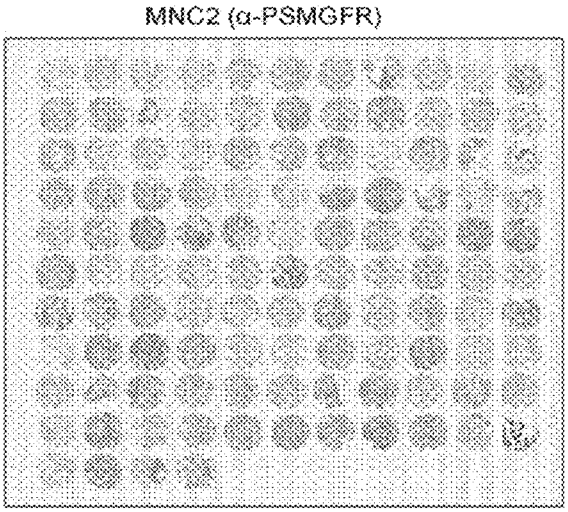
Fig. 67B
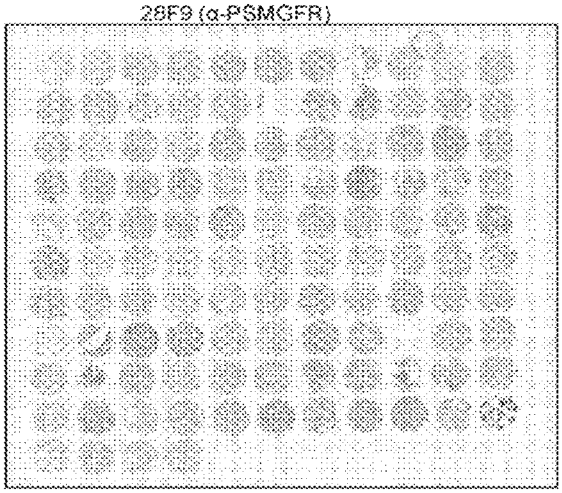
Figure 67A-67B
Breast Cancer Array Br1141

Fig. 68A
Fig. 68B
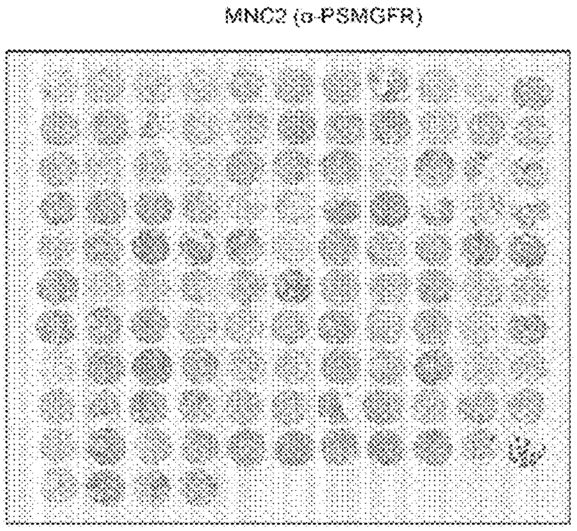
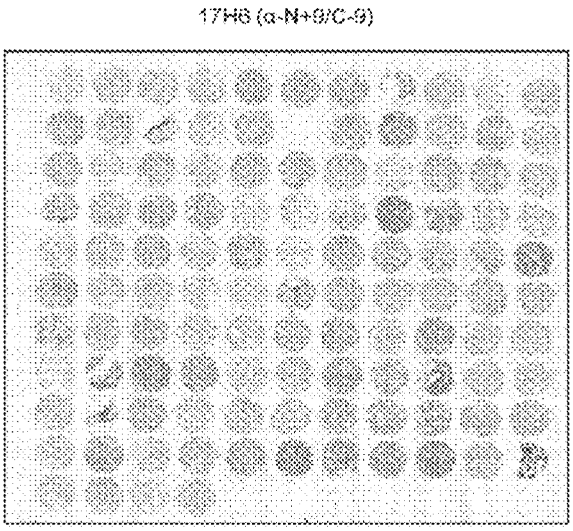
Breast Cancer Array Br1141
Figure 68A-68B Fig. 69A
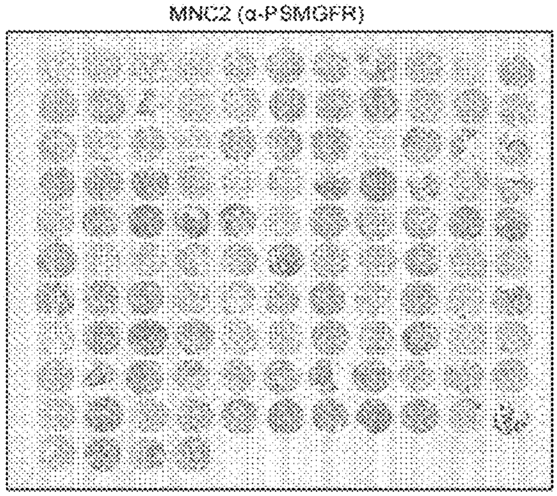
Fig. 69B
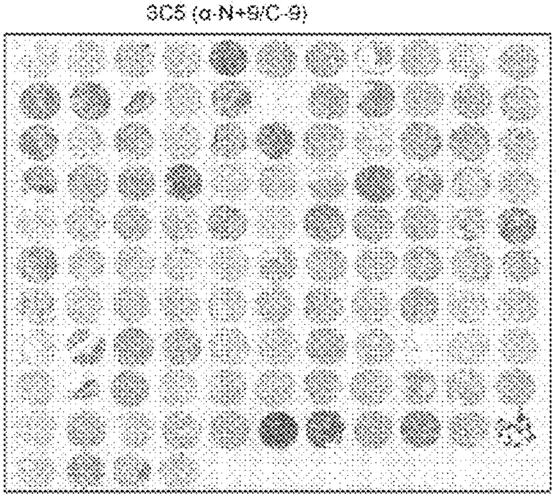
Figure 69A-69B
Breast Cancer Array Br1141

Figure 70A-70D Breast Cancer Array BR1007

Figure 70E-70G Breast Cancer Array BR1007

Fig. 71A
5E5
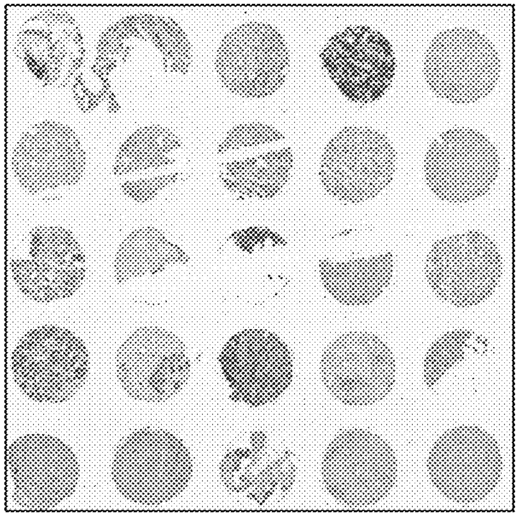
Fig. 71C
29H1 (α-N+20/C-27)
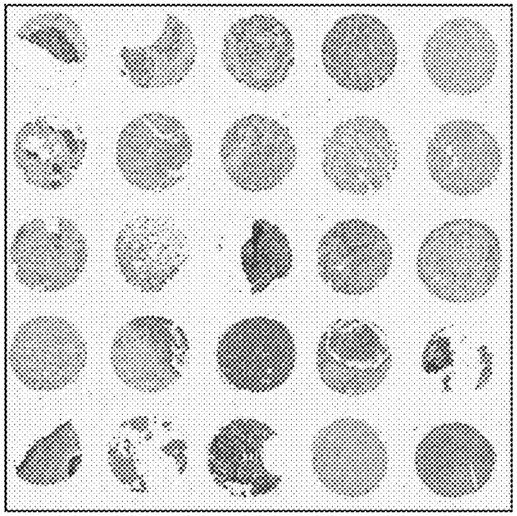
Fig. 71E
VU4H5
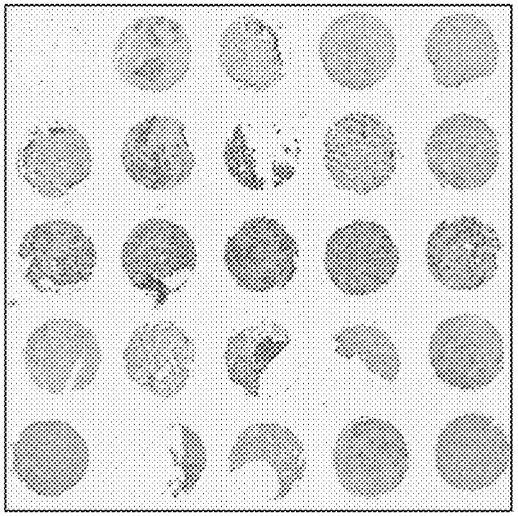
Fig. 71B
| 5E5 | | α-MUC1-FL-G |
|---|---|---|
| | 1 | 2 | 3 | 4 | 5 |
|---|---|---|---|---|---|
| A | n/a | 3 | 3 | 4 | 0 |
| B | 0 | 0 | 3 | 0 | 0.5 |
| C | 4 | 0 | 4 | 0.5 | 2 |
| D | 4 | 3 | 3 | 1 | 1 |
| E | 0.5 | 0.5 | 0 | 1 | 0 |
Fig. 71D
| 29H1-1 | | α-N+20/C-27) |
|---|---|---|
| | 1 | 2 | 3 | 4 | 5 |
|---|---|---|---|---|---|
| A | n/a | 3 | 4 | 3 | 1 |
| B | 3 | 3 | 4 | 2 | 2 |
| C | 3 | 3 | 4 | 4 | 3 |
| D | 2 | 2 | 4 | 2 | 4 |
| E | 3 | 1 | 4 | 0.5 | 2 |
Fig. 71F
| VU4H5 | | α-MUC1-FL |
|---|---|---|
| | 1 | 2 | 3 | 4 | 5 |
|---|---|---|---|---|---|
| A | n/a | 2 | 0 | 1 | 0.5 |
| B | 1 | 3 | 4 | 2 | 2 |
| C | 3 | 3 | 4 | 2 | 3 |
| D | 2 | 0.5 | 2 | 0 | 2 |
| E | 0 | 0 | 0 | 1 | 0 |
Breast Cancer Array BR1007
Figs. 71A-71F Breast Cancer Array BR1141

Breast Cancer Array BR1141

DIAGNOSTIC METHODS USING ANTI-MUC1* ANTIBODIES

CROSS-REFERENCE TO RELATED APPLICATIONS

This application is a continuation application of U.S. patent application Ser. No. 16/975,625 filed Aug. 25, 2020, which is the U.S. national phase of International Application No. PCT/US2019/019566 filed Feb. 26, 2019 which claims priority to U.S. Provisional Patent Application No. 62/791,661 filed Jan. 11, 2019, U.S. Provisional Patent Application No. 62/640,697 filed Mar. 9, 2018, and U.S. Provisional Patent Application No. 62/635,378 filed Feb. 26, 2018, the entire contents of each of which are hereby incorporated by reference. International Application No. PCT/US2019/019566 is a continuation-in-part of International Application No. PCT/US2018/062569 filed Nov. 27, 2018, the entire contents of which are hereby incorporated by reference.

DESCRIPTION OF THE XML FILE SUBMITTED ELECTRONICALLY

The instant application contains a Sequence Listing which has been submitted electronically in XML format and is hereby incorporated by reference in its entirety. Said XML copy, created on Mar. 20, 2024, is named 56699-739_301SL.xml and is 522,292 bytes in size.

BACKGROUND OF THE INVENTION

The present invention is directed to a method of diagnosing cancer and determining suitability of treating a patient suffering from cancer or metastasis of cancer characterized by aberrant expression of MUC1, with a MUC1* targeting therapeutic, comprising contacting cells or tissue of a patient diagnosed with or suspected of having cancer, with an antibody that binds to a form of MUC1 that is devoid of the tandem repeat domain, wherein the presence of specific binding of the antibody to the cleaved or truncated form of MUC1, and wherein such binding is in an abnormal pattern, indicates that a MUC1* targeting therapeutic is suitable to be used to treat the patient.

Here, we define MUC1* as a transmembrane cleavage product of MUC1 that functions as a growth factor receptor and is devoid of the tandem repeat sequences. However, MUC1 can be cleaved by different enzymes, which cleave at different sites. Which cleavage enzyme clips MUC1 may be tissue specific or patient specific. The conformation of the extra cellular domain of MUC1* may change depending on which cleavage enzyme cleaves it. Anti-MUC1* antibodies may bind to the extra cellular domain of the transmembrane receptor that remains after cleavage.

In one aspect, the antibody may bind to a peptide of Primary Sequence of MUC1 Growth Factor (PSMGFR), PSMGFR N-10, PSMGFR C-10, or may bind to PSMGFR N-10 but not to PSMGFR C-10, or may bind to PSMGFR C-10 but not to PSMGFR N-10, or may bind to the PSMGFR N+20 peptides such as N+20/C-22, N+20/C-41, or N+20/C-27 peptide, or a N+9/C-9 peptide. The antibody may bind to a peptide having a sequence that is extended N-terminally beyond the PSMGFR sequence. The antibody may bind to a peptide of sequence N+20-PSMGFR or N+9-PSMGFR. In one aspect of the invention, diagnostic assays employing anti-MUC1* antibodies or fragments thereof are used to screen patients to determine their potential benefit from a MUC1* targeting therapeutic. In one aspect of the invention, the antibody used in the diagnostic and the antibody or fragment thereof that is incorporated into the therapeutic are derived from the same antibody. The species of the diagnostic antibody and the therapeutic antibody do not need to be the same.

In one example, (i) a suspect cellular or tissue specimen, which may be a biopsy, from a patient diagnosed with cancer or suspected of developing cancer is contacted with an anti-MUC1* antibody; (ii) a normal cellular or tissue specimen from the patient or from a healthy donor is contacted with the same anti-MUC1* antibody, which may be an archived reference specimen; (iii) antibody binding is detected; (iv) the extent and pattern of antibody binding to the suspect specimen is compared to that of the normal specimen; (v) a determination that the suspect specimen overexpresses MUC1*, or expresses MUC1* in a uniform pattern as opposed to expression that is restricted to the apical border, indicates that the patient is suffering from a MUC1* positive cancer; (vi) a therapeutic agent that incorporates an anti-MUC1* antibody, or fragment thereof, is administered to the patient.

In another aspect of the invention, anti-MUC1* antibodies can be attached to an imaging agent for use in a patient as a whole body diagnostic to determine if the patient has a MUC1* positive tumor or, depending on the specific antibody used, if the patient would benefit from a therapeutic comprising all or a fragment of the antibody that is attached to the imaging agent. The species of the diagnostic antibody and the therapeutic antibody do not need to be the same. Antibodies generated in camelid species are particularly useful for in vivo diagnostic assays because camelids generated small monovalent antibodies that have a short half-life in humans.

In another aspect of the invention, anti-MUC1* antibodies, which may be attached to an imaging agent are used intra-surgically to detect or mark cancerous tissues so they can be excised during the surgery.

In another aspect of the invention, anti-MUC1* antibodies or fragments thereof that bind to a peptide having some or all of the sequence of the PSMGFR peptide are used for the diagnosis and/or treatment of breast cancers.

In another aspect of the invention, anti-MUC1* antibodies or fragments thereof that bind to a peptide having some or all of the sequence of the PSMGFR peptide, extended at the N-terminus by as many as 20 amino acids are used for the diagnosis and/or treatment of pancreatic cancers.

In another aspect of the invention, anti-MUC1* antibodies or fragments thereof that bind to a peptide having some or all of the sequence of the PSMGFR peptide, extended at the N-terminus by as many as 20 amino acids are used for the diagnosis and/or treatment of esophageal cancers.

In another aspect of the invention, anti-MUC1* antibodies or fragments thereof that bind to a peptide having some or all of the sequence of the PSMGFR peptide, extended at the N-terminus by as many as 20 amino acids are used for the diagnosis and/or treatment of prostate cancers.

In one aspect, the MUC1* targeting therapeutic may be a cancer immunotherapy. The MUC1* targeting therapeutic may be a CAR T, a BiTE, an ADC (antibody drug conjugate), a bispecific antibody or an antibody mimic.

The MUC1* targeting therapeutic may be an antibody that binds to a cleaved form of MUC1 wherein the cleaved form is the extra cellular domain of the transmembrane receptor that remains after cleavage. The antibody may bind to a peptide known as Primary Sequence of MUC1 Growth Factor (PSMGFR) or to a peptide that is N-terminally extended for up to 20 amino acids beyond the PSMGFR sequence. The antibody used in the therapeutic may be derived from the antibody used in the diagnostic assay, but need not be generated in the same species animal.

The inventive method may be an in vitro assay. The assay may be carried out on a tissue specimen, bodily fluid sample, or a blood sample.

In another aspect, the assay may be an in vivo assay. An imaging agent may be attached to the antibody.

In another aspect, the invention may comprise a second antibody, and the steps may comprise determining the ratio of the amount of a first antibody to a second antibody. The first antibody may bind to an extra cellular domain of the transmembrane receptor that remains after cleavage and the second antibody may bind to a portion of the MUC1 extra cellular domain that is N-terminal of the cleavage site, such as the tandem repeat sequences.

In another aspect, in reference to all of the above methods, the non-human, human or humanized anti-MUC1* antibody or antibody fragment or antibody-like protein may specifically bind to (i) PSMGFR region of MUC1;
(ii) PSMGFR peptide as set forth in SEQ ID NO:4;
(iii) PSMGFR N+20/C-22, a peptide having amino acid sequence of SNIKFRPGSVVVQLTLAFREGTINVHDVETQFNQYKTEAASRY (SEQ ID NO:5);
(iv) PSMGFR N+12/C-22, a peptide having amino acid sequence of SVVVQLTLAFREGTINVHDVETQFNQYKTEAASRY (SEQ ID NO:6);
(v) PSMGFR N+9/C-30, a peptide having amino acid sequence of VQLTLAFREGTINVHDVETQFNQY (SEQ ID NO:7);
(vi) PSMGFR N+20/C-41, a peptide having amino acid sequence of SNIKFRPGSVVVQLTLAFREGTIN (SEQ ID NO:8)
(vii) PSMGFR N+20/C-27, a peptide having amino acid sequence of SNIKFRPGSVVVQLTLAFREGTINVHDVETQFNQYKTE (SEQ ID NO:9); or
(viii) PSMGFR N+9/C-9, a peptide having amino acid sequence of VQLTLAFREGTINVHDVETQFNQYKTEAASRYNLTISDVSVSDVP (SEQ ID NO:10).

The antibody that binds to the extra cellular domain of the transmembrane receptor that remains after cleavage may be SDIX SRY polyclonal antibody, MNC2 monoclonal antibody, MNE6 monoclonal antibody, or monoclonal antibodies 1E4, 29H1, 31A1, 32C1, and 45C11 reactive with PSMGFR N+20/C-27; 17H6, 39H5, 3C5, 8A9 reactive with PSMGFR N+9/C-9; 18G12, 20A10, 25E6, 28F9, and 18B4 reactive with PSMGFR, as well as MNC2 and MNE6, which are also reactive with PSMGFR. These antibodies may be human, humanized, mouse, camelid, llama, alpaca, camel, rabbit, goat, hamster or other non-human species.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1A shows photographs of the breast cancer tissue arrays after they were stained with VU4H5, which is an antibody that binds to the tandem repeat domains of full-length MUC1. FIG. 1B shows graphs of the pathologist scores for the tissues pictured in FIG. 1A. FIG. 1C shows photographs of the breast cancer tissue arrays after they were stained with MNC2, which is an antibody that binds to an epitope within the PSMGFR region of MUC1*. FIG. 1D shows graphs of the pathologist scores for the tissues pictured in FIG. 1C.

FIG. 2A shows that the antibody that binds to tandem repeats of full-length MUC1 misses 30% of breast cancers. FIG. 2B shows that the anti-MUC1* antibody MNC2 recognizes 95% of breast cancers. Anti-MUC1-full-length only binds strongly to 10% of the breast tumors, while anti-MUC1* antibody MNC2 binds strongly to about 50% of breast tumors.

FIG. 3A-3B shows pie chart graphs of the pathologist scores and a photograph of breast cancer array BR1141 after staining with anti-MUC1* antibody huMNC2-scFv-Fc.

FIG. 4A-4C shows photographs, at two different magnifications, of individual breast cancer specimens from breast cancer array BR1141 after staining with anti-MUC1* antibody huMNC2-scFv-Fc. The position in the array, cancer sub-type, tumor grade, TNM (Tumor stage, Node involvement, and Metastasis) and pathologist score are indicated in figures. Standard immunohistochemistry methods were used. Antibody concentration was titered using the highest concentration at which the antibody showed expected staining of normal tissues without staining stroma. The antibody was conjugated to a biotin through its Fc region, to avoid false positive due to anti-human secondary antibodies staining host antibodies as well as B cell follicules. FIG. 4A shows the specimen at position A7 which was negative for huMNC2 reactive cells. FIG. 4B shows the specimen at position A9 which is a Grade 2 cancer, with lymph node involvement that scored +1 for huMNC2 reactivity. FIG. 4C shows the specimen at position B10 which is a larger Grade 2 tumor, with lymph node involvement that scored +2 for huMNC2 reactivity.

FIG. 5A-5B shows photographs, at two different magnifications, of individual breast cancer specimens from breast cancer array BR1141 after staining with anti-MUC1* antibody huMNC2-scFv-Fc. FIG. 5A shows the specimen at position D7 which is a Grade 2 cancer, without lymph node involvement that scored +3 for huMNC2 reactivity. FIG. 5B shows the specimen at position F6 which is a Grade 2 tumor, with lymph node involvement that scored +4 for huMNC2 reactivity.

FIG. 6A-6B shows pie chart graphs of the pathologist scores and a photograph of ovarian cancer array BC1115a after staining with anti-MUC1* antibody huMNC2-scFv-Fc.

FIG. 7A shows a photograph of a Grade 2 breast tumor that pathologist scored +4. FIG. 7B shows a photograph of a Grade 2 ovarian tumor that pathologist scored +3. FIG. 7C shows a photograph of a Grade 3 pancreatic tumor that pathologist scored +3. IHC studies of over 1,000 tumor specimens showed that huMNC2-scFv recognized 95% of Breast Cancers (90% triple negative), 83% Ovarian, 78% Pancreatic & 71% Lung Cancers.

FIG. 8A shows a photograph of a Grade 2 breast tumor that pathologist scored +2. FIG. 8B shows a photograph of a Grade 3 ovarian tumor that pathologist scored +3. FIG. 8C shows a photograph of a Grade 3 pancreatic tumor, with lymph node involvement that pathologist scored +3. FIG. 8D shows a photograph of a lung cancer that pathologist scored +3.

FIG. 9A shows normal adrenal gland tissue. FIG. 9B shows normal brain tissue. FIG. 9C shows normal breast tissue. FIG. 9D shows normal stomach tissue. FIG. 9E shows normal heart tissue. FIG. 9F shows normal kidney tissue. FIG. 9G shows normal testis tissue. FIG. 9H shows normal intestine tissue. FIG. 9I shows normal liver tissue.

FIG. 10A-10F shows photographs of normal kidney tissues after staining with anti-MUC1* antibody huMNC2-scFv-Fc. Conditions and concentrations used were identical to those used for studying cancerous tissues. FIG. 10A shows normal kidney tissue with huMNC2 reactivity limited to the apical border, which is normal expression. FIG. 10B is the same tissue at greater magnification. FIG. 10C shows another example of normal kidney tissue with undetectable huMNC2 reactivity. FIG. 10D is the same tissue at greater magnification. FIG. 10E shows another example of normal kidney tissue with huMNC2 reactivity limited to the apical border, which is normal expression. FIG. 10F is the same tissue at greater magnification. Further studies showed that less than 10% of normal kidney tissue showed huMNC2 reactivity at distal collecting tubules wherein such reactivity was strictly limited to the apical border, which is a normal expression pattern.

FIG. 11A-11B shows pie chart graphs of the pathologist scores and a photograph of esophageal cancer array BC001113 after staining with anti-MUC1* antibody huMNC2-scFv-Fc.

FIG. 12A-12F shows photographs, at two different magnifications, of individual esophageal cancer specimens from esophageal cancer array BC001113, after staining with anti-MUC1* antibody huMNC2-scFv-Fc. The position in the array, cancer sub-type, tumor grade, and pathologist score are indicated in figures. FIG. 12A shows the specimen at position A4 which was negative for huMNC2 reactive cells. FIG. 12B shows the same specimen at greater magnification. FIG. 12C shows the specimen at position D2 which the pathologist scored as trace reactivity to huMNC2. FIG. 12D shows the same specimen at greater magnification. FIG. 12E shows the specimen at position B8 which the pathologist scored as +1 reactivity to huMNC2. FIG. 12F shows the same specimen at greater magnification.

FIG. 13A-13D shows photographs, at two different magnifications, of individual esophageal cancer specimens from esophageal cancer array BC001113, after staining with anti-MUC1* antibody huMNC2-scFv-Fc. The position in the array, cancer sub-type, tumor grade, and pathologist score are indicated in figures. FIG. 13A shows the specimen at position D6, a Grade 4 tumor, which the pathologist scored +2. FIG. 13B shows the same specimen at greater magnification. FIG. 13C shows the specimen at position D5, a Grade 3 tumor, which the pathologist scored +3. FIG. 12D shows the same specimen at greater magnification.

FIG. 14A-14B shows pie chart graphs of the pathologist scores and a photograph of pancreatic cancer array PA805b after staining with anti-MUC1* antibody huMNC2-scFv-Fc.

FIG. 15A shows the specimen at position F3, a Grade 3 tumor, which the pathologist scored +3. FIG. 15B shows the same specimen at greater magnification. FIG. 15C shows the specimen at position B1, a Grade 1 tumor, which the pathologist scored +2. FIG. 15D shows the same specimen at greater magnification.

FIG. 16A-16D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 16A shows the specimen at position A2, a Grade 1 tumor, which the pathologist scored +2. FIG. 16B shows the same specimen at greater magnification. FIG. 16C shows the specimen at position C3, a Grade 2 tumor, which the pathologist scored +2. FIG. 16D shows the same specimen at greater magnification.

FIG. 17A-17D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 17A shows the specimen at position C6, a Grade 2 tumor, which the pathologist scored +2. FIG. 17B shows the same specimen at greater magnification. FIG. 17C shows the specimen at position D1, a larger Grade 3 tumor, with lymph node involvement that the pathologist scored +3. FIG. 17D shows the same specimen at greater magnification.

FIG. 18A shows the specimen at position E2, a Grade 1 tumor, which the pathologist scored +2. FIG. 18B shows the same specimen at greater magnification. FIG. 18C shows the specimen at position E10, a smaller Grade 3 tumor, with lymph node involvement that the pathologist scored +3. FIG. 18D shows the same specimen at greater magnification.

FIG. 20A shows a photograph of the pancreatic cancer array that was stained with anti-MUC1* monoclonal antibody huMNC2-scFv. FIG. 20B shows a photograph of the pancreatic cancer array that was stained with anti-MUC1* polyclonal antibody SDIX. Both polyclonal and monoclonal antibodies were generated by immunizing the animals with the PSMGFR peptide. The circled specimens are indicated because they show different staining when probed with the monoclonal versus the polyclonal antibody. The numbers beneath each specimen indicate the pathologist score, when probed with huMNC2-scFv, followed by a slash mark, then the tumor grade.

FIGS. 27A-27D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.

FIGS. 31A-31D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.

FIG. 35A-35B shows cartoons of MUC1* expression on cancer cells and on normal hematopoietic stem cells. FIG. 35A depicts MUC1* on a cancer cell being probed by anti-MUC1* monoclonal antibody, MNC2. FIG. 35B depicts MUC1* on normal hematopoietic stem cells being probed by anti-MUC1* monoclonal antibody, MNC3. Both antibodies were generated by immunizing the animal with a PSMGFR peptide. MNC2 does not bind to normal hematopoietic stem cells but MNC3 does.

FIG. 36A-36B shows FACS analysis of human hematopoietic stem cells stained with anti-PSMGFR antibodies. FIG. 36A shows a graph of FACS results showing that the SDIX polyclonal antibody and the MNC3 monoclonal antibody recognize nearly 100% of the hematopoietic stem cells but MNC2 monoclonal antibody does not bind to them. FIG. 36B shows an overlay of the FACs scans, which shows that MNC2 binding is no different than the control antibody, while MNC3 produces a clear shift in the cell populations. All three antibodies were generated by immunizing with the PSMGFR peptide.

FIG. 38A-38C lists new anti-MUC1* monoclonal antibodies that were generated by immunizing animals with one of three different peptides derived from the MUC1* extra cellular domain sequence. FIG. 38A lists monoclonal antibodies that were generated when animals were immunized with the PSMGFR peptide. FIG. 38B lists monoclonal antibodies that were generated when animals were immunized with the PSMGFR N+20/C-27 peptide. FIG. 38C lists monoclonal antibodies that were generated when animals were immunized with the PSMGFR N+9/C-9 peptide. The −1 or −2 designation refers to sister clones from the same well. Concentrations of stock antibody solutions are given.

FIG. 40A shows the Mean Fluorescence Intensity. FIG. 40B shows the percent of cells that stained positive with the respective antibody.

FIG. 41 shows a graph of an ELISA experiment testing the ability of monoclonal antibodies, generated by immunizing with the PSMGFR N+20/C-27 peptide, to bind to other peptides derived from the sequence of the MUC1* extra cellular domain. All monoclonal antibodies were first selected based on their ability to bind to the immunizing peptide. To further elucidate the epitope within that peptide to which the antibody binds, antibodies were tested for their ability to bind to the PSMGFR peptide, the N-10 peptide or the C-10 peptide.

FIG. 42A shows the Mean Fluorescence Intensity. FIG. 42B shows the percent of cells that stained positive with the respective antibody.

FIG. 43 shows a graph of an ELISA experiment testing the ability of monoclonal antibodies, generated by immunizing with the PSMGFR N+9/C-9 peptide, to bind to other peptides derived from the sequence of the MUC1* extra cellular domain. All monoclonal antibodies were first selected based on their ability to bind to the immunizing peptide. To further elucidate the epitope within that peptide to which the antibody binds, antibodies were tested for their ability to bind to the PSMGFR peptide, the N-10 peptide or the C-10 peptide.

FIG. 44A-44B shows graphs of FACS analysis of the new PSMGFR N+9/C-9 anti-MUC1* monoclonal antibodies binding to T47D breast cancer cells. FIG. 44A shows the Mean Fluorescence Intensity. FIG. 44B shows the percent of cells that stained positive with the respective antibody.

FIG. 45A shows the array stained with the SDIX polyclonal anti-MUC1* antibody, wherein the immunogen for the antibody was the PSMGFR peptide. FIG. 45B shows the array stained with the 18B4 monoclonal anti-MUC1* antibody, wherein the immunogen for the antibody was the PSMGFR peptide. FIG. 45C shows the array stained with the 1E4 monoclonal anti-MUC1* antibody, wherein the immunogen for the antibody was the PSMGFR N+20/C-27 peptide.

FIG. 46A shows a specimen stained with the SDIX polyclonal antibody. FIG. 46B shows the same tissue specimen at a greater magnification. FIG. 46C shows the adjacent tissue section stained with the 18B4 monoclonal antibody. FIG. 46D shows the same tissue specimen at a greater magnification. FIG. 46E shows the adjacent tissue section stained with the 1E4 monoclonal antibody. FIG. 46F shows the same tissue specimen at a greater magnification.

FIG. 47A-47D shows photographs of individual specimens from the pancreatic cancer array shown in FIG. 45. FIG. 47A shows a specimen stained with the SDIX polyclonal antibody. FIG. 47B shows the same tissue specimen at a greater magnification. FIG. 47C shows the adjacent tissue section stained with the 18B4 monoclonal antibody. FIG. 47D shows the same tissue specimen at a greater magnification.

FIG. 48A-48D shows photographs of individual specimens from the pancreatic cancer array shown in FIG. 45. FIG. 48A shows a specimen stained with the SDIX polyclonal antibody. FIG. 48B shows the same tissue specimen at a greater magnification. FIG. 48C shows the adjacent tissue section stained with the 18B4 monoclonal antibody. FIG. 48D shows the same tissue specimen at a greater magnification.

FIG. 49A-49D shows photographs of individual specimens from the pancreatic cancer array shown in FIG. 45. FIG. 49A shows a specimen stained with the SDIX polyclonal antibody. FIG. 49B shows the same tissue specimen at a greater magnification. FIG. 49C shows the adjacent tissue section stained with the 1E4 monoclonal antibody. FIG. 49D shows the same tissue specimen at a greater magnification. Comparing FIG. 49A to FIG. 49C, it is clear that the monoclonal antibody generated by immunizing with the PSMGFR N+20/C-27 peptide recognizes a different cell population within the tumor than that recognized by the polyclonal antibody, SDIX, that was generated by immunizing with the PSMGFR peptide.

FIG. 50A-50D shows photographs of individual specimens from the pancreatic cancer array shown in FIG. 45. FIG. 50A shows a specimen stained with the SDIX polyclonal antibody. FIG. 50B shows the same tissue specimen at a greater magnification. FIG. 50C shows the adjacent tissue section stained with the 1E4 monoclonal antibody.

FIG. 50D shows the same tissue specimen at a greater magnification. Comparing FIG. 50A to FIG. 50C, it is clear that the monoclonal antibody generated by immunizing with the PSMGFR N+20/C-27 peptide recognizes a different cell population within the tumor than that recognized by the polyclonal antibody, SDIX, that was generated by immunizing with the PSMGFR peptide.

FIG. 51A shows the array stained with the SDIX polyclonal anti-MUC1* antibody, wherein the immunogen for the antibody was the PSMGFR peptide. FIG. 51B shows the array stained with the 20A10 monoclonal anti-MUC1* antibody, wherein the immunogen for the antibody was the PSMGFR peptide. FIG. 51C shows the array stained with the 29H1 monoclonal anti-MUC1* antibody, wherein the immunogen for the antibody was the PSMGFR N+20/C-27 peptide.

FIG. 52A shows the array stained with the 17H6 monoclonal anti-MUC1* antibody, wherein the immunogen for the antibody was the PSMGFR N+9/C-9 peptide. FIG. 52B shows the array stained with the 32C1 monoclonal anti-MUC1* antibody, wherein the immunogen for the antibody was the PSMGFR N+20/C-27 peptide. FIG. 52C shows the array stained with the 45C11 monoclonal anti-MUC1* antibody, wherein the immunogen for the antibody was the PSMGFR N+20/C-27 peptide. FIG. 52D shows the array stained with the 31A1 monoclonal anti-MUC1* antibody, wherein the immunogen for the antibody was the PSMGFR N+20/C-27 peptide.

FIG. 53A shows the pancreatic cancer array stained with antibody 5E5, which is an antibody that binds to a trapped O-linked glycan in the tandem repeat domain of full-length MUC1. FIG. 53B shows the pathologist's score for each specimen in the array. FIG. 53C shows the pancreatic cancer array stained with anti-MUC1* antibody 29H1, which is an antibody that binds to the PSMGFR N+20/C-27 peptide of MUC1*. FIG. 53D shows the pathologist's score for each specimen in the array. FIG. 53E shows the pancreatic cancer array stained with antibody VU4H5, which is an antibody that binds to an epitope in the tandem repeat domain of full-length MUC1. FIG. 53F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C-27 peptide recognize epitopes that are prevalent on pancreatic cancers.

FIG. 54A-54C shows photographs of adjacent serial sections from an esophageal cancer array, which was stained by standard IHC methods with various anti-MUC1* antibodies. FIG. 54A shows the array stained with the SDIX polyclonal anti-MUC1* antibody, wherein the immunogen for the antibody was the PSMGFR peptide. FIG. 54B shows the array stained with the 20A10 monoclonal anti-MUC1* antibody, wherein the immunogen for the antibody was the PSMGFR peptide. FIG. 54C shows the array stained with the 29H1 monoclonal anti-MUC1* antibody, wherein the immunogen for the antibody was the PSMGFR N+20/C-27 peptide. FIG. 54D shows the array stained with the 31A1 monoclonal anti-MUC1* antibody, wherein the immunogen for the antibody was the PSMGFR N+20/C-27 peptide. This figure shows that antibodies SDIX and 20A10 that both bind to the PSMGFR peptide recognize the same tumor tissue specimens, albeit to differing degrees, while antibodies that bind to the PSMGFR N+20/C-27 peptide bind to more esophageal tumor specimens as well as most of those recognized by the anti-PSMGFR antibodies. These results are consistent with the idea that antibodies that bind to the PSMGFR N+20/C-27 peptide are general more specific for esophageal cancers than antibodies that bind to the PSMGFR peptide, but that certain patients may have an esophageal cancer that is better recognized by an anti-MUC1* antibody that binds to the PSMGFR peptide.

FIG. 55A shows the array stained with the SDIX polyclonal anti-MUC1* antibody, wherein the immunogen for the antibody was the PSMGFR peptide. FIG. 55B shows the array stained with the 17H6 monoclonal anti-MUC1* antibody, wherein the antibody binds to the PSMGFR N+9/C-9 peptide.

FIG. 55C shows the array stained with the MNC2 monoclonal anti-MUC1* antibody, wherein the antibody binds to the PSMGFR peptide.

FIG. 56A-56F shows photographs and graphical representations of pathologist staining scores of adjacent serial sections from a esophageal cancer array, which was stained by standard IHC methods with either antibodies that recognize full-length MUC1 or an antibody that only recognizes MUC1*. FIG. 56A shows the esophageal cancer array stained with antibody 5E5, which is an antibody that binds to a trapped O-linked glycan in the tandem repeat domain of full-length MUC1. FIG. 56B shows the pathologist's score for each specimen in the array. FIG. 56C shows the esophageal cancer array stained with anti-MUC1* antibody 29H1, which is an antibody that binds to the PSMGFR N+20/C-27 peptide of MUC1*. FIG. 56D shows the pathologist's score for each specimen in the array. FIG. 56E shows the esophageal cancer array stained with antibody VU4H5, which is an antibody that binds to an epitope in the tandem repeat domain of full-length MUC1. FIG. 56F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C-27 peptide recognize epitopes that are prevalent on esophageal cancers.

FIG. 57A-57G shows photographs of the prostate cancer array, which was stained with either antibody 5E5 or VU4H5, which both recognize full-length MUC1 or 29H1 that only recognizes MUC1* and binds to the PSMGFR N+20/C-27 peptide. FIG. 57A shows the esophageal cancer array stained with antibody 5E5. FIG. 57B shows the esophageal cancer array stained with antibody 29H1. FIG. 57B shows the esophageal cancer array stained with antibody 29H1. FIG. 57C shows the esophageal cancer array stained with antibody VU4H5. FIG. 57D shows the esophageal cancer array stained with the secondary antibody only, as a control. FIG. 57E shows the tissue marked by red box in FIG. 57A at greater magnification, wherein staining was done with 5E5. FIG. 57F shows the tissue marked by red box in FIG. 57B at greater magnification, wherein staining was done with 29H1. FIG. 57G shows the tissue marked by red box in FIG. 57C at greater magnification, wherein staining was done with VU4H5. The dashed red boxes indicate just one patient's specimen of many esophageal tumor specimens that stain negative for antibodies that recognize full-length MUC1, but highly positive when probed with anti-MUC1* antibodies, and particularly those antibodies that bind to the PSMGFR N+20/C-27 peptide.

FIG. 58A shows the array stained with the SDIX polyclonal anti-MUC1* antibody, wherein the immunogen for the antibody was the PSMGFR peptide. FIG. 58B shows the array stained with the 18B4 monoclonal anti-MUC1* antibody, wherein the antibody binds to the PSMGFR peptide. FIG. 58C shows the array stained with the 1E4 monoclonal anti-MUC1* antibody, wherein the antibody binds to the PSMGFR N+20/C-27 peptide.

FIG. 59A shows the array stained with the MNC2 monoclonal antibody that binds to the PSMGFR peptide but not the C-10 peptide. FIG. 59B shows the array stained with the 18B4 antibody that binds to the PSMGFR peptide. FIG. 59C shows the array stained with the 32C1 antibody that binds to the PSMGFR N+20/C-27 peptide. FIG. 59D shows the array stained with the SDIX polyclonal anti-MUC1* antibody, wherein the immunogen for the antibody was the PSMGFR peptide. FIG. 59E shows the array stained with the 31A1 monoclonal anti-MUC1* antibody that binds to the PSMGFR N+20/C-27 peptide.

FIG. 60A-60F shows photographs and graphical representations of pathologist staining scores of adjacent serial sections from a prostate cancer array, which was stained by standard IHC methods with either antibodies that recognize full-length MUC1 or an antibody that only recognizes MUC1*. FIG. 60A shows the prostate cancer array stained with antibody 5E5, which is an antibody that binds to a trapped O-linked glycan in the tandem repeat domain of full-length MUC1. FIG. 60B shows the pathologist's score for each specimen in the array. FIG. 60C shows the prostate cancer array stained with anti-MUC1* antibody 29H1, which is an antibody that binds to the PSMGFR N+20/C-27 peptide of MUC1*. FIG. 60D shows the pathologist's score for each specimen in the array. FIG. 60E shows the prostate cancer array stained with antibody VU4H5, which is an antibody that binds to an epitope in the tandem repeat domain of full-length MUC1. FIG. 60F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C-27 peptide recognize epitopes that are prevalent on prostate cancers.

FIG. 61A-61G shows photographs of the prostate cancer array, which was stained with either antibody 5E5 or VU4H5, which both recognize full-length MUC1 or 29H1 that only recognizes MUC1* and binds to the PSMGFR N+20/C-27 peptide. FIG. 61A shows the prostate cancer array stained with antibody 5E5. FIG. 61B shows the prostate cancer array stained with antibody 29H1. FIG. 61B shows the prostate cancer array stained with antibody 29H1. FIG. 61C shows the prostate cancer array stained with antibody VU4H5. FIG. 61D shows the prostate cancer array stained with the secondary antibody only, as a control. FIG. 61E shows the tissue marked by red box in FIG. 61A at greater magnification, wherein staining was done with 5E5. FIG. 61F shows the tissue marked by red box in FIG. 61B at greater magnification, wherein staining was done with 29H1. FIG. 61G shows the tissue marked by red box in FIG. 61C at greater magnification, wherein staining was done with VU4H5. The dashed red boxes indicate just one patient's specimen of many prostate tumor specimens that stain negative for antibodies that recognize full-length MUC1, but highly positive when probed with anti-MUC1* antibodies, and particularly those antibodies that bind to the PSMGFR N+20/C-27 peptide.

FIG. 62A shows a photograph of the breast cancer array that was stained with anti-MUC1* monoclonal antibody MNC2. FIG. 62B shows a photograph of the breast cancer array that was stained with anti-MUC1* monoclonal antibody 20A10. Both monoclonal antibodies bind to the PSMGFR peptide, the N-10 peptide but not to the C10 peptide.

FIG. 63A-63B shows photographs of adjacent serial sections of breast cancer array BR1141 that were stained with two different anti-MUC1* monoclonal antibodies. FIG. 63A shows a photograph of the breast cancer array that was stained with anti-MUC1* monoclonal antibody MNC2. FIG. 63B shows a photograph of the breast cancer array that was stained with anti-MUC1* monoclonal antibody 25E6. Both monoclonal antibodies bind to the PSMGFR peptide and to the N-10 peptide. Whereas MNC2 cannot bind to the C-10 peptide, 25E6 shows some low level of binding to the C-10 peptide, indicating that they bind to different epitopes.

FIG. 64A shows a photograph of the breast cancer array that was stained with anti-MUC1* monoclonal antibody MNC2. FIG. 64B shows a photograph of the breast cancer array that was stained with anti-MUC1* monoclonal antibody 18B4. Both monoclonal antibodies bind to the PSMGFR peptide. However, unlike MNC2, 18B4 cannot bind to the N-10 epitope, indicating that they bind to different epitopes and that 18B4 may require the 10 N-terminal amino acids of the PSMGFR peptide for binding.

FIG. 65A shows a photograph of the breast cancer array that was stained with anti-MUC1* monoclonal antibody MNC2. FIG. 65B shows a photograph of the breast cancer array that was stained with anti-MUC1* monoclonal antibody 18G12. Both monoclonal antibodies bind to the PSMGFR peptide. However, unlike MNC2, 18G12 binds to the C-10 epitope to some degree, indicating they bind to different epitope within PSMGFR peptide.

FIG. 66A shows a photograph of the breast cancer array that was stained with anti-MUC1* monoclonal antibody MNC2. FIG. 66B shows a photograph of the breast cancer array that was stained with anti-MUC1* monoclonal antibody 8A9. Monoclonal antibody MNC2 binds to the PSMGFR peptide, whereas 8A9 binds to the PSMGFR N+9/C-9 peptide. The peptides to which they bind, combined with the very different staining patterns indicates that they bind to different MUC1* epitopes.

FIG. 67A-67B shows photographs of adjacent serial sections of breast cancer array BR1141 that were stained with two different anti-MUC1* monoclonal antibodies. FIG. 67A shows a photograph of the breast cancer array that was stained with anti-MUC1* monoclonal antibody MNC2. FIG. 67B shows a photograph of the breast cancer array that was stained with anti-MUC1* monoclonal antibody 28F9. Both monoclonal antibodies bind to the PSMGFR peptide.

FIG. 68A-68B shows photographs of adjacent serial sections of breast cancer array BR1141 that were stained with two different anti-MUC1* monoclonal antibodies. FIG. 68A shows a photograph of the breast cancer array that was stained with anti-MUC1* monoclonal antibody MNC2. FIG. 68B shows a photograph of the breast cancer array that was stained with anti-MUC1* monoclonal antibody 17H6. Monoclonal antibody MNC2 binds to the PSMGFR peptide, whereas 17H6 binds to the PSMGFR N+9/C-9 peptide. The peptides to which they bind, combined with the very different staining patterns indicates that they bind to different MUC1* epitopes.

FIG. 69A-69B shows photographs of adjacent serial sections of breast cancer array BR1141 that were stained with two different anti-MUC1* monoclonal antibodies. FIG. 69A shows a photograph of the breast cancer array that was stained with anti-MUC1* monoclonal antibody MNC2. FIG. 69B shows a photograph of the breast cancer array that was stained with anti-MUC1* monoclonal antibody 3C5. Monoclonal antibody MNC2 binds to the PSMGFR peptide, whereas 3C5 binds to the PSMGFR N+9/C-9 peptide. The peptides to which they bind, combined with the very different staining patterns indicates that they bind to different MUC1* epitopes.

FIG. 70A shows a photograph of the breast cancer array that was stained with anti-MUC1* monoclonal antibody 20A10, which binds to the PSMGFR peptide. FIG. 70B shows a photograph of the breast cancer array that was stained with anti-MUC1* monoclonal antibody 29H1, which binds to the PSMGFR N+20/C-27 peptide. FIG. 70C shows a photograph of the breast cancer array that was stained with anti-MUC1* monoclonal antibody 45C11, which binds to the PSMGFR N+20/C-27 peptide. FIG. 70D shows a photograph of the breast cancer array that was stained with anti-MUC1* monoclonal antibody 32C1, which binds to the PSMGFR N+20/C-27 peptide. FIG. 70E shows a photograph of the breast cancer array that was stained with anti-MUC1* monoclonal antibody 18B4, which binds to the PSMGFR peptide. FIG. 70F shows a photograph of the breast cancer array that was stained with anti-MUC1* monoclonal antibody 31A1, which binds to the PSMGFR N+20/C-27 peptide. FIG. 70G shows a photograph of the breast cancer array that was stained with anti-MUC1* monoclonal antibody 17H6, which binds to the PSMGFR N+9/C-9 peptide.

FIG. 71A-71F shows photographs and graphical representations of pathologist staining scores of adjacent serial sections from a breast cancer array, which was stained by standard IHC methods with either antibodies that recognize full-length MUC1 or an antibody that only recognizes MUC1*. FIG. 71A shows the breast cancer array stained with antibody 5E5, which is an antibody that binds to a trapped O-linked glycan in the tandem repeat domain of full-length MUC1. FIG. 71B shows the pathologist's score for each specimen in the array. FIG. 71C shows the breast cancer array stained with anti-MUC1* antibody 29H1, which is an antibody that binds to the PSMGFR N+20/C-27 peptide of MUC1*. FIG. 71D shows the pathologist's score for each specimen in the array. FIG. 71E shows the breast cancer array stained with antibody VU4H5, which is an antibody that binds to an epitope in the tandem repeat domain of full-length MUC1. FIG. 71F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1.

FIG. 72A shows breast cancer specimens that were stained with MNC2. FIG. 72B shows breast cancer specimens that were stained with 20A10. FIG. 72C shows breast cancer specimens that were stained with 25E6. FIG. 72D shows breast cancer specimens that were stained with 28F9. FIG. 72E shows breast cancer specimens that were stained with 18G12. FIG. 72F shows breast cancer specimens that were stained with 18B4. All these antibodies bind to the PSMGFR peptide and roughly produce the same staining pattern of this breast cancer array. However, there are some differences in how these antibodies recognize individual specimens within the array, which could represent MUC1 to MUC1* cleavage by different enzymes. Referring to FIG. 39, MNC2 and 20A10 bind to the N-10 peptide but not to the C-10 peptide, indicating the 10 membrane proximal amino acids are important for their binding. Antibodies 18B4, 18G12 and 25E6 show some binding to the C-10 peptide and 28F9 shows even more binding to C-10 peptide. Notably, 18B4 does not bind to the N-10 peptide, indicating that it binds to an epitope that is more N-terminal within PSMGFR than the others. Red circles indicate specimens of interest for comparison.

FIG. 73A shows breast cancer specimens that were stained with MNC2. FIG. 73B shows breast cancer specimens that were stained with 8A9. FIG. 73C shows breast cancer specimens that were stained with 17H6. FIG. 73D shows breast cancer specimens that were stained with huMNC2-scFv-Fc. FIG. 73E shows breast cancer specimen that was stained with 3C5. FIG. 73F shows breast cancer specimens that were stained with 39H5. Referring now to the patient specimens that are marked by red circles, it is plain to see that antibodies that bind to the PSMGFR N+9/C-9 peptide recognize a population of breast cancer cells that MNC2 anti-PSMGFR antibodies miss or bind weakly to.

Figures 1A, 1B, 1C, 1D:
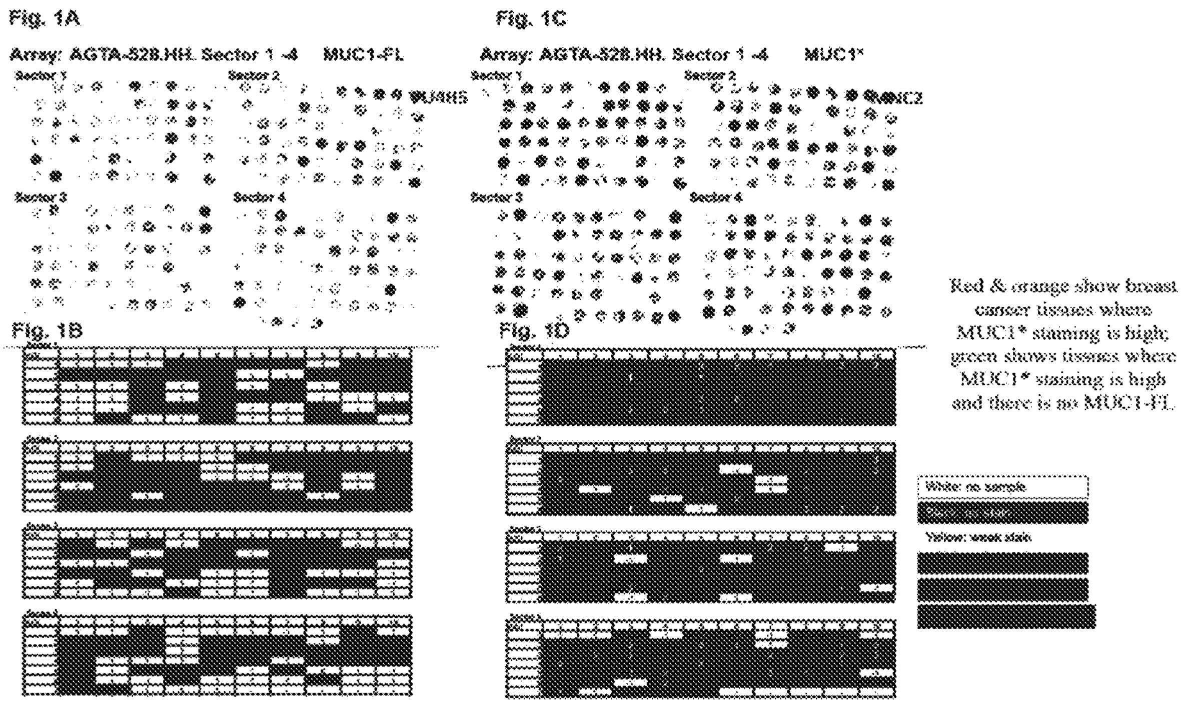
FIG. 1A-1D shows photographs of adjacent serial sections of breast cancer tissue arrays and graphical representations of the pathologist scores, according to Allred scoring system. Pathologist score is 0-3, where 0 showed no staining and 3 is the greatest staining. The graphs are also color coded, where a pathologist score zero is black, 1 is yellow, 2 is orange, and 3 is red; tissues that scored zero when probed with an antibody that recognizes full-length MUC1 but positive when probed with an antibody that recognizes MUC1* were colored green; and missing or uninterpretable tissues were scored −1.

In addition to monoclonal antibodies MNC2, MNE6, MNC3, MNC8, and 18B4, 18G12, 20A10, 25E6, 1E4, 29H1, 31A1, 32C1, 45C11, 3C5, 8A9, 17H6, and 39H5 disclosed in the present application, other monoclonal antibody sequences are recited in SEQ ID NOS: 237-349 that are made from inoculation with the PSMGFR peptide.

DETAILED DESCRIPTION OF THE PREFERRED EMBODIMENTS

In the present application, "a" and "an" are used to refer to both single and a plurality of objects.

As used herein, occasionally, in short hand, a polypeptide is indicated as being "transduced or transfected" into a cell. In these occurrences, it is understood that the nucleic acid encoding the polypeptide sequence is transduced or transfected into the cell, as it is an impossibility that a polypeptide could be transduced or transfected into a cell.

As used herein, occasionally when referring to number of cells injected into an animal or otherwise contextually wherein the number of cells is referred to, "M" refers to millions, and "K" refers to thousands.

As used herein, interchangeable designations for various monoclonal antibodies are used, such as, "MN-C2", which is interchangeable with "C2", "Min-C2" and "MNC2"; "MN-E6", which is interchangeable with "E6", "Min-E6" and "MNE6"; "MN-C3", which is interchangeable with "C3", "Min-C3" and "MNC3"; and "MN-C8", which is interchangeable with "C8", "Min-C8" and "MNC8".

As used herein, "h" or "hu" placed before an antibody construct is short-hand for human or humanized.

As used herein, the term "antibody-like" means a molecule that may be engineered such that it contains portions of antibodies but is not an antibody that would naturally occur in nature. Examples include but are not limited to CAR (chimeric antigen receptor) T cell technology and the Ylanthia® technology. The CAR technology uses an antibody epitope fused to a portion of a T cell so that the body's immune system is directed to attack a specific target protein or cell. The Ylanthia® technology consists of an "antibody-like" library that is a collection of synthetic human Fabs that are then screened for binding to peptide epitopes from target proteins. The selected Fab regions can then be engineered into a scaffold or framework so that they resemble antibodies.

As used herein, "PSMGFR" is abbreviation for Primary Sequence of the MUC1 Growth Factor Receptor which is identified by SEQ ID NO:4, and thus is not to be confused with a six amino acid sequence. "PSMGFR peptide" or "PSMGFR region" refers to a peptide or region that incorporates the Primary Sequence of the MUC1 Growth Factor Receptor (SEQ ID NO: 4).

As used herein, the term "PSMGFR" is an acronym for Primary Sequence of MUC1 Growth Factor Receptor as set forth as GTINVHDVETQFNQYKTEAAS-RYNLTISDVSVSDVPFPFSAQSGA (SEQ ID NO:4). In this regard, the "N-number" as in "N-10 PSMGFR", "N-15 PSMGFR", or "N-20 PSMGFR" refers to the number of amino acid residues that have been deleted at the N-terminal end of PSMGFR, likewise "N+10 PSMGFR", "N+15 PSMGFR", or "N+20 PSMGFR" refers to the number of amino acid residues that have been added at the N-terminal end of PSMGFR. Likewise "C-number" as in "C-10 PSMGFR", "C-15 PSMGFR", or "C-20 PSMGFR" refers to the number of amino acid residues that have been deleted at the C-terminal end of PSMGFR, and "C+10 PSMGFR", "C+15 PSMGFR", or "C+20 PSMGFR" refers to the number of amino acid residues that have been added at the C-terminal end of PSMGFR. Moreover, combinations are possible, such as, "N+20/C-27 PSMGFR", "PSMGFR N+20/C-27" or "N+20/C-27" which refer to the same peptide, in which the N terminus of PSMGFR includes 20 additional amino acids of MUC1 peptide, and is deleted 27 amino acids at the C-terminus of PSMGFR.

As used herein, when it is desired to refer to a genus of PSMGFR peptides, they are referred to as "PSMGFR group". For example, "N+20 PSMGFR group" refers to peptides that have additional 20 amino acids at the N-terminus, without regard to how the C-terminus is modified, whether amino acids have been deleted, or added and so on.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein, the "MUC1*" extra cellular domain is defined primarily by the PSMGFR sequence (GTINVHD-VETQFNQYKTEAAS-RYNLTISDVSVSDVPFPFSAQSGA (SEQ ID NO:4)). Because the exact site of MUC1 cleavage depends on the enzyme that clips it, and that the cleavage enzyme varies depending on cell type, tissue type or the time in the evolution of the cell, the exact sequence of the MUC1* extra cellular domain may vary at the N-terminus.

Other clipped amino acid sequences may include

```
                                        (SEQ ID NO: 5)
SNIKFRPGSVVVQLTLAFREGTINVHDVETQFNQYKTEAASRY;
```

or

```
                                        (SEQ ID NO: 6)
SVVVQLTLAFREGTINVHDVETQFNQYKTEAASRY.
```

As used herein "sequence identity" means homology in sequence of a particular polypeptide or nucleic acid to a reference sequence of nucleic acid or amino acid such that the function of the homologous peptide is the same as the reference peptide or nucleic acid. Such homology can be so close with the reference peptide such that at times the two sequences may be 90%, 95% or 98% identical yet possess the same function in binding or other biological activities.

As used herein, “MUC1 positive” cell refers to a cell that expresses a gene for MUC1, MUC1-Y or MUC1-Z or other MUC1 variant.

As used herein, “MUC1 negative” cell refers to a cell that does not express a gene for MUC1.

As used herein, “MUC1* positive” cell refers to a cell that expresses a gene for MUC1, wherein that gene's expressed protein is a transmembrane protein that is devoid of tandem repeats, which may be a consequence of post-translational modification, cleavage, alternative splicing, or transfecting or transducing a cell with a MUC1 protein that is devoid of tandem repeats.

As used herein, “MUC1* negative” cell refers to a cell that may or may not express a gene for MUC1 but does not express a MUC1 transmembrane protein that is devoid of tandem repeats.

As used herein, “MUC1 positive” cancer cell refers to a cancer cell that overexpresses the gene for MUC1, expresses MUC1 in an aberrant pattern, wherein its expression is not restricted to the apical border and/or expresses a MUC1 that is devoid of tandem repeats.

As used herein, “MUC1 negative” cancer cell refers to a cancer cell that may or may not express a gene for MUC1 but does not overexpress MUC1 or does not overexpress a MUC1 transmembrane protein that is devoid of tandem repeats.

As used herein, “MUC1* positive” cancer cell refers to a cancer cell that overexpresses a MUC1 transmembrane protein that is devoid of tandem repeats.

As used herein, “MUC1* negative” cancer cell refers to a cancer cell that may or may not express a gene for MUC1 but does not overexpress a MUC1 transmembrane protein that is devoid of tandem repeats.

The present invention involves, generally, diagnostic assays related to cancers that are characterized by the aberrant expression of a class of cell surface receptors characterized by interchain binding regions or increased cleavage of extra cellular domain in cancerous tissues. One such set of cancers are those characterized by the aberrant expression of mucin family proteins, such as MUC1, MUC2, MUC3, MUC4, up to and including MUC16. Much of the description of the invention herein is directed to cells and tissues that aberrantly express MUC1, as an example of the larger class of proteins involved in cancers which have extra cellular domains that are increasingly cleaved in cancers and/or have an inter-chain binding region (IBR). It is to be understood that in these instances the description is to be considered exemplary, and that the principles of the invention apply to other transmembrane proteins that function by a similar mechanism. With the disclosure herein, those of ordinary skill in the art will readily be able to identify other transmembrane proteins that function by this or a similar mechanism, and to apply the invention to those cancers characterized by aberrant expression of receptors. The invention is based on a novel mechanism involving transmembrane proteins that have regions of their extra cellular domain that self-aggregate and/or are increasingly cleaved, exemplified by MUC1, which was elucidated by the inventors.

MUC1 comprises several regions termed herein as follows. From the C-terminus inside the cell to the N-terminus outside the cell, the MUC1 protein is comprised of the following domains: 1) cytoplasmic tail; 2) transmembrane section; 3) MGFR; 4) IBR (interchain binding region) 5) UR (unique region); and 6) the tandem repeats.

One aspect of our previous invention featured the discovery that a specific region of the MUC1 receptor, i.e., the IBR, binds strongly to identical regions of other MUC1 molecules. That is, the MUC1 receptor has the ability to aggregate (i.e. self-aggregate) with other MUC1 receptors via the IBR of the respective receptors. A gold nanoparticle experiment was performed that showed that the IBR aggregates with itself which can occlude the binding of ligands to MUC1 or its cleavage product MUC1*. The boundary between the IBR and MGFR varies depending on where MUC1 is cleaved, which is determined by which cleavage enzyme cleaves it.

This self-aggregation may contribute to MUC1 receptor clustering, observed in healthy cells. The discovery that the IBR portion of the MUC1 receptor self-aggregates is consistent with the following mechanistic model for which the inventors present supporting evidence. (1) receptor clustering is associated with the healthy state because the aggregated IBR portions block access of ligands, such as growth factors, modifying enzymes and the like to the neighboring extracellular portions of the MUC1 receptor that act as the functional receptor; clustering also blocks access of intracellular tails to intracellular modifying enzymes and signaling ligands; (2) when the MUC1 receptor is cleaved at a position that releases some or all of the self-aggregating portions, the critical force that keeps the receptors clustered is lost and receptors are free to migrate within the cell membrane or interact with modifying enzymes, secreted ligands such as activating ligands or growth factors or other cell surface receptors. These interactions involve a new, inductive multimerization state, such as dimerization, that triggers a cell proliferation signaling cascade.

Cleavage of MUC1 releases the bulk of the extra cellular domain, including the tandem repeat domain and leaves a transmembrane protein with a truncated extra cellular domain comprising at least the PSMGFR region. Cleavage and release of the bulk of the tandem repeat domain, exposes binding sites of ligands that bind to and dimerize the truncated extra cellular domain, leading to activation of growth and survival pathways. We call the MUC1 cleavage product “MUC1*”.

MUC1* is a growth factor receptor that is activated by ligand induced dimerization of its truncated extra cellular domain. Bivalent antibodies that bind to PSMGFR peptide, which is the 45 amino acid sequence of the membrane proximal portion of MUC1 dimerize MUC1* and stimulate growth. The anti-PSMGFR antibody stimulated growth of T47D MUC1 positive cancer cells in a concentration dependent manner. In a similar experiment, a concentration of the anti-PSMGFR antibody, identified to maximize cancer cell proliferation, was added to a first group of T47D tumor cells, grown as described above. The same amount of the anti-PSMGFR antibody was added to a set of control cells, K293 cells. The addition of the anti-PSMGFR antibody to MUC1 tumor cells (T47D) enhanced proliferation by 180% 24 hours, but had no effect on the control cells.

Ligands that dimerize the extra cellular domain of MUC1* induce growth and survival of cells. Ligands of MUC1* that we identified are NME1, NME2, NME6, NME7-AB and alternative splice variant NME7-X1.

MUC1* is the growth factor receptor that drives the growth of cancer cells, whereas full-length MUC1 does not. Therefore, detection of an amount of MUC1* that is above normal levels is an indicator of cancer and the higher the amount of MUC1*, the worse the cancer. Cleavage of MUC1 may occur at more than one site, depending on which cleavage enzyme the tumor expresses. Cleavage of MUC1 releases the portion of the extracellular domain that contains the tandem repeats and could, depending on cleavage site, contain portions of the unique region or portions of the IBR. The amount of MUC1 that has been cleaved can be inferred by measuring the amount of full-length MUC1 that remains on cells or tissues. This can be accomplished by contacting the cells or tissues with an antibody that binds to the tandem repeats, or the unique region or the IBR. An antibody that binds to the tandem repeat domain is an antibody that is able to bind to a peptide having the sequence PDTRPAPGSTAPPAHGVTSA (SEQ ID NO:235). Commonly used antibodies that bind to the tandem repeat domain include but are not limited to VU4H5 (Santa Cruz Biotechnology, Dallas Texas Cat. No. SC-7313), HMPV, 5E5 (Sorensen et al., Glycobiology, Vol. 16, no. 2, pp. 96-107, 2006), PR81, and LDQ10. In these cases, it is most effective to measure an amount of full-length MUC1 compared to an amount of MUC1* expressed on the same cells or tissues. The ratio of MUC1*: MUC1 full-length is an indicator of cancer and cancer aggressiveness, wherein the more MUC1*, the more aggressive the cancer. Detection of an amount of MUC1* or the ratio of MUC1* to MUC1 full-length can also be used to determine the suitability of a cancer treatment where the therapeutic drug targets MUC1* or MUC1. Similarly, the effectiveness of such a therapy can be evaluated by detecting an amount of MUC1* or the ratio of MUC1* to MUC1 full-length before and after treatment, wherein a reduction in the amount of MUC1* expressed or a shift in the ratio of MUC1* to MUC1 full-length would be an indicator of efficacy.

There may be alternative splice isoforms of MUC1 that do not contain an IBR or tandem repeats. For example, MUC1-Y or MUC1-X. These alternative splice isoforms still have an extra cellular domain that is comprised of the sequence of the PSMGFR peptide, as this is the portion that interacts with growth factors to promote cancer and survival. Therefore, detection of an amount of MUC1* expressed by cells or tissues would still be a valid indicator of cancer and cancer aggressiveness.

The dominant MUC1 species on breast cancer tissue is the transmembrane cleavage product MUC1* not full-length MUC1. Breast tumor micro arrays were probed with either VU4H5 or MNC2. VU4H5 is a monoclonal antibody that only binds to full-length MUC1 because it recognizes an epitope (PDTRPAPGSTAPPAHGVTSA (SEQ ID NO:235) in the tandem repeat domain of full-length MUC1. This epitope is repeated hundreds of times within the tandem repeat domain of full-length MUC1. Therefore, antibody VU4H5 should give a stronger signal that an antibody that binds to a single epitope on the molecule. MNC2 is a monoclonal antibody that we produced by immunizing animals with the PSMGFR peptide (SEQ ID NO: 4). Transfection experiments show that MNC2 does not bind to full-length MUC1. MNC2 binds to a cryptic epitope that is exposed after MUC1 is cleaved to a form of MUC1* that comprises at least the first 35 membrane proximal amino acids of the MUC1* extra cellular domain, as it binds to the PSMGFR peptide (45 amino acids), the N-10 peptide (35 amino acids) but not to the C-10 peptide, indicating that its cognate epitope is encompassed at least in part within the 10 membrane proximal amino acids of the MUC1* extra cellular domain. Importantly, MNC2 competitively inhibits the binding of MUC1* activating growth factors NME1 and NME7-AB.

Figure 2A:
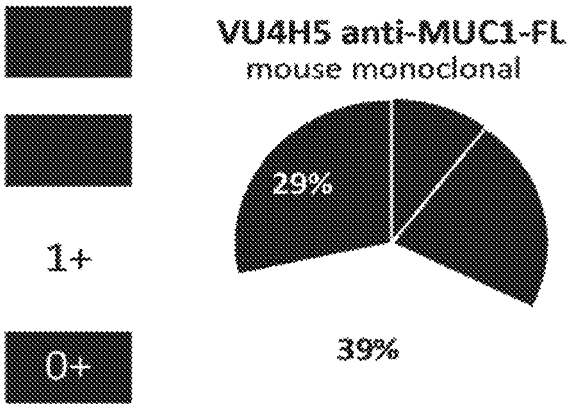
FIG. 2A-2B shows pie chart graphs of the pathologist scores of the arrays shown in FIG. 1A and FIG. 1C.
Figure 2B:
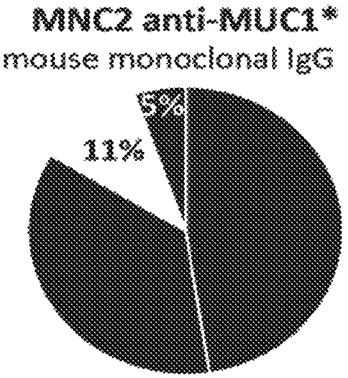

FIG. 1A-1D shows photographs of adjacent serial sections of breast cancer tissue arrays and graphical representations of the pathologist scores, according to Allred scoring system. Pathologist score is 0-3, where 0 showed no staining and 3 is the greatest staining. The graphs are also color coded, where a pathologist score zero is black, 1 is yellow, 2 is orange, and 3 is red; tissues that scored zero when probed with an antibody that recognizes full-length MUC1 but positive when probed with an antibody that recognizes MUC1* were colored green; and missing or uninterpretable tissues were scored-1. FIG. 1A shows photographs of the breast cancer tissue arrays after they were stained with VU4H5, which is an antibody that binds to the tandem repeat domains of full-length MUC1. FIG. 1B shows graphs of the pathologist scores for the tissues pictured in FIG. 1A. FIG. 1C shows photographs of the breast cancer tissue arrays after they were stained with MNC2, which is an antibody that binds to an epitope within the PSMGFR region of MUC1*. FIG. 1D shows graphs of the pathologist scores for the tissues pictured in FIG. 1C. FIG. 2A-2B shows pie chart graphs of the pathologist scores of the arrays shown in FIG. 1A and FIG. 1C. FIG. 2A shows that the antibody that binds to tandem repeats of full-length MUC1 misses 30% of breast cancers. FIG. 2B shows that the anti-MUC1* antibody MNC2 recognizes 95% of breast cancers. Anti-MUC1-full-length only binds strongly to 10% of the breast tumors, while anti-MUC1* antibody MNC2 binds strongly to about 50% of breast tumors. Together these data demonstrate that MUC1*, not full-length MUC1, is the predominant MUC1 species on cancerous tissues. Anti-MUC1* antibodies would detect or diagnose nearly all breast cancers, whereas antibodies that bind to full-length MUC1 would fail to detect about 30% of breast cancers. Further, because MUC1* is a growth factor receptor driving cancer growth, the degree of anti-MUC1* staining of a tissue or cellular specimen would be proportional to the degree or stage of cancer, whereas the expression of full-length MUC1 appears to be inversely proportional to the stage of cancer.

A wide range of cancer cells and tumor specimens were probed with anti-MUC1* antibody MNC2. MNC2 was used to detect MUC1* positive cancers in a wide range of assays, including fluorescence activated cell sorting (FACS), immunofluorescence (IF), immunohistochemistry (IHC). FACS and IF are generally used to study a cell line which is a single immortalized cell that has been propagated in a lab for decades. After decades of propagation in unnatural growth solutions, these cell lines likely show little resemblance to even a single cell within the patient's original tumor and in no way represent the tumor of a recently diagnosed patient seeking treatment. For these reasons, we analyzed thousands of tumor micro arrays, wherein each dot within the array is tumor specimen from a single patient's biopsy. In most cases, the biopsies are from recently diagnosed patients, but the accompanying anonymized patient data gives the age of the patient, cancer sub-type and cancer stage or grade. In some cases we analyzed tissue micro arrays wherein the breast cancers were all HER2+, or all ER+/PR+. In other cases. We analyzed tumor micro arrays that compared the original biopsy specimen to a later metastasis. In these studies, the recognition of tumors by MNC2 was also compared to staining using anti-full-length-MUC1 antibody VU4H5 or a new antibody 5E5 that binds to a trapped O-linked glycan in the tandem repeat domain of full-length MUC1. MNC2 and other anti-MUC1* antibodies consistently recognized tumor tissue better than VU4H5 or 5E5. Normal tissues and normal tissue micro arrays were also extensively studied to determine binding of MNC2 or its humanized singly chain form huMNC2-scFv or huMNC2-scFv-Fc to normal tissues. On normal tissues, expression of MNC2 reactive MUC1* was restricted to the apical border of ducts and glands in a small percentage of only a few tissues. In all cases, MNC2 reactive MUC1* was expressed to a much higher degree in cancerous tissues than in normal tissues and expressed over 50-100% of the cancerous tissues compared to expression of 0.2%-5% of the normal tissue that did express MNC2 reactive MUC1*.

Figures 7A, 7B, 7C:
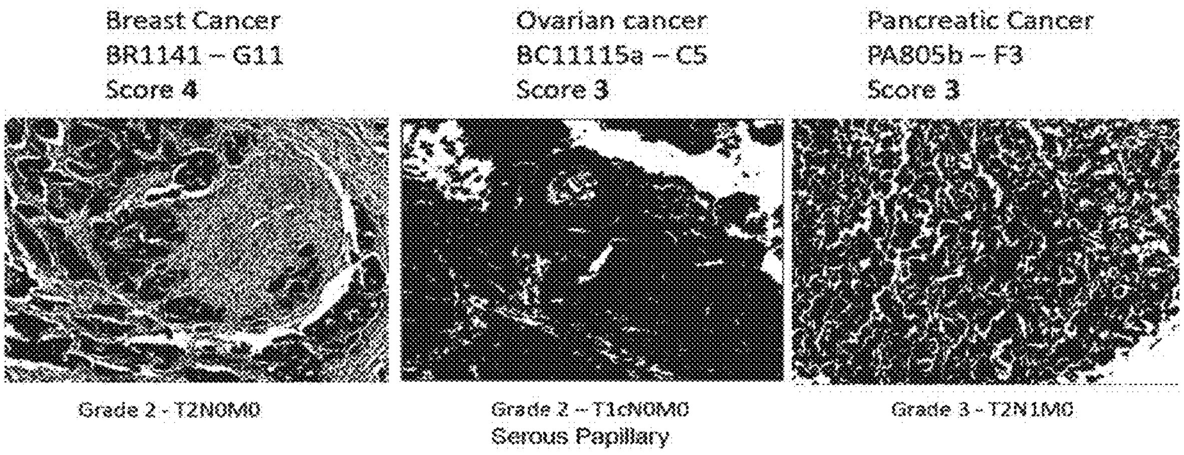
FIG. 7A-7C shows magnified photographs of different cancer sub-types after staining with anti-MUC1* antibody huMNC2-scFv-Fc.
Figures 8A, 8B, 8C, 8D:
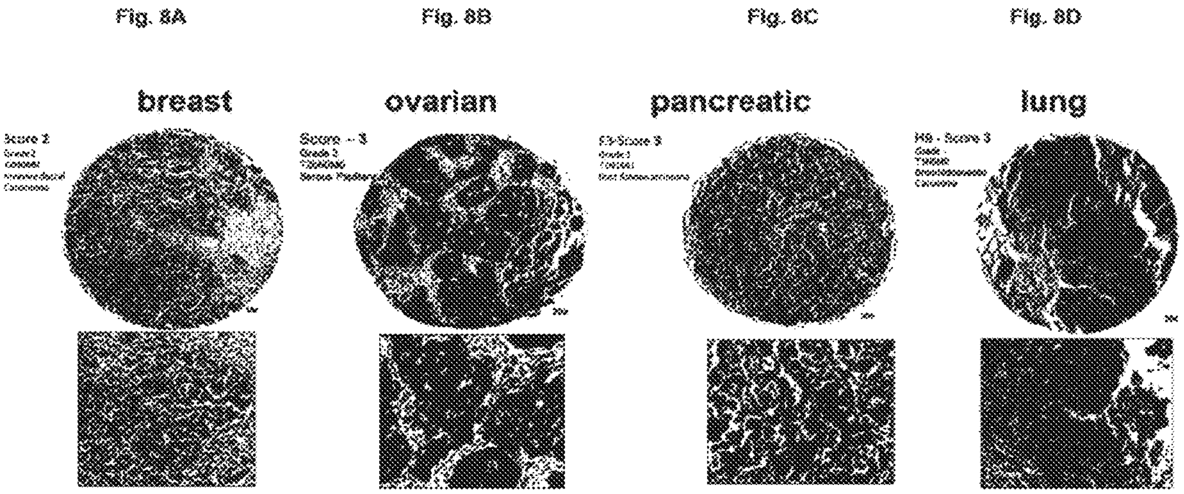
FIG. 8A-8D shows magnified photographs of different cancer sub-types after staining with anti-MUC1* antibody huMNC2-scFv-Fc.
Figures 9A, 9B, 9C, 9D, 9E, 9F, 9G, 9H, 9I:
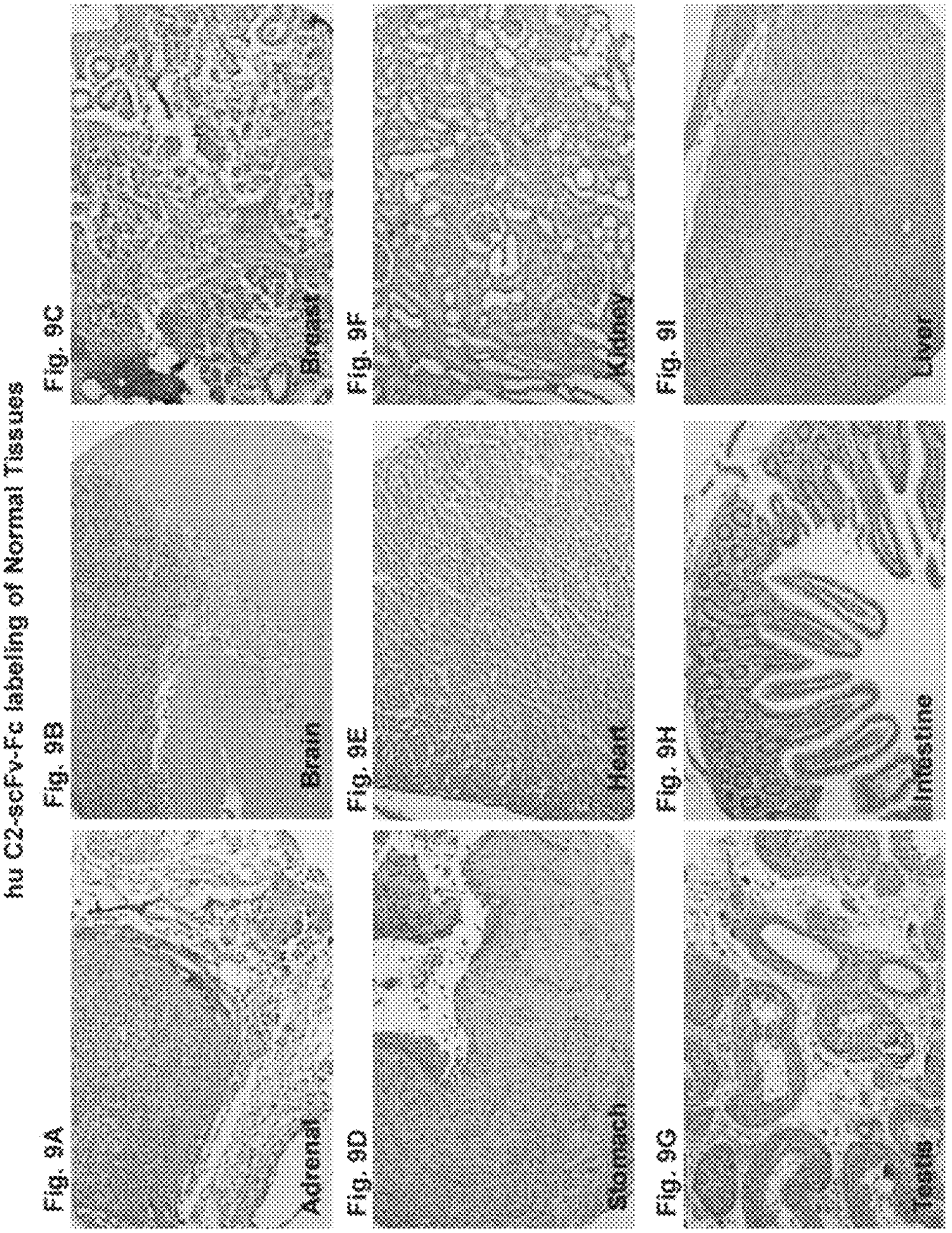
FIG. 9A-9I shows magnified photographs of various normal tissues after staining with anti-MUC1* antibody huMNC2-scFv-Fc. Conditions and concentrations used were identical to those used for studying cancerous tissues.
Figure 15A:
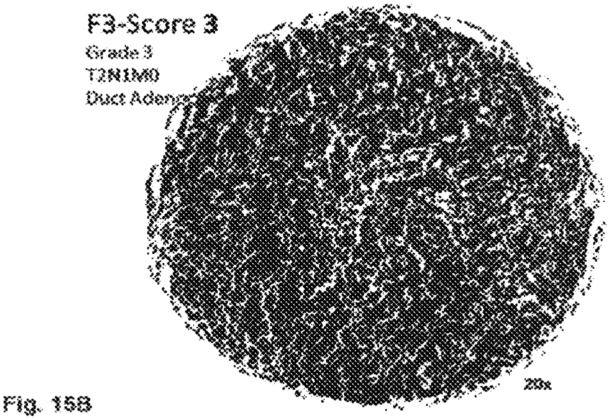
FIG. 15A-15D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures.
Figure 15C:
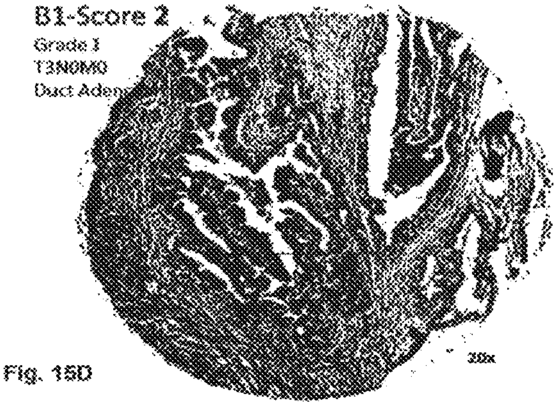
Figure 15B:
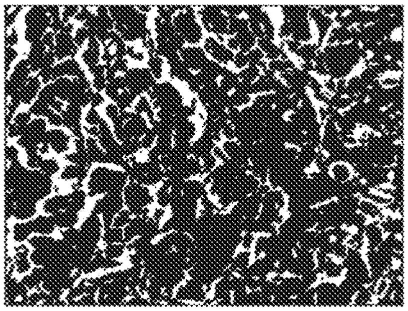
Figure 15D:
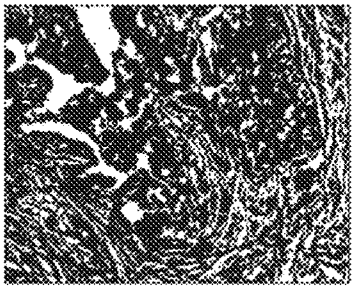
Figure 18A:
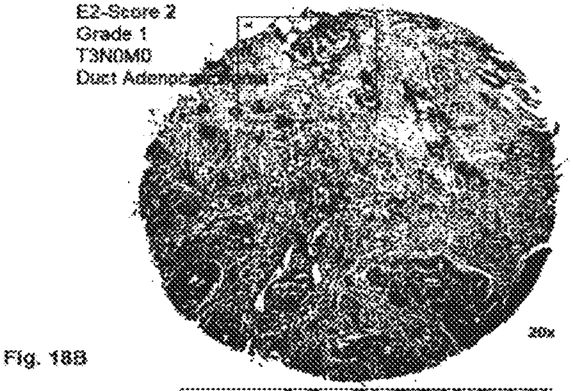
FIG. 18A-18D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures.
Figure 18B:
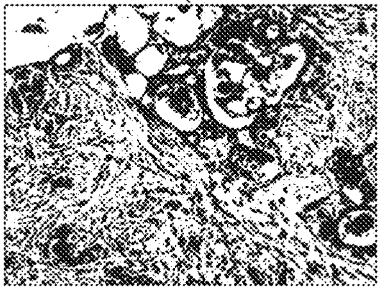
Figure 18C:
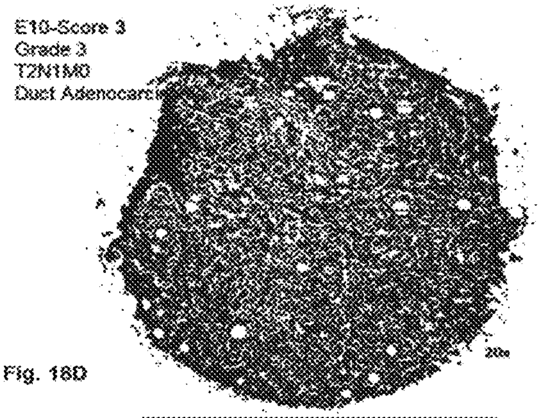
Figure 18D:
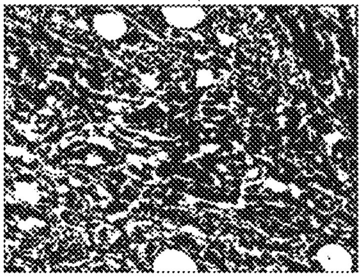
Figure 19:
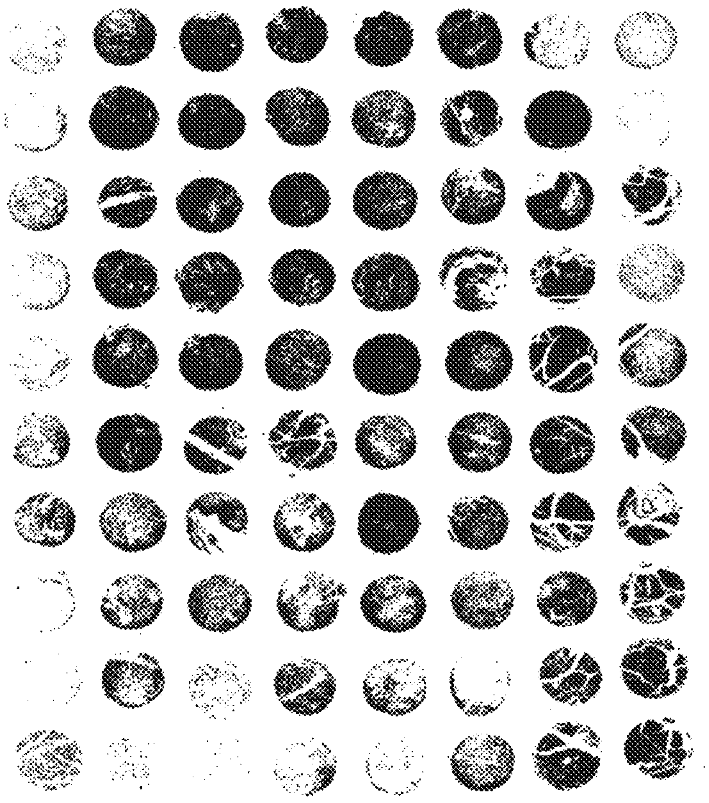
FIG. 19 shows a photograph of pancreatic cancer array PA805b that was stained with the secondary antibody alone, as a control.

FIG. 3 to FIG. 19 show that monoclonal anti-MUC1* antibody MNC2 binds to high percentages of breast, ovarian, pancreatic, lung and esophageal tumors, while having very little if any binding to normal tissues. FIG. 3A-3B shows pie chart graphs of the pathologist scores and a photograph of breast cancer array BR1141 after staining with anti-MUC1* antibody huMNC2-scFv-Fc. FIG. 4A-4C shows photographs, at two different magnifications, of individual breast cancer specimens from breast cancer array BR1141 after staining with anti-MUC1* antibody huMNC2-scFv-Fc. The position in the array, cancer sub-type, tumor grade, TNM (Tumor stage, Node involvement, and Metastasis) and pathologist score are indicated in figures. Standard immunohistochemistry methods were used. Antibody concentration was titered using the highest concentration at which the antibody showed expected staining of normal tissues without staining stroma. The antibody was conjugated to a biotin through its Fc region, to avoid false positive due to anti-human secondary antibodies staining host antibodies as well as B cell follicules. FIG. 4A shows the specimen at position A7 which was negative for huMNC2 reactive cells. FIG. 4B shows the specimen at position A9 which is a Grade 2 cancer, with lymph node involvement that scored +1 for huMNC2 reactivity. FIG. 4C shows the specimen at position B10 which is a larger Grade 2 tumor, with lymph node involvement that scored +2 for huMNC2 reactivity. FIG. 5A-5B shows photographs, at two different magnifications, of individual breast cancer specimens from breast cancer array BR1141 after staining with anti-MUC1* antibody huMNC2-scFv-Fc. FIG. 5A shows the specimen at position D7 which is a Grade 2 cancer, without lymph node involvement that scored +3 for huMNC2 reactivity. FIG. 5B shows the specimen at position F6 which is a Grade 2 tumor, with lymph node involvement that scored +4 for huMNC2 reactivity. FIG. 6A-6B shows pie chart graphs of the pathologist scores and a photograph of ovarian cancer array BC1115a after staining with anti-MUC1* antibody huMNC2-scFv-Fc. FIG. 7A-7C shows magnified photographs of different cancer sub-types after staining with anti-MUC1* antibody huMNC2-scFv-Fc. FIG. 7A shows a photograph of a Grade 2 breast tumor that pathologist scored +4. FIG. 7B shows a photograph of a Grade 2 ovarian tumor that pathologist scored +3. FIG. 7C shows a photograph of a Grade 3 pancreatic tumor that pathologist scored +3. IHC studies of over 1,000 tumor specimens showed that huMNC2-scFv recognized 95% of Breast Cancers (90% triple negative), 83% Ovarian, 78% Pancreatic and 71% Lung Cancers. FIG. 8A-8D shows magnified photographs of different cancer sub-types after staining with anti-MUC1* antibody huMNC2-scFv-Fc. FIG. 8A shows a photograph of a Grade 2 breast tumor that pathologist scored +2. FIG. 8B shows a photograph of a Grade 3 ovarian tumor that pathologist scored +3. FIG. 8C shows a photograph of a Grade 3 pancreatic tumor, with lymph node involvement that pathologist scored +3. FIG. 8D shows a photograph of a lung cancer that pathologist scored +3. FIG. 9A-9I shows magnified photographs of various normal tissues after staining with anti-MUC1* antibody huMNC2-scFv-Fc. Conditions and concentrations used were identical to those used for studying cancerous tissues. FIG. 9A shows normal adrenal gland tissue. FIG. 9B shows normal brain tissue. FIG. 9C shows normal breast tissue. FIG. 9D shows normal stomach tissue. FIG. 9E shows normal heart tissue. FIG. 9F shows normal kidney tissue. FIG. 9G shows normal testis tissue. FIG. 9H shows normal intestine tissue. FIG. 9I shows normal liver tissue. FIG. 10A-10F shows photographs of normal kidney tissues after staining with anti-MUC1* antibody huMNC2-scFv-Fc. Conditions and concentrations used were identical to those used for studying cancerous tissues. FIG. 10A shows normal kidney tissue with huMNC2 reactivity limited to the apical border, which is normal expression. FIG. 10B is the same tissue at greater magnification. FIG. 10C shows another example of normal kidney tissue with undetectable huMNC2 reactivity. FIG. 10D is the same tissue at greater magnification. FIG. 10E shows another example of normal kidney tissue with huMNC2 reactivity limited to the apical border, which is normal expression. FIG. 10F is the same tissue at greater magnification. Further studies showed that less than 10% of normal kidney tissue showed huMNC2 reactivity at distal collecting tubules wherein such reactivity was strictly limited to the apical border, which is a normal expression pattern. FIG. 11A-11B shows pie chart graphs of the pathologist scores and a photograph of esophageal cancer array BC001113 after staining with anti-MUC1* antibody huMNC2-scFv-Fc. FIG. 12A-12F shows photographs, at two different magnifications, of individual esophageal cancer specimens from esophageal cancer array BC001113, after staining with anti-MUC1* antibody huMNC2-scFv-Fc. The position in the array, cancer sub-type, tumor grade, and pathologist score are indicated in figures. FIG. 12A shows the specimen at position A4 which was negative for huMNC2 reactive cells. FIG. 12B shows the same specimen at greater magnification. FIG. 12C shows the specimen at position D2 which the pathologist scored as trace reactivity to huMNC2. FIG. 12D shows the same specimen at greater magnification. FIG. 12E shows the specimen at position B8 which the pathologist scored as +1 reactivity to huMNC2. FIG. 12F shows the same specimen at greater magnification. FIG. 13A-13D shows photographs, at two different magnifications, of individual esophageal cancer specimens from esophageal cancer array BC001113, after staining with anti-MUC1* antibody huMNC2-scFv-Fc. The position in the array, cancer sub-type, tumor grade, and pathologist score are indicated in figures. FIG. 13A shows the specimen at position D6, a Grade 4 tumor, which the pathologist scored +2. FIG. 13B shows the same specimen at greater magnification. FIG. 13C shows the specimen at position D5, a Grade 3 tumor, which the pathologist scored +3. FIG. 12D shows the same specimen at greater magnification. FIG. 14A-14B shows pie chart graphs of the pathologist scores and a photograph of pancreatic cancer array PA805b after staining with anti-MUC1* antibody huMNC2-scFv-Fc. FIG. 15A-15D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 15A shows the specimen at position F3, a Grade 3 tumor, which the pathologist scored +3. FIG. 15B shows the same specimen at greater magnification. FIG. 15C shows the specimen at position B1, a Grade 1 tumor, which the pathologist scored +2. FIG. 15D shows the same specimen at greater magnification. FIG. 16A-16D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 16A shows the specimen at position A2, a Grade 1 tumor, which the pathologist scored +2. FIG. 16B shows the same specimen at greater magnification. FIG. 16C shows the specimen at position C3, a Grade 2 tumor, which the pathologist scored +2. FIG. 16D shows the same specimen at greater magnification. FIG. 17A-17D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 17A shows the specimen at position C6, a Grade 2 tumor, which the pathologist scored +2. FIG. 17B shows the same specimen at greater magnification. FIG. 17C shows the specimen at position D1, a larger Grade 3 tumor, with lymph node involvement that the pathologist scored +3. FIG. 17D shows the same specimen at greater magnification. FIG. 18A-18D shows photographs, at two different magnifications, of individual pancreatic cancer specimens from pancreatic cancer array PA805b, after staining with anti-MUC1* antibody huMNC2-scFv-Fc. The position in the array, cancer sub-type, tumor grade, and pathologist score are indicated in figures. FIG. 18A shows the specimen at position E2, a Grade 1 tumor, which the pathologist scored +2. FIG. 18B shows the same specimen at greater magnification. FIG. 18C shows the specimen at position E10, a smaller Grade 3 tumor, with lymph node involvement that the pathologist scored +3. FIG. 18D shows the same specimen at greater magnification. FIG. 19 shows a photograph of pancreatic cancer array PA805b that was stained with the secondary antibody alone, as a control.

Although MNC2 recognized about 95% of breast tumors across all breast cancer sub-types, we noticed that some cancer sub-types did not express as much MNC2 reactive MUC1* as breast cancers. In particular, pancreatic, esophageal and prostate cancers expressed lower levels of MNC2 reactive MUC1*. Pancreatic cancer arrays showed that 78% of the tumors were MNC2 reactive but the strength of staining, which is proportional to the tumor's expression levels, was relative weak. The pie chart of FIG. 14A shows that 65% of the pancreatic tumors scored +1 or +2, only 5% scored +3 and none scored +4. The pie chart of FIG. 3A shows that more than half of the breast tumors scored +2 to +3, 6% were +4 and only 4% were negative for MNC2 MUC1* reactivity. Both arrays were stained with the same MNC2 anti-MUC1* antibody and scored by the same board-certified pathologist. We reasoned that the difference between MNC2 staining of MUC1* in breast cancer and pancreatic cancer could be due to differences in cleavage enzymes that cleave MUC1 to MUC1* at different positions that induce conformational or linear changes in the MUC1* extra cellular domain. To investigate, we stained the same pancreatic cancer array with the anti-MUC1* polyclonal antibody SDIX. Although both MNC2 and SDIX were generated by immunizing animals with the PSMGFR peptide, they showed different binding characteristics to tumor tissue. In general, SDIX recognized more pancreatic tissues and stained more robustly than MNC2, although there were cases where MNC2 recognized a tumor that SDIX did not.

Figures 20A, 20B:
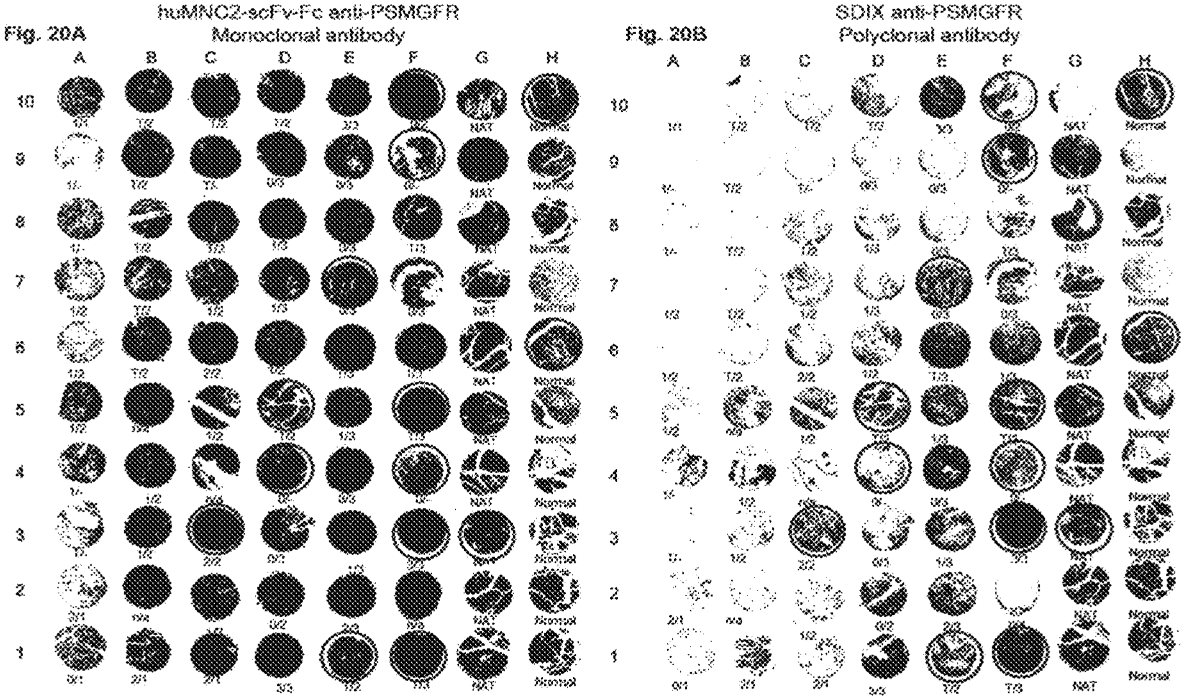
FIG. 20A-20B shows photographs of pancreatic cancer array PA805b that were stained with an anti-MUC1* monoclonal antibody or an anti-MUC1* polyclonal antibody.
Figures 21A, 21B, 21C, 21D:
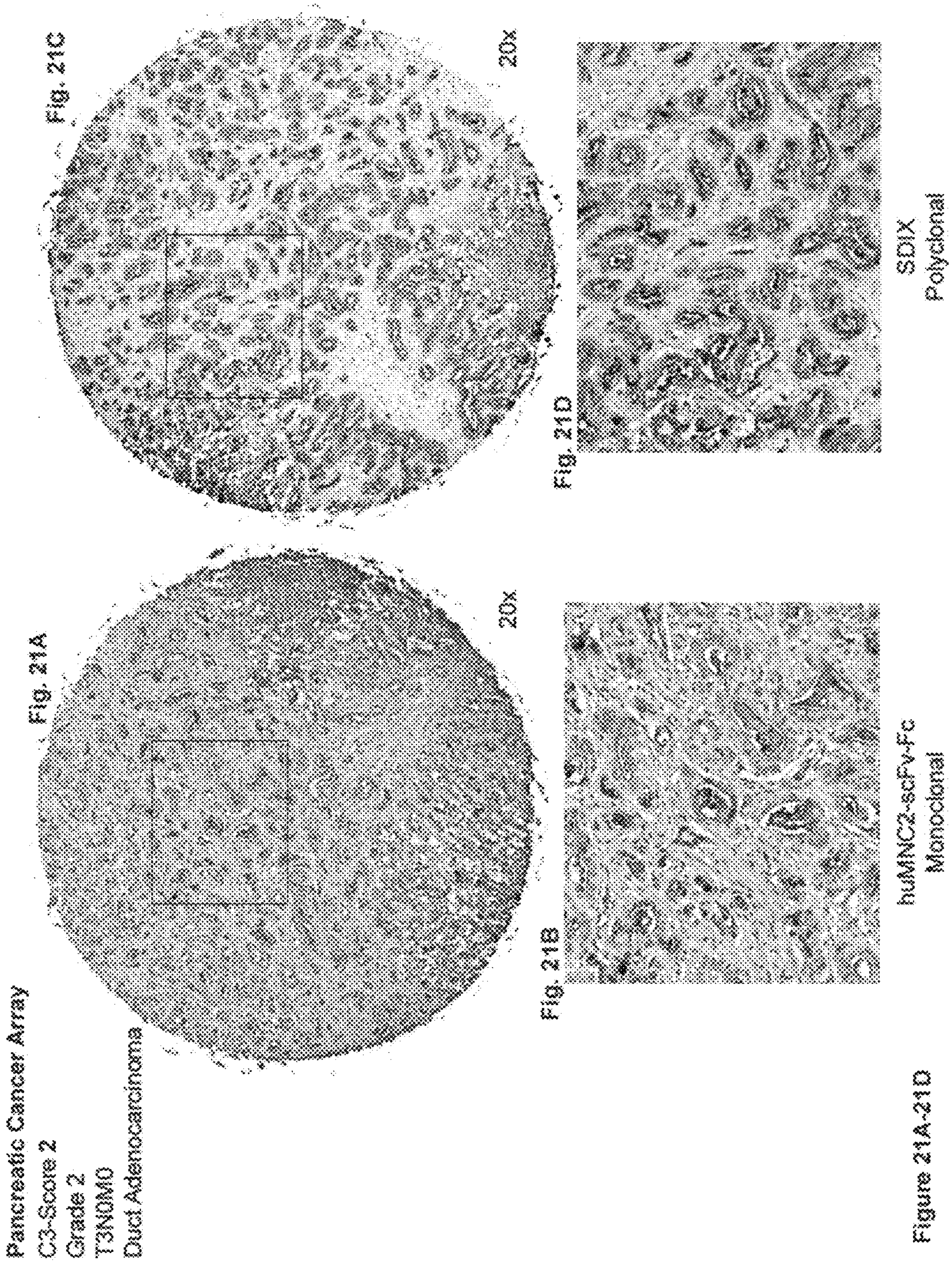
FIGS. 21A-21D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 22A, 22B, 22C, 22D:
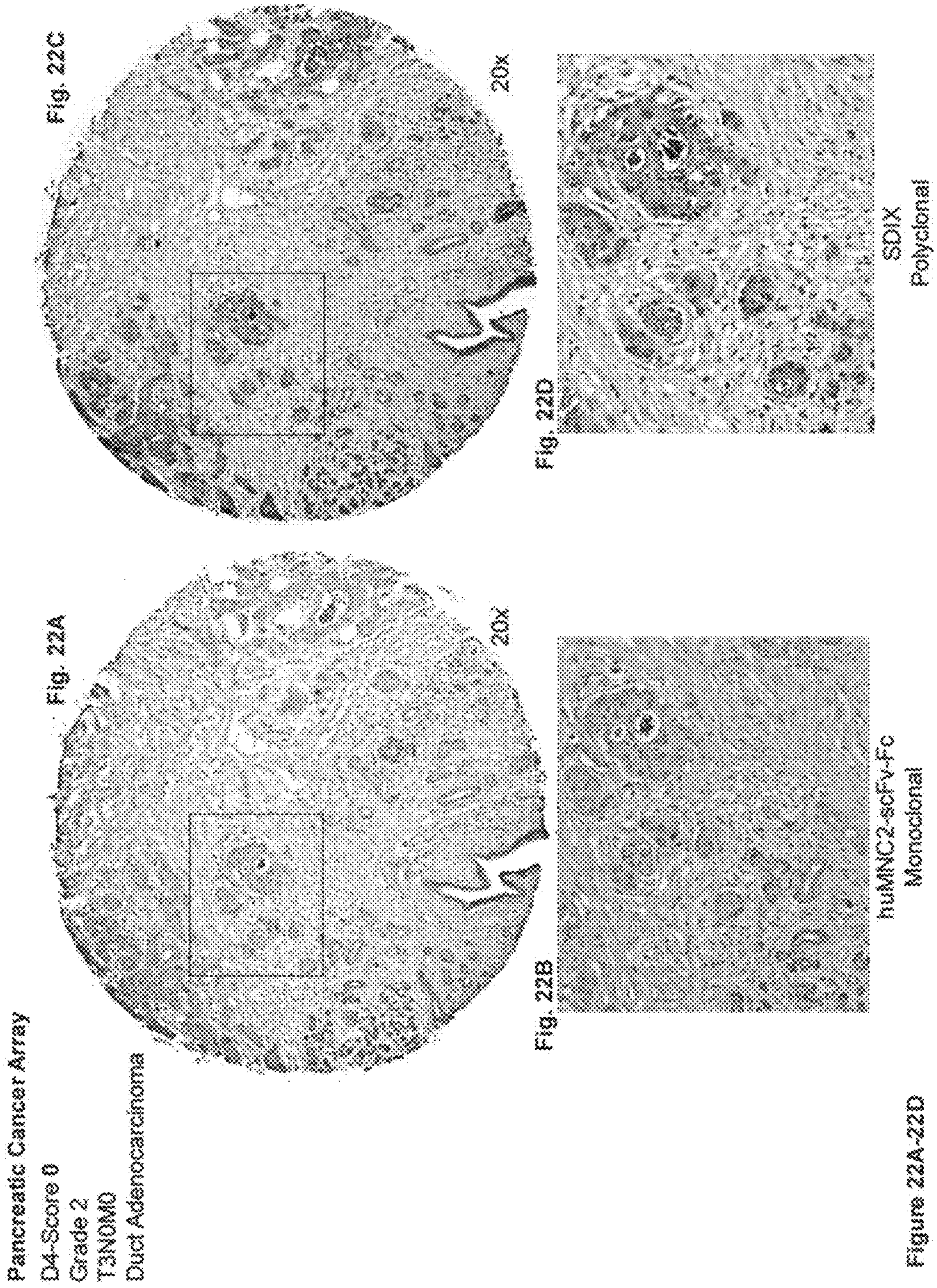
FIGS. 22A-22D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 23A, 23B, 23C, 23D:
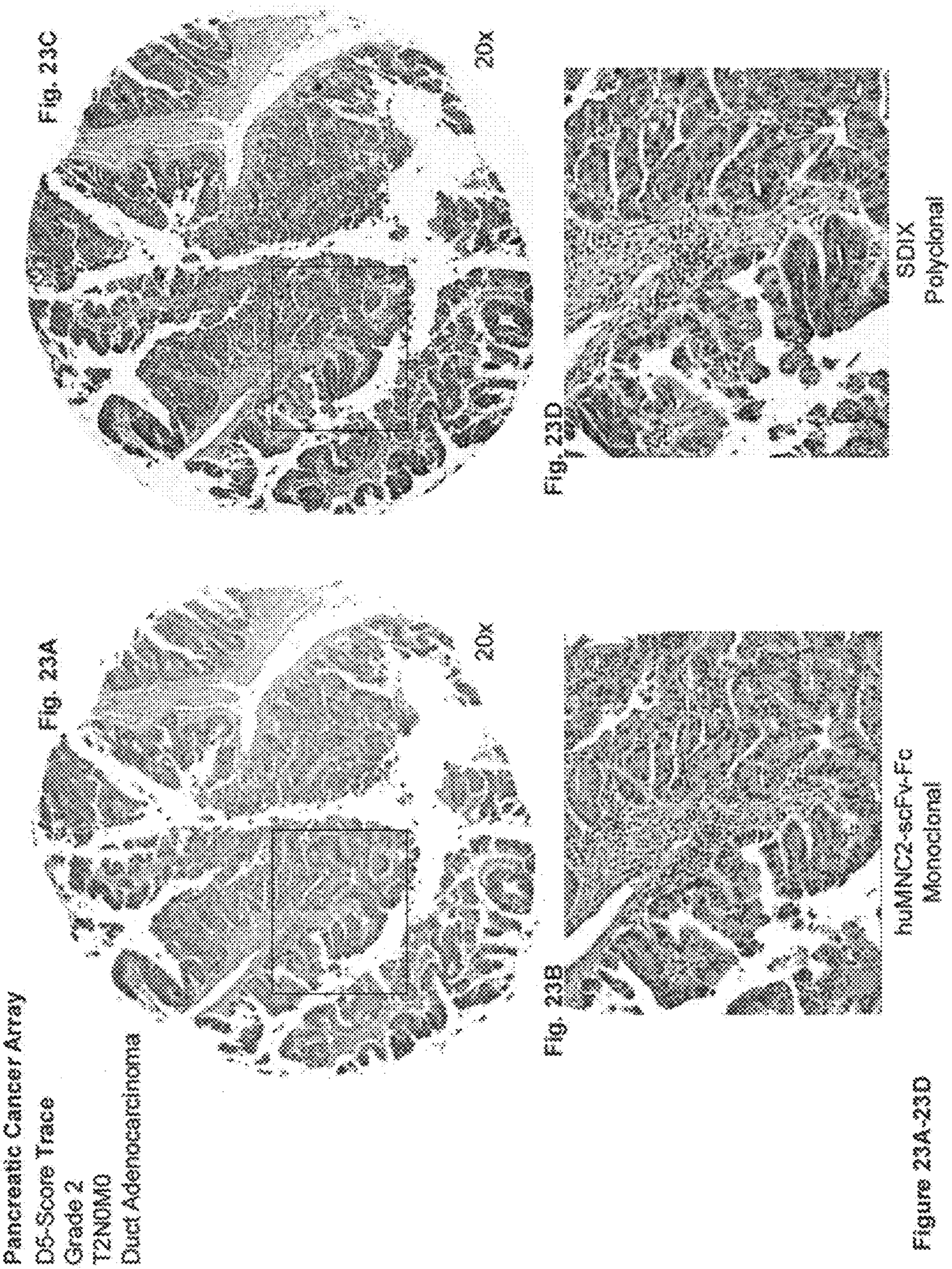
FIGS. 23A-23D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 24A, 24B, 24C, 24D:
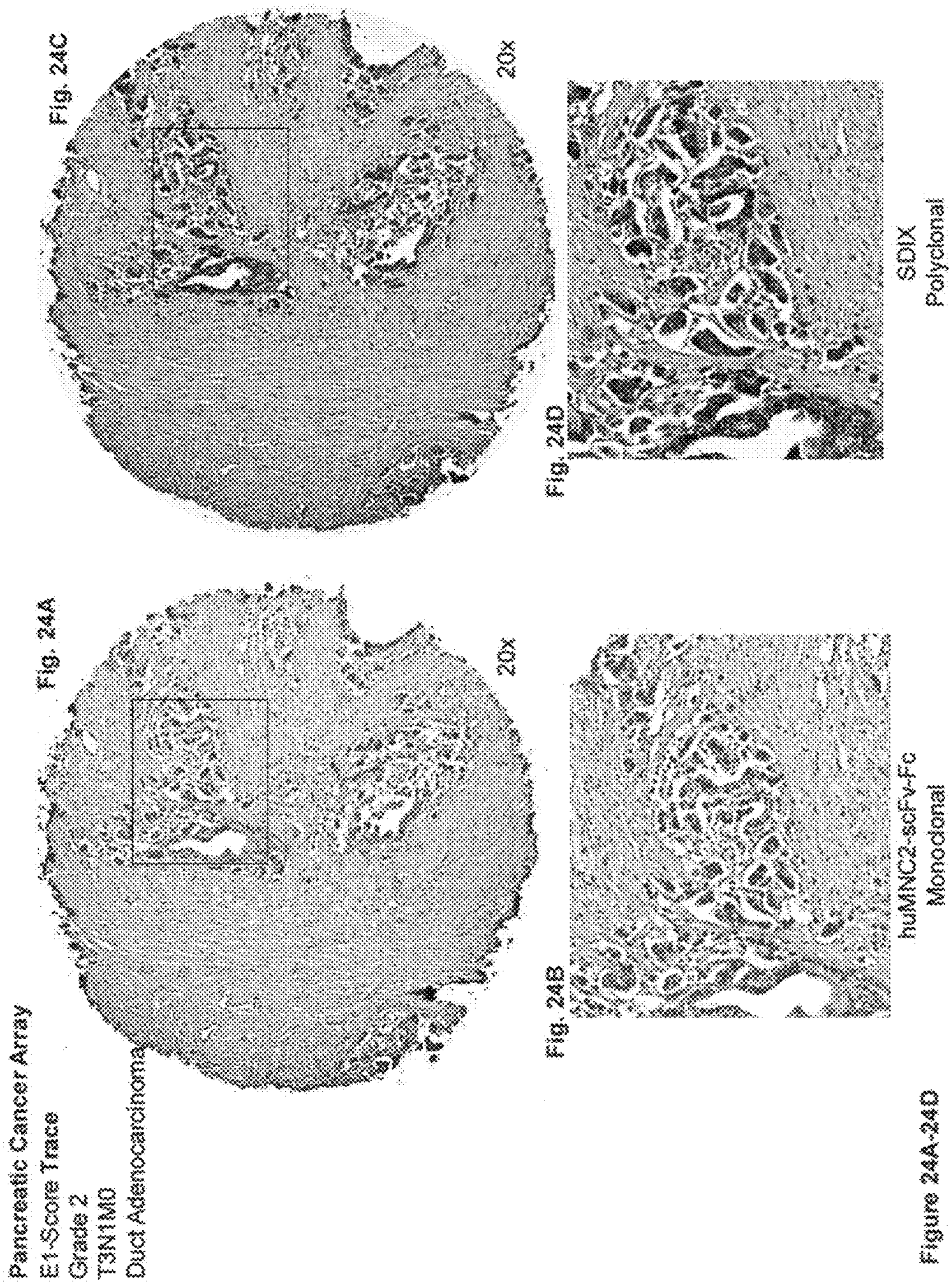
FIGS. 24A-24D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 25A, 25B, 25C, 25D:
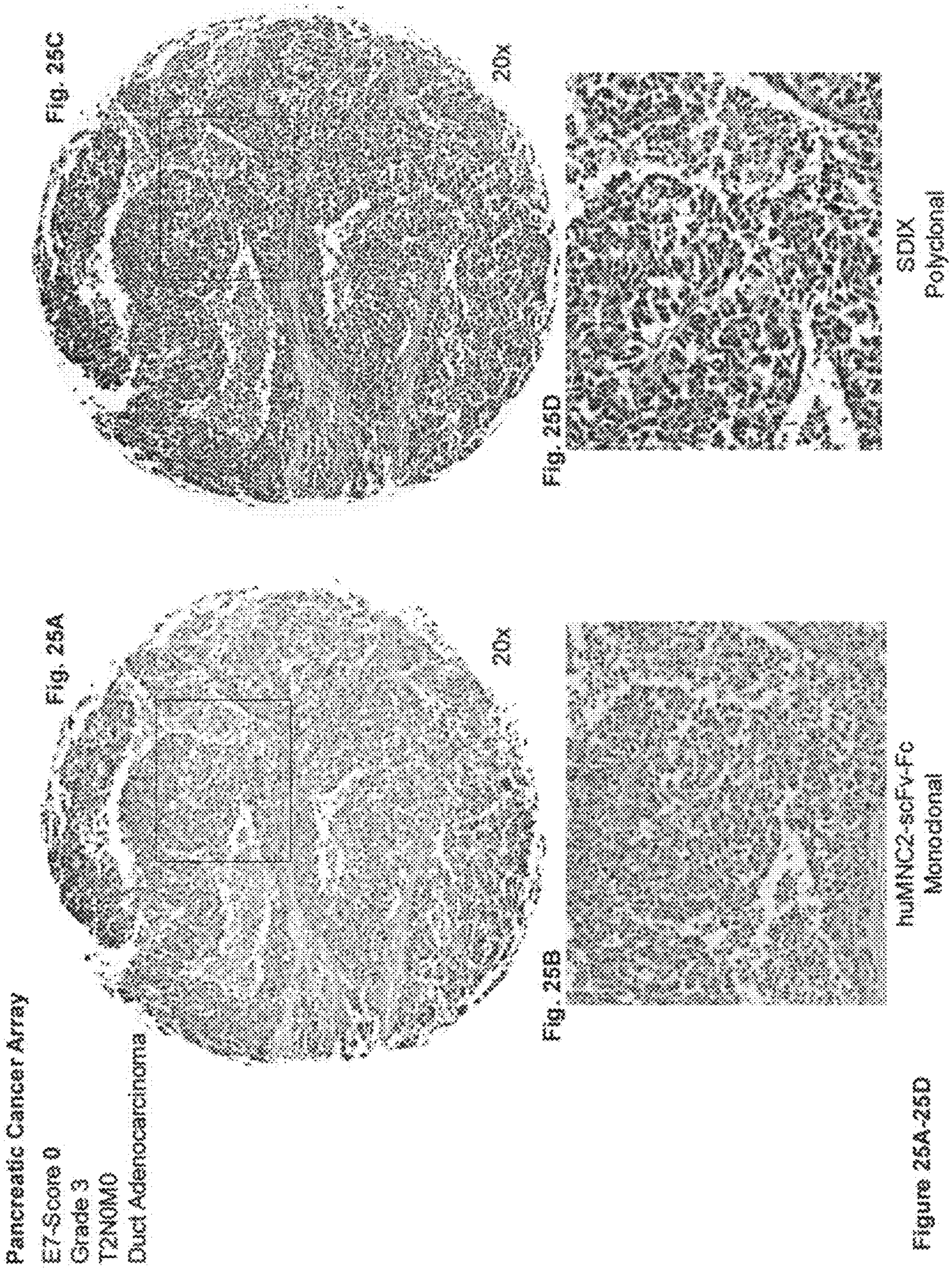
FIGS. 25A-25D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 26A, 26B, 26C, 26D:
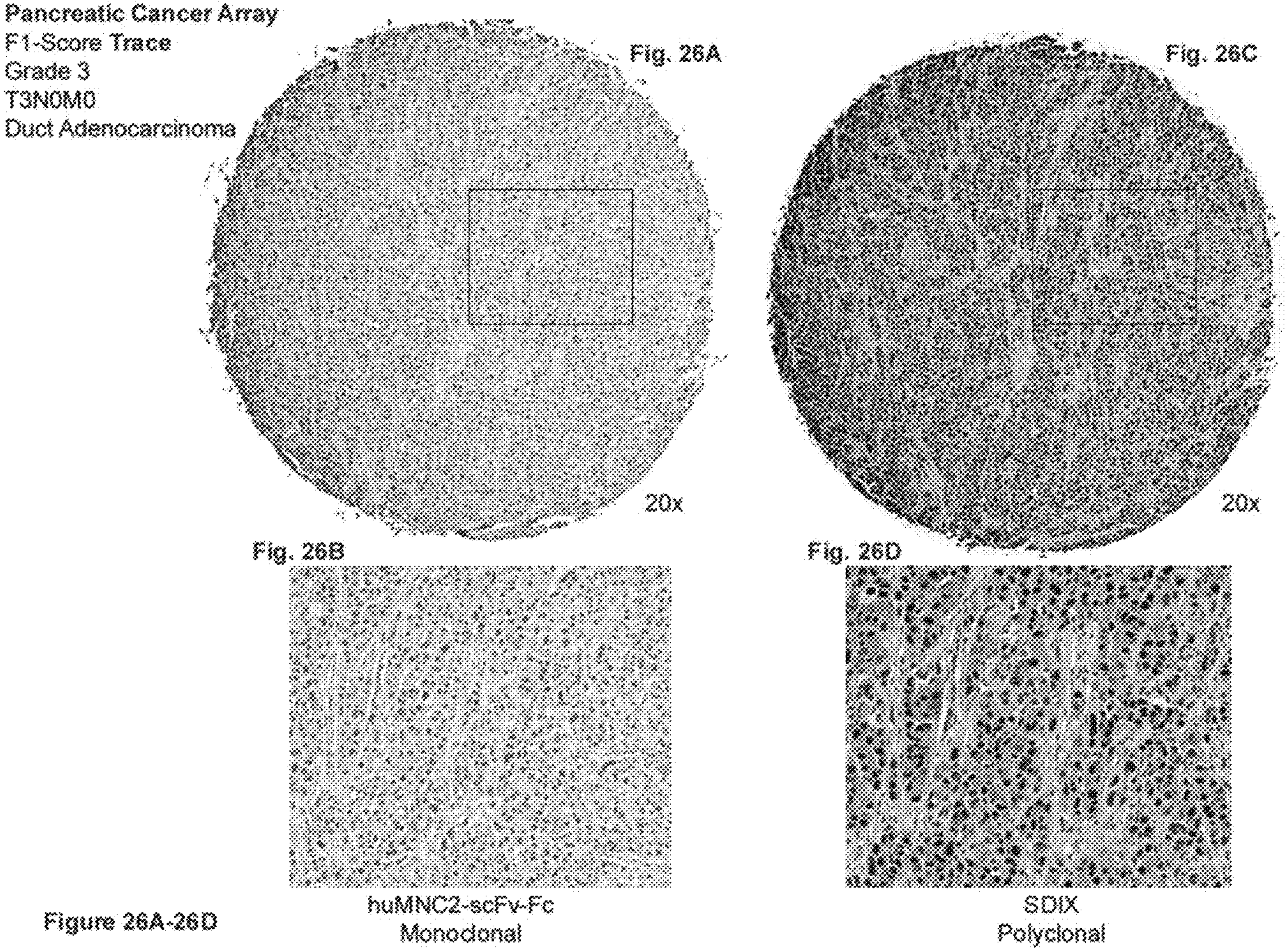
FIGS. 26A-26D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 28A, 28B, 28C, 28D:
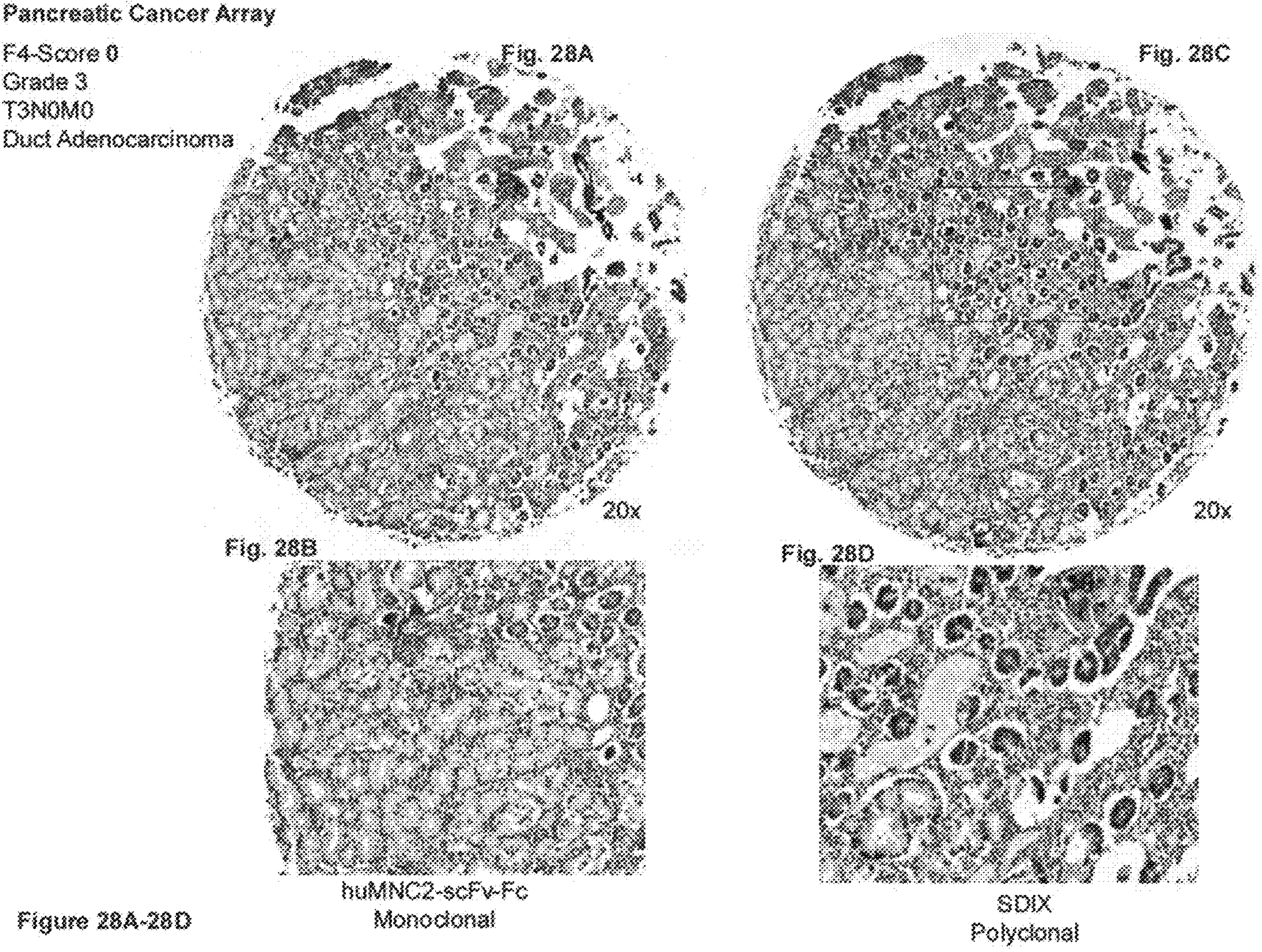
FIGS. 28A-28D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 29A, 29B, 29C, 29D:
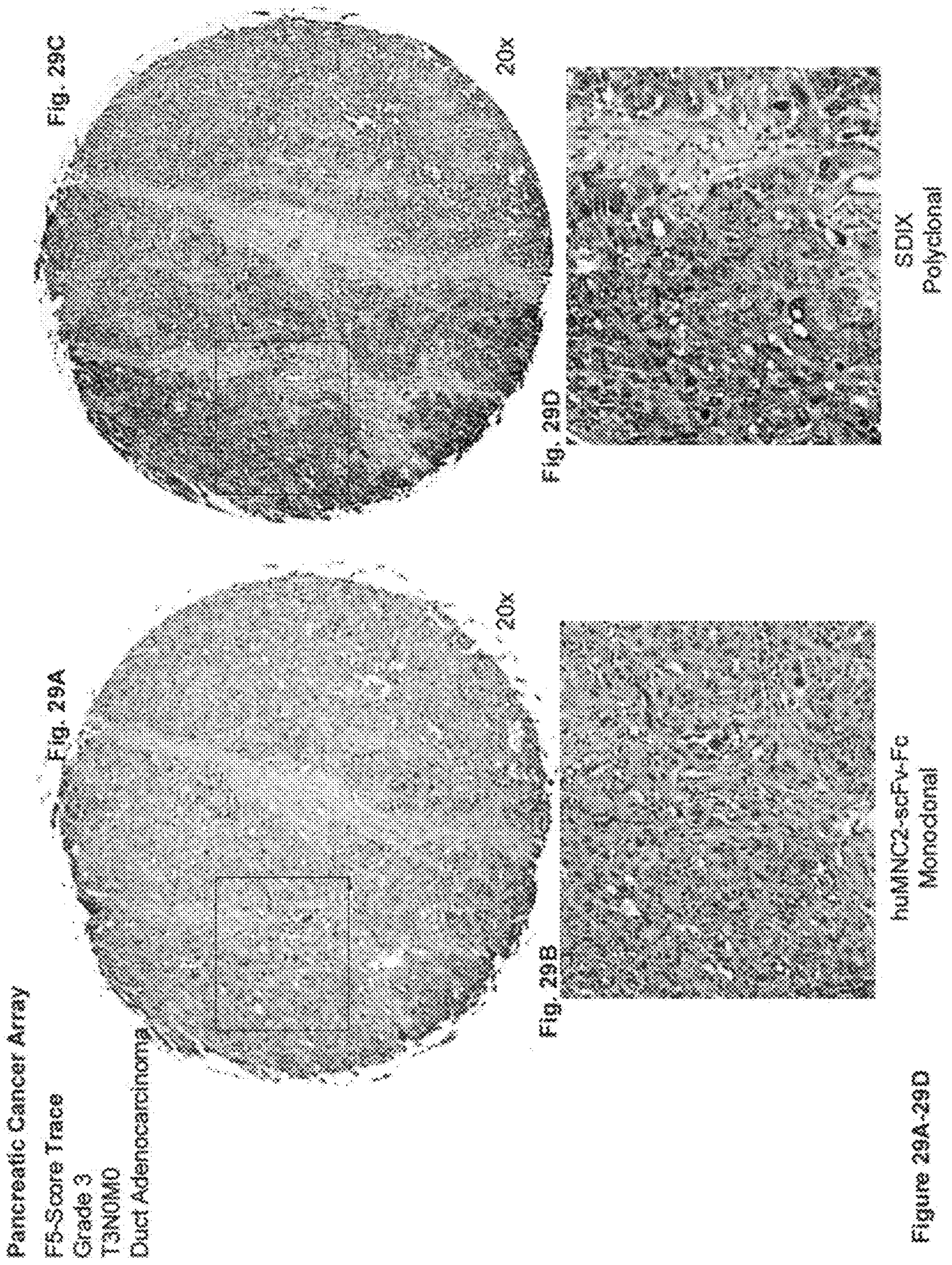
FIGS. 29A-29D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 30A, 30B, 30C, 30D:
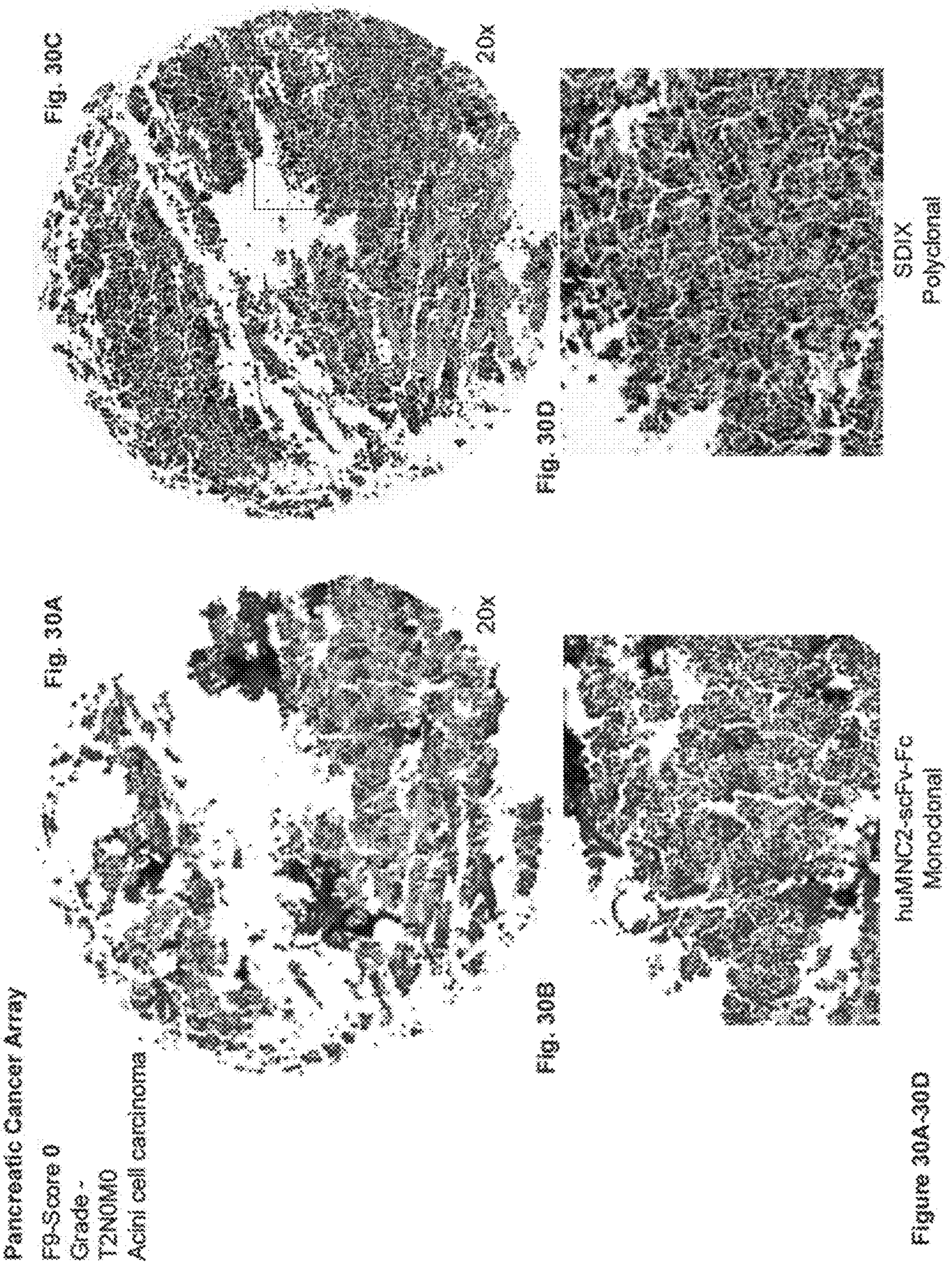
FIGS. 30A-30D show photographs of individual tumor tissue specimens from the pancreatic cancer array, comparing the staining intensity and pattern of staining when the patient sample is probed with monoclonal antibody MNC2 or polyclonal antibody SDIX, wherein both antibodies bind to the PSMGFR peptide. In the figures, (A) is stained with MNC2, (B) is the same tissue but at greater magnification, (C) is stained with SDIX, and (D) is that same tissue but shown at greater magnification.
Figures 32A, 32B, 32C, 32D:
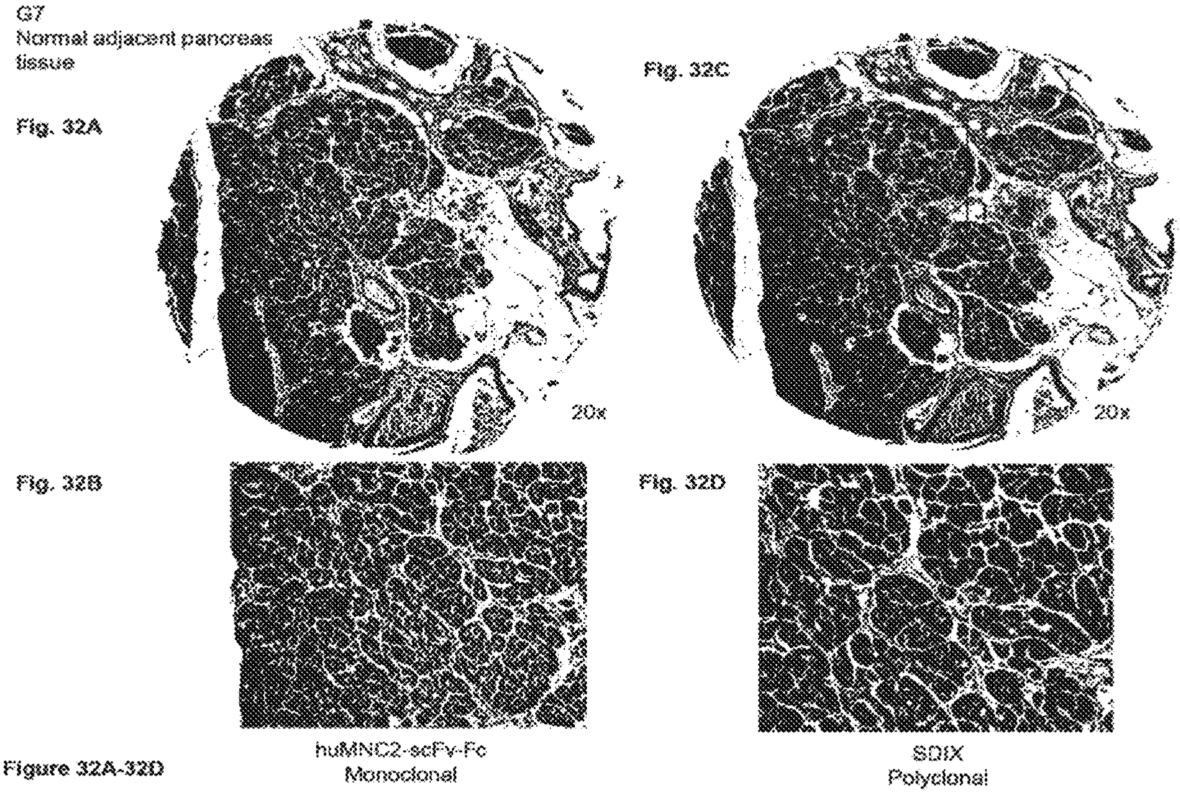
FIGS. 32A-32D show photographs of individual tissue specimens from the pancreatic cancer array, but the specimens that are shown are normal pancreatic tissues. The staining intensity and pattern of staining of monoclonal antibody MNC2 is compared to that of polyclonal antibody SDIX. In the figures, (A) is stained with MNC2, (B) is the same tissue but at greater magnification, (C) is stained with SDIX, and (D) is that same tissue but shown at greater magnification.
Figures 33A, 33B, 33C, 33D:
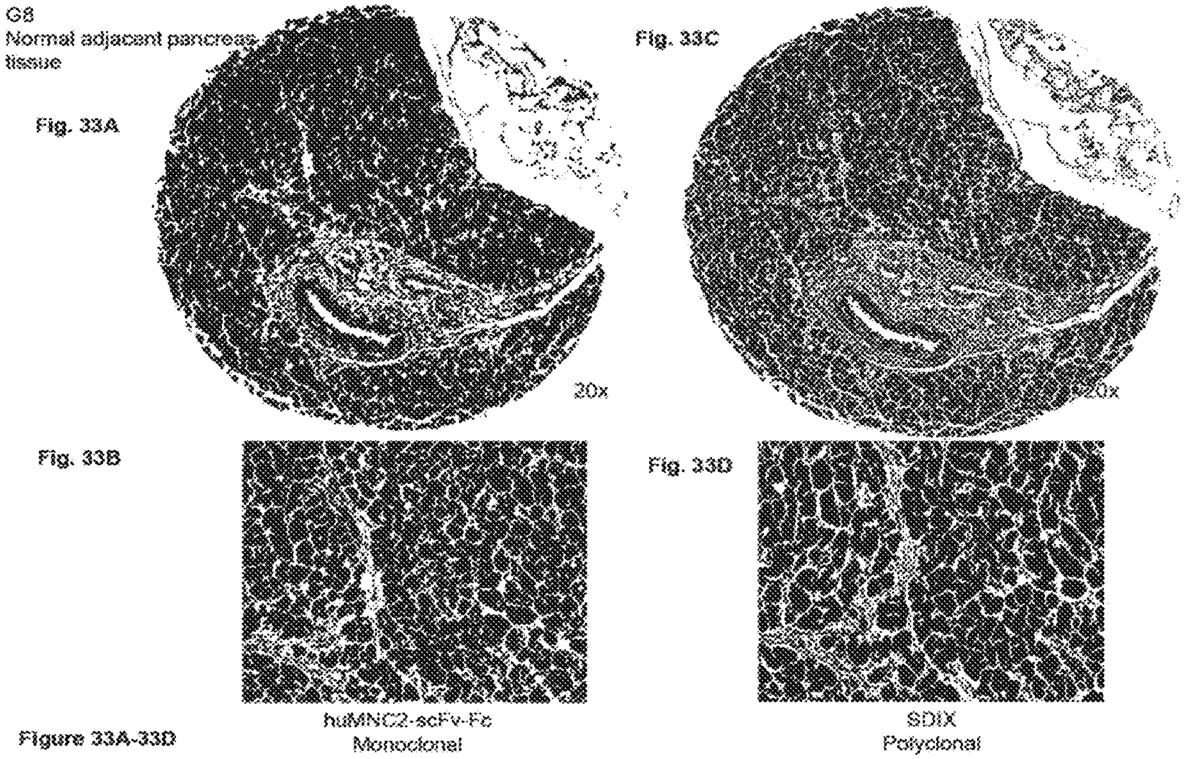
FIGS. 33A-33D show photographs of individual tissue specimens from the pancreatic cancer array, but the specimens that are shown are normal pancreatic tissues. The staining intensity and pattern of staining of monoclonal antibody MNC2 is compared to that of polyclonal antibody SDIX. In the figures, (A) is stained with MNC2, (B) is the same tissue but at greater magnification, (C) is stained with SDIX, and (D) is that same tissue but shown at greater magnification.
Figures 34A, 34B, 34C, 34D:
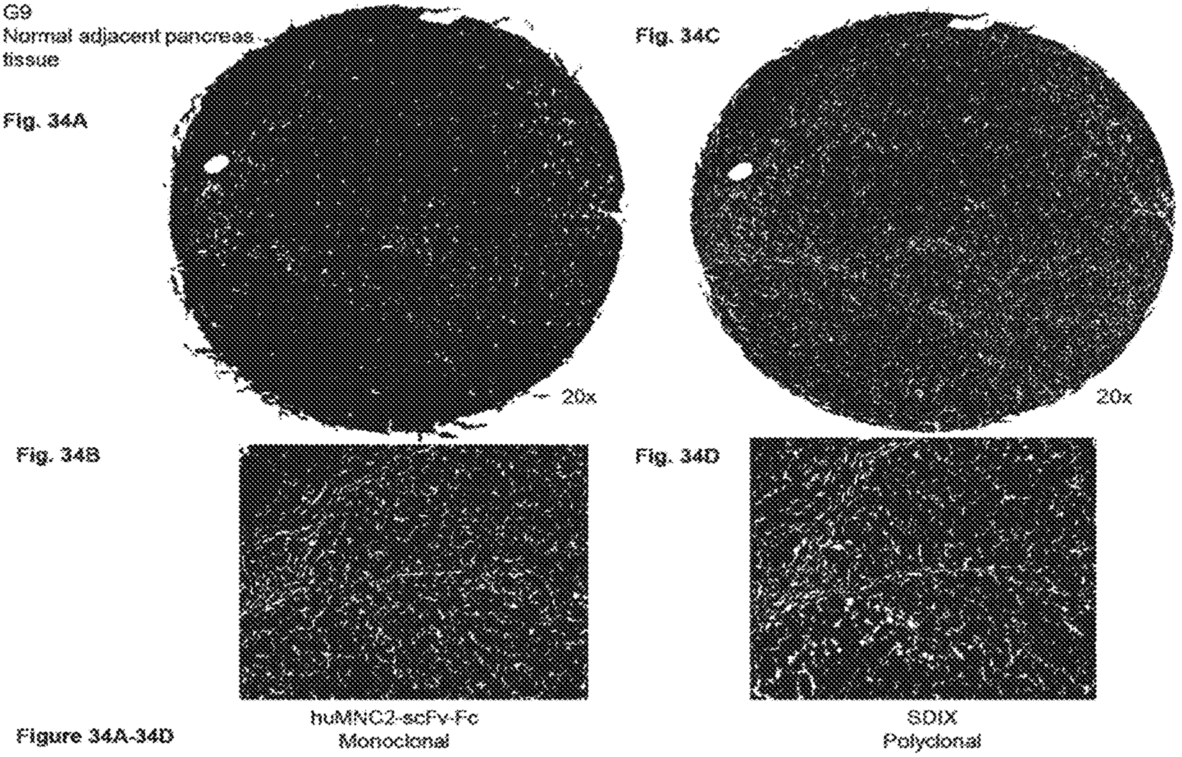
FIGS. 34A-34D show photographs of individual tissue specimens from the pancreatic cancer array, but the specimens that are shown are normal pancreatic tissues. The staining intensity and pattern of staining of monoclonal antibody MNC2 is compared to that of polyclonal antibody SDIX. In the figures, (A) is stained with MNC2, (B) is the same tissue but at greater magnification, (C) is stained with SDIX, and (D) is that same tissue but shown at greater magnification.

On cancerous tissues, MUC1* is expressed over most of the tissue and is characteristic of cancer, all anatomical barriers have broken down in cancerous tissues. In contrast, on normal tissues, expression of MUC1* is restricted to the apical border of ducts and glands. Expression of MNC2 reactive MUC1* is even further restricted. For example, FIG. 6B shows a photograph of an ovarian cancer micro array. However, Column J is made up of normal ovarian tissues. As can be seen, there is no expression of MNC2 reactive MUC1*. Normal kidney does express some MNC2 reactive MUC1*. As can be seen in FIG. 10A-10F, normal MUC1* expression is weak and restricted to the apical border of about 10% of the distal collecting tubules of normal kidney. Normal pancreas expresses MUC1* that is again tightly restricted to the apical border of acinar cells (FIG. 20). Those skilled in the art can readily identify cancerous tissues and can differentiate between MUC1* expression on normal tissue and on cancerous tissues. In general, MUC1* is grossly overexpressed on cancerous tissues and its expression is not restricted to an apical pattern of expression.

In this FIG. 20 through FIG. 34, we show that a series of pancreatic tumors showed no or minimal staining with monoclonal antibody MNC2, but staining the same tissue with the SDIX polyclonal antibody produced robust staining. Both MNC2 and SDIX were generated by immunizing animal with the same peptide: PSMGFR. However, MNC2 only recognizes a subset of those recognized by SDIX. These results strongly argue that MNC2 recognizes an epitope that is only created in a subset of the tumor. The data suggest that the MNC2 reactive subset of MUC1* can be cancer sub-type specific or patient specific, likely due to cleavage by different cleavage enzymes.

Figure 37:
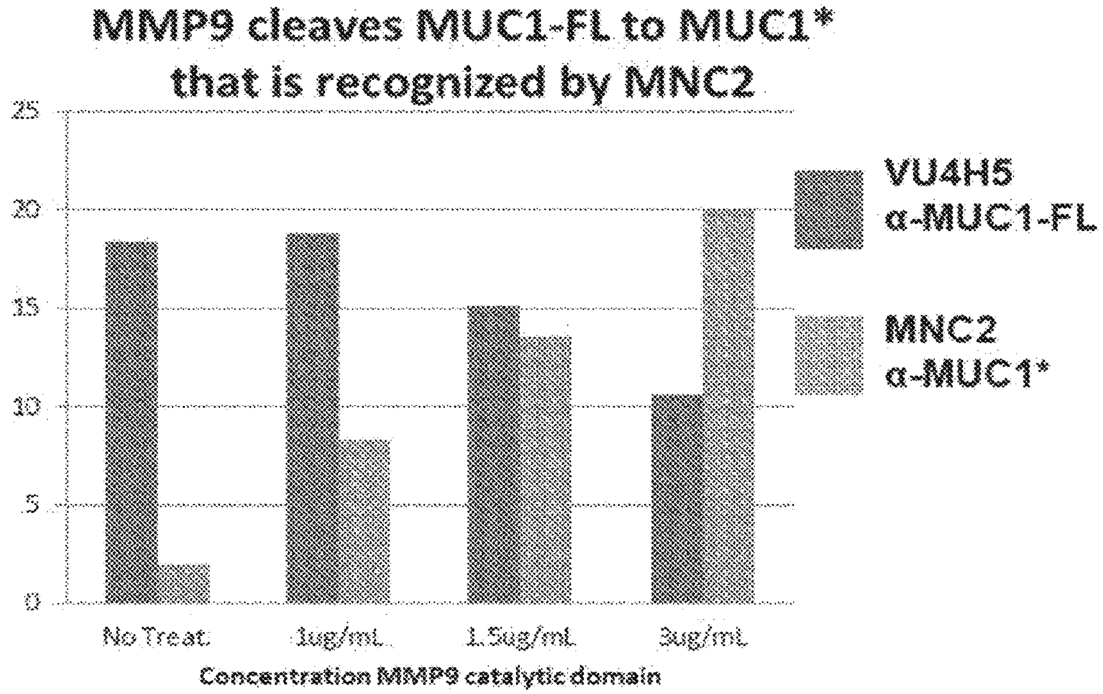
FIG. 37 shows a graph of FACS analysis of cells that express 90% full-length MUC1 after addition of a catalytic domain of cleavage enzyme MMP9, then probing with anti-full-length MUC1 antibody VU4H5 or anti-MUC1* antibody MNC2.

The hypothesis that anti-MUC1* antibody specificity is dependent on the cleavage enzyme that cleaves MUC1 to a MUC1* is supported by data shown in FIG. 35 through FIG. 37. MNC2, MNC3 and SDIX were all generated by immunizing an animal with the PSMGFR peptide. However, monoclonal antibody MNC3 recognizes nearly 100% of hematopoietic stem cells, as does the polyclonal antibody SDIX, while monoclonal antibody MNC2 does not. Conversely, MNC2 binds to nearly 95% of breast tumors, but MNC3 does not. Importantly, we demonstrated that MNC2 recognizes MUC1* after MUC1 is cleaved by cleavage enzyme MMP9, which is overexpressed in most breast cancers, but not in hematopoietic stem cells. Expression of MMP9 is predictor of poor prognosis for most solid tumor cancers (Yousef et al. BMC Cancer 2014, 14:609; Mehner et al, Oncotarget, Vol. 5, No. 9, pp 2736-2749, 2014; Radisky et al., Front Biosci (Landmark Ed); 20:1144-1163, 2015; Gong et al., Journal of Surgical Oncology 2000; 73:95-99; Latinovic et al., Arch Oncol 2013; 21 (3-4): 109-14; Sillanpaa et al., Gynecologic Oncology 104 (2007) 296-303).

In order to generate new anti-MUC1* monoclonal antibodies that were capable of recognizing a wide range of MUC1*'s that can be cancer sub-type specific, patient specific or to better address tumor heterogeneity, we immunized animals with one of the following peptides derived from the sequence of the MUC1* extra cellular domain:

(i) PSMGFR peptide (SEQ ID NO: 4)
GTINVHDVETQFNQYKTEAASRYNLTISDVSVSDVPFPFSAQSGA;

(ii) PSMGFR N+20/C-27

(SEQ ID NO: 9)
SNIKFRPGSVVVQLTLAFREGTINVHDVETQFNQYKTE;

or (iii) PSMGFR N+9/C-9

(SEQ ID NO: 10)
VQLTLAFREGTINVHDVETQFNQYKTEAASRYNLTISDVSVSDVP.

Antibody clones were isolated and a subset from each immunization was selected, first based on their ability to bind to the immunizing peptide, then secondly for their ability to recognize cancerous tissues above normal tissues. FIG. 38A to FIG. 38C shows tables of the selected antibodies, organized according to immunizing peptide. In the tables, designation of −1 or −2 indicates that these are sister clones, which after sequencing showed these were in fact the same antibody. Throughout the rest of the disclosure, antibodies are referred to without the −1 or −2 designation.

FIG. 39 through FIG. 44 show the binding characteristics of new anti-MUC1* antibodies. All antibodies were first selected by virtue of the fact that they bound to the immunizing peptide. For comparison to MNC2 and MNC3, new antibodies were tested for their ability to bind to PSMGFR, the N-10 peptide and the C-10 peptide. New anti-MUC1* antibodies were also tested by FACS to determine their ability to bind to the T47D breast cancer cell line. Because analysis of antibody binding to a single cell line that was generated from a patient decades ago, we expanded the analysis of the new antibodies to hundreds of tumor tissues across multiple cancer sub-types. The number of patients represented in each array varied. Normal tissues were also probed with the antibodies.

FIG. 45 through FIG. 52 compares the binding of the new anti-MUC1* antibodies to the SDIX polyclonal to investigate antibodies that bind to regions that are N-terminal to the PSMGFR sequence. We started with pancreatic cancer arrays because out previous work showed that although MNC2 recognized about 78% of pancreatic cancers, the binding was not so robust and some very nasty tumors were not recognized at all by MNC2 or the SDIX polyclonal.

Figures 45A, 45B, 45C:
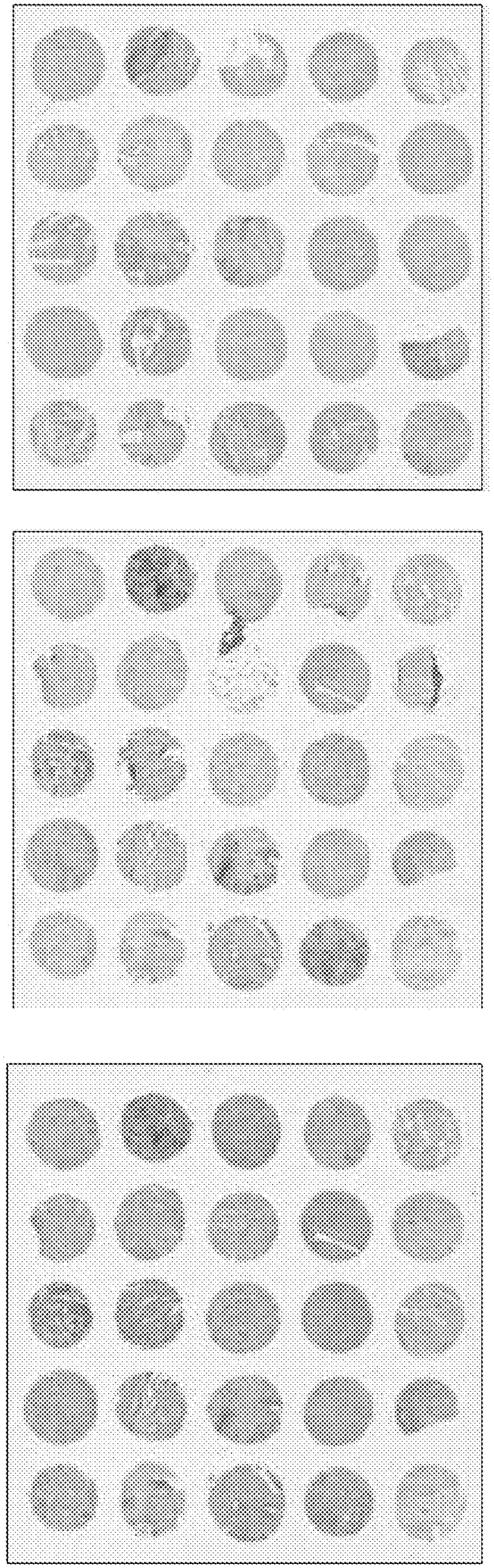
FIG. 45A-45C shows photographs of adjacent serial sections from a pancreatic cancer array, which was stained by standard IHC methods with various anti-MUC1* antibodies.
Figures 46A, 46B, 46C, 46D, 46E, 46F:
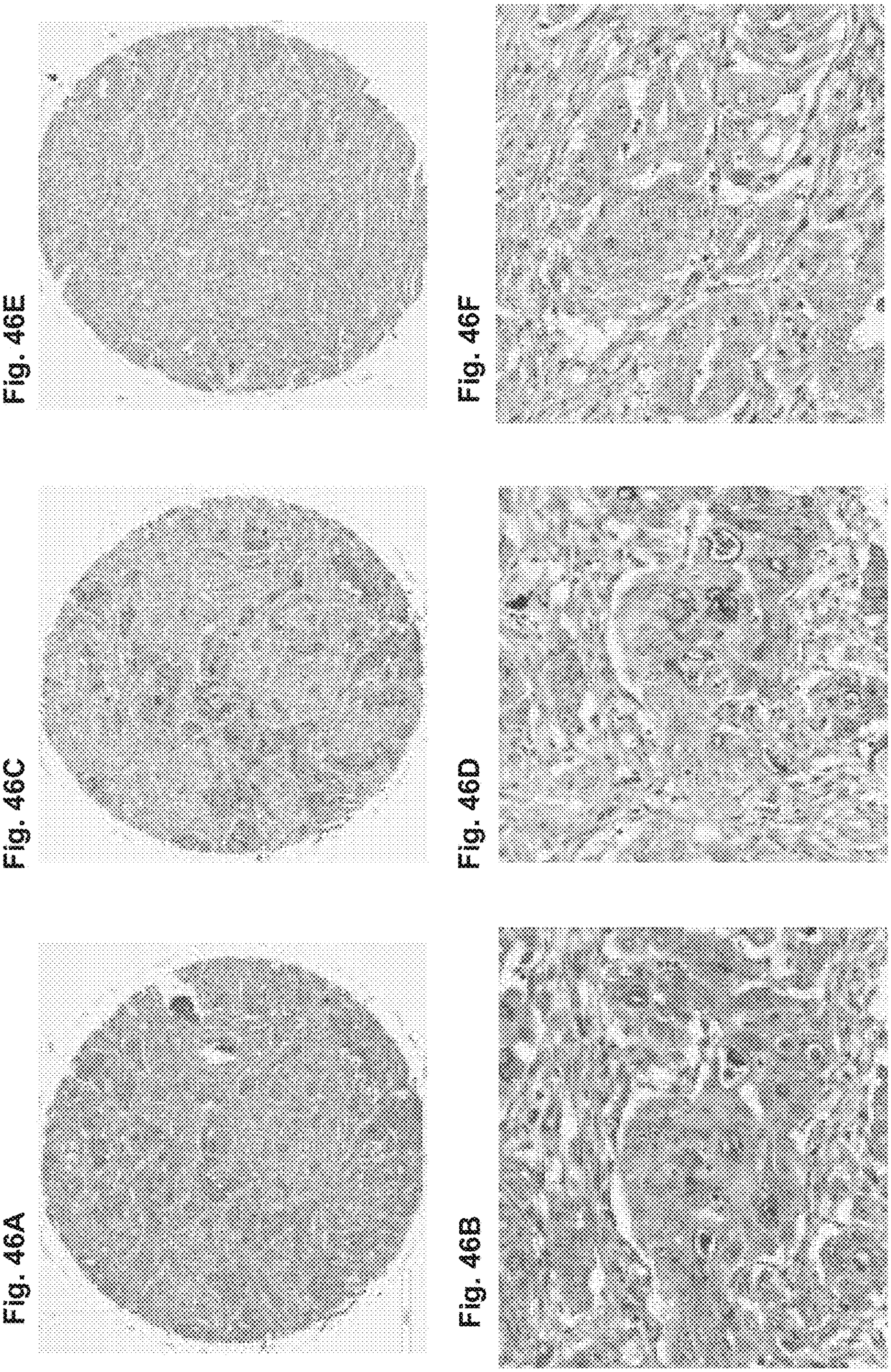
FIG. 46A-46F shows photographs of individual specimens from the pancreatic cancer array shown in FIG. 45.
Figures 51A, 51B, 51C:
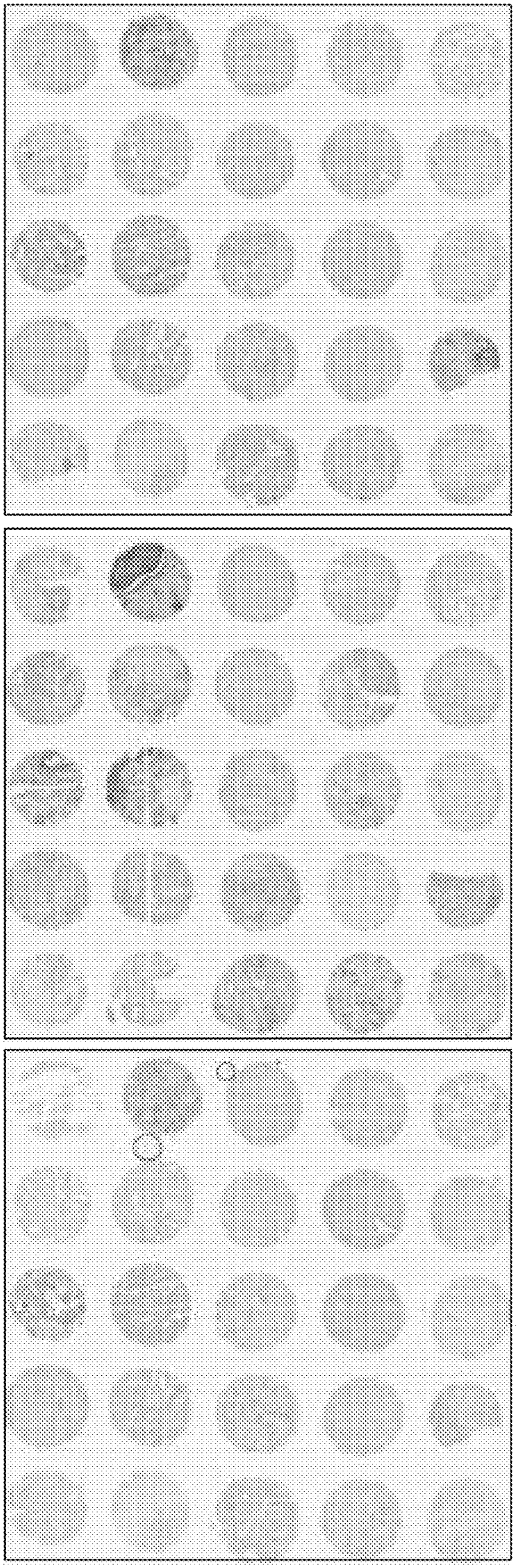
FIG. 51A-51C shows photographs of adjacent serial sections from a pancreatic cancer array, which was stained by standard IHC methods with various anti-MUC1* antibodies.
Figures 52A, 52B, 52C, 52D:
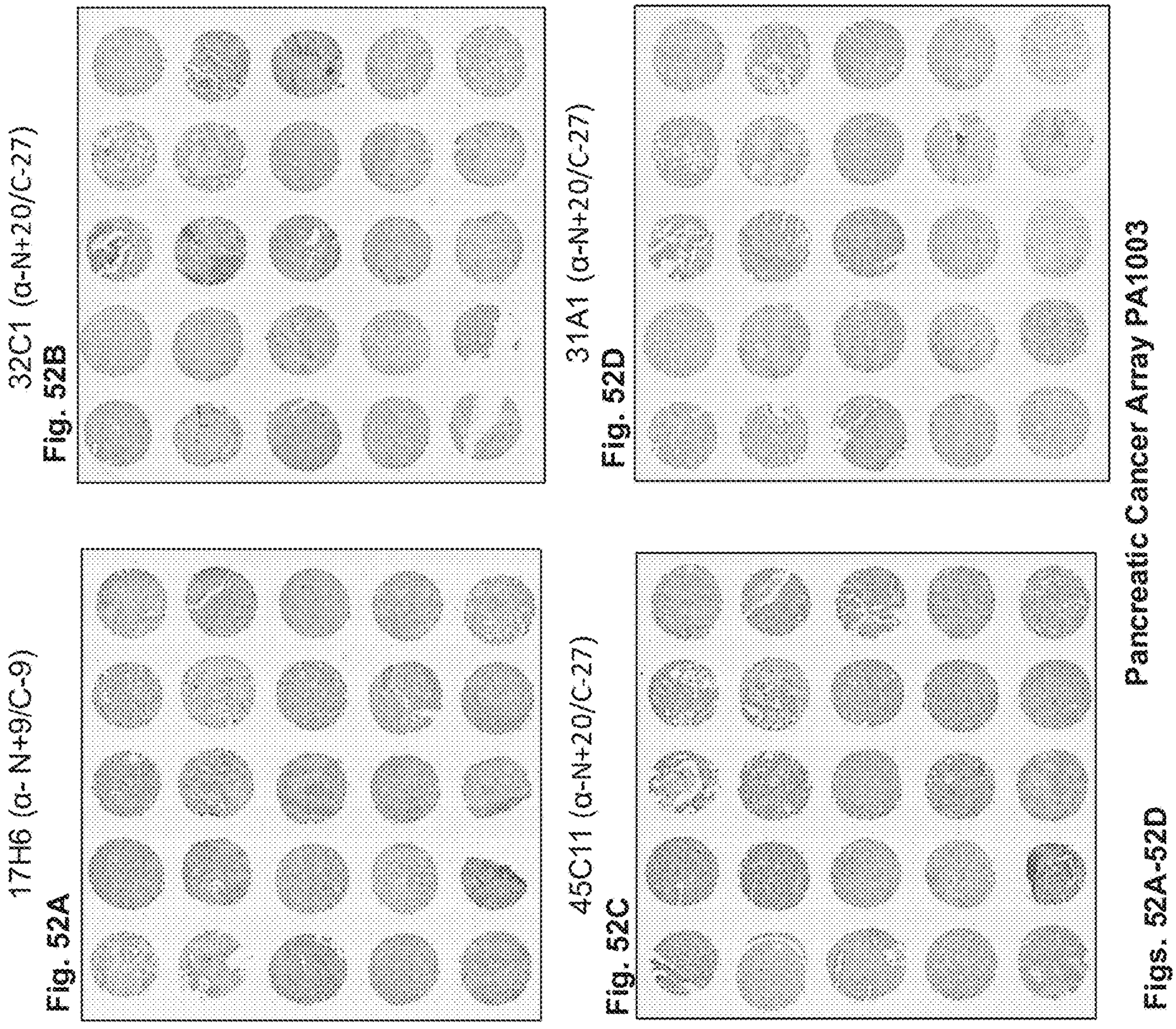
FIG. 52A-52D shows photographs of adjacent serial sections from a pancreatic cancer array, which was stained by standard IHC methods with various anti-MUC1* antibodies.

Some anti-PSMGFR antibodies, such as 18B4, appear to recognize the same pancreatic tumor tissues as the polyclonal anti-PSMGFR antibody SDIX (FIG. 45A-45BC). In this small pancreatic cancer array, anti-PSMGFR N+20/C-27 antibody 1E4 appears to recognize the same tumors as SDIX and 18B4, however, the magnified view of these tumor specimens shows that antibody 1E4 recognizes a different population of cancer cells within the tumor than the anti-PSMGFR antibodies (FIG. 46A-46F), Some of the tumors were not recognized well by SDIX but were recognized by monoclonal antibody 18B4 (FIG. 47A-48D). Other pancreatic tumors were recognized better by anti-PSMGFR N+20/C-27 antibody 1E4 (FIG. 49A-49D). Similarly, anti-PSMGFR N+20/C-27 antibody 29H1 recognizes some pancreatic tumors that are missed by anti-PSMGFR antibodies SDIX and 20A10 (FIG. 51A-51C).

These studies showed that, in general, antibodies that bind to the MUC1* extra cellular domain that is extended beyond PSMGFR at the N-terminus recognize pancreatic cancers better than SDIX polyclonal. However, antibody specificity of pancreatic tumors appears to also be patient specific. Some patient specimens stained much better with the SDIX anti-PSMGFR antibody than the new antibodies that bind to PSMGFR N+20/C-27 or PSMGFR N+9/C-9. This supports the idea that patient tumors must be probed with a panel of MUC1* antibodies to determine which treatment is best suited for elimination of their tumor. In one aspect of the invention, the therapeutic agent incorporates some or all of the antibody that is the diagnostic agent or some or all of an antibody that is derived from the antibody that is the diagnostic antibody.

Figures 53A, 53B, 53C, 53D, 53E, 53F:
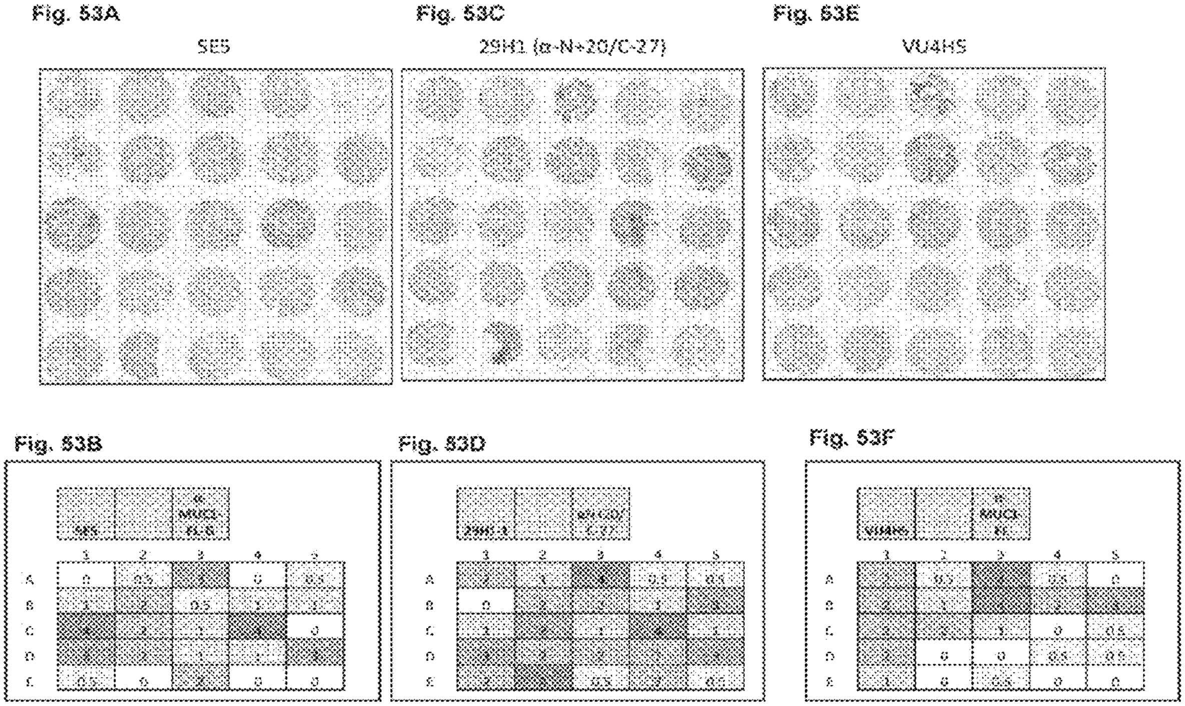
FIG. 53A-53F shows photographs and graphical representations of pathologist staining scores of adjacent serial sections from a pancreatic cancer array, which was stained by standard IHC methods with either antibodies that recognize full-length MUC1 or an antibody that only recognizes MUC1*.

FIG. 53 demonstrates that these new antibodies that are extended at the N-terminus are recognize more pancreatic tumors than antibodies that bind to full-length MUC1. This figure compares the binding of 29H1 to a standard antibody, VU4H5, that binds to the tandem repeats of full-length MUC1, and to a new antibody, 5E5 that binds to a trapped O-linked glycan that is present on some cancer cells.

We next looked at esophageal tumors and prostate tumors. These studies were motivated by our previous findings that monoclonal antibody MNC2 as well as polyclonal antibody SDIX, which both bind to the PSMGFR peptide, showed poor recognition of esophageal tumors and prostate tumors. In fact, those tumors that showed some MNC2 reactivity in the well differentiated portions of a tumor specimen, lost that reactivity in the less well differentiated portion of the same specimen. These results argued that a cleavage enzyme other than MMP9 is dominant in most esophageal and prostate cancers. These studies support that idea.

The new anti-MUC1* antibodies, which bind to peptides PSMGFR N+20/C-27 and/or PSMGFR N+9/C-9, showed markedly better recognition of esophageal and prostate tumors when compared to MNC2, SDIX, and full-length MUC1 antibodies 5E5 and VU4H5.

FIG. 54A-54C shows photographs of adjacent serial sections from an esophageal cancer array, which was stained by standard IHC methods with various anti-MUC1* antibodies. FIG. 54A shows the array stained with the SDIX polyclonal anti-MUC1* antibody, wherein the immunogen for the antibody was the PSMGFR peptide. FIG. 54B shows the array stained with the 20A10 monoclonal anti-MUC1* antibody, wherein the immunogen for the antibody was the PSMGFR peptide. FIG. 54C shows the array stained with the 29H1 monoclonal anti-MUC1* antibody, wherein the immunogen for the antibody was the PSMGFR N+20/C-27 peptide. FIG. 54D shows the array stained with the 31A1 monoclonal anti-MUC1* antibody, wherein the immunogen for the antibody was the PSMGFR N+20/C-27 peptide. This figure shows that antibodies SDIX and 20A10 that both bind to the PSMGFR peptide recognize the same tumor tissue specimens, albeit to differing degrees, while antibodies that bind to the PSMGFR N+20/C-27 peptide bind to more esophageal tumor specimens as well as most of those recognized by the anti-PSMGFR antibodies. These results are consistent with the idea that antibodies that bind to the PSMGFR N+20/C-27 peptide are general more specific for esophageal cancers than antibodies that bind to the PSMGFR peptide, but that certain patients may have an esophageal cancer that is better recognized by an anti-MUC1* antibody that binds to the PSMGFR peptide.

Figures 55A, 55B, 55C, 55D:
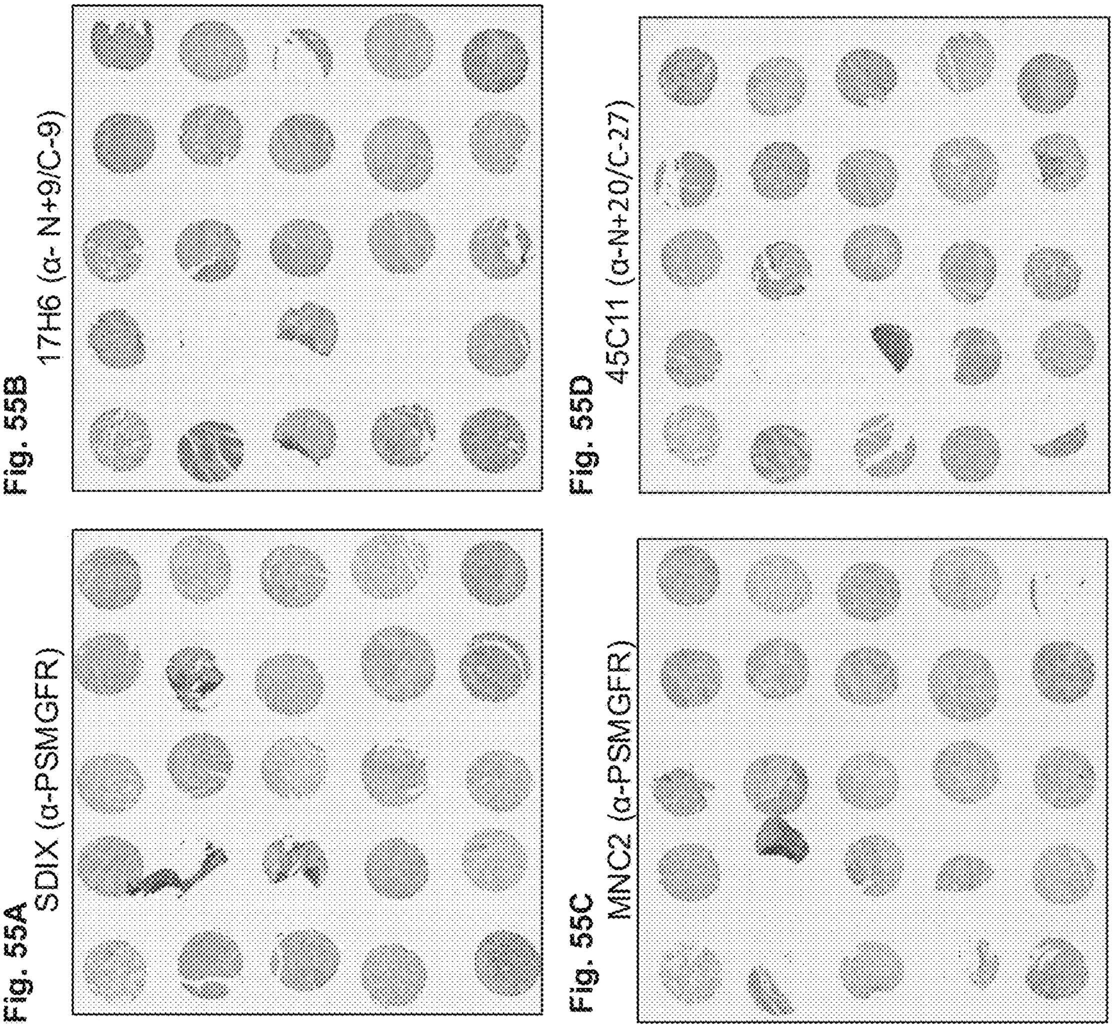
FIG. 55A-55C shows photographs of adjacent serial sections from an esophageal cancer array, which was stained by standard IHC methods with various anti-MUC1* antibodies.
FIG. 55D shows the array stained with the 45C11 monoclonal anti-MUC1* antibody, wherein the antibody binds to the PSMGFR N+20/C-27 peptide. These results are consistent with the idea that on most esophageal cancers, MUC1 is cleaved by an enzyme that exposes a cryptic epitope that is N-terminal to the PSMGFR sequence.

FIG. 55A-55C shows photographs of adjacent serial sections from an esophageal cancer array, which was stained by standard IHC methods with various anti-MUC1* antibodies. FIG. 55A shows the array stained with the SDIX polyclonal anti-MUC1* antibody, wherein the immunogen for the antibody was the PSMGFR peptide. FIG. 55B shows the array stained with the 17H6 monoclonal anti-MUC1* antibody, wherein the antibody binds to the PSMGFR N+9/C-9 peptide. FIG. 55C shows the array stained with the MNC2 monoclonal anti-MUC1* antibody, wherein the antibody binds to the PSMGFR peptide. FIG. 55D shows the array stained with the 45C11 monoclonal anti-MUC1* antibody, wherein the antibody binds to the PSMGFR N+20/C-27 peptide. These results are consistent with the idea that on most esophageal cancers, MUC1 is cleaved by an enzyme that exposes a cryptic epitope that is N-terminal to the PSMGFR sequence.

FIG. 56A-56F shows photographs and graphical representations of pathologist staining scores of adjacent serial sections from a esophageal cancer array, which was stained by standard IHC methods with either antibodies that recognize full-length MUC1 or an antibody that only recognizes MUC1*. FIG. 56A shows the esophageal cancer array stained with antibody 5E5, which is an antibody that binds to a trapped O-linked glycan in the tandem repeat domain of full-length MUC1. FIG. 56B shows the pathologist's score for each specimen in the array. FIG. 56C shows the esophageal cancer array stained with anti-MUC1* antibody 29H1, which is an antibody that binds to the PSMGFR N+20/C-27 peptide of MUC1*. FIG. 56D shows the pathologist's score for each specimen in the array. FIG. 56E shows the esophageal cancer array stained with antibody VU4H5, which is an antibody that binds to an epitope in the tandem repeat domain of full-length MUC1. FIG. 56F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C-27 peptide recognize epitopes that are prevalent on esophageal cancers.

Figures 57A, 57B, 57C, 57D:
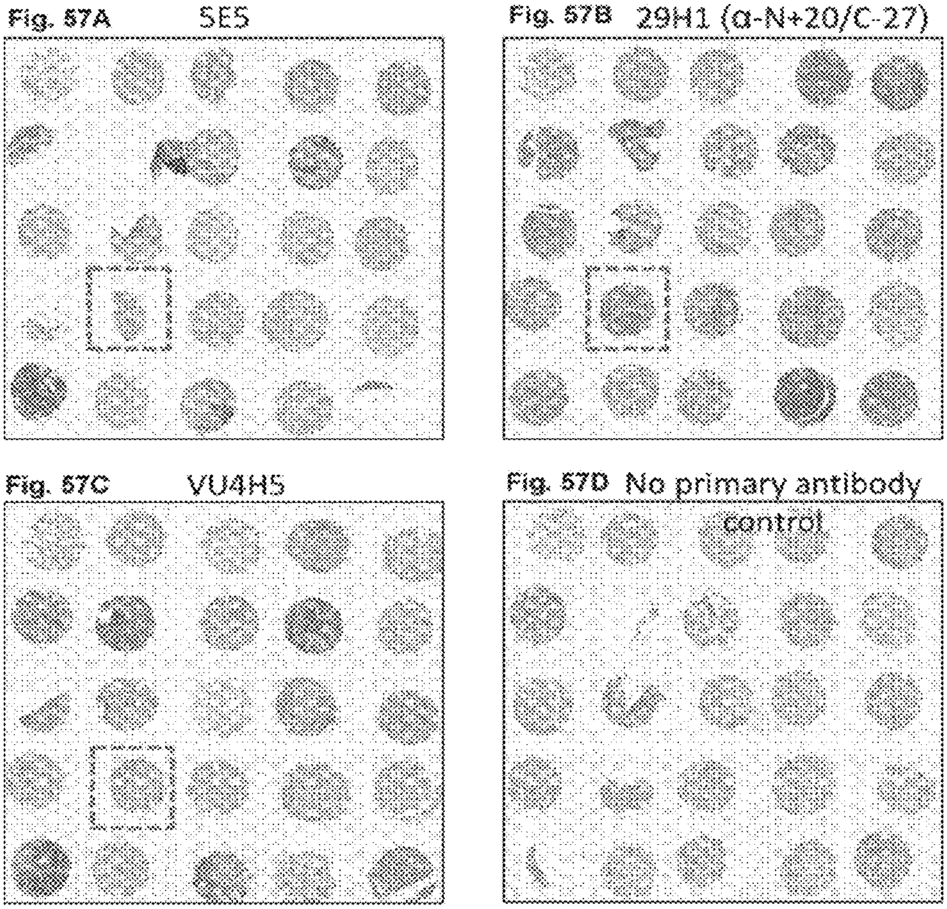

FIG. 57A-57G shows photographs of the prostate cancer array, which was stained with either antibody 5E5 or VU4H5, which both recognize full-length MUC1 or 29H1 that only recognizes MUC1* and binds to the PSMGFR N+20/C-27 peptide. FIG. 57A shows the esophageal cancer array stained with antibody 5E5. FIG. 57B shows the esophageal cancer array stained with antibody 29H1. FIG. 57B shows the esophageal cancer array stained with antibody 29H1. FIG. 57C shows the esophageal cancer array stained with antibody VU4H5. FIG. 57D shows the esophageal cancer array stained with the secondary antibody only, as a control. FIG. 57E shows the tissue marked by red box in FIG. 57A at greater magnification, wherein staining was done with 5E5. FIG. 57F shows the tissue marked by red box in FIG. 57B at greater magnification, wherein staining was done with 29H1. FIG. 57G shows the tissue marked by red box in FIG. 57C at greater magnification, wherein staining was done with VU4H5. The dashed red boxes indicate just one patient's specimen of many esophageal tumor specimens that stain negative for antibodies that recognize full-length MUC1, but highly positive when probed with anti-MUC1* antibodies, and particularly those antibodies that bind to the PSMGFR N+20/C-27 peptide.

Figures 58A, 58B, 58C:
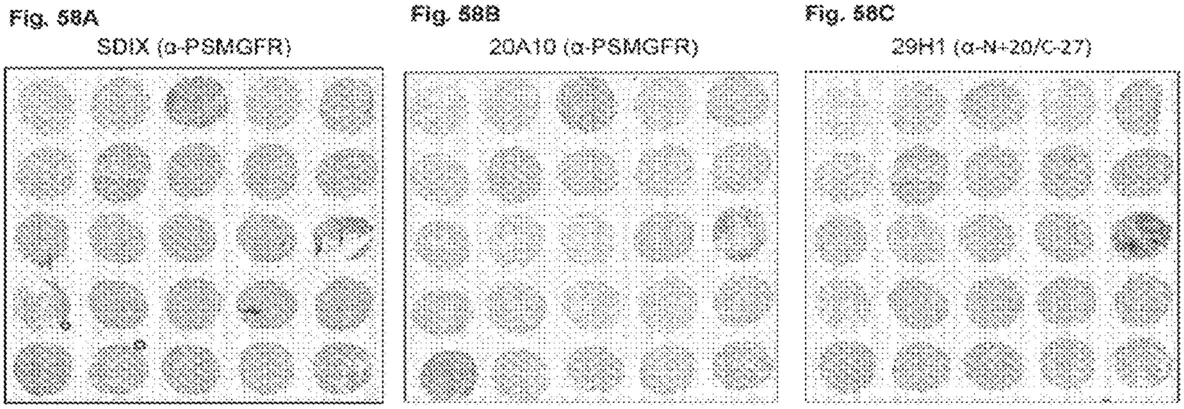
FIG. 58A-58C shows photographs of adjacent serial sections from a prostate cancer array, which was stained by standard IHC methods with various anti-MUC1* antibodies.

FIG. 58A-58C shows photographs of adjacent serial sections from a prostate cancer array, which was stained by standard IHC methods with various anti-MUC1* antibodies. FIG. 58A shows the array stained with the SDIX polyclonal anti-MUC1* antibody, wherein the immunogen for the antibody was the PSMGFR peptide. FIG. 58B shows the array stained with the 18B4 monoclonal anti-MUC1* antibody, wherein the antibody binds to the PSMGFR peptide. FIG. 58C shows the array stained with the 1E4 monoclonal anti-MUC1* antibody, wherein the antibody binds to the PSMGFR N+20/C-27 peptide.

Figures 59A, 59B, 59C, 59D, 59E:
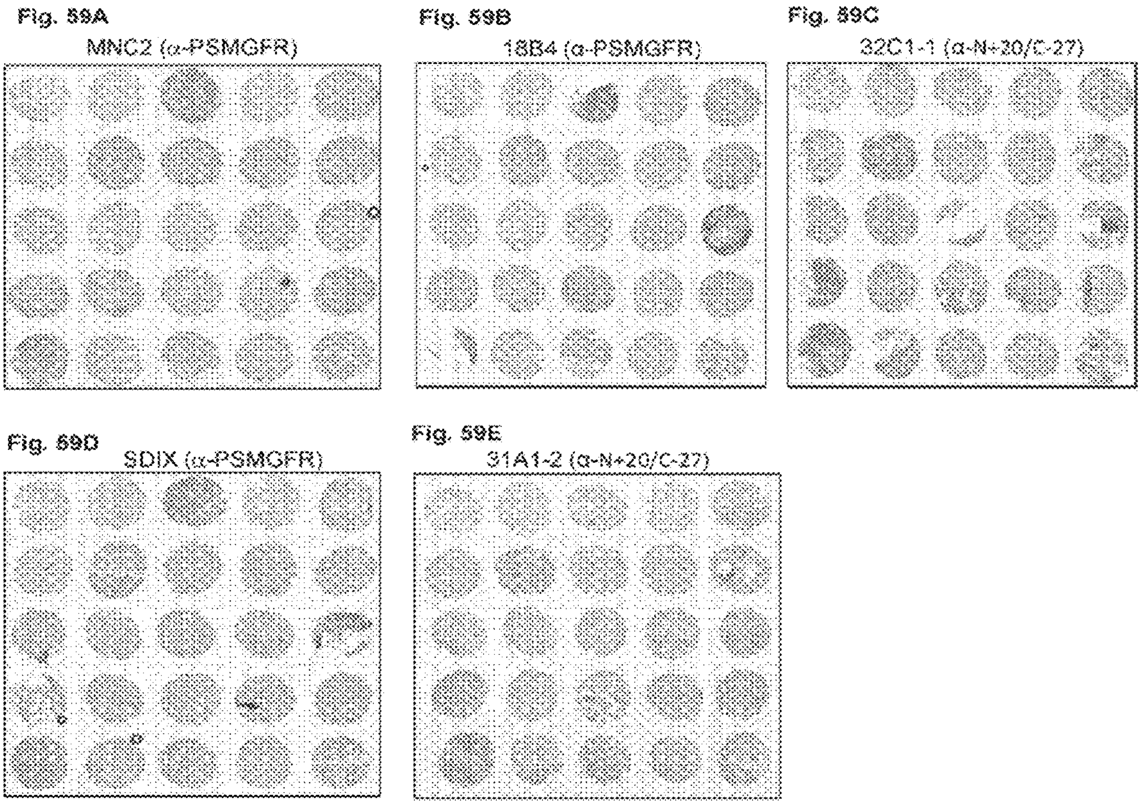
FIG. 59A-59E shows photographs of adjacent serial sections from a prostate cancer array, which was stained by standard IHC methods with various anti-MUC1* antibodies.

FIG. 59A-59E shows photographs of adjacent serial sections from a prostate cancer array, which was stained by standard IHC methods with various anti-MUC1* antibodies. FIG. 59A shows the array stained with the MNC2 monoclonal antibody that binds to the PSMGFR peptide but not the C-10 peptide. FIG. 59B shows the array stained with the 18B4 antibody that binds to the PSMGFR peptide. FIG. 59C shows the array stained with the 32C1 antibody that binds to the PSMGFR N+20/C-27 peptide. FIG. 59D shows the array stained with the SDIX polyclonal anti-MUC1* antibody, wherein the immunogen for the antibody was the PSMGFR peptide. FIG. 59E shows the array stained with the 31A1 monoclonal anti-MUC1* antibody that binds to the PSMGFR N+20/C-27 peptide.

FIG. 60A-60F shows photographs and graphical representations of pathologist staining scores of adjacent serial sections from a prostate cancer array, which was stained by standard IHC methods with either antibodies that recognize full-length MUC1 or an antibody that only recognizes MUC1*. FIG. 60A shows the prostate cancer array stained with antibody 5E5, which is an antibody that binds to a trapped O-linked glycan in the tandem repeat domain of full-length MUC1. FIG. 60B shows the pathologist's score for each specimen in the array. FIG. 60C shows the prostate cancer array stained with anti-MUC1* antibody 29H1, which is an antibody that binds to the PSMGFR N+20/C-27 peptide of MUC1*. FIG. 60D shows the pathologist's score for each specimen in the array. FIG. 60E shows the prostate cancer array stained with antibody VU4H5, which is an antibody that binds to an epitope in the tandem repeat domain of full-length MUC1. FIG. 60F shows the pathologist's score for each specimen in the array. As can be seen if the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1, and that the antibodies that bind to the PSMGFR N+20/C-27 peptide recognize epitopes that are prevalent on prostate cancers.

Figures 61A, 61B, 61C, 61D:
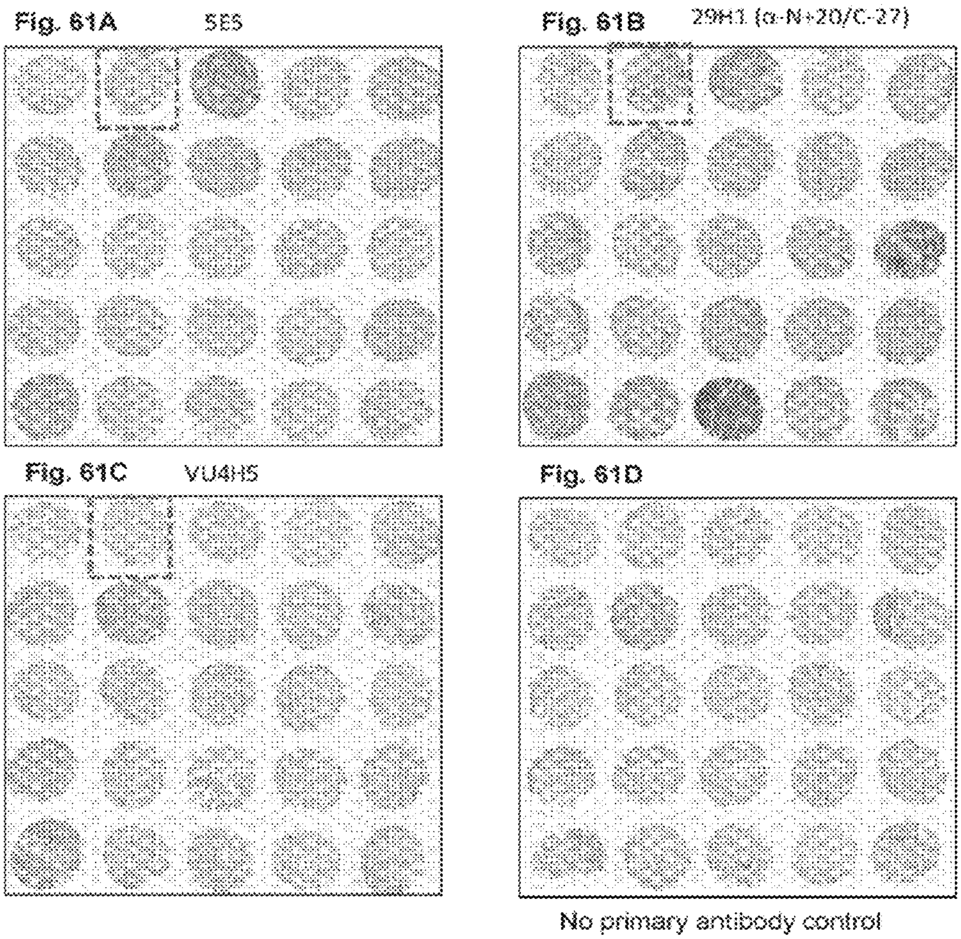

FIG. 61A-61G shows photographs of the prostate cancer array, which was stained with either antibody 5E5 or VU4H5, which both recognize full-length MUC1 or 29H1 that only recognizes MUC1* and binds to the PSMGFR N+20/C-27 peptide. FIG. 61A shows the prostate cancer array stained with antibody 5E5. FIG. 61B shows the prostate cancer array stained with antibody 29H1. FIG. 61B shows the prostate cancer array stained with antibody 29H1. FIG. 61C shows the prostate cancer array stained with antibody VU4H5. FIG. 61D shows the prostate cancer array stained with the secondary antibody only, as a control. FIG. 61E shows the tissue marked by red box in FIG. 61A at greater magnification, wherein staining was done with 5E5. FIG. 61F shows the tissue marked by red box in FIG. 61B at greater magnification, wherein staining was done with 29H1. FIG. 61G shows the tissue marked by red box in FIG. 61C at greater magnification, wherein staining was done with VU4H5. The dashed red boxes indicate just one patient's specimen of many prostate tumor specimens that stain negative for antibodies that recognize full-length MUC1, but highly positive when probed with anti-MUC1* antibodies, and particularly those antibodies that bind to the PSMGFR N+20/C-27 peptide.

MNC2 recognizes a MUC1* that is present in large percentages of breast cancers. However, tumor heterogeneity and the potential of tumor escape by proliferating a population of cells in which MUC1*, the growth factor receptor, is cleaved by a different cleavage enzyme, and thereby recognized by a different anti-MUC1* antibody, suggests that treatment with more than one anti-MUC1* antibody would be beneficial. To this end, we compared more closely the recognition of new anti-MUC1* antibodies to MNC2 (FIG. 62-FIG. 73).

Figure 62A:
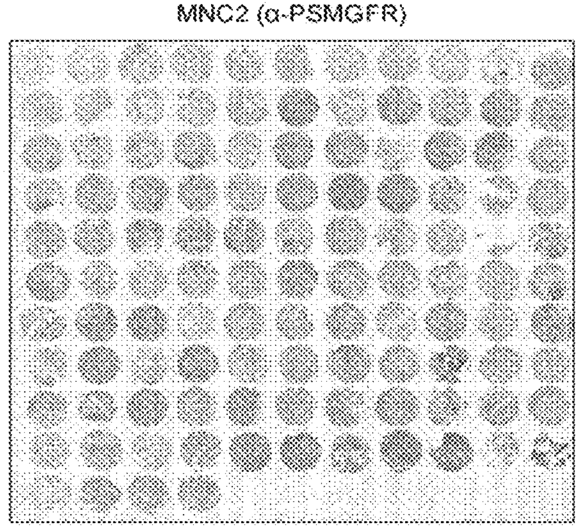
FIG. 62A-62B shows photographs of adjacent serial sections of breast cancer array BR1141 that were stained with two different anti-MUC1* monoclonal antibodies.
Figure 62B:
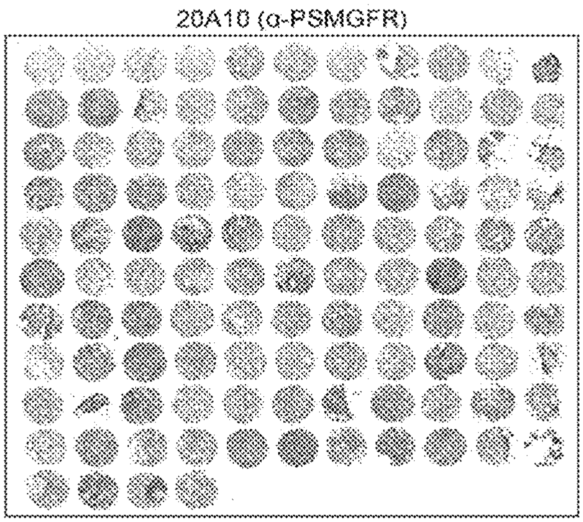
Figure 64A:
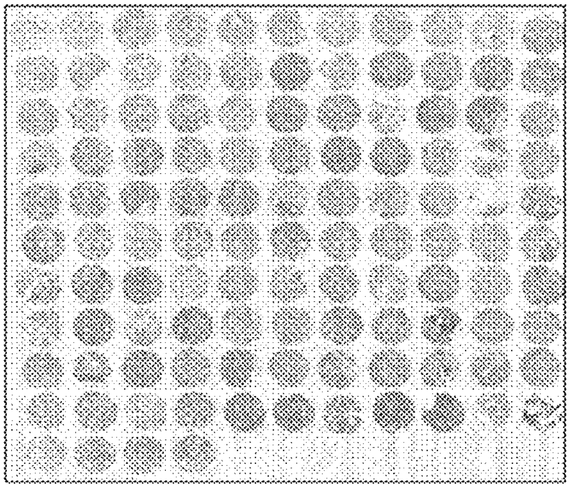
FIG. 64A-64B shows photographs of adjacent serial sections of breast cancer array BR1141 that were stained with two different anti-MUC1* monoclonal antibodies.
Figure 64B:
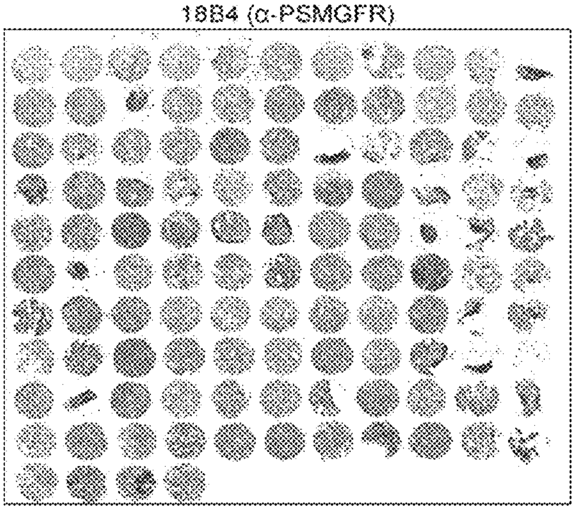
Figure 65A:
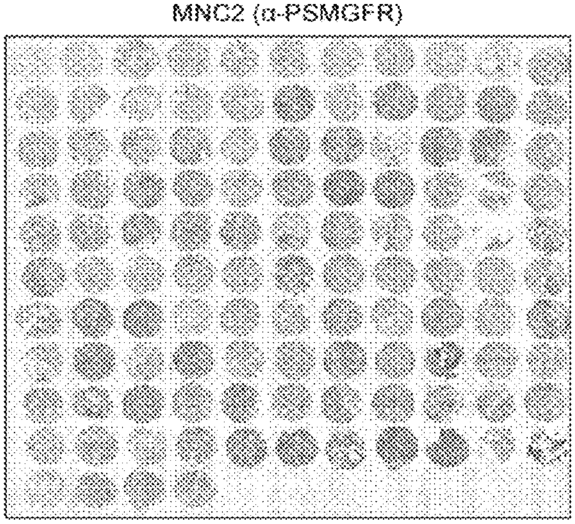
FIG. 65A-65B shows photographs of adjacent serial sections of breast cancer array BR1141 that were stained with two different anti-MUC1* monoclonal antibodies.
Figure 65B:
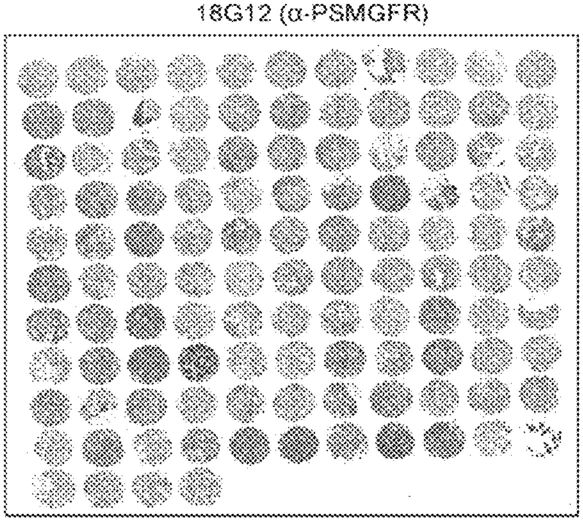
Figure 66A:
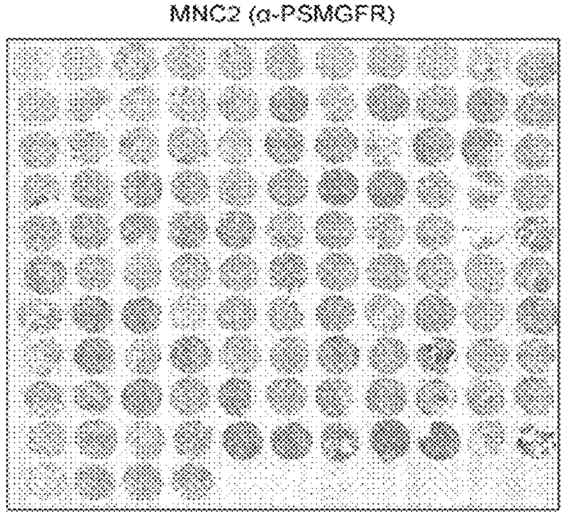
FIG. 66A-66B shows photographs of adjacent serial sections of breast cancer array BR1141 that were stained with two different anti-MUC1* monoclonal antibodies.
Figure 66B:
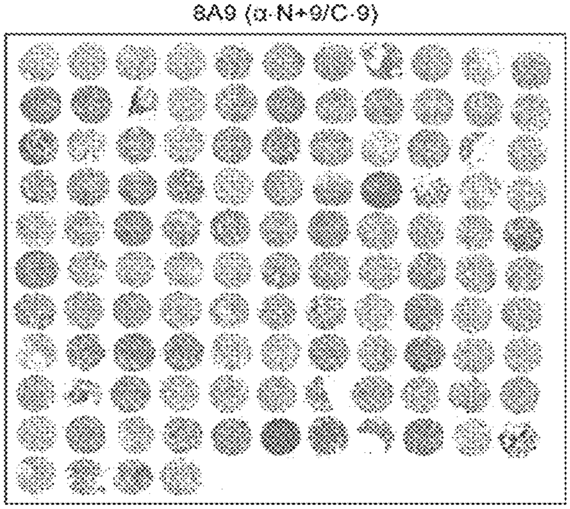
Figure 70A:
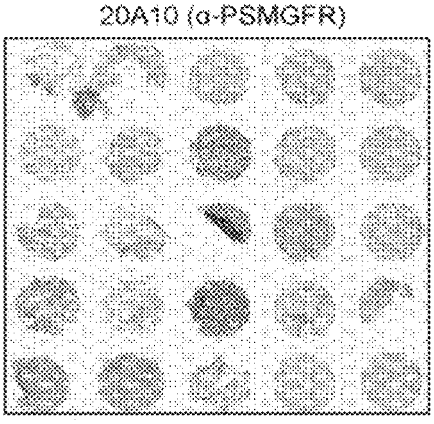
FIG. 70A-70G shows photographs of adjacent serial sections of breast cancer array BR1007 that were stained with four different anti-MUC1* monoclonal antibodies.
Figure 70B:
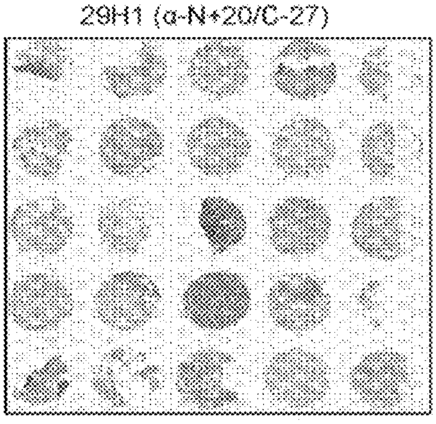
Figure 70C:
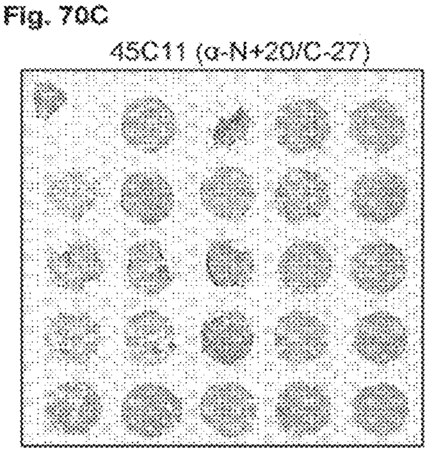
Figure 70D:
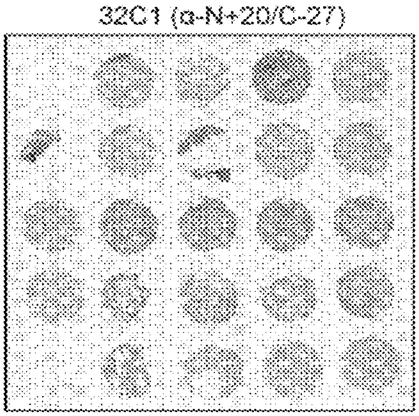
Figure 70E:
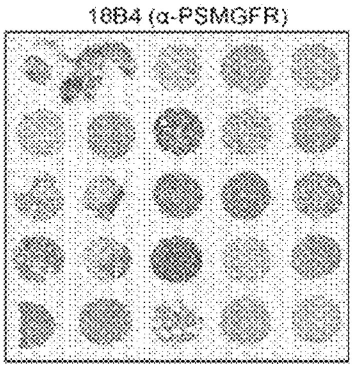
Figure 70F:
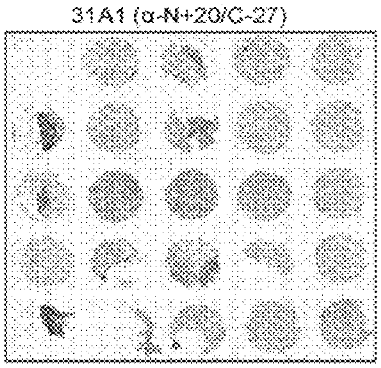
Figure 70G:
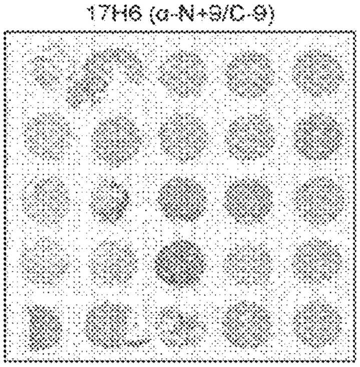
Figures 72A, 72B, 72C, 72D, 72E, 72F:
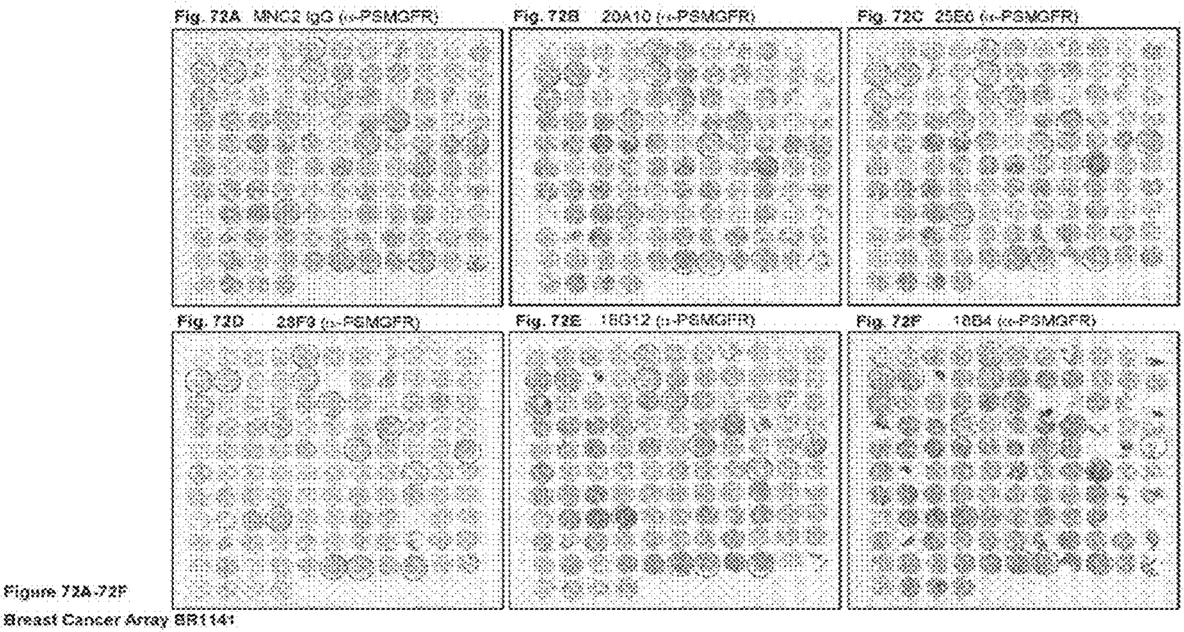
FIG. 72A-72F shows photographs of adjacent serial sections of breast cancer tissue array BR1141 that have been stained with various anti-MUC1* monoclonal antibodies, wherein all antibodies bind to the PSMGFR peptide.

Breast cancer array BR1141 was stained with either MNC2 or 20A10, which both bind to PSMGFR peptide, N-10 peptide, but not the C-10 peptide. To a first order approximation, the two antibodies recognize the same or a very close epitope of a MUC1* that is expressed in breast cancers (FIG. 62A-62B). FIG. 63A-65B shows the same breast cancer array but MNC2 compared to 25E6, 18B4 and 18G12. Recall that unlike MNC2, this set of new anti-PSMGFR antibodies are able to bind to the C-10 peptide (FIG. 41). As can be seen in the figure, there are differences between the binding of MNC2 and these new anti-PSMGFR antibodies. Differences in recognition of breast cancer populations between patients, as well as within the same tumor, are more pronounced when MNC2 is compared to anti-PSMGFR N+9/C-9 antibody 8A9 (FIG. 66A-66B) and anti-PSMGFR antibody 28F9 (FIG. 67A-67B). Referring to FIG. 41, antibody 28F9 showed the highest degree of binding to the C-10 peptide whereas MNC2 does not bind the C-10 peptide, arguing that these antibodies bind to very different epitopes on the truncated extra cellular domain of MUC1*. Differences between the binding of anti-PSMGFR N+9/C-9 antibody 3C5 and MNC2 are clearly visible in FIG. 69A-69B. Differences in breast cancer recognition between anti-PSMGFR antibodies 20A10 and 18B4 and other antibodies that bind to peptide PSMGFR N+20/C-27, such as 29H1, 45C11 and 32C1, 31A1 or antibodies that bind to the PSMGFR N+9/C-9 peptide, such as 17H6 are shown in FIG. 70A-70G.

A smaller breast cancer array, BR1007, was probed with anti-MUC1* antibody 29H1 and compared to the recognition of the same array when probed with anti-full-length-MUC1 antibodies 5E5 and VU4H5 (FIG. 71A-71F). As can be seen in the figure, antibody 5E5 recognizes some specimens that VU4H5 does not recognize, however, anti-MUC1* antibody 29H1 recognizes specimens recognized by both antibodies that recognize full-length MUC1 plus other specimens that are not recognized by either anti-MUC1 antibody. These findings show that anti-MUC1* antibodies that bind to peptides that include amino acids that are N-terminally extended beyond PSMGFR sequence are not recognizing full-length MUC1.

Figure 39:
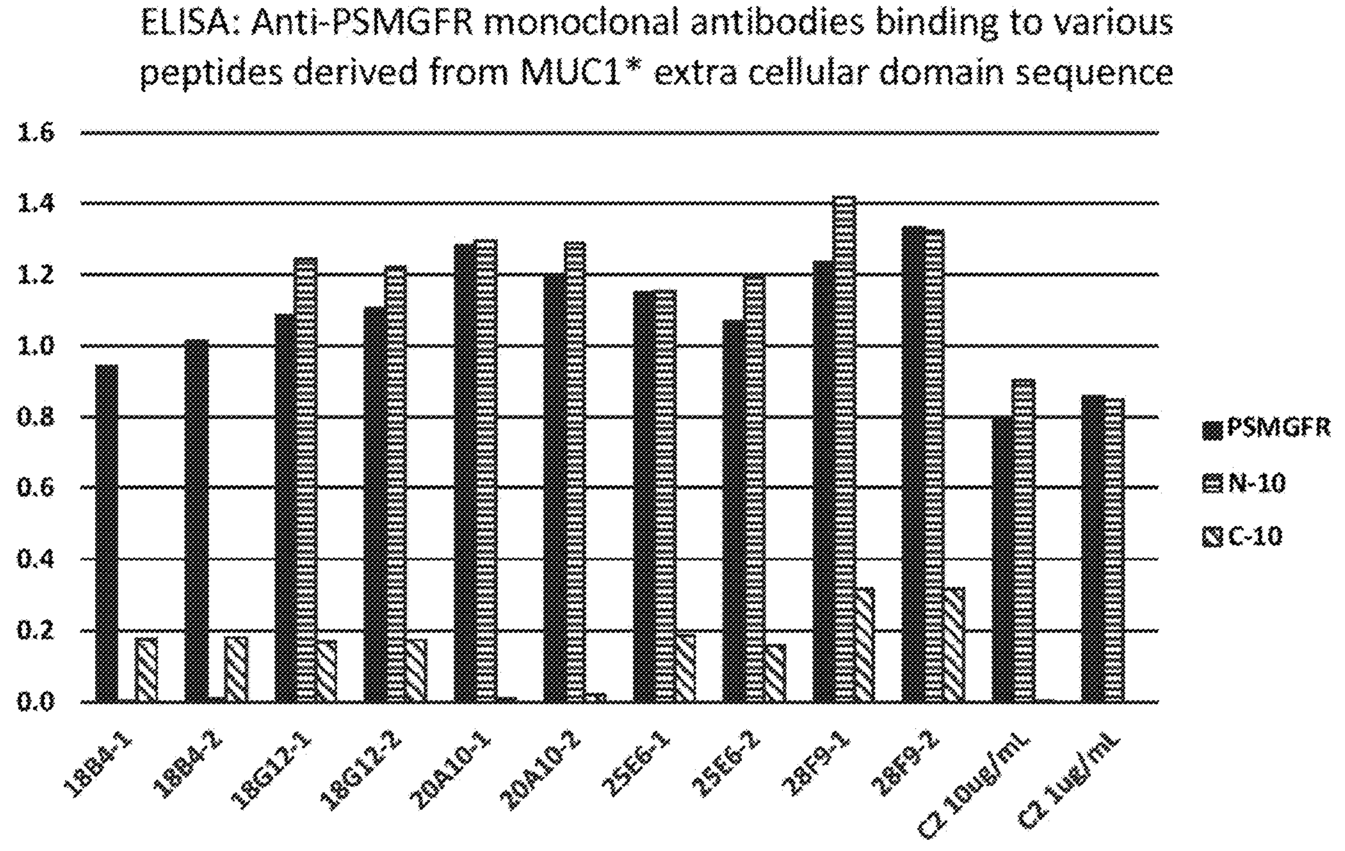
FIG. 39 shows a graph of an ELISA experiment testing the ability of monoclonal antibodies, generated by immunizing with the PSMGFR peptide, to bind to other peptides derived from the sequence of the MUC1* extra cellular domain. All monoclonal antibodies were first selected based on their ability to bind to the immunizing peptide. To further elucidate the epitope within that peptide to which the antibody binds, antibodies were tested for their ability to bind to the PSMGFR peptide, the N-10 peptide or the C-10 peptide.
Figures 40A, 40B:
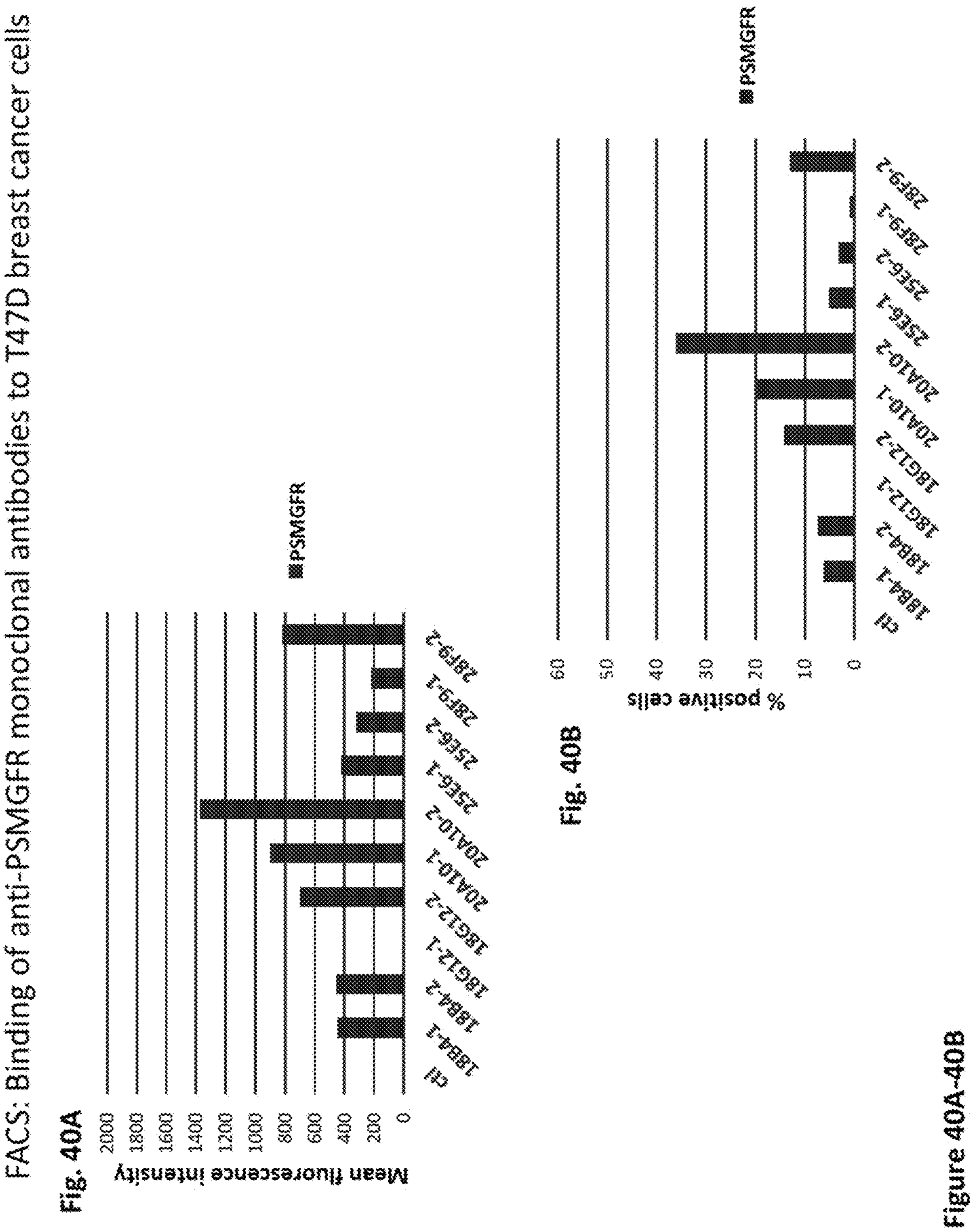
FIG. 40A-40B shows graphs of FACS analysis of the new PSMGFR anti-MUC1* monoclonal antibodies binding to T47D breast cancer cells.
Figures 42A, 42B:
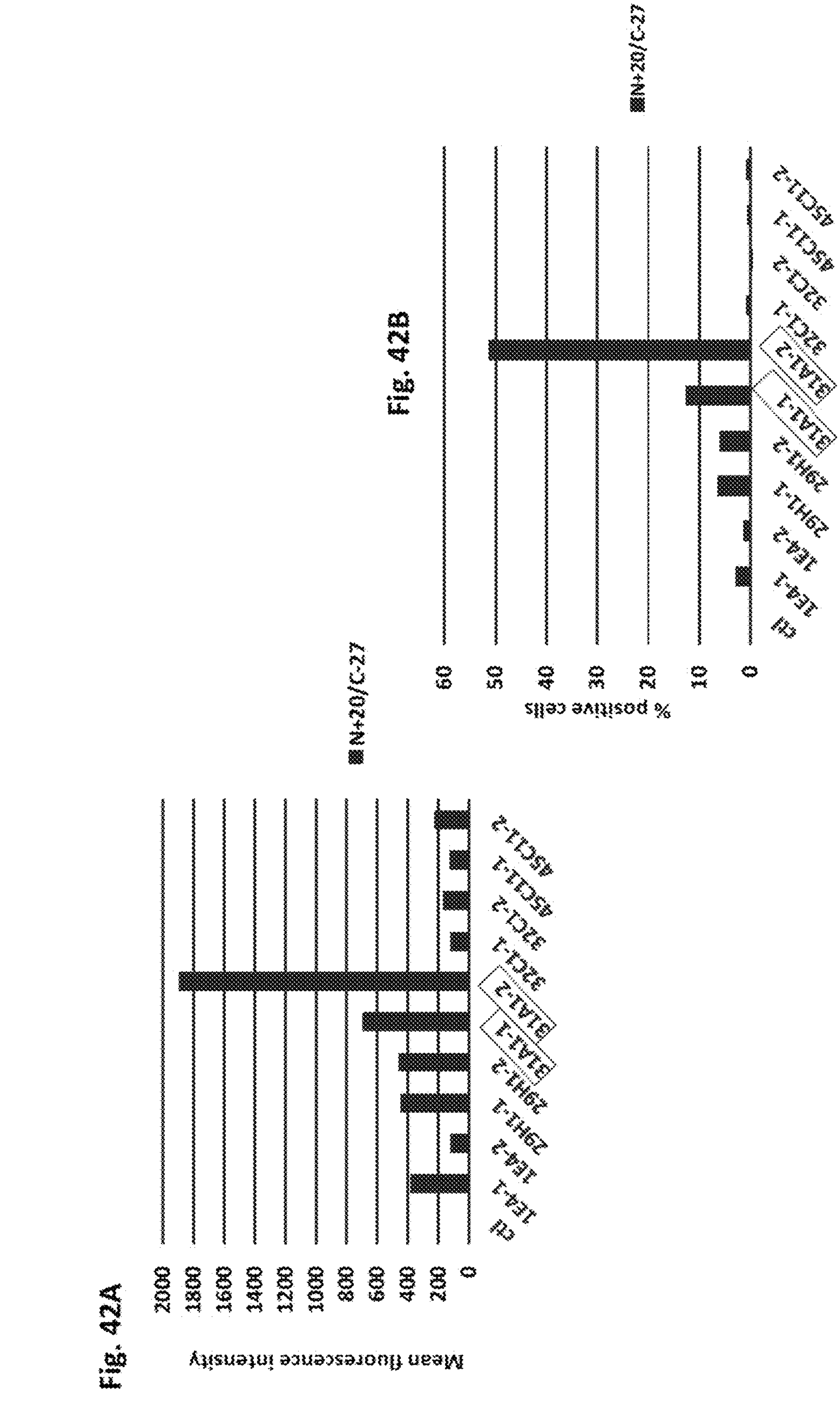
FIG. 42A-42B shows graphs of FACS analysis of the new PSMGFR N+20/C-27 anti-MUC1* monoclonal antibodies binding to T47D breast cancer cells.

In FIG. 72A-72F, the binding of MNC2 to breast cancer array BR1141 was compared to a panel of anti-PSMGFR antibodies. All these antibodies bind to the PSMGFR peptide and roughly produce the same staining pattern of this breast cancer array. However, there are some differences in how these antibodies recognize individual specimens within the array, which could represent MUC1 to MUC1* cleavage by different enzymes. Referring to FIG. 39, MNC2 and 20A10 bind to the N-10 peptide but not to the C-10 peptide, indicating the 10 membrane proximal amino acids are important for their binding. Antibodies 18B4, 18G12 and 25E6 show some binding to the C-10 peptide and 28F9 shows even more binding to C-10 peptide. Notably, 18B4 does not bind to the N-10 peptide, indicating that it binds to an epitope that is more N-terminal within PSMGFR than the others. Albeit with the previously mentioned exceptions, the recognition of tumors within this array by anti-PSMGFR antibodies was very similar.

Figures 73A, 73B, 73C, 73D, 73E, 73F:
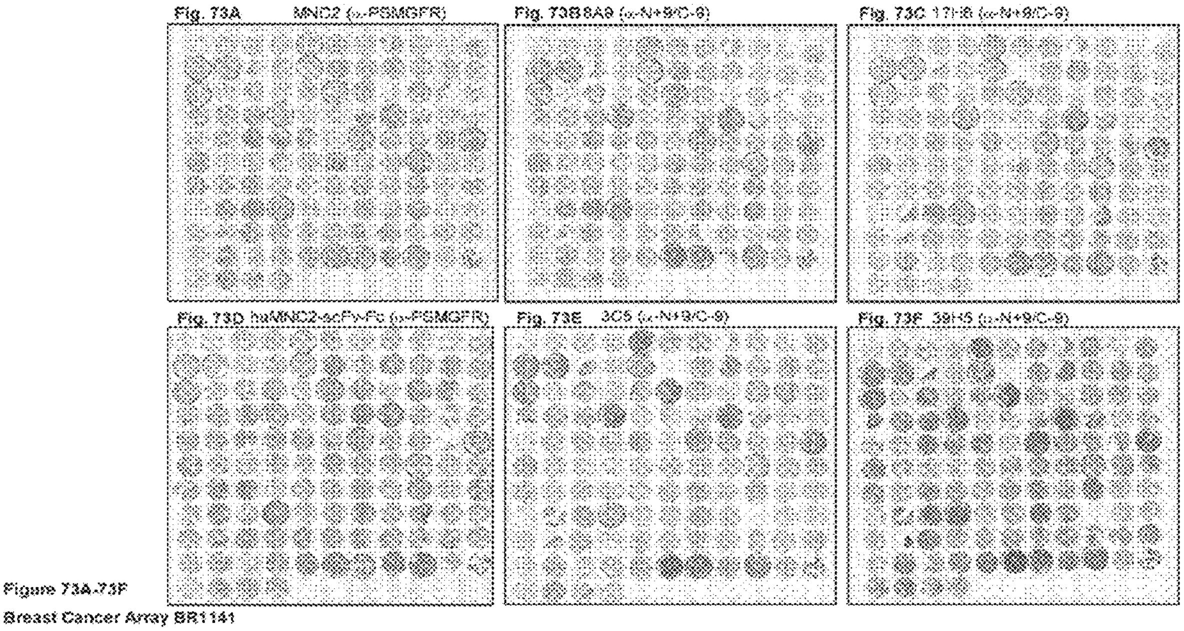
FIG. 73A-73F shows photographs of adjacent serial sections of breast cancer tissue array BR1141 that have been stained with various anti-MUC1* monoclonal antibodies, wherein antibodies that bind to the PSMGFR N+9/C-9 peptide are compared to MNC2 and its humanized single chain form, huMNC2-scFv-Fc, which both bind to PSMGFR, N-10 but not to C-10 peptides.

In contrast, antibodies that bind to the PSMGFR N+9/C-9 peptide robustly recognized a subset of tumors that was either not recognized by MNC2 or weakly recognized by MNC2 and other anti-PSMGFR antibodies (FIG. 73A-73F). The photographs shown are of adjacent serial sections of breast cancer tissue array BR1141 that have been stained with various anti-MUC1* monoclonal antibodies, wherein antibodies that bind to the PSMGFR N+9/C-9 peptide are compared to MNC2 and its humanized single chain form, huMNC2-scFv-Fc, which both bind to PSMGFR, N-10 but not to C-10 peptides. FIG. 73A shows breast cancer specimen that was stained with MNC2. FIG. 73B shows breast cancer specimen that was stained with 8A9. FIG. 73C shows breast cancer specimen that was stained with 17H6. FIG. 73D shows breast cancer specimen that was stained with huMNC2-scFv-Fc. FIG. 73E shows breast cancer specimen that was stained with 3C5. FIG. 73F shows breast cancer specimen that was stained with 39H5. Referring now to the patient specimens that are marked by red circles, it is plain to see that antibodies that bind to the PSMGFR N+9/C-9 peptide recognize a population of breast cancer cells that MNC2 anti-PSMGFR antibodies miss or bind weakly to. Anti-MUC1* antibodies 8A9, 17H6, 3C5, and 39H5 recognize a unique subset of cancer cells that are either not recognized or recognized to a lesser degree by anti-PSMGFR antibodies such as MNC2, 20A10, 25E6, 28F9, 18G12, or 18B4.

Collectively, these data show that: (i) diagnosis of MUC1 positive cancers, even within a cancer sub-type such as breast cancers, is more accurate when a tumor is probed with an anti-MUC1* antibody rather than an antibody that binds to full-length MUC1; (ii) diagnosis of MUC1 positive cancers, even within a cancer sub-type such as breast cancers, is more accurate when a tumor is probed with more than one anti-MUC1*; (iii) diagnosis of MUC1 positive cancers, even within a cancer sub-type such as breast cancers, is even more accurate when a tumor is probed with more than one anti-MUC1*, wherein the at least two different antibodies are chosen from among two different groups, wherein the groups are antibodies that bind to the PSMGFR peptide, antibodies that bind to the PSMGFR N+20/C-27 peptide, and antibodies that bind to the PSMGFR N+9/C-9 peptide.

Anti-MUC1* antibodies of the invention, which can be used for use in the diagnosis of cancers, include antibodies that bind to the PSMGFR peptide, the PSMGFR N+20/C-27 peptide, the PSMGFR N+9/C-9 peptide, or more specifically antibodies that bind to a peptide having at least 15 contiguous amino acids of the sequences below, with up to four amino acids substitutions;

(i) PSMGFR region of MUC1;

(ii) PSMGFR peptide as set forth in SEQ ID NO:4;

(iii) PSMGFR N+20/C-22, a peptide having amino acid sequence of SNIKFRPGSVVVQLTLAFREGTINVHDVETQFNQYKTEAASRY (SEQ ID NO:5);

(iv) PSMGFR N+12/C-22, a peptide having amino acid sequence of SVVVQLTLAFREGTINVHDVETQFNQYKTEAASRY (SEQ ID NO:6);

(v) PSMGFR N+9/C-30, a peptide having amino acid sequence of VQLTLAFREGTINVHDVETQFNQY (SEQ ID NO:7);

(vi) PSMGFR N+20/C-41, a peptide having amino acid sequence of SNIKFRPGSVVVQLTLAFREGTIN (SEQ ID NO:8)

(vii) PSMGFR N+20/C-27, a peptide having amino acid sequence of SNIKFRPGSVVVQLTLAFREGTINVHDVETQFNQYKTE (SEQ ID NO:9); or (viii) PSMGFR N+9/C-9, a peptide having amino acid sequence of VQLTLAFREGTINVHDVETQFNQYKTEAASRYNLTISDVSVSDVP (SEQ ID NO:10). Specifically anti-PSMGFR antibodies MNC2, MNE6, 18B4, 18G12, 20A10, 25E6, anti-PSMGFR N+20/C-27 antibodies 1E4, 29H1, 31A1, 32C1, 45C11, and anti-PSMGFR N+9/C-9 antibodies 3C5, 8A9, 17H6, and 39H5 are antibodies that can be used to diagnose cancers. These antibodies may be human, humanized or non-human. They may be antibody intact antibodies or antibody fragments. Antibodies may be generated by immunizing animals with peptides of sequences (i)-(viii) above. The animal that is immunized with the MUC1* extra cellular domain peptides to produce the antibodies may be human, rabbit, mouse, goat, donkey, camelid, llama, alpaca or other non-human species.

An antibody of the invention can be used in a diagnostic assay wherein it may be derivatized with, or attached to an imaging agent, a dye, a fluorescent entity, a color producing reagent or any other entity that renders the antibody optically, visually, electrically or radioactively detectable. Antibodies of the invention can be used in a variety of diagnostic formats.

In another example, anti-MUC1* antibodies of the invention can be attached to an imaging agent for use in a live patient as a whole body diagnostic to determine if the patient has a MUC1* positive tumor or to determine if the patient would benefit from a therapeutic comprising all, or a fragment of, an anti-MUC1* antibody, which may be derived from or have similar binding characteristics as the antibody used in the diagnostic. The species of the diagnostic antibody and the therapeutic antibody do not need to be the same. Antibodies generated in camelid species are particularly useful for in vivo diagnostic assays because camelids generate small monovalent antibodies that have a short half-life in humans.

In yet another example, anti-MUC1* antibodies of the invention may be attached to an imaging agent and used intra-surgically to detect or mark cancerous tissues so they can be excised completely during the surgery.

In one aspect of the invention, a bodily fluid or tissue specimen from a patient diagnosed with cancer or suspected to be at risk of cancer is contacted with one or more anti-MUC1* antibodies of the invention; analysis of the binding of the antibody to the cells of the specimen indicate a level of binding or a pattern of binding that is indicative of cancer. A therapeutic agent for the treatment of cancer is then administered to the patient. In one aspect of the invention the therapeutic agent comprises all or a fragment of an anti-MUC1* antibody.

In one example, diagnostic assays employing anti-MUC1* antibodies or fragments thereof are used to screen patients to determine their potential benefit from a MUC1* targeting therapeutic. The anti-MUC1* antibody used in the diagnostic and the antibody or fragment thereof that is incorporated into the therapeutic may be derived from the same antibody. The species of the diagnostic antibody and the therapeutic antibody do not need to be the same. Diagnostic assays may encompass use of one or more anti-MUC1* antibodies. A patient specimen that reacts with one or more anti-MUC1* antibodies indicates that the patient may benefit from administration of therapeutics that contain the one or more reactive antibodies, or fragments thereof.

One example, includes the steps of: (i) a suspect cellular or tissue specimen, which may be a biopsy, from a patient diagnosed with cancer or suspected of developing cancer is contacted with an anti-MUC1* antibody; (ii) a normal cellular or tissue specimen from the patient or from a healthy donor is contacted with the same anti-MUC1* antibody, which may be an archived reference specimen; (iii) antibody binding is detected; (iv) the extent and pattern of antibody binding to the suspect specimen is compared to that of the normal specimen; (v) a determination that the suspect specimen overexpresses MUC1*, or expresses MUC1* in a uniform pattern as opposed to expression that is restricted to the apical border, indicates that the patient is suffering from a MUC1* positive cancer; (vi) a therapeutic agent for the treatment of cancer is then administered to the patient, which may be a therapeutic agent that incorporates an anti-MUC1* antibody, or fragment thereof.

In one aspect of the invention, a bodily fluid or tissue specimen from a patient diagnosed with or suspected of having cancer is contacted with an anti-MUC1* antibody of the invention and a higher than normal level of MUC1* is detected or an abnormal pattern of MUC1* is detected, indicating that the patient has a MUC1* positive cancer and a therapeutic agent is then administered to the patient, which incorporates an anti-MUC1* antibody or antibody fragment. In one case the therapeutic agent into which the antibody or antibody fragment is incorporated is an immuno-oncology agent, such as a CAR T cell, an engineered NK cell or a dendritic cell. In another case, the therapeutic agent into which the antibody or antibody fragment is incorporated is a huMNC2-CAR44 T cell. In yet another aspect of the invention the therapeutic agent into which the antibody or antibody fragment is incorporated is a bispecific antibody. In yet another aspect of the invention the therapeutic agent into which the antibody or antibody fragment is incorporated is an antibody drug conjugate (ADC). In yet another aspect of the invention the therapeutic agent into which the antibody or antibody fragment is incorporated is a bispecific T cell engager (BiTE).

In another example, the diagnostic assay may comprise an anti-MUC1* antibody and a second antibody, and the steps may comprise determining the ratio of the amount of a first antibody to a second antibody. The first antibody may bind to MUC1* extra cellular domain and the second antibody may bind to a portion of the MUC1 extra cellular domain that is N-terminal of the cleavage site, such as the tandem repeat sequences. In the case of contacting a tissue specimen, the higher the ratio of MUC1* to full-length MUC1, the more progressed is the cancer and the more likely it is that the patient would benefit from a MUC1* targeting therapeutic.

The invention includes antibodies as well as antibody-like proteins, including but not limited to polyclonal, monoclonal, chimeras, humanized, single chain, antibody fragments and the like. In addition, the invention includes the use of protein scaffolds for generating antibody mimics to obtain proteins that can be characterized by binding assays described herein and The invention further includes using methods set forth here to identify antibodies that recognize specific epitopes, within the MUC1* extra cellular domain, that are differentially expressed on cancer cells.

In one aspect, the present invention is directed to a human or humanized anti-MUC1* antibody or antibody fragment or antibody-like protein that binds to a region on extracellular domain of MUC1 isoform or cleavage product that is devoid of the tandem repeat domains. The human or humanized anti-MUC1* antibody or antibody fragment or antibody-like protein may specifically bind to (i) PSMGFR region of MUC1;

(ii) PSMGFR peptide as set forth in SEQ ID NO:4;

(iii) PSMGFR N+20/C-22, a peptide having amino acid sequence of SNIKFRPGSVVVQLTLAFREGT-INVHDVETQFNQYKTEAASRY (SEQ ID NO:5);

(iv) PSMGFR N+12/C-22, a peptide having amino acid sequence of SVVVQLTLAFREGTINVHD-VETQFNQYKTEAASRY (SEQ ID NO:6);

(v) PSMGFR N+9/C-30, a peptide having amino acid sequence of VQLTLAFREGTINVHDVETQFNQY (SEQ ID NO:7);

(vi) PSMGFR N+20/C-41, a peptide having amino acid sequence of SNIKFRPGSVVVQLTLAFREGTIN (SEQ ID NO:8)

(vii) PSMGFR N+20/C-27, a peptide having amino acid sequence of SNIKFRPGSVVVQLTLAFREGT-INVHDVETQFNQYKTE (SEQ ID NO:9); or (viii) PSMGFR N+9/C-9, a peptide having amino acid sequence of VQLTLAFREGTINVHDVETQFNQYK-TEAASRYNLTISDVSVSDVP (SEQ ID NO:10).

The human or humanized antibody may be IgG1, IgG2, IgG3, IgG4 or IgM. The human or humanized antibody fragment or antibody-like protein may be scFv or scFv-Fc.

The human or humanized antibody, antibody fragment or antibody-like protein as in above may comprise a heavy chain variable region and light chain variable region which is derived from mouse monoclonal MN-E6 antibody, and has at least 80%, 90% or 95% or 98% sequence identity to the mouse monoclonal MN-E6 antibody.

The human or humanized antibody, antibody fragment or antibody-like protein according to above may include complementarity determining regions (CDRs) in the heavy chain variable region and light chain variable region having at least 90% or 95% or 98% sequence identity to CDR1, CDR2 or CDR3 regions of the antibodies 1E4, 29H1, 31A1, 32C1, and 45C11 reactive with PSMGFR N+20/C-27; 17H6, 39H5, 3C5, 8A9 reactive with PSMGFR N+9/C-9; 18G12, 20A10, 25E6, 28F9, 18B4, MNC2, and MNE6 reactive with PSMGFR.

In another aspect, the invention is directed to a human or humanized anti-MUC1* antibody or antibody fragment or antibody-like protein according to above, which inhibits the binding of NME protein to MUC1*. The NME may be NME1, NME6, NME7AB, NME7 or NME8.

In still another aspect, the invention is directed to a chimeric antigen receptor (CAR) comprising a scFv or a humanized variable region that binds to the extracellular domain of a MUC1 that is devoid of tandem repeats, a linker molecule, a transmembrane domain and a cytoplasmic domain. The single chain antibody fragment may bind to (i) PSMGFR region of MUC1;

(ii) PSMGFR peptide as set forth in SEQ ID NO:4;

(iii) PSMGFR N+20/C-22, a peptide having amino acid sequence of SNIKFRPGSVVVQLTLAFREGT-INVHDVETQFNQYKTEAASRY (SEQ ID NO:5);

(iv) PSMGFR N+12/C-22, a peptide having amino acid sequence of SVVVQLTLAFREGTINVHD-VETQFNQYKTEAASRY (SEQ ID NO:6);

(v) PSMGFR N+9/C-30, a peptide having amino acid sequence of VQLTLAFREGTINVHDVETQFNQY (SEQ ID NO:7);

(vi) PSMGFR N+20/C-41, a peptide having amino acid sequence of SNIKFRPGSVVVQLTLAFREGTIN (SEQ ID NO:8)

(vii) PSMGFR N+20/C-27, a peptide having amino acid sequence of SNIKFRPGSVVVQLTLAFREGT-INVHDVETQFNQYKTE (SEQ ID NO:9); or (viii) PSMGFR N+9/C-9, a peptide having amino acid sequence of VQLTLAFREGTINVHDVETQFNQYK-TEAASRYNLTISDVSVSDVP (SEQ ID NO:10).

In this regard, a preferred embodiment is huMNC2-CAR44 set forth in SEQ ID NO: 236)

In one aspect, the invention is directed to a method for the treatment of a person diagnosed with, suspected of having or at risk of developing a MUC1 or MUC1* positive cancer involving administering to the person an effective amount of a cancer specific antibody such as MNC2 or MNE6, or fragment thereof, wherein the antibody may be human, humanized or of a non-human species. In a particular aspect of the invention, the MUC1* targeting therapeutic is an immune cell transduced with a chimeric antigen receptor, also known as CAR T, wherein the antibody fragment of the CAR is derived from a MUC1* cancer cell specific antibody. In one aspect it is derived from MNC2. In another case it is derived from MNE6.

In another aspect, the invention is directed to a diagnostic assay for the identification of persons who might benefit from treatment of a MUC1 or MUC1* positive cancer with a therapeutic that includes an antibody, or fragment thereof, selected from the group of 1E4, 29H1, 31A1, 32C1, 45C11, 17H6, 39H5, 3C5, 8A9, 18G12, 20A10, 25E6, 28F9, 18B4, MNC2, and MNE6 antibodies. In one aspect of the invention, the anti-MUC1* antibody or a fragment thereof comprises all or part of the therapeutic and may be derived from the antibody or fragment thereof that is used for the diagnostic, wherein the therapeutic and diagnostic need not be the same species. In another instance, the anti-MUC1* antibody or fragment thereof that comprises all or part of the therapeutic is not derived from the antibody or fragment thereof that is used for the diagnostic, wherein the therapeutic and diagnostic need not be the same species.

In one aspect of the invention, the therapeutic agent targets MUC1*. In another aspect of the invention, the therapeutic that comprises some or all of an anti-MUC1* antibody is a cancer immunotherapy composition, a CAR T, a BiTE, an antibody or an antibody drug conjugate, ADC.

In one aspect of the invention, the diagnostic is a companion diagnostic to determine eligibility for treatment with the therapeutic. In another aspect of the invention, the diagnostic is used to assess efficacy of the therapeutic treatment. In yet another aspect of the invention, the diagnostic together with results of clinical trials of the therapeutic are analyzed such that results of the diagnostic can be used to predict which patients will benefit from the treatment. In another aspect of the invention, the cancer cell antibody or fragment thereof is derivatized with an imaging agent, which composition is then administered to the patient to enable visualization of reactive tumors within the patient. In this way, the antibody plus imaging agent can be used to diagnose cancer, assess response of a therapeutic treatment or assess response to a therapeutic treatment wherein the therapeutic targets MUC1* and may comprise some or all of the cancer cell antibody used in the diagnostic. In one aspect of the invention, the antibody attached to the imaging agent is a camelid antibody, including but not limited to llama, alpaca, and camel.

The diagnostic assays described here can be used on samples that may be tissues, biopsy specimens, cells, or bodily fluids taken from the test subject, patient or a normal person as a control. The diagnostic assays can be performed in vitro or in vivo. The diagnostic assays can be used intraoperatively (e.g. tissue at a surgical site can be studied without removal of the tissue from the subject). In this way, the diagnostic assay guides the surgeon to remove all the MUC1* positive tissues that are detectable, whether or not the tissues appear to be part of the tumor. In either of these studies, a primary indicator of tumorigenesis or potential for tumorigenesis is the amount of MUC1* at a cell or tissue surface that is accessible to anti-PSMGFR antibodies or cancer cell antibodies. By extension, an exposed cancer cell antibody binding epitope means that the PSMGFR region of MUC1* is also accessible to growth factors that bind to and activate growth and survival functions mediated by the MUC1* growth factor receptor. In another technique, antibodies to the MUC1* region and to the tandem repeats, IBR or UR can be exposed to the sample and a determination made of the ratio of binding of MUC1* to MUC1 full-length. A healthy sample will exhibit little or no antibody binding to the MUC1* region. A sample indicating tumorigenesis will show a non-zero ratio of anti-MUC1* antibody to anti-tandem repeat antibody or anti-IBR antibody, wherein as cancer stage/grade increases, the ratio of MUC1* to MUC1 containing tandem repeats, IBR or UR increases.

In addition to detecting an amount of MUC1* or tandem repeat containing MUC1 on cells and tissues, portions of MUC1 that contain tandem repeats, which are shed from the tissues can be detected in bodily fluids such as blood, breast milk or secretions, urine, lung efflux and the like. In these cases, a level of MUC1 cleavage to transmembrane MUC1* is inferred by measuring an amount of shed MUC1 using antibodies, including but not limited to antibodies that bind to the tandem repeats, unique regions that are N-terminal to an IBR or the IBR itself.

Measuring or inferring an amount of MUC1* on cells or tissues, that is greater than normal tissues or a prior sample from the patient, is an indicator of potential for tumor formation, existence of a tumor, or progression of a tumor, and can thereby serve as a diagnostic and/or an evaluator of the efficacy of a treatment for the patient's cancer. In one aspect, an amount of MUC1* is measured by contacting a tissue specimen with an anti-MUC1* antibody and determining that the amount of MUC1* is greater than the amount expressed on normal tissues or in a healthy person.

Sequence Listing Free Text

In the antibody sequences below, underlined sequence refers to CDR sequence and double underlined region refers to framework region.

Full-Length MUC1 Receptor (Mucin 1 Precursor, Genbank Accession Number: P15941

(SEQ ID NO: 1)
MTPGTQSPFF LLLLLTVLTV VTGSGHASST PGGEKETSAT

QRSSVPSSTE KNAVSMTSSV LSSHSPGSGS STTQGQDVTL

APATEPASGS AATWGQDVTS VPVTRPALGS TTPPAHDVTS

APDNKPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

-continued

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDTRPAPGS TAPPAHGVTS

APDTRPAPGS TAPPAHGVTS APDNRPALGS TAPPVHNVTS

ASGSASGSAS TLVHNGTSAR ATTTPASKST PFSIPSHHSD

TPTTLASHST KTDASSTHHS SVPPLTSSNH STSPQLSTGV

SFFFLSFHIS NLQFNSSLED PSTDYYQELQ RDISEMFLQI

YKQGGFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL

A Truncated MUC1 Receptor Isoform Having Nat-PSMGFR and PSIBR at its N-Terminus and Including the Transmembrane and Cytoplasmic Sequences of a Full-Length MUC1 Receptor which May be Cleaved after Translation and Prior to Expression of the Receptor on the Cell Surface:

(SEQ ID NO: 2)
GFLGLS NIKFRPGSVV VQLTLAFREG TINVHDVETQ

FNQYKTEAAS RYNLTISDVS VSDVPFPFSA QSGAGVPGWG

IALLVLVCVL VALAIVYLIA LAVCQCRRKN YGQLDIFPAR

DTYHPMSEYP TYHTHGRYVP PSSTDRSPYE KVSAGNGGSS

LSYTNPAVAA ASANL

A Truncated MUC1 Receptor Isoform Having Nat-PSMGER+PSIBR+Unique Region at its N-Terminus and Including the Transmembrane and Cytoplasmic Sequences of a Full-Length MUC1 Receptor:

(SEQ ID NO: 3)
ATTTPASKSTPFSIPSHHSDTPTTLASHSTKTDASSTHHSTVPPLTSSNH

STSPQLSTGVSFFFLSFHISNLQFNSSLEDPSTDYYQELQRDISEMFLQI

YKQGGFLGLSNIKFRPGSVVVQLTLAFREGTINVHDVETQFNQYKTEAAS

RYNLTISDVSVSDVPFPFSAQSGAGVPGWGIALLVLVCVLVALAIVYLIA

LAVCQCRRKNYGQLDIFPARDTYHPMSEYPTYHTHGRYVPPSSTDRSPYE

KVSAGNGGSSLSYTNPAVAAASANL

PSMGFR (SEQ ID NO: 4)
GTINVHDVETQFNQYKTEAASRYNLTISDVSVSDVPFPFSAQSGA

PSMGFR N+20/C-22

(SEQ ID NO: 5)
SNIKFRPGSVVVQLTLAFREGTINVHDVETQFNQYKTEAASRY

PSMGFR N+12/C-22

(SEQ ID NO: 6)
SVVVQLTLAFREGTINVHDVETQFNQYKTEAASRY

-continued

PSMGFR N+9/C-30

(SEQ ID NO: 7)

VQLTLAFREGTINVHDVETQFNQY

PSMGFR N+20/C-41

(SEQ ID NO: 8)

SNIKFRPGSVVVQLTLAFREGTIN

PSMGFR N+20/C-27

(SEQ ID NO: 9)

SNIKFRPGSVVVQLTLAFREGTINVHDVETQFNQYKTE

PSMGFR N+9/C-9

(SEQ ID NO: 10)

VQLTLAFREGTINVHDVETQFNQYKTEAASRYNLTISDVSVSDVP

Antibody 17H6 Heavy Chain - Signal sequence-FR1-CDR1-FR2-CDR2-FR3-CDR3-FR4

(SEQ ID NO: 11)

ATGAAGTTGTGGCTGAACTGGATTTTCCTTGTAACACTTTTAAATGGTAT

CCAGTGTGAGGTGAAGCTGGTGGAGTCTGGAGGAGGCTTGGTACAGCCTG

GGGGTTCTCTGAGACTCTCCTGTGCAACTTCTGGGTTCACCTTCACTGAT

TACTACATGAGCTGGGTCCGCCAGCCTCCAAGAAAGGCACTTGAGTGGTT

GGGTTTTATTAGAAACAAAGCTAATGGTTACACAGCAGAGTACAGTGCGT

CTGTGAAGGGTCGGTTCACCATCTCCAGAGATGTTTCCCAAAACCTCCTC

TATCTTCAAATGAACATCCTGAGAGCTGAGGACAGTGCCACTTATTACTG

TGCAAAAGATTACTACGGTAGTAACCCTGCCTGGTTTGCTTACTGGGGCC

AAGGGACTCTGGTCACTGTCTCTGCA

Antibody 17H6 Heavy Chain - Signal peptide-FR1-CDR1-FR2-CDR2-FR3-CDR3-FR4

(SEQ ID NO: 12)

MKLWLNWIFLVTLLNGIQCEVKLVESGGGLVQPGGSLRLSCATSGFTFTD

YYMSWVRQPPRKALEWLGFIRNKANGYTAEYSASVKGRFTISRDVSQNLL

YLQMNILRAEDSATYYCAKDYYGSNPAWFAYWGQGTLVTVSA

Antibody 17H6 Light Chain - Signal sequence-FR1-CDR1-FR2-CDR2-FR3-CDR3-FR4

(SEQ ID NO: 13)

ATGAAGTTGCCTGTGAGGCTGTTGGTGCTGATGTTCTGGATTCCTGCTTC

CAACAGTGATATTTTGATGACCCAGACTCCACTCTCCCTGCCTGTCAGTC

TTGGAGATCAAGCCTCCATCTCTTGCAGATCTAGTCAGAGCATTGTACAT

AGTAGTGGAAACACCTTTTTAGAATGGTACCTGCAGAAACCTGGCCAGTC

TCCAAAGCTCCTGATCTACAAAGTTTCCAACCGATTTTCTGGGGTCCCAG

ACAGGTTCAGTGGCAGTGGATCAGGGATAGATTTCACACTCAAGATCAGC

AGAGTGGAGGCTGAGGATCTGGGAGTTTATTACTGCTTTCAAGGTTCACA

TGTTCCTTTCACGTTCGGCTCGGGGACAAAGTTGGAAATAAAA

Antibody 17H6 Light Chain - Signal peptide-FR1-CDR1-FR2-CDR2-FR3-CDR3-FR4

(SEQ ID NO: 14)

MKLPVRLLVLMFWIPASNSDILMTQTPLSLPVSLGDQASISCRSSQSIVH

SSGNTFLEWYLQKPGQSPKLLIYKVSNRFSGVPDRFSGSGSGIDFTLKIS

RVEAEDLGVYYCFQGSHVPFTFGSGTKLEIK

Antibody 17H6 Heavy Chain CDR1

(SEQ ID NO: 15)

GATTACTACATGAGC

Antibody 17H6 Heavy Chain CDR1

(SEQ ID NO: 16)

DYYMS

-continued

Antibody 17H6 Heavy Chain CDR2

(SEQ ID NO: 17)

TTTATTAGAAACAAAGCTAATGGTTACACAGCAGAGTACAGTGCGTCTGT

GAAGGGT

Antibody 17H6 Heavy Chain CDR2

(SEQ ID NO: 18)

FIRNKANGYTAEYSASVKG

Antibody 17H6 Heavy Chain CDR3

(SEQ ID NO: 19)

GATTACTACGGTAGTAACCCTGCCTGGTTTGCTTAC

Antibody 17H6 Heavy Chain CDR3

(SEQ ID NO: 20)

DYYGSNPAWFAY

Antibody 17H6 Light Chain CDR1

(SEQ ID NO: 21)

AGATCTAGTCAGAGCATTGTACATAGTAGTGGAAACACCTTTTTAGAA

Antibody 17H6 Light Chain CDR1

(SEQ ID NO: 22)

RSSQSIVHSSGNTFLE

Antibody 17H6 Light Chain CDR2

(SEQ ID NO: 23)

AAAGTTTCCAACCGATTTTCT

Antibody 17H6 Light Chain CDR2

(SEQ ID NO: 24)

KVSNRFS

Antibody 17H6 Light Chain CDR3

(SEQ ID NO: 25)

TTTCAAGGTTCACATGTTCCTTTCACG

Antibody 17H6 Light Chain CDR3

(SEQ. ID. NO: 26)

FQGSHVPFT

Antibody 39H5 Heavy Chain - Signal sequence-FR1-CDR1-FR2-CDR2-FR3-CDR3-FR4

(SEQ ID NO: 27)

ATGGCTTGGGTGTGGACCTTGCTATTCCTGATGGCAGCTGCCCAAAGTGC

CCAAGCACAGATCCAGTTGGTGCAGTCTGGACCTGAGCTGAAGAAGCCTG

GAGAGACAGTCAAGATCTCCTGCAAGGCTTCTGGGTATACCTTCACAAAC

TATGGAATGAACTGGGTGAAGCAGGCTCCAGGAAAGGGTTTAAAGTGGAT

GGGCTGGATAAACACCTACACTGGAGAGCCAACATATGTTGGTGACTTCA

AGGGACGGTTTGCCTTCTCTTTGGAGACCTCTGCCAGCACTGCCTATTTG

CAGATCAACAACCTCAAAAATGAGGACACGGCTACATATTTTTGTGTTAG

AGGTATCCACGGCTACGTGGACTACTGGGGCCAAGGCACCACTCTCACAG

TCTCCTCA

Antibody 39H5 Heavy Chain - Signal sequence-FR1-CDR1-FR2-CDR2-FR3-CDR3-FR4

(SEQ. ID. NO: 28)

MAWVWTLLFLMAAAQSAQAQIQLVQSGPELKKPGETVKISCKASGYTFTN

YGMNWVKQAPGKGLKWMGWINTYTGEPTYVGDFKGRFAFSLETSASTAYL

QINNLKNEDTATYFCVRGIHGYVDYWGQGTTLTVSS

Antibody 39H5 Light Chain - Signal sequence-FR1-CDR1-FR2-CDR2-FR3-CDR3-FR4

(SEQ ID NO: 29)

ATGAAGTTGCCTGTTAGGCTGTTGGTGCTGATGTTCTGGATTCCTGCTTC

CAGCAGTGATGTTTTGATGACCCAAACTCCACTCTCCCTGCCTGTCAGTC

TTGGAGATCAAGCCTCCATCTCTTGCAGATCTAGTCAGAGCATTGTACAT

-continued

AGAAATGGAAACACCTATTTAGAATGGTACCTGCAGAAACCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAGTTTATTACTGCTTTCAAGGTTCACA

TCTTCCGTGGACGTTCGGTGGAGGCACCAAGCTGGAAATCAAA

Antibody 39H5 Light Chain - Signal sequence-FR1-CDR1-FR2-CDR2-FR3-CDR3-FR4

(SEQ ID NO: 30)

MKLPVRLLVLMFWIPASSSDVLMTQTPLSLPVSLGDQASISCRSSQSIVH

RNGNTYLEWYLQKPGQSPKLLIYKVSNRFSGVPDRFSGSGSGTDFTLKIS

RVEAEDLGVYYCFQGSHLPWTFGGGTKLEIK

Antibody 39H5 Heavy Chain CDR1

(SEQ ID NO: 31)

AACTATGGAATGAAC

Antibody 39H5 Heavy Chain CDR1

(SEQ ID NO: 32)

NYGMN

Antibody 39H5 Heavy Chain CDR2

(SEQ ID NO: 33)

TGGATAAACACCTACACTGGAGAGCCAACATATGTTGGTGACTTCAAGGG

A

Antibody 39H5 Heavy Chain CDR2

(SEQ ID NO: 34)

WINTYTGEPTYVGDFKG

Antibody 39H5 Heavy Chain CDR3

(SEQ ID NO: 35)

GGTATCCACGGCTACGTGGACTAC

Antibody 39H5 Heavy Chain CDR3

(SEQ ID NO: 36)

GIHGYVDY

Antibody 39H5 Light Chain CDR1

(SEQ ID NO: 37)

AGATCTAGTCAGAGCATTGTACATAGAAATGGAAACACCTATTTAGAA

Antibody 39H5 Light Chain CDR1

(SEQ ID NO: 38)

RSSQSIVHRNGNTYLE

Antibody 39H5 Light Chain CDR2

(SEQ ID NO: 39)

AAAGTTTCCAACCGATTTTCT

Antibody 39H5 Light Chain CDR2

(SEQ ID NO: 40)

KVSNRFS

Antibody 39H5 Light Chain CDR3

(SEQ ID NO: 41)

TTTCAAGGTTCACATCTTCCGTGGACG

Antibody 39H5 Light Chain CDR3

(SEQ ID NO: 42)

FQGSHLPWT

Antibody 3C5 Heavy Chain - Signal sequence-FR1-CDR1-FR2-CDR2-FR3-CDR3-FR4

(SEQ ID NO: 43)

ATGGCTTGGGTGTGGACCTTGCTGTTCCTGATGGCAGCTGCCCAAAGTGC

CCAAGCACAGATCCAGTTGGTGCAGTCTGGACCTGAGCTGAAGAAGCCTG

GAGAGACAGTCAAGATCTCCTGCAAGGCTTCTGGGTATACCTTCACAAAC

TATGGAATGAACTGGGTGAAGCAGGCTCCAGGAAAGGGTTTAAAGTGGAT

-continued

GGGCTGGATAAACACCTACACTGGAAAGCCAACATATGCTGATGACTTCA

AGGGACGGTTTGCCTTCTCTTTGGAGACCTCTGCCAGCACTGCCTATTTG

CAGATCAACAACCTCAAAAATGAGGACACGGCTACATATTTCTGTGCAAG

AGGGGGACTAGATGGTTACTACGGCTACTGGGGCCAAGGCACCACTCTCA

CAGTCTCCTCA

Antibody 3C5 Heavy Chain - Signal sequence-FR1-CDR1-FR2-CDR2-FR3-CDR3-FR4

(SEQ ID NO: 44)

MAWVWTLLFLMAAAQSAQAQIQLVQSGPELKKPGETVKISCKASGYTFTN

YGMNWVKQAPGKGLKWMGWINTYTGKPTYADDFKGRFAFSLETSASTAYL

QINNLKNEDTATYFCARGGLDGYYGYWGQGTTLTVSS

Antibody 3C5 Light Chain - Signal sequence-FR1-CDR1-FR2-CDR2-FR3-CDR3-FR4

(SEQ ID NO: 45)

ATGAGTCCTGCCCAGTTCCTGTTTCTGCTAGTGCTCTCGATTCAGGAAAC

CAACGGTGATGTTGTGATGGCTCAGACCCCACTCACTTTGTCGGTTACCA

TTGGACAACCAGCCTCCATCTCTTGCAAATCAAGTCAGAGCCTCTTACAT

AGTAAAGGAAAGACATATTTGAATTGGTTATTACAGAGGCCAGGCCAGTC

TCCAAAGCTCCTAATCTATCTGGTGTCTAAACTGGAATCTGGAGTCCCTG

ACAGGTTCAGTGGCAGTGGATCAGGGACAGATTTCACACTGAAAATCAGC

AGAGTGGAGGCTGAAGATTTGGGAGTTTATTACTGCTTGCAAACTACACA

TTTTCCGTGGACGTTCGGTGGAGGCACCAAGCTGGAAATCAAA

Antibody 3C5 Light Chain - Signal sequence-FR1-CDR1-FR2-CDR2-FR3-CDR3-FR4

(SEQ ID NO: 46)

MSPAQFLFLLVLSIQETNGDVVMAQTPLTLSVTIGQPASISCKSSQSLLH

SKGKTYLNWLLQRPGQSPKLLIYLVSKLESGVPDRFSGSGSGTDFTLKIS

RVEAEDLGVYYCLQTTHFPWTFGGGTKLEIK

Antibody 3C5 Heavy Chain CDR1

(SEQ ID NO: 47)

AACTATGGAATGAAC

Antibody 3C5 Heavy Chain CDR1

(SEQ ID NO: 48)

NYGMN

Antibody 3C5 Heavy Chain CDR2

(SEQ ID NO: 49)

TGGATAAACACCTACACTGGAAAGCCAACATATGCTGATGACTTCAAGGG

A

Antibody 3C5 Heavy Chain CDR2

(SEQ ID NO: 50)

WINTYTGKPTYADDFKG

Antibody 3C5 Heavy Chain CDR3

(SEQ ID NO: 51)

GGGGGACTAGATGGTTACTACGGCTAC

Antibody 3C5 Heavy Chain CDR3

(SEQ ID NO: 52)

GGLDGYYGY

Antibody 3C5 Light Chain CDR1

(SEQ ID NO: 53)

AAATCAAGTCAGAGCCTCTTACATAGTAAAGGAAAGACATATTTGAAT

Antibody 3C5 Light Chain CDR1

(SEQ ID NO: 54)

KSSQSLLHSKGKTYLN

-continued

Antibody 3C5 Light Chain CDR2
(SEQ ID NO: 55)
CTGGTGTCTAAACTGGAATCT

Antibody 3C5 Light Chain CDR2
(SEQ ID NO: 56)
LVSKLES

Antibody 3C5 Light Chain CDR3
(SEQ ID NO: 57)
TTGCAAACTACACATTTTCCGTGGACG

Antibody 3C5 Light Chain CDR3
(SEQ ID NO: 58)
LQTTHFPWT

Antibody 8A9 Heavy Chain - Signal sequence-FR1-CDR1-FR2-CDR2-FR3-CDR3-FR4
(SEQ ID NO: 59)
ATGAAGTTGTGGCTGAACTGGATTTTCCTTGTAACACTTTTAAATGGTAT
CCAGTGTGAGGTGGAGCTGGTGGAGTCTGGAGGAGGCTTGGTACAGCCTG
GGGGTTCTCTGAGACTCTCCTGTGCAACTTCTGGGTTCACCTTCACTGAT
CACTACATGAGCTGGGTCCGCCAGCCTCCAGGAAAGGCACTTGAGTGGTT
GGGATTTATTAGAAACAAAGCTAATGGTTACACAACAGAGTACAGTGCAT
CTGTGAAGGGTCGGTTCACCATCTCCAGAGATAATTCCCAAAGCATCCTC
TATCTTCAAATGAAAACCCTGAGAACTGAGGACAGTGCCACTTATTACTG
TGCAAGACCTTCTGACTGGGACTCCTGGTTTGCTTACTGGGGCCAAGGGA
CTCTGGTCACTGTCTCTGCA Antibody 8A9 Heavy Chain - Signal sequence-FR1-CDR1-FR2-CDR2-FR3-CDR3-FR4
(SEQ ID NO: 60)
MKLWLNWIFLVTLLNGIQCEVELVESGGGLVQPGGSLRLSCATSGFTFTD
HYMSWVRQFPGKALEWLGFIRNKANGYTTEYSASVKGRFTISRDNSQSIL
YLQMKTLRTEDSATYYCARPSDWDSWFAYWGQGTLVTVSA Antibody 8A9 Light Chain - Signal sequence-FR1-CDR1-FR2-CDR2-FR3-CDR3-FR4
(SEQ ID NO: 61)
ATGAAGTTGCCTGTTAGGCTGTTGGTGCTGATGTTCTGGATTCCTGCTTC
CAGCAGTGATGTTTTGATGACCCAAACTCCACTCTCCCTGCCTGTCAGTC
TTGGTGATCAAGCCTCCATCTCTTGCAGATCTAGTCAGAGCATTGTACAT
AGTAATGGCAACACCTATTTAGATTGGTACTTGCAGAAACCAGGCCAGTC
TCCAAAGCTCCTGATCTACAGAGTTTCCAACCGATTTTCTGGGGTCCCAG
ACAGGTTCAGTGGCAGTGGATCAGGGACAGATTTCACACTCAAGATCAGC
AGAGTGGAGGCTGAGGATCTGGGACTTTATTACTGTTTTCAAGGTTCACA
TGTTCCGTGGGCGTTCGGTGGAGGCACCAAGCTGGAAATCAAA Antibody 8A9 Light Chain - Signal sequence-FR1-CDR1-FR2-CDR2-FR3-CDR3-FR4
(SEQ ID NO: 62)
MKLPVRLLVLMFWIPASSSDVLMTQTPLSLPVSLGDQASISCRSSQSIVH
SNGNTYLDWYLQKPGQSPKLLIYRVSNRFSGVPDRFSGSGSGTDFTLKIS
RVEAEDLGLYYCFQGSHVPWAFGGGTKLEIK Antibody 8A9 Heavy Chain CDR1
(SEQ ID NO: 63)
GATCACTACATGAGC Antibody 8A9 Heavy Chain CDR1
(SEQ ID NO: 64)
DHYMS -continued Antibody 8A9 Heavy Chain CDR2
(SEQ ID NO: 65)
TTTATTAGAAACAAAGCTAATGGTTACACAACAGAGTACAGTGCATCTGT
GAAGGGT Antibody 8A9 Heavy Chain CDR2
(SEQ ID NO: 66)
FIRNKANGYTTEYSASVKG Antibody 8A9 Heavy Chain CDR3
(SEQ ID NO: 67)
CCTTCTGACTGGGACTCCTGGTTTGCTTAC Antibody 8A9 Heavy Chain CDR3
(SEQ ID NO: 68)
PSDWDSWFAY Antibody 8A9 Light Chain CDR1
(SEQ ID NO: 69)
AGATCTAGTCAGAGCATTGTACATAGTAATGGCAACACCTATTTAGAT Antibody 8A9 Light Chain CDR1
(SEQ ID NO: 70)
RSSQSIVHSNGNTYLD Antibody 8A9 Light Chain CDR2
(SEQ ID NO: 71)
AGAGTTTCCAACCGATTTTCT Antibody 8A9 Light Chain CDR2
(SEQ ID NO: 72)
RVSNRFS Antibody 8A9 Light Chain CDR3
(SEQ ID NO: 73)
TTTCAAGGTTCACATGTTCCGTGGGCG Antibody 8A9 Light Chain CDR3
(SEQ ID NO: 74)
FQGSHVPWA Antibody 18G12 Heavy Chain - Signal sequence-FR1-CDR1-FR2-CDR2-FR3-CDR3-FR4
(SEQ ID NO: 75)
ATGGGATGGAGCTATATCATCCTCTTTTTGGTCGCAACAGCTACAGGTGT
CCACTCCCAGGTCCAACTGCAGCAGTCTGGGGCTGAACTGGTGAAGCCTG
GGGCTTCAGTGAAGTTGTCCTGCAAGGCTTCTGGCTACACCTTCACCGGC
TACTTTTTGTACTGGGTGAAGCAGAGGCCTGGACAAGGCCTTGAGTGGAT
TGGGGGGATTAATCCTGACAATGGTGGTATTGACTTCAATGAGAAGTTCA
GGAACAAGGCCACACTGACTGTAGACAAATCCTCCAGCACAGCCTACATG
CAACTCAGCAGCCTGACATCTGAGGACTCTGCGGTCTATTATTGTACATT
ACTAATAGGGAACTATTGGGGCCAAGGCACCACTCTCACAGTCTCCTCA Antibody 18G12 Heavy Chain - Signal sequence-FR1-CDR1-FR2-CDR2-FR3-CDR3-FR4
(SEQ ID NO: 76)
MGWSYIILFLVATATGVHSQVQLQQSGAELVKPGASVKLSCKASGYTFTG
YFLYWVKQRPGQGLEWIGGINPDNGGIDFNEKFRNKATLTVDKSSSTAYM
QLSSLTSEDSAVYYCTLLIGNYWGQGTTLTVSS Antibody 18G12 Light Chain - Signal sequence-FR1-CDR1-FR2-CDR2-FR3-CDR3-FR4
(SEQ ID NO: 77)
ATGAGTCCTGCCCAGTTCCTGTTTCTGTTAGTGCTCTGGATTCGGGAAAC
CAATGGTGATGTTGTGATGACCCAGACTCCACTCACTTTGTCGGTAACCA
TTGGACAGCCAGCCTCCATCTCTTGCAAGTCAAGTCAGAGCCTCTTACAT
AGTGATGGAAAGACATATTTGATTTGGTTGTTACAGAGGCCAGGCCAGTC -continued TCCAAAGCGCCTAATCTATCTGGTGTCTAAACTGGACTCTGGAGTCCCTG ACAGGTTCACTGGCAGTGGATCAGGGACAGATTTCACACTGAAAATCAGC AGAGTGGAGGCTGAGGATTTGGGAGTTTATTTTTGCTGTCAAGGTACACA TTTTCCGTGGACGTTCGGTGGAGGCACCATGCTGGAAATCAAA Antibody 18G12 Light Chain - Signal sequence-FR1-CDR1-FR2-CDR2-FR3-CDR3-FR4

(SEQ ID NO: 78)

MSPAQFLFLLVLWIRETNGDVVMTQTPLTLSVTIGQPASISCKSSQSLLH SDGKTYLIWLLQRPGQSPKRLIYLVSKLDSGVPDRFTGSGSGTDFTLKIS RVEAEDLGVYFCCQGTHFPWTFGGGTMLEIK

Antibody 18G12 Heavy Chain CDR1

(SEQ ID NO: 79)

GGCTACTTTTTGTAC

Antibody 18G12 Heavy Chain CDR1

(SEQ ID NO: 80)

GYFLY

Antibody 18G12 Heavy Chain CDR2

(SEQ ID NO: 81)

GGGATTAATCCTGACAATGGTGGTATTGACTTCAATGAGAAGTTCAGGAA C

Antibody 18G12 Heavy Chain CDR2

(SEQ ID NO: 82)

GINPDNGGIDFNEKFRN

Antibody 18G12 Heavy Chain CDR3

(SEQ ID NO: 83)

CTAATAGGGAACTAT

Antibody 18G12 Heavy Chain CDR3

(SEQ ID NO: 84)

LIGNY

Antibody 18G12 Light Chain CDR1

(SEQ ID NO: 85)

AAGTCAAGTCAGAGCCTCTTACATAGTGATGGAAAGACATATTTGATT

Antibody 18G12 Light Chain CDR1

(SEQ ID NO: 86)

KSSQSLLHSDGKTYLI

Antibody 18G12 Light Chain CDR2

(SEQ ID NO: 87)

CTGGTGTCTAAACTGGACTCT

Antibody 18G12 Light Chain CDR2

(SEQ ID NO: 88)

LVSKLDS

Antibody 18G12 Light Chain CDR3

(SEQ ID NO: 89)

TGTCAAGGTACACATTTTCCGTGGACG

Antibody 18G12 Light Chain CDR3

(SEQ ID NO: 90)

CQGTHFPWT

Antibody 20A10 Heavy Chain - Signal sequence-FR1-CDR1-FR2-CDR2-FR3-CDR3-FR4

(SEQ ID NO: 91)

ATGAACTTCGGGTTCAGCTTGATTTTCCTTGTCCTTGTTTTAAAAGGTGT CCAGTGTGAAGTGATGCTGGTGGAGTCTGGGGGAGGCTTAGTGAAGCCTG GAGGGTCCCTGAAACTCTCCTGTGCAGCCTCTGGATTCACTTTCAGTACC TATGCCATGTCTTGGATTCGCCAGACTCCAGAGAAGAGGCTGGAGTGGGT CGCATCCATTGGTCGTGCTGGTTCCACCTACTATTCAGACAGTGTGAAGG

-continued

GCCGATTCACCATCTCCAGAGATAATGTCCGGAACATCCTGTACCTGCAA ATGAGCAGTCTGAGGTCTGAGGACACGGCCATGTATTACTGTGCTAGAGG CCCGATCTACAATGATTACGACGAGTTTGCTTACTGGGGCCAAGGGACTC TGGTCACTGTCTCTGCA

Antibody 20A10 Heavy Chain - Signal sequence-FR1-CDR1-FR2-CDR2-FR3-CDR3-FR4

(SEQ ID NO: 92)

MNFGFSLIFLVLVLKGVQCEVMLVESGGGLVKPGGSLKLSCAASGFTFST YAMSWIRQTPEKRLEWVASIGRAGSTYYSDSVKGRFTISRDNVRNILYLQ MSSLRSEDTAMYYCARGPIYNDYDEFAYWGQGTLVTVSA

Antibody 20A10 Light Chain - Signal sequence-FR1-CDR1-FR2-CDR2-FR3-CDR3-FR4

(SEQ ID NO: 93)

ATGGAATCACAGACTCAGGTCTTCCTCTCCCTGCTGCTCTGGGTATCTGG TACCTGTGGGAACATTATGATGACACAGTCGCCATCATCTCTGGCTGTGT CTGCAGGAGAAAAGGTCACTATGAGCTGTAAGTCCAGTCAAAGTGTTTTA TACAGTTCAAATCAGAAGAACTATTTGGCCTGGTACCAGCAGAAACCAGG GCAGTCTCCTAAACTGCTGATCTACTGGGCATCCACTAGGGAATCTGGTG TCCCTGATCGCTTCACAGGCAGTGGATCTGGGACAGATTTTACTCTTACC ATCAGCAGTGTACAAGCTGAAGACCTGGCAGTTTATTACTGTCATCAATA CCTCTCCTCGCTCACGTTCGGTGCTGGGACCAAGCTGGAGCTGAAA

Antibody 20A10 Light Chain - Signal sequence-FR1-CDR1-FR2-CDR2-FR3-CDR3-FR4

(SEQ ID NO: 94)

MESQTQVFLSLLLWVSGTCGNIMMTQSPSSLAVSAGEKVTMSCKSSQSVL YSSNQKNYLAWYQQKPGQSPKLLIYWASTRESGVPDRFTGSGSGTDFTLT ISSVQAEDLAVYYCHQYLSSLTFGAGTKLELK

Antibody 20A10 Heavy Chain CDR1

(SEQ ID NO: 95)

ACCTATGCCATGTCT

Antibody 20A10 Heavy Chain CDR1

(SEQ ID NO: 96)

TYAMS

Antibody 20A10 Heavy Chain CDR2

(SEQ ID NO: 97)

TCCATTGGTCGTGCTGGTTCCACCTACTATTCAGACAGTGTGAAGGGC

Antibody 20A10 Heavy Chain CDR2

(SEQ ID NO: 98)

SIGRAGSTYYSDSVKG

Antibody 20A10 Heavy Chain CDR3

(SEQ ID NO: 99)

GGCCCGATCTACAATGATTACGACGAGTTTGCTTAC

Antibody 20A10 Heavy Chain CDR3

(SEQ ID NO: 100)

GPIYNDYDEFAY

Antibody 20A10 Light Chain CDR1

(SEQ ID NO: 101)

AAGTCCAGTCAAAGTGTTTTATACAGTTCAAATCAGAAGAACTATTTGGC C

Antibody 20A10 Light Chain CDR1

(SEQ ID NO: 102)

KSSQSVLYSSNQKNYLA

-continued

Antibody 20A10 Light Chain CDR2
(SEQ ID NO: 103)
TGGGCATCCACTAGGGAATCT

Antibody 20A10 Light Chain CDR2
(SEQ ID NO: 104)
WASTRES

Antibody 20A10 Light Chain CDR3
(SEQ ID NO: 105)
CATCAATACCTCTCCTCGCTCACG

Antibody 20A10 Light Chain CDR3
(SEQ ID NO: 106)
HQYLSSLT

Antibody 25E6 Heavy Chain - Signal sequence-FR1-CDR1-FR2-CDR2-FR3-CDR3-FR4
(SEQ ID NO: 107)
ATGAACTTCGGGCTCAGCTTGATTTTCCTTGCCCTCATTTTAAAAGGTGT
CCAGTGTGAGGTGCAGCTGGTGGAGTCTGGGGGAGACTTAGTGAAGCCTG
GAGGGTCCCTGAAACTCTCCTGTGCAGCCTCTGGTTTCACTTTCAGTAGT
TATGGAATGTCTTGGGTTCGCCAGACTCCAGACAAGAGGCTGGAGTGGGT
CGCAACCATTAGTAATGGTGGTAGACACACCTTCTATCCAGACAGTGTGA
AGGGGCGATTCACCATCTCCAGAGACAATGCCAAGAACACCCTGTATCTG
CAAATGAGCAGTCTGAAGTCTGAGGACACAGCCATGTATTTATGTGTAAG
ACAGACTGGGACGGAGGGCTGGTTTGCTTACTGGGGCCAAGGGACTCTGG
TCACTGTCTCTGCA Antibody 25E6 Heavy Chain - Signal sequence-FR1-CDR1-FR2-CDR2-FR3-CDR3-FR4
(SEQ ID NO: 108)
MNFGLSLIFLALILKGVQCEVQLVESGGDLVKPGGSLKLSCAASGFTFSS
YGMSWVRQTPDKRLEWVATISNGGRHTFYPDSVKGRFTISRDNAKNTLYL
QMSSLKSEDTAMYLCVRQTGTEGWFAYWGQGTLVTVSA Antibody 25E6 Light Chain - Signal sequence-FR1-CDR1-FR2-CDR2-FR3-CDR3-FR4
(SEQ ID NO: 109)
ATGAGTCCTGCCCAGTTCCTGTTTCTGTTAGTGCTCTGGATTCGGGAAAC
CAACGGTGATGTTGTGATGACCCAGACTCCACTCACTTTGTCGGTTACCA
TTGGACAACCAGCCTCCATCTCTTGCAAGTCAAGTCAGAGCCTCTTAGAT
AGTGATGGAAAGACATATTTGAATTGGTTGTTACAGAGGCCAGGCCAGTC
TCCAAAGCGCCTAATCTATCTGGTGTCTAAACTGGACTCTGGAGTCCCTG
ACAGGTTCACTGGCAGTGGATCAGGGACAGATTTCACACTGAAAATCAGC
AGAGTGGAGGCTGAGGATTTGGGAGTTTATTATTGCTGGCAAGGTACACA
TTTTCCTCAGACGTTCGGTGGAGGCACCAAGCTGGAAATCAAA Antibody 25E6 Light Chain - Signal sequence-FR1-CDR1-FR2-CDR2-FR3-CDR3-FR4
(SEQ ID NO: 110)
MSPAQFLFLLVLWIRETNGDVVMTQTPLTLSVTIGQPASISCKSSQSLLD
SDGKTYLNWLLQRPGQSPKRLIYLVSKLDSGVPDRFTGSGSGTDFTLKIS
RVEAEDLGVYYCWQGTHFPQTFGGGTKLEIK Antibody 25E6 Heavy Chain CDR1
(SEQ ID NO: 111)
AGTTATGGAATGTCT Antibody 25E6 Heavy Chain CDR1
(SEQ ID NO: 112)
SYGMS Antibody 25E6 Heavy Chain CDR2
(SEQ ID NO: 113)
ACCATTAGTAATGGTGGTAGACACACCTTCTATCCAGACAGTGTGAAGGG
G Antibody 25E6 Heavy Chain CDR2
(SEQ ID NO: 114)
TISNGGRHTFYPDSVKG Antibody 25E6 Heavy Chain CDR3
(SEQ ID NO: 115)
CAGACTGGGACGGAGGGCTGGTTTGCTTAC Antibody 25E6 Heavy Chain CDR3
(SEQ ID NO: 116)
QTGTEGWFAY Antibody 25E6 Light Chain CDR1
(SEQ ID NO: 117)
AAGTCAAGTCAGAGCCTCTTAGATAGTGATGGAAAGACATATTTGAAT Antibody 25E6 Light Chain CDR1
(SEQ ID NO: 118)
KSSQSLLDSDGKTYLN Antibody 25E6 Light Chain CDR2
(SEQ ID NO: 119)
CTGGTGTCTAAACTGGACTCT Antibody 25E6 Light Chain CDR2
(SEQ ID NO: 120)
LVSKLDS Antibody 25E6 Light Chain CDR3
(SEQ ID NO: 121)
TGGCAAGGTACACATTTTCCTCAGACG Antibody 25E6 Light Chain CDR3
(SEQ ID NO: 122)
WQGTHFPQT Antibody 28F9 Heavy Chain - Signal sequence-FR1-CDR1-FR2-CDR2-FR3-CDR3-FR4
(SEQ ID NO: 123)
ATGGGATGGAGCTATATCATCCTCTTTTTGGTAGCAACAGCTACAGGTGT
CCACTCCCAGGTCCAACTGCAGCAGCCTGGGGCTGAACTGGTGCAGCCTG
GGGCTTCAGTGAAGTTGTCCTGCAAGGCTTCTGGCTACACCTTCACCGGC
TACTTTTTGTACTGGGTGAAGCAGAGGCCTGGACATGGCCTTGAGTGGAT
TGGGGGAATTCATCCTAGCAATGGTGATACTGACTTCAATGAGAAGTTCA
AGAACAAGGCCACACTGACTGTAGACATATCCTCCAGCACTGCCTACATG
CAACTCAGCAGCCTGACATCTGAGGACTCTGCGGTCTATTATTGTACATT
ACTAATAGGGGTCTACTGGGGCCAAGGCACCACTCTCACAGTCTCCTCA Antibody 28F9 Heavy Chain - Signal sequence-FR1-CDR1-FR2-CDR2-FR3-CDR3-FR4
(SEQ ID NO: 124)
MGWSYIILFLVATATGVHSQVQLQQPGAELVQPGASVKLSCKASGYTFTG
YFLYWVKQRPGHGLEWIGGIHPSNGDTDFNEKFKNKATLTVDISSSTAYM
QLSSLTSEDSAVYYCTLLIGVYWGQGTTLTVSS -continued Antibody 28F9 Light Chain - Signal sequence-
FR1-CDR1-FR2-CDR2-FR3-CDR3-FR4

(SEQ ID NO: 125)

ATGAGTCCTGCCCAGTTCCTGTTTCTGTTAGTGCTCTGGATTCGGGAAAC
CAACGGTGATGTTGTGATGACCCAGACTCCACTCACTTTGTCGGTTACCA
TTGGACAACCAGCCTCCATCTCTTGCAAGTCAAGTCAGAGCCTCTTACAT
AGTGATGGAAAGACATATTTGATTTGGTTGTTACAGAGGCCAGGCCAGTC
TCCAAAGCGCCTAATCTATCTGGTGTCTAAACTGGACTCTGGAGTCCCTG
ACAGGTTCACCGGCAGTGGATCAGGGACAGATTTCACACTGAAAATCAGC
AGAGTGGAGGCTGAGGATTTGGGAGTTTATTTTTGCTGTCAAGGTACACA
TTTTCCGTGGACGTTCGGTGGAGGCACCATGCTGGAAATCAAA

Antibody 28F9 Light Chain - Signal sequence-
FR1-CDR1-FR2-CDR2-FR3-CDR3-FR4

(SEQ ID NO: 126)

MSPAQFLFLLVLWIRETNGDVVMTQTPLTLSVTIGQPASISCKSSQSLLH
SDGKTYLIWLLQRPGQSPKRLIYLVSKLDSGVPDRFTGSGSGTDFTLKIS
RVEAEDLGVYFCCQGTHFPWTFGGGTMLEIK

Antibody 28F9 Heavy Chain CDR1

(SEQ ID NO: 127)

GGCTACTTTTTGTAC

Antibody 28F9 Heavy Chain CDR1

(SEQ ID NO: 128)

GYFLY

Antibody 28F9 Heavy Chain CDR2

(SEQ ID NO: 129)

GGAATTCATCCTAGCAATGGTGATACTGACTTCAATGAGAAGTTCAAGAA
C

Antibody 28F9 Heavy Chain CDR2

(SEQ ID NO: 130)

GIHPSNGDTDFNEKFKN

Antibody 28F9 Heavy Chain CDR3

(SEQ ID NO: 131)

CTAATAGGGGTCTAC

Antibody 28F9 Heavy Chain CDR3

(SEQ ID NO: 132)

LIGVY

Antibody 28F9 Light Chain CDR1

(SEQ ID NO: 133)

AAGTCAAGTCAGAGCCTCTTACATAGTGATGGAAAGACATATTTGATT

Antibody 28F9 Light Chain CDR1

(SEQ ID NO: 134)

KSSQSLLHSDGKTYLI

Antibody 28F9 Light Chain CDR2

(SEQ ID NO: 135)

CTGGTGTCTAAACTGGACTCT

Antibody 28F9 Light Chain CDR2

(SEQ ID NO: 136)

LVSKLDS

Antibody 28F9 Light Chain CDR3

(SEQ ID NO: 137)

TGTCAAGGTACACATTTTCCGTGGACG

Antibody 28F9 Light Chain CDR3

(SEQ ID NO: 138)

CQGTHFPWT

Antibody 18B4 Heavy Chain - Signal sequence-
FR1-CDR1-FR2-CDR2-FR3-CDR3-FR4

(SEQ ID NO: 139)

ATGTACTTGGGACTGAACTATGTATTCATAGTTTTTCTCTTAAATGGTGT
CCAGAGTGAAGTGAAACTTGAGGAGTCTGGAGGAGGCTTGGTGCAACCTG
GGGGATCCATGAAACTCTCTTGTGCTGCCTCTGGATTCACTTTTAATGAC
GCCTGGATGGACTGGGTCCGCCAGTCTCCAGAGAAGGGGCTTGAGTGGGT
TGCTGAAATTAGAAGCACAGCTAATATTCATACAACATACTATGCTGAGT
CTGTCCAAGGGAGGTTCACCATCTCAAGAGATGATTCCAAAAGTAGTGTC
TACCTGCAAATGAACAGCTTGAGAGCTGAAGACACTGGCATTTATTATTG
TACCCCATTACTCTACGGATTTGCTTACTGGGGCCAAGGGACTCTGGTCA
CTGTCTCTGCA

Antibody 18B4 Heavy Chain - Signal sequence-
FR1-CDR1-FR2-CDR2-FR3-CDR3-FR4

(SEQ ID NO: 140)

MYLGLNYVFIVFLLNGVQSEVKLEESGGGLVQPGGSMKLSCAASGFTFND
AWMDWVRQSPEKGLEWVAEIRSTANIHTTYYAESVQGRFTISRDDSKSSV
YLQMNSLRAEDTGIYYCTPLLYGFAYWGQGTLVTVSA

Antibody 18B4 Light Chain - Signal sequence-
FR1-CDR1-FR2-CDR2-FR3-CDR3-FR4

(SEQ ID NO: 141)

ATGAAGTTGCCTGTTAGGCTGTTGGTGCTGATGTTCTGGATTCCTGCTTC
CAGCAGTGATGTTGTGATGACCCAAAGTCCACTCTCCCTGCCTGTCAGTC
TTGGAGATCAAGCCTCCATCTCTTGCAGAACTAGTCAGAGCCTTGTACAC
AGTAATGGAAACACCTATTTACATTGGCACCTGCAGAAGCCAGGCCAGTC
TCCAAAGGTCCTGATCTACAAAGTTTCCAGCCGATTTTCTGGGGTCCCAG
ACAGGTTCAGTGGCAGTGGATCGGGGACAGATTTCACACTCAAGATCAGC
AGAGTGGAGGCTGAGGATCTGGGAGTTTATTTCTGCTCTCAAAATACACA
TGTTCCGTACACGTTCGGAGGGGGGACCAAGCTGGAAATAAAA

Antibody 18B4 Heavy Chain - Signal sequence-
FR1-CDR1-FR2-CDR2-FR3-CDR3-FR4

(SEQ ID NO: 142)

MKLPVRLLVLMFWIPASSSDVVMTQSPLSLPVSLGDQASISCRTSQSLVH
SNGNTYLHWHLQKPGQSPKVLIYKVSSRFSGVPDRFSGSGSGTDFTLKIS
RVEAEDLGVYFCSQNTHVPYTFGGGTKLEIK

Antibody 18B4 Heavy Chain CDR1

(SEQ ID NO: 143)

GACGCCTGGATGGAC

Antibody 18B4 Heavy Chain CDR1

(SEQ ID NO: 144)

DAWMD

Antibody 18B4 Heavy Chain CDR2

(SEQ ID NO: 145)

GAAATTAGAAGCACAGCTAATATTCATACAACATACTATGCTGAGTCTGT
CCAAGGG

Antibody 18B4 Heavy Chain CDR2

(SEQ ID NO: 146)

EIRSTANIHTTYYAESVQG

Antibody 18B4 Heavy Chain CDR3

(SEQ ID NO: 147)

TTACTCTACGGATTTGCTTAC

-continued

Antibody 18B4 Heavy Chain CDR3

(SEQ ID NO: 148)

LLYGFAY

Antibody 18B4 Light Chain CDR1

(SEQ ID NO: 149)

AGAACTAGTCAGAGCCTTGTACACAGTAATGGAAACACCTATTTACAT

Antibody 18B4 Light Chain CDR1

(SEQ ID NO: 150)

RTSQSLVHSNGNTYLH

Antibody 18B4 Light Chain CDR2

(SEQ ID NO: 151)

AAAGTTTCCAGCCGATTTTCT

Antibody 18B4 Light Chain CDR2

(SEQ ID NO: 152)

KVSSRFS

Antibody 18B4 Light Chain CDR3

(SEQ ID NO: 153)

TCTCAAAATACACATGTTCCGTACACG

Antibody 18B4 Light Chain CDR3

(SEQ ID NO: 154)

SQNTHVPYT

Antibody 1E4 Heavy Chain - Signal sequence-FR1-CDR1-FR2-CDR2-FR3-CDR3-FR4

(SEQ ID NO: 155)

ATGGAATGGCCTTGTATCTTTCTCTTCCTCCTGTCAGTAACTGAAGGTGT

CCACTCCCAGGTTCAGCTGCAGCAGTCTGGGGCTGAGCTGGTGAGGCCTG

GGTCCTCAGTGAAGATTTCCTGTAAGGCTTCTGGCTATGCATTCAGTACC

TACTGGATGAACTGGGTGAAGCAGAGGCCTGGACAGGGTCTTGAGTGGAT

TGGACAGATTTATCCTGGAGATAGTGATACTAACTACAATGGAAAGTTCA

AGGGTAAAGCCACACTGACTGCAGACAAGTCCTCCAACACAGCCTACATG

CAGCTCAGCAGCCTAACATCTGAGGACTCTGCGGTCTTTTTCTGTGCAAG

AGGTAACCACGCCTCTATGGACTACTGGGGTCAAGGAACCTCAGTCACCG

TCTCCTCA

Antibody 1E4 Heavy Chain - Signal sequence-FR1-CDR1-FR2-CDR2-FR3-CDR3-FR4

(SEQ ID NO: 156)

MEWPCIFLFLLSVTEGVHSQVQLQQSGAELVRPGSSVKISCKASGYAFST

YWMNWVKQRPGQGLEWIGQIYPGDSDTNYNGKFKGKATLTADKSSNTAYM

QLSSLTSEDSAVFFCARGNHASMDYWGQGTSVTVSS

Antibody 1E4 Light Chain - Signal sequence-FR1-CDR1-FR2-CDR2-FR3-CDR3-FR4

(SEQ ID NO: 157)

ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCAGATCTAGTCAGAGCCTTGTACAC

AGTAATGGAAACACCTATTTACATTGGTACCTGCAGAAGCCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAGTTTATTTCTGCTCTCAAAAAACACA

TGTTCCGTGGACGTTCGGTGGAGGCACCAAGCTGGAAATCAAA

-continued

Antibody 1E4 Light Chain - Signal sequence-FR1-CDR1-FR2-CDR2-FR3-CDR3-FR4

(SEQ ID NO: 158)

MKLPVRLLVLMFWIPASSSDVVMTQTPLSLPVSLGDQASISCRSSQSLVH

SNGNTYLHWYLQKPGQSPKLLIYKVSNRFSGVPDRFSGSGSGTDFTLKIS

RVEAEDLGVYFCSQKTHVPWTFGGGTKLEIK

Antibody 1E4 Heavy Chain CDR1

(SEQ ID NO: 159)

ACCTACTGGATGAAC

Antibody 1E4 Heavy Chain CDR1

(SEQ ID NO: 160)

TYWMN

Antibody 1E4 Heavy Chain CDR2

(SEQ ID NO: 161)

CAGATTTATCCTGGAGATAGTGATACTAACTACAATGGAAAGTTCAAGGG

T

Antibody 1E4 Heavy Chain CDR2

(SEQ ID NO: 162)

QIYPGDSDTNYNGKFKG

Antibody 1E4 Heavy Chain CDR3

(SEQ ID NO: 163)

GGTAACCACGCCTCTATGGACTAC

Antibody 1E4 Heavy Chain CDR3

(SEQ ID NO: 164)

GNHASMDY

Antibody 1E4 Light Chain CDR1

(SEQ ID NO: 165)

AGATCTAGTCAGAGCCTTGTACACAGTAATGGAAACACCTATTTACAT

Antibody 1E4 Light Chain CDR1

(SEQ ID NO: 166)

RSSQSLVHSNGNTYLH

Antibody 1E4 Light Chain CDR2

(SEQ ID NO: 167)

AAAGTTTCCAACCGATTTTCT

Antibody 1E4 Light Chain CDR2

(SEQ ID NO: 168)

KVSNRFS

Antibody 1E4 Light Chain CDR3

(SEQ ID NO: 169)

TCTCAAAAAACACATGTTCCGTGGACG

Antibody 1E4 Light Chain CDR3

(SEQ ID NO: 170)

SQKTHVPWT

Antibody 29H1 Heavy Chain - Signal sequence-FR1-CDR1-FR2-CDR2-FR3-CDR3-FR4

(SEQ ID NO: 171)

ATGTACTTGGGACTGAACTATGTATTCATAGTTTTTCTCTTAAATGGTGT

CCAGAGTGAAGTGAAGCTTGAGGAGTCTGGAGGAGGCTTGGTACAACCTG

GAGGATCCATGAAACTCTCTTGTGCTGCCTCTGGATTCACTTTTAGTGAC

GCCTGGATGGACTGGGTCCGCCAGTCTCCAGAGAAGGGGCTTGAATGGGT

TGCTGAAATTAGAAGCAAAGCTACTAATCATGCAACATACTATGCTGAGT

CTGTGAAAGGGAGGTTCACCATCTCAAGAGATGATTCCAAAAGTAGTGTC

TACCTGCAAATGAACAGCTTAAGAGCTGAAGACACTGGCATTTATTACTG

TACCCCCCTACTTTACGGGTTTGCTTACTGGGGCCAAGGGACTCTGGTCA

CTGTCTCTGCA

-continued

Antibody 29H1 Heavy Chain - Signal sequence-FR1-CDR1-FR2-CDR2-FR3-CDR3-FR4

(SEQ ID NO: 172)

MYLGLNYVFIVFLLNGVQSEVKLEESGGGLVQPGGSMKLSCAASGFTFSD

AWMDWVRQSPEKGLEWVAEIRSKATNHATYYAESVKGRFTISRDDSKSSV

YLQMNSLRAEDTGIYYCTPLLYGFAYWGQGTLVTVSA

Antibody 29H1 Light Chain - Signal sequence-FR1-CDR1-FR2-CDR2-FR3-CDR3-FR4

(SEQ ID NO: 173)

ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCAGATCTGGTCAGAGCCTTGTACAC

AGTAATGGACACACCTATTTACATTGGTACCTGCAGAAGCCAGGCCAGTC

TCCAAGGCTCCTGATCTACAAAGTTTCCAACCGATTTTCTGGGGTCCCAG

ACAGGTTCAGTGGCAGTGGATCAAGGGCAGATTTCACACTCAAGATCAGC

AGAGTGGAGGCTGAGGATCTGGGAGTTTATTTCTGCTCTCAAACTACACA

TGTTCCGTGGACGTTCGGTGGAGGCACCAAGCTGGAAATCAAA

Antibody 29H1 Light Chain - Signal sequence-FR1-CDR1-FR2-CDR2-FR3-CDR3-FR4

(SEQ ID NO: 174)

MKLPVRLLVLMFWIPASSSDVVMTQTPLSLPVSLGDQASISCRSGQSLVH

SNGHTYLHWYLQKPGQSPRLLIYKVSNRFSGVPDRFSGSGSRADFTLKIS

RVEAEDLGVYFCSQTTHVPWTFGGGTKLEIK

Antibody 29H1 Heavy Chain CDR1

(SEQ ID NO: 175)

GACGCCTGGATGGAC

Antibody 29H1 Heavy Chain CDR1

(SEQ ID NO: 176)

DAWMD

Antibody 29H1 Heavy Chain CDR2

(SEQ ID NO: 177)

GAAATTAGAAGCAAAGCTACTAATCATGCAACATACTATGCTGAGTCTGT

GAAAGGG

Antibody 29H1 Heavy Chain CDR2

(SEQ ID NO: 178)

EIRSKATNHATYYAESVKG

Antibody 29H1 Heavy Chain CDR3

(SEQ ID NO: 179)

CTACTTTACGGGTTTGCTTAC

Antibody 29H1 Heavy Chain CDR3

(SEQ ID NO: 180)

LLYGFAY

Antibody 29H1 Light Chain CDR1

(SEQ ID NO: 181)

AGATCTGGTCAGAGCCTTGTACACAGTAATGGACACACCTATTTACAT

Antibody 29H1 Light Chain CDR1

(SEQ ID NO: 182)

RSGQSLVHSNGHTYLH

Antibody 29H1 Light Chain CDR2

(SEQ ID NO: 183)

AAAGTTTCCAACCGATTTTCT

Antibody 29H1 Light Chain CDR2

(SEQ ID NO: 184)

KVSNRFS

-continued

Antibody 29H1 Light Chain CDR3

(SEQ ID NO: 185)

TCTCAAACTACACATGTTCCGTGGACG

Antibody 29H1 Light Chain CDR3

(SEQ ID NO: 186)

SQTTHVPWT

Antibody 31A1 Heavy Chain - Signal sequence-FR1-CDR1-FR2-CDR2-FR3-CDR3-FR4

(SEQ ID NO: 187)

ATGGAAAGGCACTGGATCTTTCTCTTCCTGTTTTCAGTAACTGCAGGTGT

CCACTCCCAGGTCCAGCTTCAGCAGTCTGGGGCTGAACTGGCAAAACCTG

GGGCCTCAGTGAAGATGTCCTGCAAGGCTTCTGGCTACACCTTTACTAGC

TACTGGATGCACTGGGTAAAACAGAGGCCTGGACAGGGTCTGGAATGGAT

TGGATACATTAATCCTAGCACTGGTTATACTGAGTACAATCAGAAGTTCA

AGGACAAGGCCACATTGACTGCAGACAAATCCTCCAGCACAGCCTACATG

CAACTGAGCAGCCTGACATCTGAGGACTCTGCAGTCTATTACTGTGCAAG

AGCCTACATTGACTACTGGGGCCAAGGCACCACTCTCACAGTCTCCTCA

Antibody 31A1 Heavy Chain - Signal sequence-FR1-CDR1-FR2-CDR2-FR3-CDR3-FR4

(SEQ ID NO: 188)

MERHWIFLFLFSVTAGVHSQVQLQQSGAELAKPGASVKMSCKASGYTFTS

YWMHWVKQRPGQGLEWIGYINPSTGYTEYNQKFKDKATLTADKSSSTAYM

QLSSLTSEDSAVYYCARAYIDYWGQGTTLTVSS

Antibody 31A1 Light Chain - Signal sequence-FR1-CDR1-FR2-CDR2-FR3-CDR3-FR4

(SEQ ID NO: 189)

ATGAAGTTGCCTGTTAGGCTGTTGGTGCTGATGTTCTGGATTCCTGCTTC

CAGCAGTGATGTTTTGATGACCCAAACTCCACTCTCCCTGCCTGTCAGTC

TTGGAGATCAAGCCTCCTTCTCTTGCAGATCTAGTCAGAGCATTGTACAT

AGTAATGGAAACACCTATTTAGAATGGTACCTGCAGAAACCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAAC

AGAGTGGAGGCTGAGGATCTGGGAGTTTATTACTGCTTTCAAGTTTCACA

TTTTCCGTGGACGTTCGGTGGAGGCACCAAGCTGGAAATCAAA

Antibody 31A1 Light Chain - Signal sequence-FR1-CDR1-FR2-CDR2-FR3-CDR3-FR4

(SEQ ID NO: 190)

MKLPVRLLVLMFWIPASSSDVLMTQTPLSLPVSLGDQASFSCRSSQSIVH

SNGNTYLEWYLQKPGQSPKLLIYKVSNRFSGVPDRFSGSGSGTDFTLKIN

RVEAEDLGVYYCFQVSHFPWTFGGGTKLEIK

Antibody 31A1 Heavy Chain CDR1

(SEQ ID NO: 191)

AGCTACTGGATGCAC

Antibody 31A1 Heavy Chain CDR1

(SEQ ID NO: 192)

SYWMH

Antibody 31A1 Heavy Chain CDR2

(SEQ ID NO: 193)

TACATTAATCCTAGCACTGGTTATACTGAGTACAATCAGAAGTTCAAGGA

C

-continued

Antibody 31A1 Heavy Chain CDR2
(SEQ ID NO: 194)
YINPSTGYTEYNQKFKD

Antibody 31A1 Heavy Chain CDR3
(SEQ ID NO: 195)
GCCTACATTGACTAC

Antibody 31A1 Heavy Chain CDR3
(SEQ ID NO: 196)
AYIDY

Antibody 31A1 Light Chain CDR1
(SEQ ID NO: 197)
AGATCTAGTCAGAGCATTGTACATAGTAATGGAAACACCTATTTAGAA Antibody 31A1 Light Chain CDR1
(SEQ ID NO: 198)
RSSQSIVHSNGNTYLE Antibody 31A1 Light Chain CDR2
(SEQ ID NO: 199)
AAAGTTTCCAACCGATTTTCT Antibody 31A1 Light Chain CDR2
(SEQ ID NO: 200)
KVSNRFS Antibody 31A1 Light Chain CDR3
(SEQ ID NO: 201)
TTTCAAGTTTCACATTTTCCGTGGACG Antibody 31A1 Light Chain CDR3
(SEQ ID NO: 202)
FQVSHFPWT Antibody 32C1 Heavy Chain - Signal sequence-FR1-CDR1-FR2-CDR2-FR3-CDR3-FR4
(SEQ ID NO: 203)
ATGTACTTGGGACTGAACTGTGTATTCATAGTTTTTCTCTTAAAAGGTGTCCAGAGTGAAGTGAAGCTTGAGGAGTCTGGAGGAGGCTTGGTGCAATCTGGAGGATCCATGAAACTCTCCTGTGTTGCCTCTGGATTCACTTTCAGTAATTACTGGATGAACTGGGTCCGCCAGTCTCCAGAGAAGGGGCTTGAGTGGGTTGCTGAAATTAGATTGAAATCTAATAATTATGCAATACATTATGCGGAGTCTGTGAAGGGGAGGTTCACCATCTCAAGAGATGATTCCAAAAGTAGTGTCTACCTGCAAATGAACAACTTAAGAGCTGAAGACACTGGCATTTATTACTGTACCAGGGTCCCGGGACTGGATGCTTACTGGGGCCAAGGGACTCTGGTCACTGTCTCTGCA Antibody 32C1 Heavy Chain - Signal sequence-FR1-CDR1-FR2-CDR2-FR3-CDR3-FR4
(SEQ ID NO: 204)
MYLGLNCVFIVFLLKGVQSEVKLEESGGGLVQSGGSMKLSCVASGFTFSNYWMNWVRQSPEKGLEWVAEIRLKSNNYAIHYAESVKGRFTISRDDSKSSVYLQMNNLRAEDTGIYYCTRVPGLDAYWGQGTLVTVSA Antibody 32C1 Light Chain - Signal sequence-FR1-CDR1-FR2-CDR2-FR3-CDR3-FR4
(SEQ ID NO: 205)
ATGAAGTTGCCTGTTAGGCTGTTGGTGCTGATGTTCTGGATTCCTGCTTCCAGCAGTGATGTTGTGATGACCCAAACTCCACTCTCCCTGCCTGTCAGTCTTGGAGATCAAGCCTCCATCTCTTGCAGATCTAGTCAGAGCCTTGTACACAGTAATGGAAACACCTATTTACATTGGTACCTGCAGAAGCCAGGCCAGTCTCCAAAGCTCCTGATCTACAAAGTTTCCAACCGATTTTCTGGGGTCCCAGACAGGTTCAGTGGCAGTGGATCAGGGACAGATTTCACACTCAAGATCAGCAGTGTGGAGGCTGAGGATCTGGGAGTTTATTTCTGCTCTCAAATTACACATGTTCCGTACACGTTCGGAGGGGGGACCAATCTGGAAATAAAA Antibody 32C1 Light Chain - Signal sequence-FR1-CDR1-FR2-CDR2-FR3-CDR3-FR4
(SEQ ID NO: 206)
MKLPVRLLVLMFWIPASSSDVVMTQTPLSLPVSLGDQASISCRSSQSLVHSNGNTYLHWYLQKPGQSPKLLIYKVSNRFSGVPDRFSGSGSGTDFTLKISSVEAEDLGVYFCSQITHVPYTFGGGTNLEIK Antibody 32C1 Heavy Chain CDR1
(SEQ ID NO: 207)
AATTACTGGATGAAC Antibody 32C1 Heavy Chain CDR1
(SEQ ID NO: 208)
NYWMN Antibody 32C1 Heavy Chain CDR2
(SEQ ID NO: 209)
GAAATTAGATTGAAATCTAATAATTATGCAATACATTATGCGGAGTCTGTGAAGGGG Antibody 32C1 Heavy Chain CDR2
(SEQ ID NO: 210)
EIRLKSNNYAIHYAESVKG Antibody 32C1 Heavy Chain CDR3
(SEQ ID NO: 211)
GTCCCGGGACTGGATGCTTAC Antibody 32C1 Heavy Chain CDR3
(SEQ ID NO: 212)
VPGLDAY Antibody 32C1 Light Chain CDR1
(SEQ ID NO: 213)
AGATCTAGTCAGAGCCTTGTACACAGTAATGGAAACACCTATTTACAT Antibody 32C1 Light Chain CDR1
(SEQ ID NO: 214)
RSSQSLVHSNGNTYLH Antibody 32C1 Light Chain CDR2
(SEQ ID NO: 215)
AAAGTTTCCAACCGATTTTCT Antibody 32C1 Light Chain CDR2
(SEQ ID NO: 216)
KVSNRFS Antibody 32C1 Light Chain CDR3
(SEQ ID NO: 217)
TCTCAAATTACACATGTTCCGTACACG Antibody 32C1 Light Chain CDR3
(SEQ ID NO: 218)
SQITHVPYT Antibody 45C11 Heavy Chain - Signal sequence-FR1-CDR1-FR2-CDR2-FR3-CDR3-FR4
(SEQ ID NO: 219)
ATGAAATGCAGCTGGGTTATCTTCTTCCTGATGGCAGTGGTTACAGGGGTCAATTCAGAGGTTCAGCTGCAGCAGTCTGGGGCAGACCTTGTGAAGCCAGGGGCCTCAGTCAAGTTGTCCTGCACAGCTTCTGGCTTCAACATTAAAGACACCTTTATGCACTGGGTGAAGCAGAGGCCTGAACAGGGCCTGGAGTGGATTGGAAGGATTGATCCTGCGAATGGTAATACTAAATATGACCCGAAATTCCAGGGCAAGGCCACTATAACAGCAGACACATCCTCCAACACAGCCTACCTGCAGCTCAGCAGCCTGACATCTGAGGACACTGCCGTCTATTACTGTGCTAA -continued

ACCGTATGGTAACTACGGCTATTACTATGCTTTGGACTACTGGGGTCAAG

GAACCTCAGTCACCGTCTCCTCA

Antibody 45C11 Heavy Chain - Signal sequence-FR1-CDR1-FR2-CDR2-FR3-CDR3-FR4
(SEQ ID NO: 220)
MKCSWVIFFLMAVVTGVNSEVQLQQSGADLVKPGASVKLSCTASGFNIKD

TFMHWVKQRPEQGLEWIGRIDPANGNTKYDPKFQGKATITADTSSNTAYL

QLSSLTSEDTAVYYCAKPYGNYGYYYALDYWGQGTSVTVSS

Antibody 45C11 Light Chain - Signal sequence-FR1-CDR1-FR2-CDR2-FR3-CDR3-FR4
(SEQ ID NO: 221)
ATGAGGTTCCAGGTTCAGGTTCTGGGGCTCCTTCTGCTCTGGATATCAGG

TGCCCAGTGTGATGTCCAGATAACCCAGTCTCCATCTTATCTTGCTGCAT

CTCCTGGAGAAACCATTACTATTAATTGCAGGGCAAGTAAGAGCATTAGC

AAATATTTAGCCTGGTATCAAGAGAAACCTGGGAAAACTAATAAGCTTCT

TATCTACTCTGGATCCACTTTGCAATCTGGAATTCCATCAAGGTTCAGTG

GCAGTGGATCTGGTACAGATTTCACTCTCACCATCAGTAGCCTGGAGCCT

GAAGATTTTGCAATGTATTACTGTCAACAGCATAATGAATTCCCGTGGAC

GTTCGGTGGAGGCACCAAGCTGGAAATCAAA

Antibody 45C11 Light Chain - Signal sequence-FR1-CDR1-FR2-CDR2-FR3-CDR3-FR4
(SEQ ID NO: 222)
MRFQVQVLGLLLLWISGAQCDVQITQSPSYLAASPGETITINCRASKSIS

KYLAWYQEKPGKTNKLLIYSGSTLQSGIPSRFSGSGSGTDFTLTISSLEP

EDFAMYYCQQHNEFPWTFGGGTKLEIK

Antibody 45C11 Heavy Chain CDR1
(SEQ ID NO: 223)
GACACCTTTATGCAC

Antibody 45C11 Heavy Chain CDR1
(SEQ ID NO: 224)
DTFMH

Antibody 45C11 Heavy Chain CDR2
(SEQ ID NO: 225)
AGGATTGATCCTGCGAATGGTAATACTAAATATGACCCGAAATTCCAGGG

C

Antibody 45C11 Heavy Chain CDR2
(SEQ ID NO: 226)
RIDPANGNTKYDPKFQG

Antibody 45C11 Heavy Chain CDR3
(SEQ ID NO: 227)
CCGTATGGTAACTACGGCTATTACTATGCTTTGGACTAC Antibody 45C11 Heavy Chain CDR3
(SEQ ID NO: 228)
PYGNYGYYYALDY Antibody 45C11 Light Chain CDR1
(SEQ ID NO: 229)
AGGGCAAGTAAGAGCATTAGCAAATATTTAGCC Antibody 45C11 Light Chain CDR1
(SEQ ID NO: 230)
RASKSISKYLA Antibody 45C11 Light Chain CDR2
(SEQ ID NO: 231)
TCTGGATCCACTTTGCAATCT -continued Antibody 45C11 Light Chain CDR2
(SEQ ID NO: 232)
SGSTLQS Antibody 45C11 Light Chain CDR3
(SEQ ID NO: 233)
CAACAGCATAATGAATTCCCGTGGACG Antibody 45C11 Light Chain CDR3
(SEQ ID NO: 234)
QQHNEFPWT Tandem repeat domain peptide
(SEQ ID NO: 235)
PDTRPAPGSTAPPAHGVTSA CAR44: CD8/HUMNC2/CD8/4-1BB/CD3
(SEQ ID NO: 236)
MALPVTALLLPLALLLHAARPEVQLVESGGGLVKPGGSLRLSCAASGFTF

SGYAMSWVRQAPGKGLEWVSTISSGGTYIYYPDSVKGRFTISRDNAKNSL

YLQMNSLRAEDTAVYYCARLGGDNYYEYFDVWGKGTTVTVSSGGGGSGGG

GSGGGGSDIVLTQSPASLAVSPGQRATITCRASKSVSTSGYSYMHWYQQK

PGQPPKLLIYLASNLESGVPARFSGSGSGTDFTLTINPVEANDTANYYCQ

HSRELPFTFGGGTKVEIKRTTTTPAPRPPTPAPTIASQPLSLRPEACRPA

AGGAVHTRGLDFACDIYIWAPLAGTCGVLLLSLVITLYCKRGRKKLLYIF

KQPFMRPVQTTQEEDGCSCRFPEEEEGGCELRVKFSRSADAPAYKQGQNQ

LYNELNLGRREEYDVLDKRRGRDPEMGGKPRRKNPQEGLYNELQKDKMAE

AYSEIGMKGERRRGKGHDGLYQGLSTATKDTYDALHMQALPPR

MIN-A2-1 LIGHT CHAIN VARIABLE REGION AMINO ACID SEQUENCE
(SEQ ID NO: 237)
DIVLTQSTEIMSASPGEKVTITCSASSSISYIHWFQQKPGTSPKLWIFGT

SNLASGVPARFSGSGSGTSYSLTVSRMEAEDTATYYCQQRSNYPFTFGSG

TKLQIKRADAAPTVS

MIN-A2-2 LIGHT CHAIN VARIABLE REGION AMINO ACID SEQUENCE
(SEQ ID NO: 238)
DIVMTQSPAIMSASPGEKVTMTCSASSSVSYMHWFQQKPGTSPKLWIYST

SNLASGAPARFSGSGSGTSYSLTVSRMESEDAATYYCQQRSSYPSTFGGG

TKLEIKRADAAPTVS

MIN-C9-1 LIGHT CHAIN VARIABLE REGION AMINO ACID SEQUENCE
(SEQ ID NO: 239)
DIVLTQTTAIMSASPGEKVTITCSASSSVSYMYWFQQKPGTSPKLWIYST

SNLASGVPARFSGSGSGTSYSLTISRMEAEDAATYYCQQRSSYPSTFGGG

TKLEIKRADAAPTVS

MIN-C9-2 LIGHT CHAIN VARIABLE REGION AMINO ACID SEQUENCE
(SEQ ID NO: 240)
DIVITQSTAIMSASPGEKVTITCSASSSVSYTYWFQQKPGTSPKLWIYST

SNLASGVPARFSGSGSGTSYSLTISRMEAEDAATYYCQQRSSYPSTFGGG

TKLEIKRADAAPTVS

-continued

MIN-D7-1 LIGHT CHAIN VARIABLE REGION
AMINO ACID SEQUENCE
(SEQ ID NO: 241)
DIVITQTPAIMSASPGEKVTMTCSASSSVSYMHWFQQKPGTSPKLWIYST
SNLASGVPARFSGSGSGTSYSLTVSRMESEDAATYYCQQRSSYPSTFGGG
TKLEIKRADAAPTVS

MIN-D7-2 LIGHT CHAIN VARIABLE REGION
AMINO ACID SEQUENCE
(SEQ ID NO: 242)
DIVLTQSTAIMSASPGEKVTMTCSASSSVSYMHWFQQKPGTSPKLWIYST
SNLASGVPARFSGSGSGTSYSLTVSRMESEDAATYYCQQRSSYPSTFGGG
TKLEIKRADAAPTVS

MIN-F2-1 LIGHT CHAIN VARIABLE REGION
AMINO ACID SEQUENCE
(SEQ ID NO: 243)
DIVMTQSPEIMSASPGEKVTITCSASSSISYIHWFQQKPGTSPKLWIFGT
SNLASGVPARFSGSGSGTSYSLTVSRMEAEDTATYYCQQRSNYPFTFGSG
TKLQIKRADAAPTVS

MIN-F2-2 LIGHT CHAIN VARIABLE REGION
AMINO ACID SEQUENCE
(SEQ ID NO: 244)
DIVITQSTEIMSASPGEKVTITCSASSSISYIHWFQQKPGTSPKLWIFGT
SNLASGVPARFSGSGSGTSYSLTVSRMEAEDTATYYCQQRSNYPFTFGSG
TKLQIKRADAAPTVS

MIN-A2-1 HEAVY CHAIN VARIABLE REGION
AMINO ACID SEQUENCE
(SEQ ID NO: 245)
EVKLQESGPELKKPGETVEISCKASGYTFTNYGMNWVKQAPGKGLKWMGW
INTYTGEPTYAGDFKGRFAFSLETSASTAYLQINTLKNEDTATYFCARSG
DGYWYYAMDYWGQGTSVTVSSAKTTPPSVY

MIN-A2-2 HEAVY CHAIN VARIABLE REGION
AMINO ACID SEQUENCE
(SEQ ID NO: 246)
EVQLQQSGPELKKPGETVKISCKASGYTFTNYGMNWVKQAPGKGLKWMGW
INTYTGEPTYAGDFKGRFAFSLETSASTAYLQINTLKNEDTATYFCARSG
DGYWYYAMDYWGQGTSVTVSSAKTTPPSVY

MIN-C9-1 HEAVY CHAIN VARIABLE REGION
AMINO ACID SEQUENCE
(SEQ ID NO: 247)
QVQLQESGPELKQPGETVKISCKASGYTFTNNGMNWVKQAPGKGLKWMGW
INTYTGEPTYADDFKGRFAFSLDTSASTAYLQINNLKNEDMATYFCARTG
TARAFYAMDYWGQGTSVTVSSTKTTAPSVY

MIN-C9-2 HEAVY CHAIN VARIABLE REGION
AMINO ACID SEQUENCE
(SEQ ID NO: 248)
QVQLQQSGPELKQPGETVKISCKASGYTFTNNGMNWVKQAPGKGLKWMGW
INTYTGEPTYADDFKGRFAFSLGTSASTAYLQINNLKNEDMATYFCARTG
TARAFYAMDYWGQGTSVTVSSTKTTAPSVY

MIN-D7-1 HEAVY CHAIN VARIABLE REGION
AMINO ACID SEQUENCE
(SEQ ID NO: 249)
EVQLEQSGPELKKPGETVKISCKASGYTFINYGMNWVKQAPGKGLKWMGW
INTYTGEPTYVDDFKGRFAFSLETSARTAYLQINNLKNEDMATYFCARTG
TTAILNGMDYWGQGTSVTVSSAKTTPPSVY

-continued

MIN-D7-2 HEAVY CHAIN VARIABLE REGION
AMINO ACID SEQUENCE
(SEQ ID NO: 250)
EVQLQQSGPELKKPGETVKISCKASGYTFTNYGMNWVKQAPGKGLKWMGW
INTYTGEPTYAGDFKGRFAFSLETSASTAYLQINTLKNEDTATYFCARSG
DGYWYYAMDYWGQGTSVTVSSAKTTPPSVY

MIN-F2-1 HEAVY CHAIN VARIABLE REGION
AMINO ACID SEQUENCE
(SEQ ID NO: 251)
EVKLEESGPELKKPGETVKISCKASGYTFINYGMNWVKQAPGKGLKWMGW
INTYTGEPTYVDDFKGRFAFSLETSARTAYLQINNLKNEDMATYFCARTG
TTAILNGMDYWGQGTSVTVSSAKTTPPSVY

MIN-F2-2 HEAVY CHAIN VARIABLE REGION
AMINO ACID SEQUENCE
(SEQ ID NO: 252)
EVQLEQSGAELVRPGASVKLSCKALGYTFTDYEMHWVKQTPVHGLEWIGA
IHPGSGGTAYNQKFKGKATLTADKSSSTAYMELSSLTSEDSAVYYCTNYG
SFAYWGQGTLVTVSAAKTTPPSVY

MIN-F2-3 HEAVY CHAIN VARIABLE REGION
AMINO ACID SEQUENCE
(SEQ ID NO: 253)
RCRLQQSGPELKKPGETVKISCKASGYTFINYGMNWVKQAPGKGLKWMGW
INTYTGEPTYVDDFKGRFAFSLETSARTAYLQINNLKNEDMATYFCARTG
TTAILNGMDYWGQGTSVTVSSAKTTPPSCL

MIN-F2-4 HEAVY CHAIN VARIABLE REGION
AMINO ACID SEQUENCE
(SEQ ID NO: 254)
EVQLEQSGPELKKPGETVKISCKASGYTFINYGMNWVKQAPGKGLKWMGW
INTYTGEPTYVDDFKGRFAFSLETSARTAYLQINNLKNEDMATYFCARTG
TTAILNGMDYWGQGTSVTVSSAKTTPPSVY

MIN-14 LIGHT CHAIN VARIABLE REGION
AMINO ACID SEQUENCE
(SEQ ID NO: 255)
DIQMTQSPSSLSASLGERVSLTCRASQDIGSSLNWLQQEPDGTIKRLIYA
TSSLDSGVPKRFSGSRSGSDYSLTISSLESEDFVDYYCLQYASSPHVRCW
DQAGAETGCCTNC

MIN-17-1 LIGHT CHAIN VARIABLE REGION
AMINO ACID SEQUENCE
(SEQ ID NO: 256)
DIVLTQSPASLAVSLGQRATISYRASKSVSTSGYSYMHWNQQKPGQPPRL
LIYLVSNLESGVPARFSGSGSGTDFTLNIHPVEEEDAATYYCQHIRELTR
SEGGPSW

MIN-17-2 LIGHT CHAIN VARIABLE REGION
AMINO ACID SEQUENCE
(SEQ ID NO: 257)
DIQMTQSPASQSASLGESVTITCLASQTIGTWLAWYQQKPGKSPQLLIYA
ATSLADGVPSRFSGSGSGTKFSFKISSLQAEDFVSYYCQQLYSTPWTFGG
GTKLEIKRADAAPTV

MIN-29 LIGHT CHAIN VARIABLE REGION
AMINO ACID SEQUENCE
(SEQ ID NO: 258)
DIVLTQSPASLAVSLGQRATISYRASKSVSTSGYSYMHWNQQKPGQPPRL
LIYLVSNLESGVPARFSGSGSGTDFTLNIHPVEEEDAATYYCQHIRELTR
SEGGPSW

-continued

MIN-34 LIGHT CHAIN VARIABLE REGION
AMINO ACID SEQUENCE
(SEQ ID NO: 259)
DIVLTQSPASLAVSLGQRATISYRASKSVSTSGYSYMHWNQQKPGQPPRL
LIYLVSNLESGVPARFSGSGSGTDFTLNIHPVEEEDAATYYCQHIRELTR
SEGGPSW

MIN-42 LIGHT CHAIN VARIABLE REGION
AMINO ACID SEQUENCE
(SEQ ID NO: 260)
DIVMTQSQKFMSTSVGDRVSVTCKASQNVGTNVGWYQQKPGQSPKALIYS
ASYRYSGVPDRFTGSGSGTDFTLTISNVQSEDLAEYFCQQYNNYPYTFGG
GTKLEIKRADAAPTV

MIN-45 LIGHT CHAIN VARIABLE REGION
AMINO ACID SEQUENCE
(SEQ ID NO: 261)
DIQMTQPPASLSASVGETVTITCRASGNIHNFLAWYQQKQGKSPQLLVYN
AKTLADGVPSRFSGSGSGTQYSLKINSLQPEDFGSYYCQHFWSTPWTFGG
GTKLEIKRADAAPTV

MIN-14 HEAVY CHAIN VARIABLE REGION
AMINO ACID SEQUENCE
(SEQ ID NO: 262)
QVQLQQPGAELVKPGASVKLSCKASGYTFTSYWMHWVKQRPGQGLEWIGE
INPSNGRTNYNEKFKSKATLTVDKSSSTAYMQLSSLTSEDSAVYYCATYG
NYWYF

MIN-17-2 HEAVY CHAIN VARIABLE REGION
AMINO ACID SEQUENCE
(SEQ ID NO: 263)
QITLKESGPGIVQPSQPFRLTCTFSGFSLSTSGIGVTWIRQPSGKGLEWL
ATIWWDDDNRYNPSLKSRLTVSKDTSNNQAFLNIITVETADTAIYYCAQS
TMVTA

MIN-17-1 HEAVY CHAIN VARIABLE REGION
AMINO ACID SEQUENCE
(SEQ ID NO: 264)
QVQLQQPGAELVKPGASVKLSCKASGYTFTSYWMHWVKQRPGQGLEWIGE
INPSNGRTNYNEK-FKSKATLTVDKSSSTAYMQLSSLTSEDSAVYYCATY
GNYWYF

MIN-29 HEAVY CHAIN VARIABLE REGION
AMINO ACID SEQUENCE
(SEQ ID NO: 265)
DVKLVESGGDLXKLTEGEDIWEGLTLCRDSDQSPLAPVSKPGRVVRPQRS
CTVIQGCVLRLQTAHLQVQGVLGIVSGDGESALHSVWIVGATTITINGCD
QLQPLLWSLANPRHVIATESESRGCTG

MIN-34 HEAVY CHAIN VARIABLE REGION
AMINO ACID SEQUENCE
(SEQ ID NO: 266)
QVQLKQSGPGLVQPSQSLSITCTVSGFSLTSYGVHWVRQSPGKGLEWLGV
IWGGGSTDYNAAFISRLSISKDNSKSQVFFKMNSLQANDTAIYYCARNDY
PAWF

MIN-42 HEAVY CHAIN VARIABLE REGION
AMINO ACID SEQUENCE
(SEQ ID NO: 267)
EVQLVESGGDLVKPGRSLKLSCAASGFTFSSFGMSWVRQTPDKRLEWVAT
ISSGGTYTYYPDSVKGRFTISRDNAKNTLYLQMSSLKSEDTAMYYCSRRF
YYDYD

-continued

MIN-45 HEAVY CHAIN VARIABLE REGION
AMINO ACID SEQUENCE
(SEQ ID NO: 268)
EVQLQQSGPELVKPGASVKISCKASGYSFTGYFMSWVMQSHGKSLEWIGR
INPYNGDTFYNQKFKGKATLTVDKSSTTAHIELRSLASEDSAVYYCARKG
LYG

DESCRIBES MIN-A2-1 LIGHT CHAIN VARIABLE
COMPLEMENTARITY DETERMINING REGION1 (CDR1)
AMINO ACID SEQUENCE.
(SEQ ID NO: 269)
SASSSISYIH

DESCRIBES MIN-A2-2 LIGHT CHAIN VARIABLE
COMPLEMENTARITY DETERMINING REGION1 (CDR1)
AMINO ACID SEQUENCE.
(SEQ ID NO: 270)
SASSSVSYMH

DESCRIBES MIN-C9-1 LIGHT CHAIN VARIABLE
COMPLEMENTARITY DETERMINING REGION1 (CDR1)
AMINO ACID SEQUENCE.
(SEQ ID NO: 271)
SASSSVSYMY

DESCRIBES MIN-C9-2 LIGHT CHAIN VARIABLE
COMPLEMENTARITY DETERMINING REGION1 (CDR1)
AMINO ACID SEQUENCE.
(SEQ ID NO: 272)
SASSSVSYTY

DESCRIBES MIN-D7-1 LIGHT CHAIN VARIABLE
COMPLEMENTARITY DETERMINING REGION1 (CDR1)
AMINO ACID SEQUENCE.
(SEQ ID NO: 273)
SASSSVSYMH

DESCRIBES MIN-D7-2 LIGHT CHAIN VARIABLE
COMPLEMENTARITY DETERMINING REGION1 (CDR1)
AMINO ACID SEQUENCE.
(SEQ ID NO: 274)
SASSSVSYMH

DESCRIBES MIN-F2-1 LIGHT CHAIN VARIABLE
COMPLEMENTARITY DETERMINING REGION1 (CDR1)
AMINO ACID SEQUENCE.
(SEQ ID NO: 275)
SASSSISYIH

DESCRIBES MIN-F2-2 LIGHT CHAIN VARIABLE
COMPLEMENTARITY DETERMINING REGION1 (CDR1)
AMINO ACID SEQUENCE.
(SEQ ID NO: 276)
SASSSISYIH

DESCRIBES MIN-A2-1 LIGHT CHAIN VARIABLE
COMPLEMENTARITY DETERMINING REGION2 (CDR2)
AMINO ACID SEQUENCE.
(SEQ ID NO: 277)
GTSNLAS

DESCRIBES MIN-A2-2 LIGHT CHAIN VARIABLE
COMPLEMENTARITY DETERMINING REGION2 (CDR2)
AMINO ACID SEQUENCE.
(SEQ ID NO: 278)
STSNLAS

DESCRIBES MIN-C9-1 LIGHT CHAIN VARIABLE
COMPLEMENTARITY DETERMINING REGION2 (CDR2)
AMINO ACID SEQUENCE.
(SEQ ID NO: 279)
STSNLAS

DESCRIBES MIN-C9-2 LIGHT CHAIN VARIABLE
COMPLEMENTARITY DETERMINING REGION2 (CDR2)
AMINO ACID SEQUENCE.
(SEQ ID NO: 280)
STSNLAS

-continued

DESCRIBES MIN-D7-1 LIGHT CHAIN VARIABLE COMPLEMENTARITY DETERMINING REGION2 (CDR2) AMINO ACID SEQUENCE.

(SEQ ID NO: 281)
STSNLAS

DESCRIBES MIN-D7-2 LIGHT CHAIN VARIABLE COMPLEMENTARITY DETERMINING REGION2 (CDR2) AMINO ACID SEQUENCE.

(SEQ ID NO: 282)
STSNLAS

DESCRIBES MIN-F2-1 LIGHT CHAIN VARIABLE COMPLEMENTARITY DETERMINING REGION2 (CDR2) AMINO ACID SEQUENCE.

(SEQ ID NO: 283)
GTSNLAS

DESCRIBES MIN-F2-2 LIGHT CHAIN VARIABLE COMPLEMENTARITY DETERMINING REGION2 (CDR2) AMINO ACID SEQUENCE.

(SEQ ID NO: 284)
GTSNLAS

DESCRIBES MIN-A2-1 LIGHT CHAIN VARIABLE COMPLEMENTARITY DETERMINING REGION3 (CDR3) AMINO ACID SEQUENCE.

(SEQ ID NO: 285)
QQRSNYPFT

DESCRIBES MIN-A2-2 LIGHT CHAIN VARIABLE COMPLEMENTARITY DETERMINING REGION3 (CDR3) AMINO ACID SEQUENCE.

(SEQ ID NO: 286)
QQRSSYPST

DESCRIBES MIN-C9-1 LIGHT CHAIN VARIABLE COMPLEMENTARITY DETERMINING REGION3 (CDR3) AMINO ACID SEQUENCE.

(SEQ ID NO: 287)
QQRSSYPST

DESCRIBES MIN-C9-2 LIGHT CHAIN VARIABLE COMPLEMENTARITY DETERMINING REGION3 (CDR3) AMINO ACID SEQUENCE.

(SEQ ID NO: 288)
QQRSSYPST

DESCRIBES MIN-D7-1 LIGHT CHAIN VARIABLE COMPLEMENTARITY DETERMINING REGION3 (CDR3) AMINO ACID SEQUENCE.

(SEQ ID NO: 289)
QQRSSYPST

DESCRIBES MIN-D7-2 LIGHT CHAIN VARIABLE COMPLEMENTARITY DETERMINING REGION3 (CDR3) AMINO ACID SEQUENCE.

(SEQ ID NO: 290)
QQRSSYPST

DESCRIBES MIN-F2-1 LIGHT CHAIN VARIABLE COMPLEMENTARITY DETERMINING REGION3 (CDR3) AMINO ACID SEQUENCE.

(SEQ ID NO: 291)
QQRSNYPFT

DESCRIBES MIN-F2-2 LIGHT CHAIN VARIABLE COMPLEMENTARITY DETERMINING REGION3 (CDR3) AMINO ACID SEQUENCE.

(SEQ ID NO: 292)
QQRSNYPFT

DESCRIBES MIN-A2-1 HEAVY CHAIN VARIABLE COMPLEMENTARITY DETERMINING REGION1 (CDR1) AMINO ACID SEQUENCE.

(SEQ ID NO: 293)
NYGMN

-continued

DESCRIBES MIN-A2-2 HEAVY CHAIN VARIABLE COMPLEMENTARITY DETERMINING REGION1 (CDR1) AMINO ACID SEQUENCE.

(SEQ ID NO: 294)
NYGMN

DESCRIBES MIN-C9-1 HEAVY CHAIN VARIABLE COMPLEMENTARITY DETERMINING REGION1 (CDR1) AMINO ACID SEQUENCE.

(SEQ ID NO: 295)
NNGMN

DESCRIBES MIN-C9-2 HEAVY CHAIN VARIABLE COMPLEMENTARITY DETERMINING REGION1 (CDR1) AMINO ACID SEQUENCE.

(SEQ ID NO: 296)
NNGMN

DESCRIBES MIN-D7-1 HEAVY CHAIN VARIABLE COMPLEMENTARITY DETERMINING REGION1 (CDR1) AMINO ACID SEQUENCE.

(SEQ ID NO: 297)
NYGMN

DESCRIBES MIN-D7-2 HEAVY CHAIN VARIABLE COMPLEMENTARITY DETERMINING REGION1 (CDR1) AMINO ACID SEQUENCE.

(SEQ ID NO: 298)
NYGMN

DESCRIBES MIN-F2-1 HEAVY CHAIN VARIABLE COMPLEMENTARITY DETERMINING REGION1 (CDR1) AMINO ACID SEQUENCE.

(SEQ ID NO: 299)
NYGMN

DESCRIBES MIN-F2-2 HEAVY CHAIN VARIABLE COMPLEMENTARITY DETERMINING REGION1 (CDR1) AMINO ACID SEQUENCE.

(SEQ ID NO: 300)
DYEMH

DESCRIBES MIN-F2-3 HEAVY CHAIN VARIABLE COMPLEMENTARITY DETERMINING REGION1 (CDR1) AMINO ACID SEQUENCE.

(SEQ ID NO: 301)
NYGMN

DESCRIBES MIN-F2-4 HEAVY CHAIN VARIABLE COMPLEMENTARITY DETERMINING REGION1 (CDR1) AMINO ACID SEQUENCE.

(SEQ ID NO: 302)
NYGMN

DESCRIBES MIN-A2-1 HEAVY CHAIN VARIABLE COMPLEMENTARITY DETERMINING REGION2 (CDR2) AMINO ACID SEQUENCE.

(SEQ ID NO: 303)
WINTYTGEPTYAGDFKG

DESCRIBES MIN-A2-2 HEAVY CHAIN VARIABLE COMPLEMENTARITY DETERMINING REGION2 (CDR2) AMINO ACID SEQUENCE.

(SEQ ID NO: 304)
WINTYTGEPTYAGDFKG

DESCRIBES MIN-C9-1 HEAVY CHAIN VARIABLE COMPLEMENTARITY DETERMINING REGION2 (CDR2) AMINO ACID SEQUENCE.

(SEQ ID NO: 305)
WINTYTGEPTYADDFKG

DESCRIBES MIN-C9-2 HEAVY CHAIN VARIABLE COMPLEMENTARITY DETERMINING REGION2 (CDR2) AMINO ACID SEQUENCE.

(SEQ ID NO: 306)
WINTYTGEPTYADDFKG

-continued

DESCRIBES MIN-D7-1 HEAVY CHAIN VARIABLE COMPLEMENTARITY DETERMINING REGION2 (CDR2) AMINO ACID SEQUENCE.

(SEQ ID NO: 307)

WINTYTGEPTYVDDFKG

DESCRIBES MIN-D7-2 HEAVY CHAIN VARIABLE COMPLEMENTARITY DETERMINING REGION2 (CDR2) AMINO ACID SEQUENCE.

(SEQ ID NO: 308)

WINTYTGEPTYAGDFKG

DESCRIBES MIN-F2-1 HEAVY CHAIN VARIABLE COMPLEMENTARITY DETERMINING REGION2 (CDR2) AMINO ACID SEQUENCE.

(SEQ ID NO: 309)

WINTYTGEPTYVDDFKG

DESCRIBES MIN-F2-2 HEAVY CHAIN VARIABLE COMPLEMENTARITY DETERMINING REGION2 (CDR2) AMINO ACID SEQUENCE.

(SEQ ID NO: 310)

AIHPGSGGTAYNQKFKG

DESCRIBES MIN-F2-3 HEAVY CHAIN VARIABLE COMPLEMENTARITY DETERMINING REGION2 (CDR2) AMINO ACID SEQUENCE.

(SEQ ID NO: 311)

WINTYTGEPTYVDDFKG

DESCRIBES MIN-F2-4 HEAVY CHAIN VARIABLE COMPLEMENTARITY DETERMINING REGION2 (CDR2) AMINO ACID SEQUENCE.

(SEQ ID NO: 312)

WINTYTGEPTYVDDFKG

DESCRIBES MIN-A2-1 HEAVY CHAIN VARIABLE COMPLEMENTARITY DETERMINING REGION3 (CDR3) AMINO ACID SEQUENCE.

(SEQ ID NO: 313)

SGDGYWYYA

DESCRIBES MIN-A2-2 HEAVY CHAIN VARIABLE COMPLEMENTARITY DETERMINING REGION3 (CDR3) AMINO ACID SEQUENCE.

(SEQ ID NO: 314)

SGDGYWYYA

DESCRIBES MIN-C9-1 HEAVY CHAIN VARIABLECOMPLEMENTARITY DETERMINING REGION3 (CDR3) AMINO ACID SEQUENCE.

(SEQ ID NO: 315)

TGTARAFYA

DESCRIBES MIN-C9-2 HEAVY CHAIN VARIABLECOMPLEMENTARITY DETERMINING REGION3 (CDR3) AMINO ACID SEQUENCE.

(SEQ ID NO: 316)

TGTARAFYA

DESCRIBES MIN-D7-1 HEAVY CHAIN VARIABLE COMPLEMENTARITY DETERMINING REGION3 (CDR3) AMINO ACID SEQUENCE.

(SEQ ID NO: 317)

TGTTAILNG

DESCRIBES MIN-D7-2 HEAVY CHAIN VARIABLE COMPLEMENTARITY DETERMINING REGION3 (CDR3) AMINO ACID SEQUENCE.

(SEQ ID NO: 318)

SGDGYWYYA

DESCRIBES MIN-F2-1 HEAVY CHAIN VARIABLE COMPLEMENTARITY DETERMINING REGION3 (CDR3) AMINO ACID SEQUENCE.

(SEQ ID NO: 319)

TGTTAILNG

-continued

DESCRIBES MIN-F2-2 HEAVY CHAIN VARIABLE COMPLEMENTARITY DETERMINING REGION3 (CDR3) AMINO ACID SEQUENCE.

(SEQ ID NO: 320)

YGSFA

DESCRIBES MIN-F2-3 HEAVY CHAIN VARIABLE COMPLEMENTARITY DETERMINING REGION3 (CDR3) AMINO ACID SEQUENCE.

(SEQ ID NO: 321)

TGTTAILNG

DESCRIBES MIN-F2-4 HEAVY CHAIN VARIABLE COMPLEMENTARITY DETERMINING REGION3 (CDR3) AMINO ACID SEQUENCE.

(SEQ ID NO: 322)

TGTTAILNG

DESCRIBES MIN-14 LIGHT CHAIN VARIABLE COMPLEMENTARITY DETERMINING REGION1 (CDR1) AMINO ACID SEQUENCE.

(SEQ ID NO: 323)

RASQDIGSSLN

DESCRIBES MIN-17-1 LIGHT CHAIN VARIABLE COMPLEMENTARITY DETERMINING REGION1 (CDR1) AMINO ACID SEQUENCE.

(SEQ ID NO: 324)

RASKSVSTSGYSYMH

DESCRIBES MIN-17-2 LIGHT CHAIN VARIABLE COMPLEMENTARITY DETERMINING REGION1 (CDR1) AMINO ACID SEQUENCE.

(SEQ ID NO: 325)

LASQTIGTWLA

DESCRIBES MIN-29 LIGHT CHAIN VARIABLE COMPLEMENTARITY DETERMINING REGION1 (CDR1) AMINO ACID SEQUENCE.

(SEQ ID NO: 326)

RASKSVSTSGYSYMH

DESCRIBES MIN-34 LIGHT CHAIN VARIABLE COMPLEMENTARITY DETERMINING REGION1 (CDR1) AMINO ACID SEQUENCE.

(SEQ ID NO: 327)

RASKSVSTSGYSYMH

DESCRIBES MIN-42 LIGHT CHAIN VARIABLE COMPLEMENTARITY DETERMINING REGION1 (CDR1) AMINO ACID SEQUENCE.

(SEQ ID NO: 328)

KASQNVGTNVG

DESCRIBES MIN-45 LIGHT CHAIN VARIABLE COMPLEMENTARITY DETERMINING REGION1 (CDR1) AMINO ACID SEQUENCE.

(SEQ ID NO: 329)

RASGNIHNFLA

DESCRIBES MIN-14 LIGHT CHAIN VARIABLE COMPLEMENTARITY DETERMINING REGION2 (CDR2) AMINO ACID SEQUENCE.

(SEQ ID NO: 330)

ATSSLDS

DESCRIBES MIN-17-1 LIGHT CHAIN VARIABLE COMPLEMENTARITY DETERMINING REGION2 (CDR2) AMINO ACID SEQUENCE.

(SEQ ID NO: 331)

LVSNLES

DESCRIBES MIN-17-2 LIGHT CHAIN VARIABLE COMPLEMENTARITY DETERMINING REGION2 (CDR2) AMINO ACID SEQUENCE.

(SEQ ID NO: 332)

AATSLAD

-continued

DESCRIBES MIN-29 LIGHT CHAIN VARIABLE COMPLEMENTARITY DETERMINING REGION2 (CDR2) AMINO ACID SEQUENCE.
(SEQ ID NO: 333)
LVSNLES

DESCRIBES MIN-34 LIGHT CHAIN VARIABLE COMPLEMENTARITY DETERMINING REGION2 (CDR2) AMINO ACID SEQUENCE.
(SEQ ID NO: 334)
LVSNLES

DESCRIBES MIN-42 LIGHT CHAIN VARIABLE COMPLEMENTARITY DETERMINING REGION2 (CDR2) AMINO ACID SEQUENCE.
(SEQ ID NO: 335)
SASYRYS

DESCRIBES MIN-45 LIGHT CHAIN VARIABLE COMPLEMENTARITY DETERMINING REGION2 (CDR2)AMINO ACID SEQUENCE.
(SEQ ID NO: 336)
NAKTLAD

DESCRIBES MIN-14 HEAVY CHAIN COMPLEMENTARITY DETERMINING REGION1 (CDR1) AMINO ACID SEQUENCE.
(SEQ ID NO: 337)
SYWMH

DESCRIBES MIN-17-1 HEAVY CHAIN COMPLEMENTARITY DETERMINING REGION1 (CDR1) AMINO ACID SEQUENCE.
(SEQ ID NO: 338)
SYWMH

DESCRIBES MIN-17-2 HEAVY CHAIN COMPLEMENTARITY DETERMINING REGION1 (CDR1) AMINO ACID SEQUENCE.
(SEQ ID NO: 339)
GIGVT

DESCRIBES MIN-34 HEAVY CHAIN COMPLEMENTARITY DETERMINING REGION1 (CDR1) AMINO ACID SEQUENCE.
(SEQ ID NO: 340)
SYGVH

DESCRIBES MIN-42 HEAVY CHAIN COMPLEMENTARITY DETERMINING REGION1 (CDR1) AMINO ACID SEQUENCE.
(SEQ ID NO: 341)
SFGMS

DESCRIBES MIN-45 HEAVY CHAIN COMPLEMENTARITY DETERMINING REGION1 (CDR1) AMINO ACID SEQUENCE.
(SEQ ID NO: 342)
GYFMS

DESCRIBES MIN-14 HEAVY CHAIN COMPLEMENTARITY DETERMINING REGION2 (CDR2) AMINO ACID SEQUENCE.
(SEQ ID NO: 343)
EINPSNGRTNYNEKFKS

DESCRIBES MIN-17-1 HEAVY CHAIN COMPLEMENTARITY DETERMINING REGION2 (CDR2) AMINO ACID SEQUENCE.
(SEQ ID NO: 344)
EINPSNGRTNYNEKFKS

DESCRIBES MIN-17-2 HEAVY CHAIN COMPLEMENTARITY DETERMINING REGION2 (CDR2) AMINO ACID SEQUENCE.
(SEQ ID NO: 345)
TIWWDDDNRYNPSLKS

-continued

DESCRIBES MIN-29 HEAVY CHAIN COMPLEMENTARITY DETERMINING REGION2 (CDR2) AMINO ACID SEQUENCE.
(SEQ ID NO: 346)
GIVSGDGESALHSVWIVG

DESCRIBES MIN-34 HEAVY CHAIN COMPLEMENTARITY DETERMINING REGION2 (CDR2) AMINO ACID SEQUENCE.
(SEQ ID NO: 347)
VIWGGGSTDYNAAFIS

DESCRIBES MIN-42 HEAVY CHAIN COMPLEMENTARITY DETERMINING REGION2 (CDR2) AMINO ACID SEQUENCE.
(SEQ ID NO: 348)
TISSGGTYTYYPDSVKG

DESCRIBES MIN-45 HEAVY CHAIN COMPLEMENTARITY DETERMINING REGION2 (CDR2) AMINO ACID SEQUENCE.
(SEQ ID NO: 349)
RINPYNGDTFYNQKFKG

HUMANIZED E6 HEAVY CHAIN VARIABLE REGION SEQUENCE:
(SEQ ID NO: 350)
EVQLVESGGGLVKPGGSLRLSCAASGFTFSRYGMSWVRQAPGKRLEWVST

ISGGGTYIYYPDSVKGRFTISRDNAKNTLYLQMNSLRAEDTAVYYCTRDN

YGRNYDYGMDYWGQGTLVTVSS

HUMANIZED E6 HEAVY CHAIN VARIABLE COMPLEMENTARITY DETERMINING REGIONS 1 (CDR1) SEQUENCE:
(SEQ ID NO: 351)
RYGMS

HUMANIZED E6 HEAVY CHAIN VARIABLE COMPLEMENTARITY DETERMINING REGIONS 2 (CDR2) SEQUENCE:
(SEQ ID NO: 352)
TISGGGTYIYYPDSVKG

HUMANIZED E6 HEAVY CHAIN VARIABLE COMPLEMENTARITY DETERMINING REGIONS 3 (CDR3) SEQUENCE:
(SEQ ID NO: 353)
DNYGRNYDYGMDY

HUMANIZED E6 LIGHT CHAIN VARIABLE REGION SEQUENCE:
(SEQ ID NO: 354)
EIVLTQSPATLSLSPGERATLTCSATSSVSYIHWYQQRPGQSPRLLIYST

SNLASGIPARFSGSGSGSDYTLTISSLEPEDFAVYYCQQRSSSPFTFGSG

TKVEIK

HUMANIZED E6 LIGHT CHAIN VARIABLE COMPLEMENTARITY DETERMINING REGIONS 1 (CDR1) SEQUENCE:
(SEQ ID NO: 355)
SATSSVSYIH

HUMANIZED E6 LIGHT CHAIN VARIABLE COMPLEMENTARITY DETERMINING REGIONS 2 (CDR2) SEQUENCE:
(SEQ ID NO: 356)
STSNLAS

HUMANIZED E6 LIGHT CHAIN VARIABLE COMPLEMENTARITY DETERMINING REGIONS 3 (CDR3) SEQUENCE:
(SEQ ID NO: 357)
QQRSSSPFT

-continued

HUMANIZED C2 HEAVY CHAIN VARIABLE REGION SEQUENCE:

(SEQ ID NO: 358)

EVQLVESGGGLVKPGGSLRLSCAASGFTFSGYAMSWVRQAPGKGLEWVST

ISSGGTYIYYPDSVKGRFTISRDNAKNSLYLQMNSLRAEDTAVYYCARLG

GDNYYEYFDVWGKGTTVTVSS

HUMANIZED C2 HEAVY CHAIN VARIABLE COMPLEMENTARITY DETERMINING REGIONS 1 (CDR1) SEQUENCE:

(SEQ ID NO: 359)

GYAMS

HUMANIZED C2 HEAVY CHAIN VARIABLE COMPLEMENTARITY DETERMINING REGIONS 2 (CDR2) SEQUENCE:

(SEQ ID NO: 360)

TISSGGTYIYYPDSVKG

HUMANIZED C2 HEAVY CHAIN VARIABLE COMPLEMENTARITY DETERMINING REGIONS 3 (CDR3) SEQUENCE:

(SEQ ID NO: 361)

LGGDNYYEYFDV

HUMANIZED C2 LIGHT CHAIN VARIABLE REGION SEQUENCE:

(SEQ ID NO: 362)

DIVLTQSPASLAVSPGQRATITCRASKSVSTSGYSYMHWYQQKPGQPPKL

LIYLASNLESGVPARFSGSGSGTDFTLTINPVEANDTANYYCQHSRELPF

TFGGGTKVEIKRT

HUMANIZED C2 LIGHT CHAIN VARIABLE COMPLEMENTARITY DETERMINING REGIONS 1 (CDR1) SEQUENCE:

(SEQ ID NO: 363)

RASKSVSTSGYSYMH

HUMANIZED C2 LIGHT CHAIN VARIABLE COMPLEMENTARITY DETERMINING REGIONS 2 (CDR2) SEQUENCE:

(SEQ ID NO: 364)

LASNLES

HUMANIZED C2 LIGHT CHAIN VARIABLE COMPLEMENTARITY DETERMINING REGIONS 3 (CDR3) SEQUENCE:

(SEQ ID NO: 365)

QHSRELPFT

HUMANIZED C2 LIGHT CHAIN VARIABLE COMPLEMENTARITY DETERMINING REGIONS 3 (CDR3) SEQUENCE:

(SEQ ID NO: 366)

LQSKNFPPT

PSECTAG2 C2 SCFV-FC (SEQ ID NO: 367)

METDTLLLWVLLLWVPGSTGDAAQPAEVQLVESGGGLVKPGGSLRLSCAA

SGFTFSGYAMSWVRQAPGKGLEWVSTISSGGTYIYYPDSVKGRFTISRDN

AKNSLYLQMNSLRAEDTAVYYCARLGGDNYYEYFDVWGKGTTVTVSSGGG

GSGGGGSGGGGSDIVLTQSPASLAVSPGQRATITCRASKSVSTSGYSYMH

WYQQKPGQPPKLLIYLASNLESGVPARFSGSGSGTDFTLTINPVEANDTA

NYYCQHSRELPFTFGGGTKVEIKRTEPKSCDKTHTCPPCPAPELLGGPSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENN

-continued

YKTTPPVLDSDGSFFLYSKLTVDKSRWQQGNVFSCSVMHEALHNHYTQKS

LSLSPGK**

PSECTAG2 E6 SCFV-FC (SEQ ID NO: 368)

METDTLLLWVLLLWVPGSTGDAAQPAEVQLVESGGGLVKPGGSLRLSCAA

SGFTFSRYGMSWVRQAPGKRLEWVSTISGGGTYIYYPDSVKGRFTISRDN

AKNTLYLQMNSLRAEDTAVYYCTRDNYGRNYDYGMDYWGQGTLVTVSSGG

GGSGGGGSGGGGSEIVLTQSPATLSLSPGERATLTCSATSSVSYIHWYQQ

RPGQSPRLLIYSTSNLASGIPARFSGSGSGSDYTLTISSLEPEDFAVYYC

QQRSSSPFTFGSGTKVEIKEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K**

HUMANIZED C2 SCFV (VH-VL) SEQUENCE:

(SEQ ID NO: 369)

EVQLVESGGGLVKPGGSLRLSCAASGFTFSGYAMSWVRQAPGKGLEWVST

ISSGGTYIYYPDSVKGRFTISRDNAKNSLYLQMNSLRAEDTAVYYCARLG

GDNYYEYFDVWGKGTTVTVSSGGGGSGGGGSGGGGSDIVLTQSPASLAVS

PGQRATITCRASKSVSTSGYSYMHWYQQKPGQPPKLLIYLASNLESGVPA

RFSGSGSGTDFTLTINPVEANDTANYYCQHSRELPFTFGGGTKVEIKRT

HUMANIZED E6 SCFV (VL-VH) SEQUENCE:

(SEQ ID NO: 370)

DIVLTQSPASLAVSPGQRATITCRASKSVSTSGYSYMHWYQQKPGQPPKL

LIYLASNLESGVPARFSGSGSGTDFTLTINPVEANDTANYYCQHSRELPF

TFGGGTKVEIKRTGGGGSGGGGSGGGGSEVQLVESGGGLVKPGGSLRLSC

AASGFTFSGYAMSWVRQAPGKGLEWVSTISSGGTYIYYPDSVKGRFTISR

DNAKNSLYLQMNSLRAEDTAVYYCARLGGDNYYEYFDVWGKGTTVTVSS

HUMANIZED C3 HEAVY CHAIN VARIABLE REGION SEQUENCE:

(SEQ ID NO: 371)

QVQLVQSGAEVKKPGASVKVSCKASGYTFTDYAMNWVRQAPGQGLEWMGV

ISTFSGNTNFNQKFKGRVTMTTDTSTSTAYMELRSLRSDDTAVYYCARSD

YYGPYFDYWGQGTTLTVSS

HUMANIZED C3 HEAVY CHAIN VARIABLE COMPLEMENTARITY DETERMINING REGIONS 1 (CDR1) SEQUENCE:

(SEQ ID NO: 372)

DYAMN

HUMANIZED C3 HEAVY CHAIN VARIABLE COMPLEMENTARITY DETERMINING REGIONS 2 (CDR2) SEQUENCE:

(SEQ ID NO: 373)

VISTFSGNTNFNQKFKG

HUMANIZED C3 HEAVY CHAIN VARIABLE COMPLEMENTARITY DETERMINING REGIONS 3 (CDR3) SEQUENCE:

(SEQ ID NO: 374)

SDYYGPYFDY

-continued

HUMANIZED C3 LIGHT CHAIN VARIABLE REGION SEQUENCE:
(SEQ ID NO: 375)
DIVMTQTPLSLSVTPGQPASISCRSSQTIVHSNGNTYLEWYLQKPGQSPQ

LLIYKVSNRFSGVPDRFSGSGSGTDFTLKISRVEAEDVGVYYCFQGSHVP

FTFGGGTKVEIKRT

HUMANIZED C3 LIGHT CHAIN VARIABLE COMPLEMENTARITY DETERMINING REGIONS 1 (CDR1) SEQUENCE:
(SEQ ID NO: 376)
RSSQTIVHSNGNTYLE

HUMANIZED C3 LIGHT CHAIN VARIABLE COMPLEMENTARITY DETERMINING REGIONS 2 (CDR2) SEQUENCE:
(SEQ ID NO: 377)
KVSNRFS

HUMANIZED C3 LIGHT CHAIN VARIABLE COMPLEMENTARITY DETERMINING REGIONS 3 (CDR3) SEQUENCE:
(SEQ ID NO: 378)
FQGSHVPFT

HUMANIZED C8 HEAVY CHAIN VARIABLE REGION SEQUENCE:
(SEQ ID NO: 379)
EVQLVESGGGLVKPGGSLRLSCAASGFTFSGYAMSWVRQAPGKGLEWVST

ISSGGTYIYYPDSVKGRFTISRDNAKNSLYLQMNSLRAEDTAVYYCARLG

GDNYYEYWGKGTTVTVSS

HUMANIZED C8 HEAVY CHAIN VARIABLE COMPLEMENTARITY DETERMINING REGION1 (CDR1) SEQUENCE:
(SEQ ID NO: 380)
GYAMS

HUMANIZED C8 HEAVY CHAIN VARIABLE

-continued

COMPLEMENTARITY DETERMINING REGION2 (CDR2) SEQUENCE:
(SEQ ID NO: 381)
TISSGGTYIYYPDSVKG

HUMANIZED C8 HEAVY CHAIN VARIABLE COMPLEMENTARITY DETERMINING REGION3 (CDR3) SEQUENCE:
(SEQ ID NO: 382)
LGGDNYYEY

HUMANIZED C8 LIGHT CHAIN VARIABLE REGION SEQUENCE
(SEQ ID NO: 383)
DIVMTQSPDSLAVSLGERATINCRASKSVSTSGYSYMHWYQQKPGQPPKL

LIYLVSNLESGVPDRFSGSGSGTDFTLTISSLQAEDVAVYYCQHIRELTR

SEFGGGTKVEIKRT

HUMANIZED C8 LIGHT CHAIN VARIABLE COMPLEMENTARITY DETERMINING REGION1 (CDR1) SEQUENCE:
(SEQ ID NO: 384)
RASKSVSTSGYSYM

HUMANIZED C8 LIGHT CHAIN VARIABLE COMPLEMENTARITY DETERMINING REGION2 (CDR2) SEQUENCE:
(SEQ ID NO: 385)
LVSNLES

HUMANIZED C8 LIGHT CHAIN VARIABLE COMPLEMENTARITY DETERMINING REGION3 (CDR3) SEQUENCE:
(SEQ ID NO: 386)
QHIRELTRSE

All of the references cited herein are incorporated by reference in their entirety.

Those skilled in the art will recognize, or be able to ascertain using no more than routine experimentation, many equivalents to the specific embodiments of the invention specifically described herein.

What is claimed is:

1. An anti-MUC1* antibody or antibody fragment comprising the following six complementarity determining regions (CDRs):

SEQ ID NOs: 144, 146, 148, 150, 152, and 154,
SEQ ID NOs: 80, 82, 84, 86, 88, and 90,
SEQ ID NOs: 112, 114, 116, 118, 120, and 122,
SEQ ID NOs: 128, 130, 132, 134, 136, and 138,
SEQ ID NOs: 160, 162, 164, 166, 168, and 170,
SEQ ID NOs: 176, 178, 180, 182, 184, and 186,
SEQ ID NOs: 192, 194, 196, 198, 200, and 202,
SEQ ID NOs: 208, 210, 212, 214, 216, and 218,
SEQ ID NOs: 224, 226, 228, 230, 232, and 234,
SEQ ID NOs: 48, 50, 52, 54, 56, and 58,
SEQ ID NOs: 64, 66, 68, 70, 72, and 74,
SEQ ID NOs: 16, 18, 20, 22, 24, and 26, or
SEQ ID NOs: 32, 34, 36, 38, 40, and 42;

wherein the six CDRs of each antibody or antibody fragment are heavy chain CDR1, heavy chain CDR2, heavy chain CDR3, light chain CDR1, light chain CDR2, and light chain CDR3, respectively.

2. The anti-MUC1* antibody or antibody fragment of claim 1, wherein the antibody or antibody fragment comprises the following six CDRs: SEQ ID NOs: 144, 146, 148, 150, 152, and 154.

3. The anti-MUC1* antibody or antibody fragment of claim 1, wherein the antibody or antibody fragment comprises the following six CDRs: SEQ ID NOs: 80, 82, 84, 86, 88, and 90.

4. The anti-MUC1* antibody or antibody fragment of claim 1, wherein the antibody or antibody fragment comprises the following six CDRs: SEQ ID NOs: 112, 114, 116, 118, 120, and 122.

5. The anti-MUC1* antibody or antibody fragment of claim 1, wherein the antibody or antibody fragment is humanized.

6. A conjugate comprising the anti-MUC1* antibody or antibody fragment of claim 1 attached to an imaging agent, a dye, a fluorescent entity, a color producing reagent or any other entity that renders the antibody or antibody fragment optically, visually, electrically or radioactively detectable.

7. A method of diagnosing cancer in a subject comprising contacting a cell or tissue of the subject with the conjugate of claim 6.

8. The method of claim 7, wherein the contacting is carried out in vitro.

9. The method of claim 7, wherein the contacting is carried out in vivo.

10. The method of claim 7, wherein the diagnosing further comprises: a) determining that: i. an amount of the antibody or antibody fragment of the conjugate of claim 6 binding to the cell or tissue is greater than an amount of the antibody or antibody fragment of the conjugate of claim 6 bound to a normal cell or normal tissue; or ii. a pattern of the antibody or antibody fragment of the conjugate of claim 6 binding to the cell or tissue is not restricted to an apical border of the cell or tissue; and b) concluding that the subject is suffering from a MUC1* positive cancer.

11. A method of determining suitability of treating a patient suffering from cancer or metastasis of cancer with a MUC1* targeting therapeutic agent comprising the anti-MUC1* antibody or antibody fragment of claim 1, the method comprising contacting a cell or tissue from the patient with the conjugate of claim 6.

12. The method of claim 11, further comprising: a) determining that the conjugate binds specifically to the cell or tissue; and b) concluding that the patient is suitable for treatment with the MUC1* targeting therapeutic agent comprising the anti-MUC1* antibody or antibody fragment of claim 1.

13. A method of treating a MUC1* positive cancer in a subject, comprising: a) determining that the conjugate of claim 6 specifically binds to a cell or tissue of the MUC1* positive cancer; and b) administering a MUC1* targeting therapeutic agent comprising the anti-MUC1* antibody or antibody fragment of claim 1, to the subject.

14. The method of claim 13, wherein the MUC1* targeting therapeutic agent comprises a T cell comprising a chimeric antigen receptor (CAR) comprising the anti-MUC1* antibody or antibody fragment of claim 1.

15. The method of claim 13, wherein the MUC1* targeting therapeutic agent comprises a bispecific T cell engager comprising the anti-MUC1* antibody or antibody fragment of claim 1.

16. The method of claim 13, wherein the MUC1* targeting therapeutic agent comprises an antibody drug conjugate comprising the anti-MUC1* antibody or antibody fragment of claim 1.

* * * * *

SEQUENCE LISTING

```
Sequence total quantity: 386
SEQ ID NO: 1            moltype = AA  length = 1255
FEATURE                 Location/Qualifiers
REGION                  1..1255
                        note = Full-length MUC1 Receptor (Mucin 1 precursor,
                         Genbank Accession number: P15941
source                  1..1255
                        mol_type = protein
                        organism = synthetic construct
SEQUENCE: 1
MTPGTQSPFF LLLLLTVLTV VTGSGHASST PGGEKETSAT QRSSVPSSTE KNAVSMTSSV  60
LSSHSPGSGS STTQGQDVTL APATEPASGS AATWGQDVTS VPVTRPALGS TTPPAHDVTS  120
APDNKPAPGS TAPPAHGVTS APDTRPAPGS TAPPAHGVTS APDTRPAPGS TAPPAHGVTS  180
APDTRPAPGS TAPPAHGVTS APDTRPAPGS TAPPAHGVTS APDTRPAPGS TAPPAHGVTS  240
APDTRPAPGS TAPPAHGVTS APDTRPAPGS TAPPAHGVTS APDTRPAPGS TAPPAHGVTS  300
APDTRPAPGS TAPPAHGVTS APDTRPAPGS TAPPAHGVTS APDTRPAPGS TAPPAHGVTS  360
APDTRPAPGS TAPPAHGVTS APDTRPAPGS TAPPAHGVTS APDTRPAPGS TAPPAHGVTS  420
APDTRPAPGS TAPPAHGVTS APDTRPAPGS TAPPAHGVTS APDTRPAPGS TAPPAHGVTS  480
APDTRPAPGS TAPPAHGVTS APDTRPAPGS TAPPAHGVTS APDTRPAPGS TAPPAHGVTS  540
APDTRPAPGS TAPPAHGVTS APDTRPAPGS TAPPAHGVTS APDTRPAPGS TAPPAHGVTS  600
APDTRPAPGS TAPPAHGVTS APDTRPAPGS TAPPAHGVTS APDTRPAPGS TAPPAHGVTS  660
APDTRPAPGS TAPPAHGVTS APDTRPAPGS TAPPAHGVTS APDTRPAPGS TAPPAHGVTS  720
APDTRPAPGS TAPPAHGVTS APDTRPAPGS TAPPAHGVTS APDTRPAPGS TAPPAHGVTS  780
APDTRPAPGS TAPPAHGVTS APDTRPAPGS TAPPAHGVTS APDTRPAPGS TAPPAHGVTS  840
APDTRPAPGS TAPPAHGVTS APDTRPAPGS TAPPAHGVTS APDTRPAPGS TAPPAHGVTS  900
APDTRPAPGS TAPPAHGVTS APDTRPAPGS TAPPAHGVTS APDNRPALGS TAPPVHNVTS  960
ASGSASGSAS TLVHNGTSAR ATTTPASKST PFSIPSHHSD TPTTLASHST KTDASSTHHS  1020
SVPPLTSSNH STSPQLSTGV SFFFLSFHIS NLQFNSSLED PSTDYYQELQ RDISEMFLQI  1080
YKQGGFLGLS NIKFRPGSVV VQLTLAFREG TINVHDVETQ FNQYKTEAAS RYNLTISDVS  1140
VSDVPFPFSA QSGAGVPGWG IALLVLVCVL VALAIVYLIA LAVCQCRRKN YGQLDIFPAR  1200
```

-continued

```
DTYHPMSEYP TYHTHGRYVP PSSTDRSPYE KVSAGNGGSS LSYTNPAVAA ASANL       1255

SEQ ID NO: 2            moltype = AA  length = 171
FEATURE                 Location/Qualifiers
REGION                  1..171
                        note = A truncated MUC1 receptor isoform having nat-PSMGFR
                         and PSIBR at its N-terminus and including the
                         transmembrane and cytoplasmic sequences of a full-length
                         MUC1 receptor which may be cleaved after translation and
                         prior to expression of the receptor on the
source                  1..171
                        mol_type = protein
                        organism = synthetic construct
SEQUENCE: 2
GFLGLSNIKF RPGSVVVQLT LAFREGTINV HDVETQFNQY KTEAASRYNL TISDVSVSDV  60
PFPFSAQSGA GVPGWGIALL VLVCVLVALA IVYLIALAVC QCRRKNYGQL DIFPARDTYH  120
PMSEYPTYHT HGRYVPPSST DRSPYEKVSA GNGGSSLSYT NPAVAAASAN L           171

SEQ ID NO: 3            moltype = AA  length = 275
FEATURE                 Location/Qualifiers
REGION                  1..275
                        note = A truncated MUC1 receptor isoform having nat-PSMGFR
                         + PSIBR + Unique Region at its N-terminus and including
                         the transmembrane and cytoplasmic sequences of a
                         full-length MUC1 receptor
source                  1..275
                        mol_type = protein
                        organism = synthetic construct
SEQUENCE: 3
ATTTPASKST PFSIPSHHSD TPTTLASHST KTDASSTHHS TVPPLTSSNH STSPQLSTGV  60
SFFFLSFHIS NLQFNSSLED PSTDYYQELQ RDISEMFLQI YKQGGFLGLS NIKFRPGSVV  120
VQLTLAFREG TINVHDVETQ FNQYKTEAAS RYNLTISDVS VSDVPFPFSA QSGAGVPGWG  180
IALLVLVCVL VALAIVYLIA LAVCQCRRKN YGQLDIFPAR DTYHPMSEYP TYHTHGRYVP  240
PSSTDRSPYE KVSAGNGGSS LSYTNPAVAA ASANL                             275

SEQ ID NO: 4            moltype = AA  length = 45
FEATURE                 Location/Qualifiers
REGION                  1..45
                        note = PSMGFR
source                  1..45
                        mol_type = protein
                        organism = synthetic construct
SEQUENCE: 4
GTINVHDVET QFNQYKTEAA SRYNLTISDV SVSDVPFPFS AQSGA                  45

SEQ ID NO: 5            moltype = AA  length = 43
FEATURE                 Location/Qualifiers
REGION                  1..43
                        note = PSMGFR N+20/C-22
source                  1..43
                        mol_type = protein
                        organism = synthetic construct
SEQUENCE: 5
SNIKFRPGSV VVQLTLAFRE GTINVHDVET QFNQYKTEAA SRY                    43

SEQ ID NO: 6            moltype = AA  length = 35
FEATURE                 Location/Qualifiers
REGION                  1..35
                        note = PSMGFR N+12/C-22
source                  1..35
                        mol_type = protein
                        organism = synthetic construct
SEQUENCE: 6
SVVVQLTLAF REGTINVHDV ETQFNQYKTE AASRY                             35

SEQ ID NO: 7            moltype = AA  length = 24
FEATURE                 Location/Qualifiers
REGION                  1..24
                        note = PSMGFR N+9/C-30
source                  1..24
                        mol_type = protein
                        organism = synthetic construct
SEQUENCE: 7
VQLTLAFREG TINVHDVETQ FNQY                                         24

SEQ ID NO: 8            moltype = AA  length = 24
FEATURE                 Location/Qualifiers
REGION                  1..24
                        note = PSMGFR N+20/C-41
```

-continued

```
source                  1..24
                        mol_type = protein
                        organism = synthetic construct
SEQUENCE: 8
SNIKFRPGSV VVQLTLAFRE GTIN                                          24

SEQ ID NO: 9            moltype = AA  length = 38
FEATURE                 Location/Qualifiers
REGION                  1..38
                        note = PSMGFR N+20/C-27
source                  1..38
                        mol_type = protein
                        organism = synthetic construct
SEQUENCE: 9
SNIKFRPGSV VVQLTLAFRE GTINVHDVET QFNQYKTE                           38

SEQ ID NO: 10           moltype = AA  length = 45
FEATURE                 Location/Qualifiers
REGION                  1..45
                        note = PSMGFR N+9/C-9
source                  1..45
                        mol_type = protein
                        organism = synthetic construct
SEQUENCE: 10
VQLTLAFREG TINVHDVETQ FNQYKTEAAS RYNLTISDVS VSDVP                   45

SEQ ID NO: 11           moltype = DNA  length = 426
FEATURE                 Location/Qualifiers
misc_feature            1..426
                        note = Antibody 17H6 Heavy chain - Signal
                         sequence-FR1-CDR1-FR2-CDR2-FR3-CDR3-FR4
source                  1..426
                        mol_type = other DNA
                        organism = synthetic construct
SEQUENCE: 11
atgaagttgt ggctgaactg gattttcctt gtaacacttt taaatggtat ccagtgtgag  60
gtgaagctgg tggagtctgg aggaggcttg gtacagcctg gggggttctct gagactctcc 120
tgtgcaactt ctgggttcac cttcactgat tactacatga gctgggtccg ccagcctcca  180
agaaaggcac ttgagtggtt gggttttatt agaaacaaag ctaatggtta cacagcagag  240
tacagtgcgt ctgtgaaggg tcggttcacc atctccagag atgtttccca aaacctcctc  300
tatcttcaaa tgaacatcct gagagctgag gacagtgcca cttattactg tgcaaaagat  360
tactacggta gtaaccctgc ctggtttgct tactggggcc aagggactct ggtcactgtc  420
tctgca                                                              426

SEQ ID NO: 12           moltype = AA  length = 142
FEATURE                 Location/Qualifiers
REGION                  1..142
                        note = Antibody 17H6 Heavy chain - Signal
                         peptide-FR1-CDR1-FR2-CDR2-FR3-CDR3-FR4
source                  1..142
                        mol_type = protein
                        organism = synthetic construct
SEQUENCE: 12
MKLWLNWIFL VTLLNGIQCE VKLVESGGGL VQPGGSLRLS CATSGFTFTD YYMSWVRQPP  60
RKALEWLGFI RNKANGYTAE YSASVKGRFT ISRDVSQNLL YLQMNILRAE DSATYYCAKD  120
YYGSNPAWFA YWGQGTLVTV SA                                            142

SEQ ID NO: 13           moltype = DNA  length = 393
FEATURE                 Location/Qualifiers
misc_feature            1..393
                        note = Antibody 17H6 Light chain - Signal
                         sequence-FR1-CDR1-FR2-CDR2-FR3-CDR3-FR4
source                  1..393
                        mol_type = other DNA
                        organism = synthetic construct
SEQUENCE: 13
atgaagttgc ctgtgaggct gttggtgctg atgttctgga ttcctgcttc caacagtgat  60
attttgatga cccagactcc actctccctg cctgtcagtc ttggagatca agcctccatc  120
tcttgcagat ctagtcagag cattgtacat agtagtggaa acaccttttt agaatggtac  180
ctgcagaaac ctggccagtc tccaaagctc ctgatctaca aagtttccaa ccgattttct  240
ggggtcccag acaggttcag tggcagtgga tcagggatag atttcacact caagatcagc  300
agagtggagg ctgaggatct gggagtttat tactgctttc aaggttcaca tgttcctttc  360
acgttcggct cggggacaaa gttggaaata aaa                                393

SEQ ID NO: 14           moltype = AA  length = 131
FEATURE                 Location/Qualifiers
REGION                  1..131
                        note = Antibody 17H6 Light chain - Signal
                         peptide-FR1-CDR1-FR2-CDR2-FR3-CDR3-FR4
```

```
source                  1..131
                        mol_type = protein
                        organism = synthetic construct
SEQUENCE: 14
MKLPVRLLVL MFWIPASNSD ILMTQTPLSL PVSLGDQASI SCRSSQSIVH SSGNTFLEWY  60
LQKPGQSPKL LIYKVSNRFS GVPDRFSGSG SGIDFTLKIS RVEAEDLGVY YCFQGSHVPF  120
TFGSGTKLEI K                                                      131

SEQ ID NO: 15           moltype = DNA  length = 15
FEATURE                 Location/Qualifiers
misc_feature            1..15
                        note = Antibody 17H6 Heavy Chain CDR1
source                  1..15
                        mol_type = other DNA
                        organism = synthetic construct
SEQUENCE: 15
gattactaca tgagc                                                  15

SEQ ID NO: 16           moltype = AA  length = 5
FEATURE                 Location/Qualifiers
REGION                  1..5
                        note = Antibody 17H6 Heavy Chain CDR1
source                  1..5
                        mol_type = protein
                        organism = synthetic construct
SEQUENCE: 16
DYYMS                                                             5

SEQ ID NO: 17           moltype = DNA  length = 57
FEATURE                 Location/Qualifiers
misc_feature            1..57
                        note = Antibody 17H6 Heavy Chain CDR2
source                  1..57
                        mol_type = other DNA
                        organism = synthetic construct
SEQUENCE: 17
tttattagaa acaaagctaa tggttacaca gcagagtaca gtgcgtctgt gaagggt     57

SEQ ID NO: 18           moltype = AA  length = 19
FEATURE                 Location/Qualifiers
REGION                  1..19
                        note = Antibody 17H6 Heavy Chain CDR
source                  1..19
                        mol_type = protein
                        organism = synthetic construct
SEQUENCE: 18
FIRNKANGYT AEYSASVKG                                              19

SEQ ID NO: 19           moltype = DNA  length = 36
FEATURE                 Location/Qualifiers
misc_feature            1..36
                        note = Antibody 17H6 Heavy Chain CDR3
source                  1..36
                        mol_type = other DNA
                        organism = synthetic construct
SEQUENCE: 19
gattactacg gtagtaaccc tgcctggttt gcttac                           36

SEQ ID NO: 20           moltype = AA  length = 12
FEATURE                 Location/Qualifiers
REGION                  1..12
                        note = Antibody 17H6 Heavy Chain CDR3
source                  1..12
                        mol_type = protein
                        organism = synthetic construct
SEQUENCE: 20
DYYGSNPAWF AY                                                     12

SEQ ID NO: 21           moltype = DNA  length = 48
FEATURE                 Location/Qualifiers
misc_feature            1..48
                        note = Antibody 17H6 Light Chain CDR1
source                  1..48
                        mol_type = other DNA
                        organism = synthetic construct
SEQUENCE: 21
agatctagtc agagcattgt acatagtagt ggaaacacct ttttagaa              48

SEQ ID NO: 22           moltype = AA  length = 16
```

-continued

```
FEATURE                Location/Qualifiers
REGION                 1..16
                       note = Antibody 17H6 Light Chain CDR1
source                 1..16
                       mol_type = protein
                       organism = synthetic construct
SEQUENCE: 22
RSSQSIVHSS GNTFLE                                            16

SEQ ID NO: 23          moltype = DNA  length = 21
FEATURE                Location/Qualifiers
misc_feature           1..21
                       note = Antibody 17H6 Light Chain CDR2
source                 1..21
                       mol_type = other DNA
                       organism = synthetic construct
SEQUENCE: 23
aaagtttcca accgattttc t                                      21

SEQ ID NO: 24          moltype = AA  length = 7
FEATURE                Location/Qualifiers
REGION                 1..7
                       note = Antibody 17H6 Light Chain CDR2
source                 1..7
                       mol_type = protein
                       organism = synthetic construct
SEQUENCE: 24
KVSNRFS                                                      7

SEQ ID NO: 25          moltype = DNA  length = 27
FEATURE                Location/Qualifiers
misc_feature           1..27
                       note = Antibody 17H6 Light Chain CDR3
source                 1..27
                       mol_type = other DNA
                       organism = synthetic construct
SEQUENCE: 25
tttcaaggtt cacatgttcc tttcacg                                27

SEQ ID NO: 26          moltype = AA  length = 9
FEATURE                Location/Qualifiers
REGION                 1..9
                       note = Antibody 17H6 Light Chain CDR3
source                 1..9
                       mol_type = protein
                       organism = synthetic construct
SEQUENCE: 26
FQGSHVPFT                                                    9

SEQ ID NO: 27          moltype = DNA  length = 408
FEATURE                Location/Qualifiers
misc_feature           1..408
                       note = Antibody 39H5 Heavy chain - Signal
                        sequence-FR1-CDR1-FR2-CDR2-FR3-CDR3-FR4
source                 1..408
                       mol_type = other DNA
                       organism = synthetic construct
SEQUENCE: 27
atggcttggg tgtggacctt gctattcctg atggcagctg cccaaagtgc ccaagcacag  60
atccagttgg tgcagtctgg acctgagctg aagaagcctg gagagacagt caagatctcc  120
tgcaaggctt ctgggtatac cttcacaaac tatggaatga actgggtgaa gcaggctcca  180
ggaaagggtt taaagtggat gggctggata aacacctaca ctggagagcc aacatatgtt  240
ggtgacttca agggacggtt tgccttctct ttggagacct ctgccagcac tgcctatttg  300
cagatcaaca acctcaaaaa tgaggacacg gctacatatt tttgtgttag aggtatccac  360
ggctacgtgg actactgggg ccaaggcacc actctcacag tctcctca             408

SEQ ID NO: 28          moltype = AA  length = 136
FEATURE                Location/Qualifiers
REGION                 1..136
                       note = Antibody 39H5 Heavy chain - Signal
                        sequence-FR1-CDR1-FR2-CDR2-FR3-CDR3-FR4
source                 1..136
                       mol_type = protein
                       organism = synthetic construct
SEQUENCE: 28
MAWVWTLLFL MAAAQSAQAQ IQLVQSGPEL KKPGETVKIS CKASGYTFTN YGMNWVKQAP  60
GKGLKWMGWI NTYTGEPTYV GDFKGRFAFS LETSASTAYL QINNLKNEDT ATYFCVRGIH  120
GYVDYWGQGT TLTVSS                                            136
```

-continued

```
SEQ ID NO: 29          moltype = DNA  length = 393
FEATURE                Location/Qualifiers
misc_feature           1..393
                       note = Antibody 39H5 Light chain - Signal
                        sequence-FR1-CDR1-FR2-CDR2-FR3-CDR3-FR4
source                 1..393
                       mol_type = other DNA
                       organism = synthetic construct
SEQUENCE: 29
atgaagttgc ctgttaggct gttggtgctg atgttctgga ttcctgcttc cagcagtgat  60
gttttgatga cccaaactcc actctccctg cctgtcagtc ttggagatca agcctccatc  120
tcttgcagat ctagtcagag cattgtacat agaaatggaa acacctattt agaatggtac  180
ctgcagaaac caggccagtc tccaaagctc ctgatctaca aagtttccaa ccgattttct  240
ggggtcccag acaggttcag tggcagtgga tcagggacag atttcacact caagatcagc  300
agagtggagg ctgaggatct gggagtttat tactgctttc aaggttcaca tcttccgtgg  360
acgttcggtg gaggcaccaa gctggaaatc aaa                               393

SEQ ID NO: 30          moltype = AA  length = 131
FEATURE                Location/Qualifiers
REGION                 1..131
                       note = Antibody 39H5 Light chain - Signal
                        sequence-FR1-CDR1-FR2-CDR2-FR3-CDR3-FR4
source                 1..131
                       mol_type = protein
                       organism = synthetic construct
SEQUENCE: 30
MKLPVRLLVL MFWIPASSSD VLMTQTPLSL PVSLGDQASI SCRSSQSIVH RNGNTYLEWY  60
LQKPGQSPKL LIYKVSNRFS GVPDRFSGSG SGTDFTLKIS RVEAEDLGVY YCFQGSHLPW  120
TFGGGTKLEI K                                                       131

SEQ ID NO: 31          moltype = DNA  length = 15
FEATURE                Location/Qualifiers
misc_feature           1..15
                       note = Antibody 39H5 Heavy Chain CDR1
source                 1..15
                       mol_type = other DNA
                       organism = synthetic construct
SEQUENCE: 31
aactatggaa tgaac                                                   15

SEQ ID NO: 32          moltype = AA  length = 5
FEATURE                Location/Qualifiers
REGION                 1..5
                       note = Antibody 39H5 Heavy Chain CDR1
source                 1..5
                       mol_type = protein
                       organism = synthetic construct
SEQUENCE: 32
NYGMN                                                              5

SEQ ID NO: 33          moltype = DNA  length = 51
FEATURE                Location/Qualifiers
misc_feature           1..51
                       note = Antibody 39H5 Heavy Chain CDR2
source                 1..51
                       mol_type = other DNA
                       organism = synthetic construct
SEQUENCE: 33
tggataaaca cctacactgg agagccaaca tatgttggtg acttcaaggg a           51

SEQ ID NO: 34          moltype = AA  length = 17
FEATURE                Location/Qualifiers
REGION                 1..17
                       note = Antibody 39H5 Heavy Chain CDR2
source                 1..17
                       mol_type = protein
                       organism = synthetic construct
SEQUENCE: 34
WINTYTGEPT YVGDFKG                                                 17

SEQ ID NO: 35          moltype = DNA  length = 24
FEATURE                Location/Qualifiers
misc_feature           1..24
                       note = Antibody 39H5 Heavy Chain CDR3
source                 1..24
                       mol_type = other DNA
                       organism = synthetic construct
SEQUENCE: 35
ggtatccacg gctacgtgga ctac                                         24
```

```
SEQ ID NO: 36           moltype = AA  length = 8
FEATURE                 Location/Qualifiers
REGION                  1..8
                        note = Antibody 39H5 Heavy Chain CDR3
source                  1..8
                        mol_type = protein
                        organism = synthetic construct
SEQUENCE: 36
GIHGYVDY                                                          8

SEQ ID NO: 37           moltype = DNA  length = 48
FEATURE                 Location/Qualifiers
misc_feature            1..48
                        note = Antibody 39H5 Light Chain CDR1
source                  1..48
                        mol_type = other DNA
                        organism = synthetic construct
SEQUENCE: 37
agatctagtc agagcattgt acatagaaat ggaaacacct atttagaa              48

SEQ ID NO: 38           moltype = AA  length = 16
FEATURE                 Location/Qualifiers
REGION                  1..16
                        note = Antibody 39H5 Light Chain CDR1
source                  1..16
                        mol_type = protein
                        organism = synthetic construct
SEQUENCE: 38
RSSQSIVHRN GNTYLE                                                 16

SEQ ID NO: 39           moltype = DNA  length = 21
FEATURE                 Location/Qualifiers
misc_feature            1..21
                        note = Antibody 39H5 Light Chain CDR2
source                  1..21
                        mol_type = other DNA
                        organism = synthetic construct
SEQUENCE: 39
aaagtttcca accgattttc t                                           21

SEQ ID NO: 40           moltype = AA  length = 7
FEATURE                 Location/Qualifiers
REGION                  1..7
                        note = Antibody 39H5 Light Chain CDR2
source                  1..7
                        mol_type = protein
                        organism = synthetic construct
SEQUENCE: 40
KVSNRFS                                                           7

SEQ ID NO: 41           moltype = DNA  length = 27
FEATURE                 Location/Qualifiers
misc_feature            1..27
                        note = Antibody 39H5 Light Chain CDR3
source                  1..27
                        mol_type = other DNA
                        organism = synthetic construct
SEQUENCE: 41
tttcaaggtt cacatcttcc gtggacg                                     27

SEQ ID NO: 42           moltype = AA  length = 9
FEATURE                 Location/Qualifiers
REGION                  1..9
                        note = Antibody 39H5 Light Chain CDR3
source                  1..9
                        mol_type = protein
                        organism = synthetic construct
SEQUENCE: 42
FQGSHLPWT                                                         9

SEQ ID NO: 43           moltype = DNA  length = 411
FEATURE                 Location/Qualifiers
misc_feature            1..411
                        note = Antibody 3C5 Heavy chain - Signal
                         sequence-FR1-CDR1-FR2-CDR2-FR3-CDR3-FR4
source                  1..411
                        mol_type = other DNA
                        organism = synthetic construct
```

-continued

```
SEQUENCE: 43
atggcttggg tgtggacctt gctgttcctg atggcagctg cccaaagtgc ccaagcacag  60
atccagttgg tgcagtctgg acctgagctg aagaagcctg gagagacagt caagatctcc  120
tgcaaggctt ctgggtatac cttcacaaac tatggaatga actgggtgaa gcaggctcca  180
ggaaagggtt taaagtggat gggctggata aacacctaca ctggaaagcc aacatatgct  240
gatgacttca agggacggtt tgccttctct ttggagacct ctgccagcac tgcctatttg  300
cagatcaaca acctcaaaaa tgaggacacg gctacatatt tctgtgcaag agggggacta  360
gatggttact acggctactg gggccaaggc accactctca cagtctcctc a           411

SEQ ID NO: 44          moltype = AA  length = 137
FEATURE                Location/Qualifiers
REGION                 1..137
                       note = Antibody 3C5 Heavy chain - Signal
                        sequence-FR1-CDR1-FR2-CDR2-FR3-CDR3-FR4
source                 1..137
                       mol_type = protein
                       organism = synthetic construct
SEQUENCE: 44
MAWVWTLLFL MAAAQSAQAQ IQLVQSGPEL KKPGETVKIS CKASGYTFTN YGMNWVKQAP  60
GKGLKWMGWI NTYTGKPTYA DDFKGRFAFS LETSASTAYL QINNLKNEDT ATYFCARGGL  120
DGYYGYWGQG TTLTVSS                                                 137

SEQ ID NO: 45          moltype = DNA  length = 393
FEATURE                Location/Qualifiers
misc_feature           1..393
                       note = Antibody 3C5 Light chain - Signal
                        sequence-FR1-CDR1-FR2-CDR2-FR3-CDR3-FR4
source                 1..393
                       mol_type = other DNA
                       organism = synthetic construct
SEQUENCE: 45
atgagtcctg cccagttcct gtttctgcta gtgctctcga ttcaggaaac caacggtgat  60
gttgtgatgg ctcagacccc actcactttg tcggttacca ttggacaacc agcctccatc  120
tcttgcaaat caagtcagag cctcttacat agtaaaggaa agacatattt gaattggtta  180
ttacagaggc caggccagtc tccaaagctc ctaatctatc tggtgtctaa actggaatct  240
ggagtccctg acaggttcag tggcagtgga tcagggacag atttcacact gaaaatcagc  300
agagtggagg ctgaagattt gggagtttat tactgcttgc aaactacaca ttttccgtgg  360
acgttcggtg gaggcaccaa gctggaaatc aaa                               393

SEQ ID NO: 46          moltype = AA  length = 131
FEATURE                Location/Qualifiers
REGION                 1..131
                       note = Antibody 3C5 Light chain - Signal
                        sequence-FR1-CDR1-FR2-CDR2-FR3-CDR3-FR4
source                 1..131
                       mol_type = protein
                       organism = synthetic construct
SEQUENCE: 46
MSPAQFLFLL VLSIQETNGD VVMAQTPLTL SVTIGQPASI SCKSSQSLLH SKGKTYLNWL  60
LQRPGQSPKL LIYLVSKLES GVPDRFSGSG SGTDFTLKIS RVEAEDLGVY YCLQTTHFPW  120
TFGGGTKLEI K                                                       131

SEQ ID NO: 47          moltype = DNA  length = 15
FEATURE                Location/Qualifiers
misc_feature           1..15
                       note = Antibody 3C5 Heavy Chain CDR1
source                 1..15
                       mol_type = other DNA
                       organism = synthetic construct
SEQUENCE: 47
aactatggaa tgaac                                                   15

SEQ ID NO: 48          moltype = AA  length = 5
FEATURE                Location/Qualifiers
REGION                 1..5
                       note = Antibody 3C5 Heavy Chain CDR1
source                 1..5
                       mol_type = protein
                       organism = synthetic construct
SEQUENCE: 48
NYGMN                                                              5

SEQ ID NO: 49          moltype = DNA  length = 51
FEATURE                Location/Qualifiers
misc_feature           1..51
                       note = Antibody 3C5 Heavy Chain CDR2
source                 1..51
                       mol_type = other DNA
                       organism = synthetic construct
```

```
SEQUENCE: 49
tggataaaca cctacactgg aaagccaaca tatgctgatg acttcaaggg a          51

SEQ ID NO: 50          moltype = AA  length = 17
FEATURE                Location/Qualifiers
REGION                 1..17
                       note = Antibody 3C5 Heavy Chain CDR2
source                 1..17
                       mol_type = protein
                       organism = synthetic construct
SEQUENCE: 50
WINTYTGKPT YADDFKG                                                17

SEQ ID NO: 51          moltype = DNA  length = 27
FEATURE                Location/Qualifiers
misc_feature           1..27
                       note = Antibody 3C5 Heavy Chain CDR3
source                 1..27
                       mol_type = other DNA
                       organism = synthetic construct
SEQUENCE: 51
gggggactag atggttacta cggctac                                     27

SEQ ID NO: 52          moltype = AA  length = 9
FEATURE                Location/Qualifiers
REGION                 1..9
                       note = Antibody 3C5 Heavy Chain CDR3
source                 1..9
                       mol_type = protein
                       organism = synthetic construct
SEQUENCE: 52
GGLDGYYGY                                                         9

SEQ ID NO: 53          moltype = DNA  length = 48
FEATURE                Location/Qualifiers
misc_feature           1..48
                       note = Antibody 3C5 Light Chain CDR1
source                 1..48
                       mol_type = other DNA
                       organism = synthetic construct
SEQUENCE: 53
aaatcaagtc agagcctctt acatagtaaa ggaaagacat atttgaat              48

SEQ ID NO: 54          moltype = AA  length = 16
FEATURE                Location/Qualifiers
REGION                 1..16
                       note = Antibody 3C5 Light Chain CDR1
source                 1..16
                       mol_type = protein
                       organism = synthetic construct
SEQUENCE: 54
KSSQSLLHSK GKTYLN                                                 16

SEQ ID NO: 55          moltype = DNA  length = 21
FEATURE                Location/Qualifiers
misc_feature           1..21
                       note = Antibody 3C5 Light Chain CDR2
source                 1..21
                       mol_type = other DNA
                       organism = synthetic construct
SEQUENCE: 55
ctggtgtcta aactggaatc t                                           21

SEQ ID NO: 56          moltype = AA  length = 7
FEATURE                Location/Qualifiers
REGION                 1..7
                       note = Antibody 3C5 Light Chain CDR2
source                 1..7
                       mol_type = protein
                       organism = synthetic construct
SEQUENCE: 56
LVSKLES                                                           7

SEQ ID NO: 57          moltype = DNA  length = 27
FEATURE                Location/Qualifiers
misc_feature           1..27
                       note = Antibody 3C5 Light Chain CDR3
source                 1..27
                       mol_type = other DNA
```

```
                      organism = synthetic construct
SEQUENCE: 57
ttgcaaacta cacattttcc gtggacg                                      27

SEQ ID NO: 58         moltype = AA  length = 9
FEATURE               Location/Qualifiers
REGION                1..9
                      note = Antibody 3C5 Light Chain CDR3
source                1..9
                      mol_type = protein
                      organism = synthetic construct
SEQUENCE: 58
LQTTHFPWT                                                          9

SEQ ID NO: 59         moltype = DNA  length = 420
FEATURE               Location/Qualifiers
misc_feature          1..420
                      note = Antibody 8A9 Heavy chain - Signal
                       sequence-FR1-CDR1-FR2-CDR2-FR3-CDR3-FR4
source                1..420
                      mol_type = other DNA
                      organism = synthetic construct
SEQUENCE: 59
atgaagttgt ggctgaactg gattttcctt gtaacacttt taaatggtat ccagtgtgag  60
gtggagctgg tggagtctgg aggaggcttg gtacagcctg gggggttctct gagactctcc  120
tgtgcaactt ctgggttcac cttcactgat cactacatga gctgggtccg ccagcctcca  180
ggaaaggcac ttgagtggtt gggatttatt agaaacaaag ctaatggtta cacaacagag  240
tacagtgcat ctgtgaaggg tcggttcacc atctccagag ataattccca aagcatcctc  300
tatcttcaaa tgaaaaccct gagaactgag gacagtgcca cttattactg tgcaagacct  360
tctgactggg actcctggtt tgcttactgg ggccaaggga ctctggtcac tgtctctgca  420

SEQ ID NO: 60         moltype = AA  length = 140
FEATURE               Location/Qualifiers
REGION                1..140
                      note = Antibody 8A9 Heavy chain - Signal
                       sequence-FR1-CDR1-FR2-CDR2-FR3-CDR3-FR4
source                1..140
                      mol_type = protein
                      organism = synthetic construct
SEQUENCE: 60
MKLWLNWIFL VTLLNGIQCE VELVESGGGL VQPGGSLRLS CATSGFTFTD HYMSWVRQPP  60
GKALEWLGFI RNKANGYTTE YSASVKGRFT ISRDNSQSIL YLQMKTLRTE DSATYYCARP  120
SDWDSWFAYW GQGTLVTVSA                                              140

SEQ ID NO: 61         moltype = DNA  length = 393
FEATURE               Location/Qualifiers
misc_feature          1..393
                      note = Antibody 8A9 Light chain - Signal
                       sequence-FR1-CDR1-FR2-CDR2-FR3-CDR3-FR4
source                1..393
                      mol_type = other DNA
                      organism = synthetic construct
SEQUENCE: 61
atgaagttgc ctgttaggct gttggtgctg atgttctgga ttcctgcttc cagcagtgat  60
gttttgatga cccaaactcc actctccctg cctgtcagtc ttggtgatca agcctccatc  120
tcttgcagat ctagtcagag cattgtacat agtaatggca acacctattt agattggtac  180
ttgcagaaac caggccagtc tccaaagctc ctgatctaca gagtttccaa ccgattttct  240
ggggtcccag acaggttcag tggcagtgga tcagggacag atttcacact caagatcagc  300
agagtggagg ctgaggatct gggactttat tactgttttc aaggttcaca tgttccgtgg  360
gcgttcggtg gaggcaccaa gctggaaatc aaa                               393

SEQ ID NO: 62         moltype = AA  length = 131
FEATURE               Location/Qualifiers
REGION                1..131
                      note = Antibody 8A9 Light chain - Signal
                       sequence-FR1-CDR1-FR2-CDR2-FR3-CDR3-FR4
source                1..131
                      mol_type = protein
                      organism = synthetic construct
SEQUENCE: 62
MKLPVRLLVL MFWIPASSSD VLMTQTPLSL PVSLGDQASI SCRSSQSIVH SNGNTYLDWY  60
LQKPGQSPKL LIYRVSNRFS GVPDRFSGSG SGTDFTLKIS RVEAEDLGLY YCFQGSHVPW  120
AFGGGTKLEI K                                                       131

SEQ ID NO: 63         moltype = DNA  length = 15
FEATURE               Location/Qualifiers
misc_feature          1..15
                      note = Antibody 8A9 Heavy Chain CDR1
source                1..15
```

-continued

```
                      mol_type = other DNA
                      organism = synthetic construct
SEQUENCE: 63
gatcactaca tgagc                                                   15

SEQ ID NO: 64         moltype = AA  length = 5
FEATURE               Location/Qualifiers
REGION                1..5
                      note = Antibody 8A9 Heavy Chain CDR1
source                1..5
                      mol_type = protein
                      organism = synthetic construct
SEQUENCE: 64
DHYMS                                                              5

SEQ ID NO: 65         moltype = DNA  length = 57
FEATURE               Location/Qualifiers
misc_feature          1..57
                      note = Antibody 8A9 Heavy Chain CDR2
source                1..57
                      mol_type = other DNA
                      organism = synthetic construct
SEQUENCE: 65
tttattagaa acaaagctaa tggttacaca acagagtaca gtgcatctgt gaagggt     57

SEQ ID NO: 66         moltype = AA  length = 19
FEATURE               Location/Qualifiers
REGION                1..19
                      note = Antibody 8A9 Heavy Chain CDR2
source                1..19
                      mol_type = protein
                      organism = synthetic construct
SEQUENCE: 66
FIRNKANGYT TEYSASVKG                                               19

SEQ ID NO: 67         moltype = DNA  length = 30
FEATURE               Location/Qualifiers
misc_feature          1..30
                      note = Antibody 8A9 Heavy Chain CDR3
source                1..30
                      mol_type = other DNA
                      organism = synthetic construct
SEQUENCE: 67
ccttctgact gggactcctg gtttgcttac                                   30

SEQ ID NO: 68         moltype = AA  length = 10
FEATURE               Location/Qualifiers
REGION                1..10
                      note = Antibody 8A9 Heavy Chain CDR3
source                1..10
                      mol_type = protein
                      organism = synthetic construct
SEQUENCE: 68
PSDWDSWFAY                                                         10

SEQ ID NO: 69         moltype = DNA  length = 48
FEATURE               Location/Qualifiers
misc_feature          1..48
                      note = Antibody 8A9 Light Chain CDR1
source                1..48
                      mol_type = other DNA
                      organism = synthetic construct
SEQUENCE: 69
agatctagtc agagcattgt acatagtaat ggcaacacct atttagat               48

SEQ ID NO: 70         moltype = AA  length = 16
FEATURE               Location/Qualifiers
REGION                1..16
                      note = Antibody 8A9 Light Chain CDR1
source                1..16
                      mol_type = protein
                      organism = synthetic construct
SEQUENCE: 70
RSSQSIVHSN GNTYLD                                                  16

SEQ ID NO: 71         moltype = DNA  length = 21
FEATURE               Location/Qualifiers
misc_feature          1..21
                      note = Antibody 8A9 Light Chain CDR2
```

```
source                  1..21
                        mol_type = other DNA
                        organism = synthetic construct
SEQUENCE: 71
agagtttcca accgattttc t                                             21

SEQ ID NO: 72           moltype = AA  length = 7
FEATURE                 Location/Qualifiers
REGION                  1..7
                        note = Antibody 8A9 Light Chain CDR2
source                  1..7
                        mol_type = protein
                        organism = synthetic construct
SEQUENCE: 72
RVSNRFS                                                             7

SEQ ID NO: 73           moltype = DNA  length = 27
FEATURE                 Location/Qualifiers
misc_feature            1..27
                        note = Antibody 8A9 Light Chain CDR3
source                  1..27
                        mol_type = other DNA
                        organism = synthetic construct
SEQUENCE: 73
tttcaaggtt cacatgttcc gtgggcg                                       27

SEQ ID NO: 74           moltype = AA  length = 9
FEATURE                 Location/Qualifiers
REGION                  1..9
                        note = Antibody 8A9 Light Chain CDR3
source                  1..9
                        mol_type = protein
                        organism = synthetic construct
SEQUENCE: 74
FQGSHVPWA                                                           9

SEQ ID NO: 75           moltype = DNA  length = 399
FEATURE                 Location/Qualifiers
misc_feature            1..399
                        note = Antibody 18G12 Heavy chain - Signal
                         sequence-FR1-CDR1-FR2-CDR2-FR3-CDR3-FR4
source                  1..399
                        mol_type = other DNA
                        organism = synthetic construct
SEQUENCE: 75
atgggatgga gctatatcat cctctttttg gtcgcaacag ctacaggtgt ccactcccag  60
gtccaactgc agcagtctgg ggctgaactg gtgaagcctg gggcttcagt gaagttgtcc  120
tgcaaggctt ctggctacac cttcaccggc tactttttgt actgggtgaa gcagaggcct  180
ggacaaggcc ttgagtggat tggggggatt aatcctgaca atggtggtat tgacttcaat  240
gagaagttca ggaacaaggc cacactgact gtagacaaat cctccagcac agcctacatg  300
caactcagca gcctgacatc tgaggactct gcggtctatt attgtacatt actaataggg  360
aactattggg gccaaggcac cactctcaca gtctcctca                          399

SEQ ID NO: 76           moltype = AA  length = 133
FEATURE                 Location/Qualifiers
REGION                  1..133
                        note = Antibody 18G12 Heavy chain - Signal
                         sequence-FR1-CDR1-FR2-CDR2-FR3-CDR3-FR4
source                  1..133
                        mol_type = protein
                        organism = synthetic construct
SEQUENCE: 76
MGWSYIILFL VATATGVHSQ VQLQQSGAEL VKPGASVKLS CKASGYTFTG YFLYWVKQRP  60
GQGLEWIGGI NPDNGGIDFN EKFRNKATLT VDKSSSTAYM QLSSLTSEDS AVYYCTLLIG  120
NYWGQGTTLT VSS                                                      133

SEQ ID NO: 77           moltype = DNA  length = 393
FEATURE                 Location/Qualifiers
misc_feature            1..393
                        note = Antibody 18G12 Light chain - Signal
                         sequence-FR1-CDR1-FR2-CDR2-FR3-CDR3-FR4
source                  1..393
                        mol_type = other DNA
                        organism = synthetic construct
SEQUENCE: 77
atgagtcctg cccagttcct gtttctgtta gtgctctgga ttcgggaaac caatggtgat  60
gttgtgatga cccagactcc actcactttg tcggtaacca ttggacagcc agcctccatc  120
tcttgcaagt caagtcagag cctcttacat agtgatggaa agacatattt gatttggttg  180
ttacagaggc caggccagtc tccaaagcgc ctaatctatc tggtgtctaa actggactct  240
```

-continued

```
ggagtccctg acaggttcac tggcagtgga tcagggacag atttcacact gaaaatcagc  300
agagtggagg ctgaggattt gggagtttat ttttgctgtc aaggtacaca ttttccgtgg  360
acgttcggtg gaggcaccat gctggaaatc aaa                                393

SEQ ID NO: 78           moltype = AA  length = 131
FEATURE                 Location/Qualifiers
REGION                  1..131
                        note = Antibody 18G12 Light chain - Signal
                         sequence-FR1-CDR1-FR2-CDR2-FR3-CDR3-FR4
source                  1..131
                        mol_type = protein
                        organism = synthetic construct
SEQUENCE: 78
MSPAQFLFLL VLWIRETNGD VVMTQTPLTL SVTIGQPASI SCKSSQSLLH SDGKTYLIWL  60
LQRPGQSPKR LIYLVSKLDS GVPDRFTGSG SGTDFTLKIS RVEAEDLGVY FCCQGTHFPW  120
TFGGGTMLEI K                                                        131

SEQ ID NO: 79           moltype = DNA  length = 15
FEATURE                 Location/Qualifiers
misc_feature            1..15
                        note = Antibody 18G12 Heavy Chain CDR1
source                  1..15
                        mol_type = other DNA
                        organism = synthetic construct
SEQUENCE: 79
ggctactttt tgtac                                                    15

SEQ ID NO: 80           moltype = AA  length = 5
FEATURE                 Location/Qualifiers
REGION                  1..5
                        note = Antibody 18G12 Heavy Chain CDR1
source                  1..5
                        mol_type = protein
                        organism = synthetic construct
SEQUENCE: 80
GYFLY                                                               5

SEQ ID NO: 81           moltype = DNA  length = 51
FEATURE                 Location/Qualifiers
misc_feature            1..51
                        note = Antibody 18G12 Heavy Chain CDR2
source                  1..51
                        mol_type = other DNA
                        organism = synthetic construct
SEQUENCE: 81
gggattaatc ctgacaatgg tggtattgac ttcaatgaga agttcaggaa c            51

SEQ ID NO: 82           moltype = AA  length = 17
FEATURE                 Location/Qualifiers
REGION                  1..17
                        note = Antibody 18G12 Heavy Chain CDR2
source                  1..17
                        mol_type = protein
                        organism = synthetic construct
SEQUENCE: 82
GINPDNGGID FNEKFRN                                                  17

SEQ ID NO: 83           moltype = DNA  length = 15
FEATURE                 Location/Qualifiers
misc_feature            1..15
                        note = Antibody 18G12 Heavy Chain CDR3
source                  1..15
                        mol_type = other DNA
                        organism = synthetic construct
SEQUENCE: 83
ctaataggga actat                                                    15

SEQ ID NO: 84           moltype = AA  length = 5
FEATURE                 Location/Qualifiers
REGION                  1..5
                        note = Antibody 18G12 Heavy Chain CDR3
source                  1..5
                        mol_type = protein
                        organism = synthetic construct
SEQUENCE: 84
LIGNY                                                               5

SEQ ID NO: 85           moltype = DNA  length = 48
FEATURE                 Location/Qualifiers
```

-continued

```
misc_feature          1..48
                      note = Antibody 18G12 Light Chain CDR1
source                1..48
                      mol_type = other DNA
                      organism = synthetic construct
SEQUENCE: 85
aagtcaagtc agagcctctt acatagtgat ggaaagacat atttgatt              48

SEQ ID NO: 86         moltype = AA  length = 16
FEATURE               Location/Qualifiers
REGION                1..16
                      note = Antibody 18G12 Light Chain CDR1
source                1..16
                      mol_type = protein
                      organism = synthetic construct
SEQUENCE: 86
KSSQSLLHSD GKTYLI                                                 16

SEQ ID NO: 87         moltype = DNA  length = 21
FEATURE               Location/Qualifiers
misc_feature          1..21
                      note = Antibody 18G12 Light Chain CDR2
source                1..21
                      mol_type = other DNA
                      organism = synthetic construct
SEQUENCE: 87
ctggtgtcta aactggactc t                                           21

SEQ ID NO: 88         moltype = AA  length = 7
FEATURE               Location/Qualifiers
REGION                1..7
                      note = Antibody 18G12 Light Chain CDR2
source                1..7
                      mol_type = protein
                      organism = synthetic construct
SEQUENCE: 88
LVSKLDS                                                           7

SEQ ID NO: 89         moltype = DNA  length = 27
FEATURE               Location/Qualifiers
misc_feature          1..27
                      note = Antibody 18G12 Light Chain CDR3
source                1..27
                      mol_type = other DNA
                      organism = synthetic construct
SEQUENCE: 89
tgtcaaggta cacattttcc gtggacg                                     27

SEQ ID NO: 90         moltype = AA  length = 9
FEATURE               Location/Qualifiers
REGION                1..9
                      note = Antibody 18G12 Light Chain CDR3
source                1..9
                      mol_type = protein
                      organism = synthetic construct
SEQUENCE: 90
CQGTHFPWT                                                         9

SEQ ID NO: 91         moltype = DNA  length = 417
FEATURE               Location/Qualifiers
misc_feature          1..417
                      note = Antibody 20A10 Heavy chain - Signal
                       sequence-FR1-CDR1-FR2-CDR2-FR3-CDR3-FR4
source                1..417
                      mol_type = other DNA
                      organism = synthetic construct
SEQUENCE: 91
atgaacttcg ggttcagctt gattttcctt gtccttgttt taaaaggtgt ccagtgtgaa  60
gtgatgctgg tggagtctgg gggaggctta gtgaagcctg gagggtccct gaaactctcc  120
tgtgcagcct ctggattcac tttcagtacc tatgccatgt cttggattcg ccagactcca  180
gagaagaggc tggagtgggt cgcatccatt ggtcgtgctg gttccaccta ctattcagac  240
agtgtgaagg gccgattcac catctccaga gataatgtcc ggaacatcct gtacctgcaa  300
atgagcagtc tgaggtctga ggacacggcc atgtattact gtgctagagg cccgatctac  360
aatgattacg acgagtttgc ttactggggc caagggactc tggtcactgt ctctgca     417

SEQ ID NO: 92         moltype = AA  length = 139
FEATURE               Location/Qualifiers
REGION                1..139
                      note = Antibody 20A10 Heavy chain - Signal
```

```
                         sequence-FR1-CDR1-FR2-CDR2-FR3-CDR3-FR4
source                  1..139
                        mol_type = protein
                        organism = synthetic construct
SEQUENCE: 92
MNFGFSLIFL VLVLKGVQCE VMLVESGGGL VKPGGSLKLS CAASGFTFST YAMSWIRQTP  60
EKRLEWVASI GRAGSTYYSD SVKGRFTISR DNVRNILYLQ MSSLRSEDTA MYYCARGPIY  120
NDYDEFAYWG QGTLVTVSA                                               139

SEQ ID NO: 93           moltype = DNA  length = 396
FEATURE                 Location/Qualifiers
misc_feature            1..396
                        note = Antibody 20A10 Light chain - Signal
                         sequence-FR1-CDR1-FR2-CDR2-FR3-CDR3-FR4
source                  1..396
                        mol_type = other DNA
                        organism = synthetic construct
SEQUENCE: 93
atggaatcac agactcaggt cttcctctcc ctgctgctct gggtatctgg tacctgtggg  60
aacattatga tgacacagtc gccatcatct ctggctgtgt ctgcaggaga aaaggtcact  120
atgagctgta agtccagtca aagtgtttta tacagttcaa atcagaagaa ctatttggcc  180
tggtaccagc agaaaccagg gcagtctcct aaactgctga tctactgggc atccactagg  240
gaatctggtg tccctgatcg cttcacaggc agtggatctg ggacagattt tactcttacc  300
atcagcagtg tacaagctga agacctggca gtttattact gtcatcaata cctctcctcg  360
ctcacgttcg gtgctgggac caagctggag ctgaaa                            396

SEQ ID NO: 94           moltype = AA  length = 132
FEATURE                 Location/Qualifiers
REGION                  1..132
                        note = Antibody 20A10 Light chain - Signal
                         sequence-FR1-CDR1-FR2-CDR2-FR3-CDR3-FR4
source                  1..132
                        mol_type = protein
                        organism = synthetic construct
SEQUENCE: 94
MESQTQVFLS LLLWVSGTCG NIMMTQSPSS LAVSAGEKVT MSCKSSQSVL YSSNQKNYLA  60
WYQQKPGQSP KLLIYWASTR ESGVPDRFTG SGSGTDFTLT ISSVQAEDLA VYYCHQYLSS  120
LTFGAGTKLE LK                                                      132

SEQ ID NO: 95           moltype = DNA  length = 15
FEATURE                 Location/Qualifiers
misc_feature            1..15
                        note = Antibody 20A10 Heavy Chain CDR1
source                  1..15
                        mol_type = other DNA
                        organism = synthetic construct
SEQUENCE: 95
acctatgcca tgtct                                                   15

SEQ ID NO: 96           moltype = AA  length = 5
FEATURE                 Location/Qualifiers
REGION                  1..5
                        note = Antibody 20A10 Heavy Chain CDR1
source                  1..5
                        mol_type = protein
                        organism = synthetic construct
SEQUENCE: 96
TYAMS                                                              5

SEQ ID NO: 97           moltype = DNA  length = 48
FEATURE                 Location/Qualifiers
misc_feature            1..48
                        note = Antibody 20A10 Heavy Chain CDR2
source                  1..48
                        mol_type = other DNA
                        organism = synthetic construct
SEQUENCE: 97
tccattggtc gtgctggttc cacctactat tcagacagtg tgaagggc               48

SEQ ID NO: 98           moltype = AA  length = 16
FEATURE                 Location/Qualifiers
REGION                  1..16
                        note = Antibody 20A10 Heavy Chain CDR2
source                  1..16
                        mol_type = protein
                        organism = synthetic construct
SEQUENCE: 98
SIGRAGSTYY SDSVKG                                                  16
```

-continued

```
SEQ ID NO: 99          moltype = DNA  length = 36
FEATURE                Location/Qualifiers
misc_feature           1..36
                       note = Antibody 20A10 Heavy Chain CDR3
source                 1..36
                       mol_type = other DNA
                       organism = synthetic construct
SEQUENCE: 99
ggccccgatct acaatgatta cgacgagttt gcttac                      36

SEQ ID NO: 100         moltype = AA  length = 12
FEATURE                Location/Qualifiers
REGION                 1..12
                       note = Antibody 20A10 Heavy Chain CDR3
source                 1..12
                       mol_type = protein
                       organism = synthetic construct
SEQUENCE: 100
GPIYNDYDEF AY                                                 12

SEQ ID NO: 101         moltype = DNA  length = 51
FEATURE                Location/Qualifiers
misc_feature           1..51
                       note = Antibody 20A10 Light Chain CDR1
source                 1..51
                       mol_type = other DNA
                       organism = synthetic construct
SEQUENCE: 101
aagtccagtc aaagtgtttt atacagttca aatcagaaga actatttggc c      51

SEQ ID NO: 102         moltype = AA  length = 17
FEATURE                Location/Qualifiers
REGION                 1..17
                       note = Antibody 20A10 Light Chain CDR1
source                 1..17
                       mol_type = protein
                       organism = synthetic construct
SEQUENCE: 102
KSSQSVLYSS NQKNYLA                                            17

SEQ ID NO: 103         moltype = DNA  length = 21
FEATURE                Location/Qualifiers
misc_feature           1..21
                       note = Antibody 20A10 Light Chain CDR2
source                 1..21
                       mol_type = other DNA
                       organism = synthetic construct
SEQUENCE: 103
tgggcatcca ctagggaatc t                                       21

SEQ ID NO: 104         moltype = AA  length = 7
FEATURE                Location/Qualifiers
REGION                 1..7
                       note = Antibody 20A10 Light Chain CDR2
source                 1..7
                       mol_type = protein
                       organism = synthetic construct
SEQUENCE: 104
WASTRES                                                       7

SEQ ID NO: 105         moltype = DNA  length = 24
FEATURE                Location/Qualifiers
misc_feature           1..24
                       note = Antibody 20A10 Light Chain CDR3
source                 1..24
                       mol_type = other DNA
                       organism = synthetic construct
SEQUENCE: 105
catcaatacc tctcctcgct cacg                                    24

SEQ ID NO: 106         moltype = AA  length = 8
FEATURE                Location/Qualifiers
REGION                 1..8
                       note = Antibody 20A10 Light Chain CDR3
source                 1..8
                       mol_type = protein
                       organism = synthetic construct
SEQUENCE: 106
HQYLSSLT                                                      8
```

-continued

```
SEQ ID NO: 107         moltype = DNA  length = 414
FEATURE                Location/Qualifiers
misc_feature           1..414
                       note = Antibody 25E6 Heavy chain - Signal
                        sequence-FR1-CDR1-FR2-CDR2-FR3-CDR3-FR4
source                 1..414
                       mol_type = other DNA
                       organism = synthetic construct
SEQUENCE: 107
atgaacttcg ggctcagctt gattttcctt gccctcattt taaaaggtgt ccagtgtgag  60
gtgcagctgg tggagtctgg gggagactta gtgaagcctg gagggtccct gaaactctcc  120
tgtgcagcct ctggtttcac tttcagtagt tatggaatgt cttgggttcg ccagactcca  180
gacaagaggc tggagtgggt cgcaaccatt agtaatggtg gtagacacac cttctatcca  240
gacagtgtga aggggcgatt caccatctcc agagacaatg ccaagaacac cctgtatctg  300
caaatgagca gtctgaagtc tgaggacaca gccatgtatt tatgtgtaag acagactggg  360
acggagggct ggtttgctta ctggggccaa gggactctgg tcactgtctc tgca        414

SEQ ID NO: 108         moltype = AA  length = 138
FEATURE                Location/Qualifiers
REGION                 1..138
                       note = Antibody 25E6 Heavy chain - Signal
                        sequence-FR1-CDR1-FR2-CDR2-FR3-CDR3-FR4
source                 1..138
                       mol_type = protein
                       organism = synthetic construct
SEQUENCE: 108
MNFGLSLIFL ALILKGVQCE VQLVESGGDL VKPGGSLKLS CAASGFTFSS YGMSWVRQTP  60
DKRLEWVATI SNGGRHTFYP DSVKGRFTIS RDNAKNTLYL QMSSLKSEDT AMYLCVRQTG  120
TEGWFAYWGQ GTLVTVSA                                                 138

SEQ ID NO: 109         moltype = DNA  length = 393
FEATURE                Location/Qualifiers
misc_feature           1..393
                       note = Antibody 25E6 Light chain - Signal
                        sequence-FR1-CDR1-FR2-CDR2-FR3-CDR3-FR4
source                 1..393
                       mol_type = other DNA
                       organism = synthetic construct
SEQUENCE: 109
atgagtcctg cccagttcct gtttctgtta gtgctctgga ttcgggaaac caacggtgat  60
gttgtgatga cccagactcc actcactttg tcggttacca ttggacaacc agcctccatc  120
tcttgcaagt caagtcagag cctcttagat agtgatggaa agacatattt gaattggttg  180
ttacagaggc caggccagtc tccaaagcgc ctaatctatc tggtgtctaa actggactct  240
ggagtccctg acaggttcac tggcagtgga tcagggacag atttcacact gaaaatcagc  300
agagtggagg ctgaggattt gggagtttat tattgctggc aaggtacaca ttttcctcag  360
acgttcggtg gaggcaccaa gctggaaatc aaa                                393

SEQ ID NO: 110         moltype = AA  length = 131
FEATURE                Location/Qualifiers
REGION                 1..131
                       note = Antibody 25E6 Light chain - Signal
                        sequence-FR1-CDR1-FR2-CDR2-FR3-CDR3-FR4
source                 1..131
                       mol_type = protein
                       organism = synthetic construct
SEQUENCE: 110
MSPAQFLFLL VLWIRETNGD VVMTQTPLTL SVTIGQPASI SCKSSQSLLD SDGKTYLNWL  60
LQRPGQSPKR LIYLVSKLDS GVPDRFTGSG SGTDFTLKIS RVEAEDLGVY YCWQGTHFPQ  120
TFGGGTKLEI K                                                        131

SEQ ID NO: 111         moltype = DNA  length = 15
FEATURE                Location/Qualifiers
misc_feature           1..15
                       note = Antibody 25E6 Heavy Chain CDR1
source                 1..15
                       mol_type = other DNA
                       organism = synthetic construct
SEQUENCE: 111
agttatggaa tgtct                                                    15

SEQ ID NO: 112         moltype = AA  length = 5
FEATURE                Location/Qualifiers
REGION                 1..5
                       note = Antibody 25E6 Heavy Chain CDR1
source                 1..5
                       mol_type = protein
                       organism = synthetic construct
SEQUENCE: 112
```

```
SYGMS                                                        5

SEQ ID NO: 113          moltype = DNA  length = 51
FEATURE                 Location/Qualifiers
misc_feature            1..51
                        note = Antibody 25E6 Heavy Chain CDR2
source                  1..51
                        mol_type = other DNA
                        organism = synthetic construct
SEQUENCE: 113
accattagta atggtggtag acacaccttc tatccagaca gtgtgaaggg g     51

SEQ ID NO: 114          moltype = AA  length = 17
FEATURE                 Location/Qualifiers
REGION                  1..17
                        note = Antibody 25E6 Heavy Chain CDR2
source                  1..17
                        mol_type = protein
                        organism = synthetic construct
SEQUENCE: 114
TISNGGRHTF YPDSVKG                                           17

SEQ ID NO: 115          moltype = DNA  length = 30
FEATURE                 Location/Qualifiers
misc_feature            1..30
                        note = Antibody 25E6 Heavy Chain CDR3
source                  1..30
                        mol_type = other DNA
                        organism = synthetic construct
SEQUENCE: 115
cagactggga cggagggctg gtttgcttac                             30

SEQ ID NO: 116          moltype = AA  length = 10
FEATURE                 Location/Qualifiers
REGION                  1..10
                        note = Antibody 25E6 Heavy Chain CDR3
source                  1..10
                        mol_type = protein
                        organism = synthetic construct
SEQUENCE: 116
QTGTEGWFAY                                                   10

SEQ ID NO: 117          moltype = DNA  length = 48
FEATURE                 Location/Qualifiers
misc_feature            1..48
                        note = Antibody 25E6 Light Chain CDR1
source                  1..48
                        mol_type = other DNA
                        organism = synthetic construct
SEQUENCE: 117
aagtcaagtc agagcctctt agatagtgat ggaaagacat atttgaat         48

SEQ ID NO: 118          moltype = AA  length = 16
FEATURE                 Location/Qualifiers
REGION                  1..16
                        note = Antibody 25E6 Light Chain CDR1
source                  1..16
                        mol_type = protein
                        organism = synthetic construct
SEQUENCE: 118
KSSQSLLDSD GKTYLN                                            16

SEQ ID NO: 119          moltype = DNA  length = 21
FEATURE                 Location/Qualifiers
misc_feature            1..21
                        note = Antibody 25E6 Light Chain CDR2
source                  1..21
                        mol_type = other DNA
                        organism = synthetic construct
SEQUENCE: 119
ctggtgtcta aactggactc t                                      21

SEQ ID NO: 120          moltype = AA  length = 7
FEATURE                 Location/Qualifiers
REGION                  1..7
                        note = Antibody 25E6 Light Chain CDR2
source                  1..7
                        mol_type = protein
                        organism = synthetic construct
```

```
SEQUENCE: 120
LVSKLDS                                                   7

SEQ ID NO: 121         moltype = DNA  length = 27
FEATURE                Location/Qualifiers
misc_feature           1..27
                       note = Antibody 25E6 Light Chain CDR3
source                 1..27
                       mol_type = other DNA
                       organism = synthetic construct
SEQUENCE: 121
tggcaaggta cacattttcc tcagacg                              27

SEQ ID NO: 122         moltype = AA  length = 9
FEATURE                Location/Qualifiers
REGION                 1..9
                       note = Antibody 25E6 Light Chain CDR3
source                 1..9
                       mol_type = protein
                       organism = synthetic construct
SEQUENCE: 122
WQGTHFPQT                                                 9

SEQ ID NO: 123         moltype = DNA  length = 399
FEATURE                Location/Qualifiers
misc_feature           1..399
                       note = Antibody 28F9 Heavy chain - Signal
                        sequence-FR1-CDR1-FR2-CDR2-FR3-CDR3-FR4
source                 1..399
                       mol_type = other DNA
                       organism = synthetic construct
SEQUENCE: 123
atgggatgga gctatatcat cctctttttg gtagcaacag ctacaggtgt ccactcccag  60
gtccaactgc agcagcctgg ggctgaactg gtgcagcctg gggcttcagt gaagttgtcc  120
tgcaaggctt ctggctacac cttcaccggc tactttttgt actgggtgaa gcagaggcct  180
ggacatggcc ttgagtggat tggggggaatt catcctagca atggtgatac tgacttcaat  240
gagaagttca agaacaaggc cacactgact gtagacatat cctccagcac tgcctacatg  300
caactcagca gcctgacatc tgaggactct gcggtctatt attgtacatt actaataggg  360
gtctactggg gccaaggcac cactctcaca gtctcctca                   399

SEQ ID NO: 124         moltype = AA  length = 133
FEATURE                Location/Qualifiers
REGION                 1..133
                       note = Antibody 28F9 Heavy chain - Signal
                        sequence-FR1-CDR1-FR2-CDR2-FR3-CDR3-FR4
source                 1..133
                       mol_type = protein
                       organism = synthetic construct
SEQUENCE: 124
MGWSYIILFL VATATGVHSQ VQLQQPGAEL VQPGASVKLS CKASGYTFTG YFLYWVKQRP  60
GHGLEWIGGI HPSNGDTDFN EKFKNKATLT VDISSSTAYM QLSSLTSEDS AVYYCTLLIG  120
VYWGQGTTLT VSS                                            133

SEQ ID NO: 125         moltype = DNA  length = 393
FEATURE                Location/Qualifiers
misc_feature           1..393
                       note = Antibody 28F9 Light chain - Signal
                        sequence-FR1-CDR1-FR2-CDR2-FR3-CDR3-FR4
source                 1..393
                       mol_type = other DNA
                       organism = synthetic construct
SEQUENCE: 125
atgagtcctg cccagttcct gtttctgtta gtgctctgga ttcgggaaac caacggtgat  60
gttgtgatga cccagactcc actcactttg tcggttacca ttggacaacc agcctccatc  120
tcttgcaagt caagtcagag cctcttacat agtgatggaa agacatattt gatttggttg  180
ttacagaggc caggccagtc tccaaagcgc ctaatctatc tggtgtctaa actggactct  240
ggagtccctg acaggttcac cggcagtgga tcagggacag atttcacact gaaaatcagc  300
agagtggagg ctgaggattt gggagtttat ttttgctgtc aaggtacaca ttttccgtgg  360
acgttcggtg gaggcaccat gctggaaatc aaa                       393

SEQ ID NO: 126         moltype = AA  length = 131
FEATURE                Location/Qualifiers
REGION                 1..131
                       note = Antibody 28F9 Light chain - Signal
                        sequence-FR1-CDR1-FR2-CDR2-FR3-CDR3-FR4
source                 1..131
                       mol_type = protein
                       organism = synthetic construct
SEQUENCE: 126
```

```
MSPAQFLFLL VLWIRETNGD VVMTQTPLTL SVTIGQPASI SCKSSQSLLH SDGKTYLIWL  60
LQRPGQSPKR LIYLVSKLDS GVPDRFTGSG SGTDFTLKIS RVEAEDLGVY FCCQGTHFPW  120
TFGGGTMLEI K                                                      131

SEQ ID NO: 127          moltype = DNA  length = 15
FEATURE                 Location/Qualifiers
misc_feature            1..15
                        note = Antibody 28F9 Heavy Chain CDR1
source                  1..15
                        mol_type = other DNA
                        organism = synthetic construct
SEQUENCE: 127
ggctactttt tgtac                                                  15

SEQ ID NO: 128          moltype = AA  length = 5
FEATURE                 Location/Qualifiers
REGION                  1..5
                        note = Antibody 28F9 Heavy Chain CDR1
source                  1..5
                        mol_type = protein
                        organism = synthetic construct
SEQUENCE: 128
GYFLY                                                             5

SEQ ID NO: 129          moltype = DNA  length = 51
FEATURE                 Location/Qualifiers
misc_feature            1..51
                        note = Antibody 28F9 Heavy Chain CDR2
source                  1..51
                        mol_type = other DNA
                        organism = synthetic construct
SEQUENCE: 129
ggaattcatc ctagcaatgg tgatactgac ttcaatgaga agttcaagaa c          51

SEQ ID NO: 130          moltype = AA  length = 17
FEATURE                 Location/Qualifiers
REGION                  1..17
                        note = Antibody 28F9 Heavy Chain CDR2
source                  1..17
                        mol_type = protein
                        organism = synthetic construct
SEQUENCE: 130
GIHPSNGDTD FNEKFKN                                                17

SEQ ID NO: 131          moltype = DNA  length = 15
FEATURE                 Location/Qualifiers
misc_feature            1..15
                        note = Antibody 28F9 Heavy Chain CDR3
source                  1..15
                        mol_type = other DNA
                        organism = synthetic construct
SEQUENCE: 131
ctaatagggg tctac                                                  15

SEQ ID NO: 132          moltype = AA  length = 5
FEATURE                 Location/Qualifiers
REGION                  1..5
                        note = Antibody 28F9 Heavy Chain CDR3
source                  1..5
                        mol_type = protein
                        organism = synthetic construct
SEQUENCE: 132
LIGVY                                                             5

SEQ ID NO: 133          moltype = DNA  length = 48
FEATURE                 Location/Qualifiers
misc_feature            1..48
                        note = Antibody 28F9 Light Chain CDR1
source                  1..48
                        mol_type = other DNA
                        organism = synthetic construct
SEQUENCE: 133
aagtcaagtc agagcctctt acatagtgat ggaaagacat atttgatt              48

SEQ ID NO: 134          moltype = AA  length = 16
FEATURE                 Location/Qualifiers
REGION                  1..16
                        note = Antibody 28F9 Light Chain CDR1
source                  1..16
```

```
                        mol_type = protein
                        organism = synthetic construct
SEQUENCE: 134
KSSQSLLHSD GKTYLI                                                  16

SEQ ID NO: 135          moltype = DNA  length = 21
FEATURE                 Location/Qualifiers
misc_feature            1..21
                        note = Antibody 28F9 Light Chain CDR2
source                  1..21
                        mol_type = other DNA
                        organism = synthetic construct
SEQUENCE: 135
ctggtgtcta aactggactc t                                            21

SEQ ID NO: 136          moltype = AA  length = 7
FEATURE                 Location/Qualifiers
REGION                  1..7
                        note = Antibody 28F9 Light Chain CDR2
source                  1..7
                        mol_type = protein
                        organism = synthetic construct
SEQUENCE: 136
LVSKLDS                                                            7

SEQ ID NO: 137          moltype = DNA  length = 27
FEATURE                 Location/Qualifiers
misc_feature            1..27
                        note = Antibody 28F9 Light Chain CDR3
source                  1..27
                        mol_type = other DNA
                        organism = synthetic construct
SEQUENCE: 137
tgtcaaggta cacattttcc gtggacg                                      27

SEQ ID NO: 138          moltype = AA  length = 9
FEATURE                 Location/Qualifiers
REGION                  1..9
                        note = Antibody 28F9 Light Chain CDR3
source                  1..9
                        mol_type = protein
                        organism = synthetic construct
SEQUENCE: 138
CQGTHFPWT                                                          9

SEQ ID NO: 139          moltype = DNA  length = 411
FEATURE                 Location/Qualifiers
misc_feature            1..411
                        note = Antibody 18B4 Heavy chain - Signal
                         sequence-FR1-CDR1-FR2-CDR2-FR3-CDR3-FR4
source                  1..411
                        mol_type = other DNA
                        organism = synthetic construct
SEQUENCE: 139
atgtacttgg gactgaacta tgtattcata gtttttctct taaatggtgt ccagagtgaa  60
gtgaaacttg aggagtctgg aggaggcttg gtgcaacctg ggggatccat gaaactctct  120
tgtgctgcct ctggattcac ttttaatgac gcctggatgg actgggtccg ccagtctcca  180
gagaaggggc ttgagtgggt tgctgaaatt agaagcacag ctaatattca tacaacatac  240
tatgctgagt ctgtccaagg gaggttcacc atctcaagag atgattccaa aagtagtgtc  300
tacctgcaaa tgaacagctt gagagctgaa gacactggca tttattattg taccccatta  360
ctctacggat ttgcttactg gggccaaggg actctggtca ctgtctctgc a          411

SEQ ID NO: 140          moltype = AA  length = 137
FEATURE                 Location/Qualifiers
REGION                  1..137
                        note = Antibody 18B4 Heavy chain - Signal
                         sequence-FR1-CDR1-FR2-CDR2-FR3-CDR3-FR4
source                  1..137
                        mol_type = protein
                        organism = synthetic construct
SEQUENCE: 140
MYLGLNYVFI VFLLNGVQSE VKLEESGGGL VQPGGSMKLS CAASGFTFND AWMDWVRQSP  60
EKGLEWVAEI RSTANIHTTY YAESVQGRFT ISRDDSKSSV YLQMNSLRAE DTGIYYCTPL  120
LYGFAYWGQG TLVTVSA                                                 137

SEQ ID NO: 141          moltype = DNA  length = 393
FEATURE                 Location/Qualifiers
misc_feature            1..393
                        note = Antibody 18B4 Light chain - Signal
```

```
                         sequence-FR1-CDR1-FR2-CDR2-FR3-CDR3-FR4
source                  1..393
                        mol_type = other DNA
                        organism = synthetic construct
SEQUENCE: 141
atgaagttgc ctgttaggct gttggtgctg atgttctgga ttcctgcttc cagcagtgat  60
gttgtgatga cccaaagtcc actctccctg cctgtcagtc ttggagatca agcctccatc  120
tcttgcagaa ctagtcagag ccttgtacac agtaatggaa acacctattt acattggcac  180
ctgcagaagc caggccagtc tccaaaggtc ctgatctaca aagtttccag ccgattttct  240
ggggtcccag acaggttcag tggcagtgga tcggggacag atttcacact caagatcagc  300
agagtggagg ctgaggatct gggagtttat ttctgctctc aaaatacaca tgttccgtac  360
acgttcggag gggggaccaa gctggaaata aaa                                393

SEQ ID NO: 142          moltype = AA  length = 131
FEATURE                 Location/Qualifiers
REGION                  1..131
                        note = Antibody 18B4 Heavy chain - Signal
                         sequence-FR1-CDR1-FR2-CDR2-FR3-CDR3-FR4
source                  1..131
                        mol_type = protein
                        organism = synthetic construct
SEQUENCE: 142
MKLPVRLLVL MFWIPASSSD VVMTQSPLSL PVSLGDQASI SCRTSQSLVH SNGNTYLHWH  60
LQKPGQSPKV LIYKVSSRFS GVPDRFSGSG SGTDFTLKIS RVEAEDLGVY FCSQNTHVPY  120
TFGGGTKLEI K                                                        131

SEQ ID NO: 143          moltype = DNA  length = 15
FEATURE                 Location/Qualifiers
misc_feature            1..15
                        note = Antibody 18B4 Heavy Chain CDR1
source                  1..15
                        mol_type = other DNA
                        organism = synthetic construct
SEQUENCE: 143
gacgcctgga tggac                                                    15

SEQ ID NO: 144          moltype = AA  length = 5
FEATURE                 Location/Qualifiers
REGION                  1..5
                        note = Antibody 18B4 Heavy Chain CDR1
source                  1..5
                        mol_type = protein
                        organism = synthetic construct
SEQUENCE: 144
DAWMD                                                               5

SEQ ID NO: 145          moltype = DNA  length = 57
FEATURE                 Location/Qualifiers
misc_feature            1..57
                        note = Antibody 18B4 Heavy Chain CDR2
source                  1..57
                        mol_type = other DNA
                        organism = synthetic construct
SEQUENCE: 145
gaaattagaa gcacagctaa tattcataca acatactatg ctgagtctgt ccaaggg     57

SEQ ID NO: 146          moltype = AA  length = 19
FEATURE                 Location/Qualifiers
REGION                  1..19
                        note = Antibody 18B4 Heavy Chain CDR2
source                  1..19
                        mol_type = protein
                        organism = synthetic construct
SEQUENCE: 146
EIRSTANIHT TYYAESVQG                                                19

SEQ ID NO: 147          moltype = DNA  length = 21
FEATURE                 Location/Qualifiers
misc_feature            1..21
                        note = Antibody 18B4 Heavy Chain CDR3
source                  1..21
                        mol_type = other DNA
                        organism = synthetic construct
SEQUENCE: 147
ttactctacg gatttgctta c                                             21

SEQ ID NO: 148          moltype = AA  length = 7
FEATURE                 Location/Qualifiers
REGION                  1..7
```

```
                        note = Antibody 18B4 Heavy Chain CDR3
source                  1..7
                        mol_type = protein
                        organism = synthetic construct
SEQUENCE: 148
LLYGFAY                                                         7

SEQ ID NO: 149          moltype = DNA  length = 48
FEATURE                 Location/Qualifiers
misc_feature            1..48
                        note = Antibody 18B4 Light Chain CDR1
source                  1..48
                        mol_type = other DNA
                        organism = synthetic construct
SEQUENCE: 149
agaactagtc agagccttgt acacagtaat ggaaacacct atttacat            48

SEQ ID NO: 150          moltype = AA  length = 16
FEATURE                 Location/Qualifiers
REGION                  1..16
                        note = Antibody 18B4 Light Chain CDR1
source                  1..16
                        mol_type = protein
                        organism = synthetic construct
SEQUENCE: 150
RTSQSLVHSN GNTYLH                                               16

SEQ ID NO: 151          moltype = DNA  length = 21
FEATURE                 Location/Qualifiers
misc_feature            1..21
                        note = Antibody 18B4 Light Chain CDR2
source                  1..21
                        mol_type = other DNA
                        organism = synthetic construct
SEQUENCE: 151
aaagtttcca gccgattttc t                                         21

SEQ ID NO: 152          moltype = AA  length = 7
FEATURE                 Location/Qualifiers
REGION                  1..7
                        note = Antibody 18B4 Light Chain CDR2
source                  1..7
                        mol_type = protein
                        organism = synthetic construct
SEQUENCE: 152
KVSSRFS                                                         7

SEQ ID NO: 153          moltype = DNA  length = 27
FEATURE                 Location/Qualifiers
misc_feature            1..27
                        note = Antibody 18B4 Light Chain CDR3
source                  1..27
                        mol_type = other DNA
                        organism = synthetic construct
SEQUENCE: 153
tctcaaaata cacatgttcc gtacacg                                   27

SEQ ID NO: 154          moltype = AA  length = 9
FEATURE                 Location/Qualifiers
REGION                  1..9
                        note = Antibody 18B4 Light Chain CDR3
source                  1..9
                        mol_type = protein
                        organism = synthetic construct
SEQUENCE: 154
SQNTHVPYT                                                       9

SEQ ID NO: 155          moltype = DNA  length = 408
FEATURE                 Location/Qualifiers
misc_feature            1..408
                        note = Antibody 1E4 Heavy chain - Signal
                         sequence-FR1-CDR1-FR2-CDR2-FR3-CDR3-FR4
source                  1..408
                        mol_type = other DNA
                        organism = synthetic construct
SEQUENCE: 155
atggaatggc cttgtatctt tctcttcctc ctgtcagtaa ctgaaggtgt ccactcccag  60
gttcagctgc agcagtctgg ggctgagctg gtgaggcctg ggtcctcagt gaagatttcc  120
tgtaaggctt ctggctatgc attcagtacc tactggatga actgggtgaa gcagaggcct  180
```

-continued

```
ggacagggtc ttgagtggat tggacagatt tatcctggag atagtgatac taactacaat  240
ggaaagttca agggtaaagc cacactgact gcagacaagt cctccaacac agcctacatg  300
cagctcagca gcctaacatc tgaggactct gcggtctttt tctgtgcaag aggtaaccac  360
gcctctatgg actactgggg tcaaggaacc tcagtcaccg tctcctca              408

SEQ ID NO: 156         moltype = AA  length = 136
FEATURE                Location/Qualifiers
REGION                 1..136
                       note = Antibody 1E4 Heavy chain - Signal
                        sequence-FR1-CDR1-FR2-CDR2-FR3-CDR3-FR4
source                 1..136
                       mol_type = protein
                       organism = synthetic construct
SEQUENCE: 156
MEWPCIFLFL LSVTEGVHSQ VQLQQSGAEL VRPGSSVKIS CKASGYAFST YWMNWVKQRP  60
GQGLEWIGQI YPGDSDTNYN GKFKGKATLT ADKSSNTAYM QLSSLTSEDS AVFFCARGNH  120
ASMDYWGQGT SVTVSS                                                  136

SEQ ID NO: 157         moltype = DNA  length = 393
FEATURE                Location/Qualifiers
misc_feature           1..393
                       note = Antibody 1E4 Light chain - Signal
                        sequence-FR1-CDR1-FR2-CDR2-FR3-CDR3-FR4
source                 1..393
                       mol_type = other DNA
                       organism = synthetic construct
SEQUENCE: 157
atgaagttgc ctgttaggct gttggtgctg atgttctgga ttcctgcttc cagcagtgat  60
gttgtgatga cccaaactcc actctccctg cctgtcagtc ttggagatca agcctccatc  120
tcttgcagat ctagtcagag ccttgtacac agtaatggaa acacctattt acattggtac  180
ctgcagaagc caggccagtc tccaaagctc ctgatctaca aagtttccaa ccgattttct  240
ggggtcccag acaggttcag tggcagtgga tcagggacag atttcacact caagatcagc  300
agagtggagg ctgaggatct gggagtttat ttctgctctc aaaaaacaca tgttccgtgg  360
acgttcggtg gaggcaccaa gctggaaatc aaa                               393

SEQ ID NO: 158         moltype = AA  length = 131
FEATURE                Location/Qualifiers
REGION                 1..131
                       note = Antibody 1E4 Light chain - Signal
                        sequence-FR1-CDR1-FR2-CDR2-FR3-CDR3-FR4
source                 1..131
                       mol_type = protein
                       organism = synthetic construct
SEQUENCE: 158
MKLPVRLLVL MFWIPASSSD VVMTQTPLSL PVSLGDQASI SCRSSQSLVH SNGNTYLHWY  60
LQKPGQSPKL LIYKVSNRFS GVPDRFSGSG SGTDFTLKIS RVEAEDLGVY FCSQKTHVPW  120
TFGGGTKLEI K                                                       131

SEQ ID NO: 159         moltype = DNA  length = 15
FEATURE                Location/Qualifiers
misc_feature           1..15
                       note = Antibody 1E4 Heavy Chain CDR1
source                 1..15
                       mol_type = other DNA
                       organism = synthetic construct
SEQUENCE: 159
acctactgga tgaac                                                   15

SEQ ID NO: 160         moltype = AA  length = 5
FEATURE                Location/Qualifiers
REGION                 1..5
                       note = Antibody 1E4 Heavy Chain CDR1
source                 1..5
                       mol_type = protein
                       organism = synthetic construct
SEQUENCE: 160
TYWMN                                                              5

SEQ ID NO: 161         moltype = DNA  length = 51
FEATURE                Location/Qualifiers
misc_feature           1..51
                       note = Antibody 1E4 Heavy Chain CDR2
source                 1..51
                       mol_type = other DNA
                       organism = synthetic construct
SEQUENCE: 161
cagatttatc ctggagatag tgatactaac tacaatggaa agttcaaggg t           51

SEQ ID NO: 162         moltype = AA  length = 17
```

```
FEATURE                Location/Qualifiers
REGION                 1..17
                       note = Antibody 1E4 Heavy Chain CDR2
source                 1..17
                       mol_type = protein
                       organism = synthetic construct
SEQUENCE: 162
QIYPGDSDTN YNGKFKG                                          17

SEQ ID NO: 163         moltype = DNA  length = 24
FEATURE                Location/Qualifiers
misc_feature           1..24
                       note = Antibody 1E4 Heavy Chain CDR3
source                 1..24
                       mol_type = other DNA
                       organism = synthetic construct
SEQUENCE: 163
ggtaaccacg cctctatgga ctac                                  24

SEQ ID NO: 164         moltype = AA  length = 8
FEATURE                Location/Qualifiers
REGION                 1..8
                       note = Antibody 1E4 Heavy Chain CDR3
source                 1..8
                       mol_type = protein
                       organism = synthetic construct
SEQUENCE: 164
GNHASMDY                                                    8

SEQ ID NO: 165         moltype = DNA  length = 48
FEATURE                Location/Qualifiers
misc_feature           1..48
                       note = Antibody 1E4 Light Chain CDR1
source                 1..48
                       mol_type = other DNA
                       organism = synthetic construct
SEQUENCE: 165
agatctagtc agagccttgt acacagtaat ggaaacacct atttacat        48

SEQ ID NO: 166         moltype = AA  length = 16
FEATURE                Location/Qualifiers
REGION                 1..16
                       note = Antibody 1E4 Light Chain CDR1
source                 1..16
                       mol_type = protein
                       organism = synthetic construct
SEQUENCE: 166
RSSQSLVHSN GNTYLH                                           16

SEQ ID NO: 167         moltype = DNA  length = 21
FEATURE                Location/Qualifiers
misc_feature           1..21
                       note = Antibody 1E4 Light Chain CDR2
source                 1..21
                       mol_type = other DNA
                       organism = synthetic construct
SEQUENCE: 167
aaagtttcca accgattttc t                                     21

SEQ ID NO: 168         moltype = AA  length = 7
FEATURE                Location/Qualifiers
REGION                 1..7
                       note = Antibody 1E4 Light Chain CDR2
source                 1..7
                       mol_type = protein
                       organism = synthetic construct
SEQUENCE: 168
KVSNRFS                                                     7

SEQ ID NO: 169         moltype = DNA  length = 27
FEATURE                Location/Qualifiers
misc_feature           1..27
                       note = Antibody 1E4 Light Chain CDR3
source                 1..27
                       mol_type = other DNA
                       organism = synthetic construct
SEQUENCE: 169
tctcaaaaaa cacatgttcc gtggacg                               27
```

-continued

```
SEQ ID NO: 170          moltype = AA  length = 9
FEATURE                 Location/Qualifiers
REGION                  1..9
                        note = Antibody 1E4 Light Chain CDR3
source                  1..9
                        mol_type = protein
                        organism = synthetic construct
SEQUENCE: 170
SQKTHVPWT                                                         9

SEQ ID NO: 171          moltype = DNA  length = 411
FEATURE                 Location/Qualifiers
misc_feature            1..411
                        note = Antibody 29H1 Heavy chain - Signal
                         sequence-FR1-CDR1-FR2-CDR2-FR3-CDR3-FR4
source                  1..411
                        mol_type = other DNA
                        organism = synthetic construct
SEQUENCE: 171
atgtacttgg gactgaacta tgtattcata gtttttctct taaatggtgt ccagagtgaa  60
gtgaagcttg aggagtctgg aggaggcttg gtacaacctg gaggatccat gaaactctct  120
tgtgctgcct ctggattcac ttttagtgac gcctggatgg actgggtccg ccagtctcca  180
gagaaggggc ttgaatgggt tgctgaaatt agaagcaaag ctactaatca tgcaacatac  240
tatgctgagt ctgtgaaagg gaggttcacc atctcaagag atgattccaa aagtagtgtc  300
tacctgcaaa tgaacagctt aagagctgaa gacactggca tttattactg tacccccta   360
ctttacgggt ttgcttactg gggccaaggg actctggtca ctgtctctgc a           411

SEQ ID NO: 172          moltype = AA  length = 137
FEATURE                 Location/Qualifiers
REGION                  1..137
                        note = Antibody 29H1 Heavy chain - Signal
                         sequence-FR1-CDR1-FR2-CDR2-FR3-CDR3-FR4
source                  1..137
                        mol_type = protein
                        organism = synthetic construct
SEQUENCE: 172
MYLGLNYVFI VFLLNGVQSE VKLEESGGGL VQPGGSMKLS CAASGFTFSD AWMDWVRQSP  60
EKGLEWVAEI RSKATNHATY YAESVKGRFT ISRDDSKSSV YLQMNSLRAE DTGIYYCTPL  120
LYGFAYWGQG TLVTVSA                                                137

SEQ ID NO: 173          moltype = DNA  length = 393
FEATURE                 Location/Qualifiers
misc_feature            1..393
                        note = Antibody 29H1 Light chain - Signal
                         sequence-FR1-CDR1-FR2-CDR2-FR3-CDR3-FR4
source                  1..393
                        mol_type = other DNA
                        organism = synthetic construct
SEQUENCE: 173
atgaagttgc ctgttaggct gttggtgctg atgttctgga ttcctgcttc cagcagtgat  60
gttgtgatga cccaaactcc actctccctg cctgtcagtc ttggagatca agcctccatc  120
tcttgcagat ctggtcagag ccttgtacac agtaatggac acacctattt acattggtac  180
ctgcagaagc caggccagtc tccaaggctc ctgatctaca aagtttccaa ccgatttttct  240
ggggtcccag acaggttcag tggcagtgga tcaagggcag atttcacact caagatcagc  300
agagtggagg ctgaggatct gggagtttat ttctgctctc aaactacaca tgttccgtgg  360
acgttcggtg gaggcaccaa gctggaaatc aaa                              393

SEQ ID NO: 174          moltype = AA  length = 131
FEATURE                 Location/Qualifiers
REGION                  1..131
                        note = Antibody 29H1 Light chain - Signal
                         sequence-FR1-CDR1-FR2-CDR2-FR3-CDR3-FR4
source                  1..131
                        mol_type = protein
                        organism = synthetic construct
SEQUENCE: 174
MKLPVRLLVL MFWIPASSSD VVMTQTPLSL PVSLGDQASI SCRSGQSLVH SNGHTYLHWY  60
LQKPGQSPRL LIYKVSNRFS GVPDRFSGSG SRADFTLKIS RVEAEDLGVY FCSQTTHVPW  120
TFGGGTKLEI K                                                      131

SEQ ID NO: 175          moltype = DNA  length = 15
FEATURE                 Location/Qualifiers
misc_feature            1..15
                        note = Antibody 29H1 Heavy Chain CDR1
source                  1..15
                        mol_type = other DNA
                        organism = synthetic construct
SEQUENCE: 175
gacgcctgga tggac                                                  15
```

```
SEQ ID NO: 176          moltype = AA  length = 5
FEATURE                 Location/Qualifiers
REGION                  1..5
                        note = Antibody 29H1 Heavy Chain CDR1
source                  1..5
                        mol_type = protein
                        organism = synthetic construct
SEQUENCE: 176
DAWMD                                                                5

SEQ ID NO: 177          moltype = DNA  length = 57
FEATURE                 Location/Qualifiers
misc_feature            1..57
                        note = Antibody 29H1 Heavy Chain CDR2
source                  1..57
                        mol_type = other DNA
                        organism = synthetic construct
SEQUENCE: 177
gaaattagaa gcaaagctac taatcatgca acatactatg ctgagtctgt gaaaggg     57

SEQ ID NO: 178          moltype = AA  length = 19
FEATURE                 Location/Qualifiers
REGION                  1..19
                        note = Antibody 29H1 Heavy Chain CDR2
source                  1..19
                        mol_type = protein
                        organism = synthetic construct
SEQUENCE: 178
EIRSKATNHA TYYAESVKG                                                 19

SEQ ID NO: 179          moltype = DNA  length = 21
FEATURE                 Location/Qualifiers
misc_feature            1..21
                        note = Antibody 29H1 Heavy Chain CDR3
source                  1..21
                        mol_type = other DNA
                        organism = synthetic construct
SEQUENCE: 179
ctactttacg ggtttgctta c                                              21

SEQ ID NO: 180          moltype = AA  length = 7
FEATURE                 Location/Qualifiers
REGION                  1..7
                        note = Antibody 29H1 Heavy Chain CDR3
source                  1..7
                        mol_type = protein
                        organism = synthetic construct
SEQUENCE: 180
LLYGFAY                                                              7

SEQ ID NO: 181          moltype = DNA  length = 48
FEATURE                 Location/Qualifiers
misc_feature            1..48
                        note = Antibody 29H1 Light Chain CDR1
source                  1..48
                        mol_type = other DNA
                        organism = synthetic construct
SEQUENCE: 181
agatctggtc agagccttgt acacagtaat ggacacacct atttacat                 48

SEQ ID NO: 182          moltype = AA  length = 16
FEATURE                 Location/Qualifiers
REGION                  1..16
                        note = Antibody 29H1 Light Chain CDR1
source                  1..16
                        mol_type = protein
                        organism = synthetic construct
SEQUENCE: 182
RSGQSLVHSN GHTYLH                                                    16

SEQ ID NO: 183          moltype = DNA  length = 21
FEATURE                 Location/Qualifiers
misc_feature            1..21
                        note = Antibody 29H1 Light Chain CDR2
source                  1..21
                        mol_type = other DNA
                        organism = synthetic construct
SEQUENCE: 183
```

-continued

```
aaagtttcca accgattttc t                                         21

SEQ ID NO: 184         moltype = AA  length = 7
FEATURE                Location/Qualifiers
REGION                 1..7
                       note = Antibody 29H1 Light Chain CDR2
source                 1..7
                       mol_type = protein
                       organism = synthetic construct
SEQUENCE: 184
KVSNRFS                                                         7

SEQ ID NO: 185         moltype = DNA  length = 27
FEATURE                Location/Qualifiers
misc_feature           1..27
                       note = Antibody 29H1 Light Chain CDR3
source                 1..27
                       mol_type = other DNA
                       organism = synthetic construct
SEQUENCE: 185
tctcaaacta cacatgttcc gtggacg                                   27

SEQ ID NO: 186         moltype = AA  length = 9
FEATURE                Location/Qualifiers
REGION                 1..9
                       note = Antibody 29H1 Light Chain CDR3
source                 1..9
                       mol_type = protein
                       organism = synthetic construct
SEQUENCE: 186
SQTTHVPWT                                                       9

SEQ ID NO: 187         moltype = DNA  length = 399
FEATURE                Location/Qualifiers
misc_feature           1..399
                       note = Antibody 31A1 Heavy chain - Signal
                        sequence-FR1-CDR1-FR2-CDR2-FR3-CDR3-FR4
source                 1..399
                       mol_type = other DNA
                       organism = synthetic construct
SEQUENCE: 187
atggaaaggc actggatctt tctcttcctg ttttcagtaa ctgcaggtgt ccactcccag  60
gtccagcttc agcagtctgg ggctgaactg gcaaaacctg gggcctcagt gaagatgtcc  120
tgcaaggctt ctggctacac ctttactagc tactggatgc actgggtaaa acagaggcct  180
ggacagggtc tggaatggat tggatacatt aatcctagca ctggttatac tgagtacaat  240
cagaagttca aggacaaggc cacattgact gcagacaaat cctccagcac agcctacatg  300
caactgagca gcctgacatc tgaggactct gcagtctatt actgtgcaag agcctacatt  360
gactactggg gccaaggcac cactctcaca gtctcctca                      399

SEQ ID NO: 188         moltype = AA  length = 133
FEATURE                Location/Qualifiers
REGION                 1..133
                       note = Antibody 31A1 Heavy chain - Signal
                        sequence-FR1-CDR1-FR2-CDR2-FR3-CDR3-FR4
source                 1..133
                       mol_type = protein
                       organism = synthetic construct
SEQUENCE: 188
MERHWIFLFL FSVTAGVHSQ VQLQQSGAEL AKPGASVKMS CKASGYTFTS YWMHWVKQRP  60
GQGLEWIGYI NPSTGYTEYN QKFKDKATLT ADKSSSTAYM QLSSLTSEDS AVYYCARAYI  120
DYWGQGTTLT VSS                                                  133

SEQ ID NO: 189         moltype = DNA  length = 393
FEATURE                Location/Qualifiers
misc_feature           1..393
                       note = Antibody 31A1 Light chain - Signal
                        sequence-FR1-CDR1-FR2-CDR2-FR3-CDR3-FR4
source                 1..393
                       mol_type = other DNA
                       organism = synthetic construct
SEQUENCE: 189
atgaagttgc ctgttaggct gttggtgctg atgttctgga ttcctgcttc cagcagtgat  60
gttttgatga cccaaactcc actctccctg cctgtcagtc ttggagatca agcctccttc  120
tcttgcagat ctagtcagag cattgtacat agtaatggaa acacctattt agaatggtac  180
ctgcagaaac caggccagtc tccaaagctc ctgatctaca aagtttccaa ccgattttct  240
ggggtcccag acaggttcag tggcagtgga tcagggacag atttcacact caagatcaac  300
agagtggagg ctgaggatct gggagtttat tactgctttc aagtttcaca ttttccgtgg  360
acgttcggtg gaggcaccaa gctggaaatc aaa                            393
```

```
SEQ ID NO: 190          moltype = AA  length = 131
FEATURE                 Location/Qualifiers
REGION                  1..131
                        note = Antibody 31A1 Light chain - Signal
                         sequence-FR1-CDR1-FR2-CDR2-FR3-CDR3-FR4
source                  1..131
                        mol_type = protein
                        organism = synthetic construct
SEQUENCE: 190
MKLPVRLLVL MFWIPASSSD VLMTQTPLSL PVSLGDQASF SCRSSQSIVH SNGNTYLEWY  60
LQKPGQSPKL LIYKVSNRFS GVPDRFSGSG SGTDFTLKIN RVEAEDLGVY YCFQVSHFPW  120
TFGGGTKLEI K                                                       131

SEQ ID NO: 191          moltype = DNA  length = 15
FEATURE                 Location/Qualifiers
misc_feature            1..15
                        note = Antibody 31A1 Heavy Chain CDR1
source                  1..15
                        mol_type = other DNA
                        organism = synthetic construct
SEQUENCE: 191
agctactgga tgcac                                                   15

SEQ ID NO: 192          moltype = AA  length = 5
FEATURE                 Location/Qualifiers
REGION                  1..5
                        note = Antibody 31A1 Heavy Chain CDR1
source                  1..5
                        mol_type = protein
                        organism = synthetic construct
SEQUENCE: 192
SYWMH                                                              5

SEQ ID NO: 193          moltype = DNA  length = 51
FEATURE                 Location/Qualifiers
misc_feature            1..51
                        note = Antibody 31A1 Heavy Chain CDR2
source                  1..51
                        mol_type = other DNA
                        organism = synthetic construct
SEQUENCE: 193
tacattaatc ctagcactgg ttatactgag tacaatcaga agttcaagga c           51

SEQ ID NO: 194          moltype = AA  length = 17
FEATURE                 Location/Qualifiers
REGION                  1..17
                        note = Antibody 31A1 Heavy Chain CDR2
source                  1..17
                        mol_type = protein
                        organism = synthetic construct
SEQUENCE: 194
YINPSTGYTE YNQKFKD                                                 17

SEQ ID NO: 195          moltype = DNA  length = 15
FEATURE                 Location/Qualifiers
misc_feature            1..15
                        note = Antibody 31A1 Heavy Chain CDR3
source                  1..15
                        mol_type = other DNA
                        organism = synthetic construct
SEQUENCE: 195
gcctacattg actac                                                   15

SEQ ID NO: 196          moltype = AA  length = 5
FEATURE                 Location/Qualifiers
REGION                  1..5
                        note = Antibody 31A1 Heavy Chain CDR3
source                  1..5
                        mol_type = protein
                        organism = synthetic construct
SEQUENCE: 196
AYIDY                                                              5

SEQ ID NO: 197          moltype = DNA  length = 48
FEATURE                 Location/Qualifiers
misc_feature            1..48
                        note = Antibody 31A1 Light Chain CDR1
source                  1..48
                        mol_type = other DNA
```

```
                        organism = synthetic construct
SEQUENCE: 197
agatctagtc agagcattgt acatagtaat ggaaacacct atttagaa              48

SEQ ID NO: 198          moltype = AA  length = 16
FEATURE                 Location/Qualifiers
REGION                  1..16
                        note = Antibody 31A1 Light Chain CDR1
source                  1..16
                        mol_type = protein
                        organism = synthetic construct
SEQUENCE: 198
RSSQSIVHSN GNTYLE                                                 16

SEQ ID NO: 199          moltype = DNA  length = 21
FEATURE                 Location/Qualifiers
misc_feature            1..21
                        note = Antibody 31A1 Light Chain CDR2
source                  1..21
                        mol_type = other DNA
                        organism = synthetic construct
SEQUENCE: 199
aaagtttcca accgattttc t                                           21

SEQ ID NO: 200          moltype = AA  length = 7
FEATURE                 Location/Qualifiers
REGION                  1..7
                        note = Antibody 31A1 Light Chain CDR2
source                  1..7
                        mol_type = protein
                        organism = synthetic construct
SEQUENCE: 200
KVSNRFS                                                           7

SEQ ID NO: 201          moltype = DNA  length = 27
FEATURE                 Location/Qualifiers
misc_feature            1..27
                        note = Antibody 31A1 Light Chain CDR3
source                  1..27
                        mol_type = other DNA
                        organism = synthetic construct
SEQUENCE: 201
tttcaagttt cacattttcc gtggacg                                     27

SEQ ID NO: 202          moltype = AA  length = 9
FEATURE                 Location/Qualifiers
REGION                  1..9
                        note = Antibody 31A1 Light Chain CDR3
source                  1..9
                        mol_type = protein
                        organism = synthetic construct
SEQUENCE: 202
FQVSHFPWT                                                         9

SEQ ID NO: 203          moltype = DNA  length = 411
FEATURE                 Location/Qualifiers
misc_feature            1..411
                        note = Antibody 32C1 Heavy chain - Signal
                         sequence-FR1-CDR1-FR2-CDR2-FR3-CDR3-FR4
source                  1..411
                        mol_type = other DNA
                        organism = synthetic construct
SEQUENCE: 203
atgtacttgg gactgaactg tgtattcata gtttttctct taaaaggtgt ccagagtgaa  60
gtgaagcttg aggagtctgg aggaggcttg gtgcaatctg gaggatccat gaaactctcc  120
tgtgttgcct ctggattcac tttcagtaat tactggatga actgggtccg ccagtctcca  180
gagaaggggc ttgagtgggt tgctgaaatt agattgaaat ctaataatta tgcaatacat  240
tatgcggagt ctgtgaaggg gaggttcacc atctcaagag atgattccaa aagtagtgtc  300
tacctgcaaa tgaacaactt aagagctgaa gacactggca tttattactg taccagggtc  360
ccgggactgg atgcttactg gggccaaggg actctggtca ctgtctctgc a           411

SEQ ID NO: 204          moltype = AA  length = 137
FEATURE                 Location/Qualifiers
REGION                  1..137
                        note = Antibody 32C1 Heavy chain - Signal
                         sequence-FR1-CDR1-FR2-CDR2-FR3-CDR3-FR4
source                  1..137
                        mol_type = protein
                        organism = synthetic construct
```

-continued

```
SEQUENCE: 204
MYLGLNCVFI VFLLKGVQSE VKLEESGGGL VQSGGSMKLS CVASGFTFSN YWMNWVRQSP  60
EKGLEWVAEI RLKSNNYAIH YAESVKGRFT ISRDDSKSSV YLQMNNLRAE DTGIYYCTRV  120
PGLDAYWGQG TLVTVSA                                                137

SEQ ID NO: 205         moltype = DNA  length = 393
FEATURE                Location/Qualifiers
misc_feature           1..393
                       note = Antibody 32C1 Light chain - Signal
                        sequence-FR1-CDR1-FR2-CDR2-FR3-CDR3-FR4
source                 1..393
                       mol_type = other DNA
                       organism = synthetic construct
SEQUENCE: 205
atgaagttgc ctgttaggct gttggtgctg atgttctgga ttcctgcttc cagcagtgat  60
gttgtgatga cccaaactcc actctccctg cctgtcagtc ttggagatca agcctccatc  120
tcttgcagat ctagtcagag ccttgtacac agtaatggaa acacctattt acattggtac  180
ctgcagaagc caggccagtc tccaaagctc ctgatctaca aagtttccaa ccgattttct  240
ggggtcccag acaggttcag tggcagtgga tcagggacag atttcacact caagatcagc  300
agtgtggagg ctgaggatct gggagtttat ttctgctctc aaattacaca tgttccgtac  360
acgttcggag gggggaccaa tctggaaata aaa                              393

SEQ ID NO: 206         moltype = AA  length = 131
FEATURE                Location/Qualifiers
REGION                 1..131
                       note = Antibody 32C1 Light chain - Signal
                        sequence-FR1-CDR1-FR2-CDR2-FR3-CDR3-FR4
source                 1..131
                       mol_type = protein
                       organism = synthetic construct
SEQUENCE: 206
MKLPVRLLVL MFWIPASSSD VVMTQTPLSL PVSLGDQASI SCRSSQSLVH SNGNTYLHWY  60
LQKPGQSPKL LIYKVSNRFS GVPDRFSGSG SGTDFTLKIS SVEAEDLGVY FCSQITHVPY  120
TFGGGTNLEI K                                                      131

SEQ ID NO: 207         moltype = DNA  length = 15
FEATURE                Location/Qualifiers
misc_feature           1..15
                       note = Antibody 32C1 Heavy Chain CDR1
source                 1..15
                       mol_type = other DNA
                       organism = synthetic construct
SEQUENCE: 207
aattactgga tgaac                                                  15

SEQ ID NO: 208         moltype = AA  length = 5
FEATURE                Location/Qualifiers
REGION                 1..5
                       note = Antibody 32C1 Heavy Chain CDR1
source                 1..5
                       mol_type = protein
                       organism = synthetic construct
SEQUENCE: 208
NYWMN                                                             5

SEQ ID NO: 209         moltype = DNA  length = 57
FEATURE                Location/Qualifiers
misc_feature           1..57
                       note = Antibody 32C1 Heavy Chain CDR2
source                 1..57
                       mol_type = other DNA
                       organism = synthetic construct
SEQUENCE: 209
gaaattagat tgaaatctaa taattatgca atacattatg cggagtctgt gaagggg    57

SEQ ID NO: 210         moltype = AA  length = 19
FEATURE                Location/Qualifiers
REGION                 1..19
                       note = Antibody 32C1 Heavy Chain CDR2
source                 1..19
                       mol_type = protein
                       organism = synthetic construct
SEQUENCE: 210
EIRLKSNNYA IHYAESVKG                                              19

SEQ ID NO: 211         moltype = DNA  length = 21
FEATURE                Location/Qualifiers
misc_feature           1..21
                       note = Antibody 32C1 Heavy Chain CDR3
```

-continued

```
source                  1..21
                        mol_type = other DNA
                        organism = synthetic construct
SEQUENCE: 211
gtcccgggac tggatgctta c                                                  21

SEQ ID NO: 212          moltype = AA  length = 7
FEATURE                 Location/Qualifiers
REGION                  1..7
                        note = Antibody 32C1 Heavy Chain CDR3
source                  1..7
                        mol_type = protein
                        organism = synthetic construct
SEQUENCE: 212
VPGLDAY                                                                  7

SEQ ID NO: 213          moltype = DNA  length = 48
FEATURE                 Location/Qualifiers
misc_feature            1..48
                        note = Antibody 32C1 Light Chain CDR1
source                  1..48
                        mol_type = other DNA
                        organism = synthetic construct
SEQUENCE: 213
agatctagtc agagccttgt acacagtaat ggaaacacct atttacat                     48

SEQ ID NO: 214          moltype = AA  length = 16
FEATURE                 Location/Qualifiers
REGION                  1..16
                        note = Antibody 32C1 Light Chain CDR1
source                  1..16
                        mol_type = protein
                        organism = synthetic construct
SEQUENCE: 214
RSSQSLVHSN GNTYLH                                                        16

SEQ ID NO: 215          moltype = DNA  length = 21
FEATURE                 Location/Qualifiers
misc_feature            1..21
                        note = Antibody 32C1 Light Chain CDR2
source                  1..21
                        mol_type = other DNA
                        organism = synthetic construct
SEQUENCE: 215
aaagtttcca accgattttc t                                                  21

SEQ ID NO: 216          moltype = AA  length = 7
FEATURE                 Location/Qualifiers
REGION                  1..7
                        note = Antibody 32C1 Light Chain CDR2
source                  1..7
                        mol_type = protein
                        organism = synthetic construct
SEQUENCE: 216
KVSNRFS                                                                  7

SEQ ID NO: 217          moltype = DNA  length = 27
FEATURE                 Location/Qualifiers
misc_feature            1..27
                        note = Antibody 32C1 Light Chain CDR3
source                  1..27
                        mol_type = other DNA
                        organism = synthetic construct
SEQUENCE: 217
tctcaaatta cacatgttcc gtacacg                                            27

SEQ ID NO: 218          moltype = AA  length = 9
FEATURE                 Location/Qualifiers
REGION                  1..9
                        note = Antibody 32C1 Light Chain CDR3
source                  1..9
                        mol_type = protein
                        organism = synthetic construct
SEQUENCE: 218
SQITHVPYT                                                                9

SEQ ID NO: 219          moltype = DNA  length = 423
FEATURE                 Location/Qualifiers
misc_feature            1..423
```

```
                        note = Antibody 45C11 Heavy chain - Signal
                         sequence-FR1-CDR1-FR2-CDR2-FR3-CDR3-FR4
source                  1..423
                        mol_type = other DNA
                        organism = synthetic construct
SEQUENCE: 219
atgaaatgca gctgggttat cttcttcctg atggcagtgg ttacaggggt caattcagag  60
gttcagctgc agcagtctgg ggcagacctt gtgaagccag ggcctcagt caagttgtcc  120
tgcacagctt ctggcttcaa cattaaagac acctttatgc actgggtgaa gcagaggcct  180
gaacagggcc tggagtggat tggaaggatt gatcctgcga atggtaatac taaatatgac  240
ccgaaattcc agggcaaggc cactataaca gcagacacat cctccaacac agcctacctg  300
cagctcagca gcctgacatc tgaggacact gccgtctatt actgtgctaa accgtatggt  360
aactacggct attactatgc tttggactac tggggtcaag gaacctcagt caccgtctcc  420
tca                                                                423

SEQ ID NO: 220          moltype = AA  length = 141
FEATURE                 Location/Qualifiers
REGION                  1..141
                        note = Antibody 45C11 Heavy chain - Signal
                         sequence-FR1-CDR1-FR2-CDR2-FR3-CDR3-FR4
source                  1..141
                        mol_type = protein
                        organism = synthetic construct
SEQUENCE: 220
MKCSWVIFFL MAVVTGVNSE VQLQQSGADL VKPGASVKLS CTASGFNIKD TFMHWVKQRP  60
EQGLEWIGRI DPANGNTKYD PKFQGKATIT ADTSSNTAYL QLSSLTSEDT AVYYCAKPYG  120
NYGYYYALDY WGQGTSVTVS S                                            141

SEQ ID NO: 221          moltype = DNA  length = 381
FEATURE                 Location/Qualifiers
misc_feature            1..381
                        note = Antibody 45C11 Light chain - Signal
                         sequence-FR1-CDR1-FR2-CDR2-FR3-CDR3-FR4
source                  1..381
                        mol_type = other DNA
                        organism = synthetic construct
SEQUENCE: 221
atgaggttcc aggttcaggt tctggggctc cttctgctct ggatatcagg tgcccagtgt  60
gatgtccaga taacccagtc tccatcttat cttgctgcat ctcctggaga aaccattact  120
attaattgca gggcaagtaa gagcattagc aaatatttag cctggtatca agagaaacct  180
gggaaaacta ataagcttct tatctactct ggatccactt tgcaatctgg aattccatca  240
aggttcagtg gcagtggatc tggtacagat ttcactctca ccatcagtag cctggagcct  300
gaagattttg caatgtatta ctgtcaacag cataatgaat tcccgtggac gttcggtgga  360
ggcaccaagc tggaaatcaa a                                            381

SEQ ID NO: 222          moltype = AA  length = 127
FEATURE                 Location/Qualifiers
REGION                  1..127
                        note = Antibody 45C11 Light chain - Signal
                         sequence-FR1-CDR1-FR2-CDR2-FR3-CDR3-FR4
source                  1..127
                        mol_type = protein
                        organism = synthetic construct
SEQUENCE: 222
MRFQVQVLGL LLLWISGAQC DVQITQSPSY LAASPGETIT INCRASKSIS KYLAWYQEKP  60
GKTNKLLIYS GSTLQSGIPS RFSGSGSGTD FTLTISSLEP EDFAMYYCQQ HNEFPWTFGG  120
GTKLEIK                                                            127

SEQ ID NO: 223          moltype = DNA  length = 15
FEATURE                 Location/Qualifiers
misc_feature            1..15
                        note = Antibody 45C11 Heavy Chain CDR1
source                  1..15
                        mol_type = other DNA
                        organism = synthetic construct
SEQUENCE: 223
gacaccttta tgcac                                                   15

SEQ ID NO: 224          moltype = AA  length = 5
FEATURE                 Location/Qualifiers
REGION                  1..5
                        note = Antibody 45C11 Heavy Chain CDR1
source                  1..5
                        mol_type = protein
                        organism = synthetic construct
SEQUENCE: 224
DTFMH                                                              5

SEQ ID NO: 225          moltype = DNA  length = 51
```

-continued

```
FEATURE                Location/Qualifiers
misc_feature           1..51
                       note = Antibody 45C11 Heavy Chain CDR2
source                 1..51
                       mol_type = other DNA
                       organism = synthetic construct
SEQUENCE: 225
aggattgatc ctgcgaatgg taatactaaa tatgacccga aattccaggg c          51

SEQ ID NO: 226         moltype = AA  length = 17
FEATURE                Location/Qualifiers
REGION                 1..17
                       note = Antibody 45C11 Heavy Chain CDR2
source                 1..17
                       mol_type = protein
                       organism = synthetic construct
SEQUENCE: 226
RIDPANGNTK YDPKFQG                                                17

SEQ ID NO: 227         moltype = DNA  length = 39
FEATURE                Location/Qualifiers
misc_feature           1..39
                       note = Antibody 45C11 Heavy Chain CDR3
source                 1..39
                       mol_type = other DNA
                       organism = synthetic construct
SEQUENCE: 227
ccgtatggta actacggcta ttactatgct ttggactac                        39

SEQ ID NO: 228         moltype = AA  length = 13
FEATURE                Location/Qualifiers
REGION                 1..13
                       note = Antibody 45C11 Heavy Chain CDR3
source                 1..13
                       mol_type = protein
                       organism = synthetic construct
SEQUENCE: 228
PYGNYGYYYA LDY                                                    13

SEQ ID NO: 229         moltype = DNA  length = 33
FEATURE                Location/Qualifiers
misc_feature           1..33
                       note = Antibody 45C11 Light Chain CDR1
source                 1..33
                       mol_type = other DNA
                       organism = synthetic construct
SEQUENCE: 229
agggcaagta agagcattag caaatattta gcc                              33

SEQ ID NO: 230         moltype = AA  length = 11
FEATURE                Location/Qualifiers
REGION                 1..11
                       note = Antibody 45C11 Light Chain CDR1
source                 1..11
                       mol_type = protein
                       organism = synthetic construct
SEQUENCE: 230
RASKSISKYL A                                                      11

SEQ ID NO: 231         moltype = DNA  length = 21
FEATURE                Location/Qualifiers
misc_feature           1..21
                       note = Antibody 45C11 Light Chain CDR2
source                 1..21
                       mol_type = other DNA
                       organism = synthetic construct
SEQUENCE: 231
tctggatcca ctttgcaatc t                                           21

SEQ ID NO: 232         moltype = AA  length = 7
FEATURE                Location/Qualifiers
REGION                 1..7
                       note = Antibody 45C11 Light Chain CDR2
source                 1..7
                       mol_type = protein
                       organism = synthetic construct
SEQUENCE: 232
SGSTLQS                                                           7
```

-continued

```
SEQ ID NO: 233         moltype = DNA  length = 27
FEATURE                Location/Qualifiers
misc_feature           1..27
                       note = Antibody 45C11 Light Chain CDR3
source                 1..27
                       mol_type = other DNA
                       organism = synthetic construct
SEQUENCE: 233
caacagcata atgaattccc gtggacg                                       27

SEQ ID NO: 234         moltype = AA  length = 9
FEATURE                Location/Qualifiers
REGION                 1..9
                       note = Antibody 45C11 Light Chain CDR3
source                 1..9
                       mol_type = protein
                       organism = synthetic construct
SEQUENCE: 234
QQHNEFPWT                                                           9

SEQ ID NO: 235         moltype = AA  length = 20
FEATURE                Location/Qualifiers
REGION                 1..20
                       note = Tandem repeat domain peptide
source                 1..20
                       mol_type = protein
                       organism = synthetic construct
SEQUENCE: 235
PDTRPAPGST APPAHGVTSA                                               20

SEQ ID NO: 236         moltype = AA  length = 493
FEATURE                Location/Qualifiers
REGION                 1..493
                       note = CAR44: CD8/HUMNC2/CD8/4-1BB/CD3
source                 1..493
                       mol_type = protein
                       organism = synthetic construct
SEQUENCE: 236
MALPVTALLL PLALLLHAAR PEVQLVESGG GLVKPGGSLR LSCAASGFTF SGYAMSWVRQ  60
APGKGLEWVS TISSGGTYIY YPDSVKGRFT ISRDNAKNSL YLQMNSLRAE DTAVYYCARL  120
GGDNYYEYFD VWGKGTTVTV SSGGGGSGGG GSGGGGSDIV LTQSPASLAV SPGQRATITC  180
RASKSVSTSG YSYMHWYQQK PGQPPKLLIY LASNLESGVP ARFSGSGSGT DFTLTINPVE  240
ANDTANYYCQ HSRELPFTFG GGTKVEIKRT TTTPAPRPPT PAPTIASQPL SLRPEACRPA  300
AGGAVHTRGL DFACDIYIWA PLAGTCGVLL LSLVITLYCK RGRKKLLYIF KQPFMRPVQT  360
TQEEDGCSCR FPEEEEGGCE LRVKFSRSAD APAYKQGQNQ LYNELNLGRR EEYDVLDKRR  420
GRDPEMGGKP RRKNPQEGLY NELQKDKMAE AYSEIGMKGE RRRGKGHDGL YQGLSTATKD  480
TYDALHMQAL PPR                                                      493

SEQ ID NO: 237         moltype = AA  length = 115
FEATURE                Location/Qualifiers
REGION                 1..115
                       note = MIN- A2-1 light chain variable region amino acid
                        sequence
source                 1..115
                       mol_type = protein
                       organism = synthetic construct
SEQUENCE: 237
DIVLTQSTEI MSASPGEKVT ITCSASSSIS YIHWFQQKPG TSPKLWIFGT SNLASGVPAR  60
FSGSGSGTSY SLTVSRMEAE DTATYYCQQR SNYPFTFGSG TKLQIKRADA APTVS       115

SEQ ID NO: 238         moltype = AA  length = 115
FEATURE                Location/Qualifiers
REGION                 1..115
                       note = MIN-A2-2 light chain variable region amino acid
                        sequence
source                 1..115
                       mol_type = protein
                       organism = synthetic construct
SEQUENCE: 238
DIVMTQSPAI MSASPGEKVT MTCSASSSVS YMHWFQQKPG TSPKLWIYST SNLASGAPAR  60
FSGSGSGTSY SLTVSRMESE DAATYYCQQR SSYPSTFGGG TKLEIKRADA APTVS       115

SEQ ID NO: 239         moltype = AA  length = 115
FEATURE                Location/Qualifiers
REGION                 1..115
                       note = MIN-C9-1 light chain variable region amino acid
                        sequence
source                 1..115
                       mol_type = protein
```

```
                          organism = synthetic construct
SEQUENCE: 239
DIVLTQTTAI MSASPGEKVT ITCSASSSVS YMYWFQQKPG TSPKLWIYST SNLASGVPAR  60
FSGSGSGTSY SLTISRMEAE DAATYYCQQR SSYPSTFGGG TKLEIKRADA APTVS       115

SEQ ID NO: 240            moltype = AA  length = 115
FEATURE                   Location/Qualifiers
REGION                    1..115
                          note = MIN-C9-2 light chain variable region amino acid
                           sequence
source                    1..115
                          mol_type = protein
                          organism = synthetic construct
SEQUENCE: 240
DIVITQSTAI MSASPGEKVT ITCSASSSVS YTYWFQQKPG TSPKLWIYST SNLASGVPAR  60
FSGSGSGTSY SLTISRMEAE DAATYYCQQR SSYPSTFGGG TKLEIKRADA APTVS       115

SEQ ID NO: 241            moltype = AA  length = 115
FEATURE                   Location/Qualifiers
REGION                    1..115
                          note = MIN-D7-1 light chain variable region amino acid
                           sequence
source                    1..115
                          mol_type = protein
                          organism = synthetic construct
SEQUENCE: 241
DIVITQTPAI MSASPGEKVT MTCSASSSVS YMHWFQQKPG TSPKLWIYST SNLASGVPAR  60
FSGSGSGTSY SLTVSRMESE DAATYYCQQR SSYPSTFGGG TKLEIKRADA APTVS       115

SEQ ID NO: 242            moltype = AA  length = 115
FEATURE                   Location/Qualifiers
REGION                    1..115
                          note = MIN-D7-2 light chain variable region amino acid
                           sequence
source                    1..115
                          mol_type = protein
                          organism = synthetic construct
SEQUENCE: 242
DIVLTQSTAI MSASPGEKVT MTCSASSSVS YMHWFQQKPG TSPKLWIYST SNLASGVPAR  60
FSGSGSGTSY SLTVSRMESE DAATYYCQQR SSYPSTFGGG TKLEIKRADA APTVS       115

SEQ ID NO: 243            moltype = AA  length = 115
FEATURE                   Location/Qualifiers
REGION                    1..115
                          note = MIN-F2-1 light chain variable region amino acid
                           sequence
source                    1..115
                          mol_type = protein
                          organism = synthetic construct
SEQUENCE: 243
DIVMTQSPEI MSASPGEKVT ITCSASSSIS YIHWFQQKPG TSPKLWIFGT SNLASGVPAR  60
FSGSGSGTSY SLTVSRMEAE DTATYYCQQR SNYPFTFGSG TKLQIKRADA APTVS       115

SEQ ID NO: 244            moltype = AA  length = 115
FEATURE                   Location/Qualifiers
REGION                    1..115
                          note = MIN-F2-2 light chain variable region amino acid
                           sequence
source                    1..115
                          mol_type = protein
                          organism = synthetic construct
SEQUENCE: 244
DIVITQSTEI MSASPGEKVT ITCSASSSIS YIHWFQQKPG TSPKLWIFGT SNLASGVPAR  60
FSGSGSGTSY SLTVSRMEAE DTATYYCQQR SNYPFTFGSG TKLQIKRADA APTVS       115

SEQ ID NO: 245            moltype = AA  length = 130
FEATURE                   Location/Qualifiers
REGION                    1..130
                          note = MIN-A2-1 heavy chain variable region amino acid
                           sequence
source                    1..130
                          mol_type = protein
                          organism = synthetic construct
SEQUENCE: 245
EVKLQESGPE LKKPGETVEI SCKASGYTFT NYGMNWVKQA PGKGLKWMGW INTYTGEPTY  60
AGDFKGRFAF SLETSASTAY LQINTLKNED TATYFCARSG DGYWYYAMDY WGQGTSVTVS  120
SAKTTPPSVY                                                         130

SEQ ID NO: 246            moltype = AA  length = 130
```

-continued

```
FEATURE                Location/Qualifiers
REGION                 1..130
                       note = MIN-A2-2 heavy chain variable region amino acid
                        sequence
source                 1..130
                       mol_type = protein
                       organism = synthetic construct
SEQUENCE: 246
EVQLQQSGPE LKKPGETVKI SCKASGYTFT NYGMNWVKQA PGKGLKWMGW INTYTGEPTY  60
AGDFKGRFAF SLETSASTAY LQINTLKNED TATYFCARSG DGYWYYAMDY WGQGTSVTVS  120
SAKTTPPSVY                                                        130

SEQ ID NO: 247         moltype = AA  length = 130
FEATURE                Location/Qualifiers
REGION                 1..130
                       note = MIN-C9-1 heavy chain variable region amino acid
                        sequence
source                 1..130
                       mol_type = protein
                       organism = synthetic construct
SEQUENCE: 247
QVQLQESGPE LKQPGETVKI SCKASGYTFT NNGMNWVKQA PGKGLKWMGW INTYTGEPTY  60
ADDFKGRFAF SLDTSASTAY LQINNLKNED MATYFCARTG TARAFYAMDY WGQGTSVTVS  120
STKTTAPSVY                                                        130

SEQ ID NO: 248         moltype = AA  length = 130
FEATURE                Location/Qualifiers
REGION                 1..130
                       note = MIN-C9-2 heavy chain variable region amino acid
                        sequence
source                 1..130
                       mol_type = protein
                       organism = synthetic construct
SEQUENCE: 248
QVQLQQSGPE LKQPGETVKI SCKASGYTFT NNGMNWVKQA PGKGLKWMGW INTYTGEPTY  60
ADDFKGRFAF SLGTSASTAY LQINNLKNED MATYFCARTG TARAFYAMDY WGQGTSVTVS  120
STKTTAPSVY                                                        130

SEQ ID NO: 249         moltype = AA  length = 130
FEATURE                Location/Qualifiers
REGION                 1..130
                       note = MIN-D7-1 heavy chain variable region amino acid
                        sequence
source                 1..130
                       mol_type = protein
                       organism = synthetic construct
SEQUENCE: 249
EVQLEQSGPE LKKPGETVKI SCKASGYTFI NYGMNWVKQA PGKGLKWMGW INTYTGEPTY  60
VDDFKGRFAF SLETSARTAY LQINNLKNED MATYFCARTG TTAILNGMDY WGQGTSVTVS  120
SAKTTPPSVY                                                        130

SEQ ID NO: 250         moltype = AA  length = 130
FEATURE                Location/Qualifiers
REGION                 1..130
                       note = MIN-D7-2 heavy chain variable region amino acid
                        sequence
source                 1..130
                       mol_type = protein
                       organism = synthetic construct
SEQUENCE: 250
EVQLQQSGPE LKKPGETVKI SCKASGYTFT NYGMNWVKQA PGKGLKWMGW INTYTGEPTY  60
AGDFKGRFAF SLETSASTAY LQINTLKNED TATYFCARSG DGYWYYAMDY WGQGTSVTVS  120
SAKTTPPSVY                                                        130

SEQ ID NO: 251         moltype = AA  length = 130
FEATURE                Location/Qualifiers
REGION                 1..130
                       note = MIN-F2-1 heavy chain variable region amino acid
                        sequence
source                 1..130
                       mol_type = protein
                       organism = synthetic construct
SEQUENCE: 251
EVKLEESGPE LKKPGETVKI SCKASGYTFI NYGMNWVKQA PGKGLKWMGW INTYTGEPTY  60
VDDFKGRFAF SLETSARTAY LQINNLKNED MATYFCARTG TTAILNGMDY WGQGTSVTVS  120
SAKTTPPSVY                                                        130

SEQ ID NO: 252         moltype = AA  length = 124
FEATURE                Location/Qualifiers
```

```
REGION                  1..124
                        note = MIN-F2-2 heavy chain variable region amino acid
                         sequence
source                  1..124
                        mol_type = protein
                        organism = synthetic construct
SEQUENCE: 252
EVQLEQSGAE LVRPGASVKL SCKALGYTFT DYEMHWVKQT PVHGLEWIGA IHPGSGGTAY  60
NQKFKGKATL TADKSSSTAY MELSSLTSED SAVYYCTNYG SFAYWGQGTL VTVSAAKTTP  120
PSVY                                                               124

SEQ ID NO: 253          moltype = AA  length = 130
FEATURE                 Location/Qualifiers
REGION                  1..130
                        note = MIN-F2-3 heavy chain variable region amino acid
                         sequence
source                  1..130
                        mol_type = protein
                        organism = synthetic construct
SEQUENCE: 253
RCRLQQSGPE LKKPGETVKI SCKASGYTFI NYGMNWVKQA PGKGLKWMGW INTYTGEPTY  60
VDDFKGRFAF SLETSARTAY LQINNLKNED MATYFCARTG TTAILNGMDY WGQGTSVTVS  120
SAKTTPPSCL                                                         130

SEQ ID NO: 254          moltype = AA  length = 130
FEATURE                 Location/Qualifiers
REGION                  1..130
                        note = MIN-F2-4 heavy chain variable region amino acid
                         sequence
source                  1..130
                        mol_type = protein
                        organism = synthetic construct
SEQUENCE: 254
EVQLEQSGPE LKKPGETVKI SCKASGYTFI NYGMNWVKQA PGKGLKWMGW INTYTGEPTY  60
VDDFKGRFAF SLETSARTAY LQINNLKNED MATYFCARTG TTAILNGMDY WGQGTSVTVS  120
SAKTTPPSVY                                                         130

SEQ ID NO: 255          moltype = AA  length = 113
FEATURE                 Location/Qualifiers
REGION                  1..113
                        note = MIN-14 light chain variable region amino acid
                         sequence
source                  1..113
                        mol_type = protein
                        organism = synthetic construct
SEQUENCE: 255
DIQMTQSPSS LSASLGERVS LTCRASQDIG SSLNWLQQEP DGTIKRLIYA TSSLDSGVPK  60
RFSGSRSGSD YSLTISSLES EDFVDYYCLQ YASSPHVRCW DQAGAETGCC TNC         113

SEQ ID NO: 256          moltype = AA  length = 107
FEATURE                 Location/Qualifiers
REGION                  1..107
                        note = MIN-17-1 light chain variable region amino acid
                         sequence
source                  1..107
                        mol_type = protein
                        organism = synthetic construct
SEQUENCE: 256
DIVLTQSPAS LAVSLGQRAT ISYRASKSVS TSGYSYMHWN QQKPGQPPRL LIYLVSNLES  60
GVPARFSGSG SGTDFTLNIH PVEEEDAATY YCQHIRELTR SEGGPSW                107

SEQ ID NO: 257          moltype = AA  length = 115
FEATURE                 Location/Qualifiers
REGION                  1..115
                        note = MIN-17-2 light chain variable region amino acid
                         sequence
source                  1..115
                        mol_type = protein
                        organism = synthetic construct
SEQUENCE: 257
DIQMTQSPAS QSASLGESVT ITCLASQTIG TWLAWYQQKP GKSPQLLIYA ATSLADGVPS  60
RFSGSGSGTK FSFKISSLQA EDFVSYYCQQ LYSTPWTFGG GTKLEIKRAD AAPTV       115

SEQ ID NO: 258          moltype = AA  length = 107
FEATURE                 Location/Qualifiers
REGION                  1..107
                        note = MIN-29 light chain variable region amino acid
                         sequence
source                  1..107
```

-continued

```
                         mol_type = protein
                         organism = synthetic construct
SEQUENCE: 258
DIVLTQSPAS LAVSLGQRAT ISYRASKSVS TSGYSYMHWN QQKPGQPPRL LIYLVSNLES  60
GVPARFSGSG SGTDFTLNIH PVEEEDAATY YCQHIRELTR SEGGPSW                107

SEQ ID NO: 259           moltype = AA  length = 107
FEATURE                  Location/Qualifiers
REGION                   1..107
                         note = MIN-34 light chain variable region amino acid
                          sequence
source                   1..107
                         mol_type = protein
                         organism = synthetic construct
SEQUENCE: 259
DIVLTQSPAS LAVSLGQRAT ISYRASKSVS TSGYSYMHWN QQKPGQPPRL LIYLVSNLES  60
GVPARFSGSG SGTDFTLNIH PVEEEDAATY YCQHIRELTR SEGGPSW                107

SEQ ID NO: 260           moltype = AA  length = 115
FEATURE                  Location/Qualifiers
REGION                   1..115
                         note = MIN-42 light chain variable region amino acid
                          sequence
source                   1..115
                         mol_type = protein
                         organism = synthetic construct
SEQUENCE: 260
DIVMTQSQKF MSTSVGDRVS VTCKASQNVG TNVGWYQQKP GQSPKALIYS ASYRYSGVPD  60
RFTGSGSGTD FTLTISNVQS EDLAEYFCQQ YNNYPYTFGG GTKLEIKRAD AAPTV       115

SEQ ID NO: 261           moltype = AA  length = 115
FEATURE                  Location/Qualifiers
REGION                   1..115
                         note = MIN-45 light chain variable region amino acid
                          sequence
source                   1..115
                         mol_type = protein
                         organism = synthetic construct
SEQUENCE: 261
DIQMTQPPAS LSASVGETVT ITCRASGNIH NFLAWYQQKQ GKSPQLLVYN AKTLADGVPS  60
RFSGSGSGTQ YSLKINSLQP EDFGSYYCQH FWSTPWTFGG GTKLEIKRAD AAPTV       115

SEQ ID NO: 262           moltype = AA  length = 105
FEATURE                  Location/Qualifiers
REGION                   1..105
                         note = MIN-14 heavy chain variable region amino acid
                          sequence
source                   1..105
                         mol_type = protein
                         organism = synthetic construct
SEQUENCE: 262
QVQLQQPGAE LVKPGASVKL SCKASGYTFT SYWMHWVKQR PGQGLEWIGE INPSNGRTNY  60
NEKFKSKATL TVDKSSSTAY MQLSSLTSED SAVYYCATYG NYWYF                  105

SEQ ID NO: 263           moltype = AA  length = 105
FEATURE                  Location/Qualifiers
REGION                   1..105
                         note = MIN-17-2 heavy chain variable region amino acid
                          sequence
source                   1..105
                         mol_type = protein
                         organism = synthetic construct
SEQUENCE: 263
QITLKESGPG IVQPSQPFRL TCTFSGFSLS TSGIGVTWIR QPSGKGLEWL ATIWWDDDNR  60
YNPSLKSRLT VSKDTSNNQA FLNIITVETA DTAIYYCAQS TMVTA                  105

SEQ ID NO: 264           moltype = AA  length = 105
FEATURE                  Location/Qualifiers
REGION                   1..105
                         note = MIN-17-1 heavy chain variable region amino acid
                          sequence
source                   1..105
                         mol_type = protein
                         organism = synthetic construct
SEQUENCE: 264
QVQLQQPGAE LVKPGASVKL SCKASGYTFT SYWMHWVKQR PGQGLEWIGE INPSNGRTNY  60
NEKFKSKATL TVDKSSSTAY MQLSSLTSED SAVYYCATYG NYWYF                  105

SEQ ID NO: 265           moltype = AA  length = 127
```

```
FEATURE                Location/Qualifiers
REGION                 1..127
                       note = MIN-29 heavy chain variable region amino acid
                        sequence
SITE                   12
                       note = misc_feature - Xaa can be any naturally occurring
                        amino acid
source                 1..127
                       mol_type = protein
                       organism = synthetic construct
SEQUENCE: 265
DVKLVESGGD LXKLTEGEDI WEGLTLCRDS DQSPLAPVSK PGRVVRPQRS CTVIQGCVLR  60
LQTAHLQVQG VLGIVSGDGE SALHSVWIVG ATTITINGCD QLQPLLWSLA NPRHVIATES  120
ESRGCTG                                                            127

SEQ ID NO: 266         moltype = AA  length = 104
FEATURE                Location/Qualifiers
REGION                 1..104
                       note = MIN-34 heavy chain variable region amino acid
                        sequence
source                 1..104
                       mol_type = protein
                       organism = synthetic construct
SEQUENCE: 266
QVQLKQSGPG LVQPSQSLSI TCTVSGFSLT SYGVHWVRQS PGKGLEWLGV IWGGGSTDYN  60
AAFISRLSIS KDNSKSQVFF KMNSLQANDT AIYYCARNDY PAWF                   104

SEQ ID NO: 267         moltype = AA  length = 105
FEATURE                Location/Qualifiers
REGION                 1..105
                       note = MIN-42 heavy chain variable region amino acid
                        sequence
source                 1..105
                       mol_type = protein
                       organism = synthetic construct
SEQUENCE: 267
EVQLVESGGD LVKPGRSLKL SCAASGFTFS SFGMSWVRQT PDKRLEWVAT ISSGGTYTYY  60
PDSVKGRFTI SRDNAKNTLY LQMSSLKSED TAMYYCSRRF YYDYD                  105

SEQ ID NO: 268         moltype = AA  length = 103
FEATURE                Location/Qualifiers
REGION                 1..103
                       note = MIN-45 heavy chain variable region amino acid
                        sequence
source                 1..103
                       mol_type = protein
                       organism = synthetic construct
SEQUENCE: 268
EVQLQQSGPE LVKPGASVKI SCKASGYSFT GYFMSWVMQS HGKSLEWIGR INPYNGDTFY  60
NQKFKGKATL TVDKSSTTAH IELRSLASED SAVYYCARKG LYG                    103

SEQ ID NO: 269         moltype = AA  length = 10
FEATURE                Location/Qualifiers
REGION                 1..10
                       note = MIN-A2-1 light chain variable complementarity
                        determining region 1 (CDR1) amino acid sequence
source                 1..10
                       mol_type = protein
                       organism = synthetic construct
SEQUENCE: 269
SASSSISYIH                                                         10

SEQ ID NO: 270         moltype = AA  length = 10
FEATURE                Location/Qualifiers
REGION                 1..10
                       note = MIN-A2-2 light chain variable complementarity
                        determining region 1 (CDR1) amino acid sequence
source                 1..10
                       mol_type = protein
                       organism = synthetic construct
SEQUENCE: 270
SASSSVSYMH                                                         10

SEQ ID NO: 271         moltype = AA  length = 10
FEATURE                Location/Qualifiers
REGION                 1..10
                       note = MIN-C9-1 light chain variable complementarity
                        determining region 1 (CDR1) amino acid sequence
source                 1..10
```

```
                        mol_type = protein
                        organism = synthetic construct
SEQUENCE: 271
SASSSVSYMY                                                   10

SEQ ID NO: 272          moltype = AA  length = 10
FEATURE                 Location/Qualifiers
REGION                  1..10
                        note = MIN-C9-2 light chain variable complementarity
                         determining region 1 (CDR1) amino acid sequence
source                  1..10
                        mol_type = protein
                        organism = synthetic construct
SEQUENCE: 272
SASSSVSYTY                                                   10

SEQ ID NO: 273          moltype = AA  length = 10
FEATURE                 Location/Qualifiers
REGION                  1..10
                        note = MIN-D7-1 light chain variable complementarity
                         determining region 1 (CDR1) amino acid sequence
source                  1..10
                        mol_type = protein
                        organism = synthetic construct
SEQUENCE: 273
SASSSVSYMH                                                   10

SEQ ID NO: 274          moltype = AA  length = 10
FEATURE                 Location/Qualifiers
REGION                  1..10
                        note = MIN-D7-2 light chain variable complementarity
                         determining region 1 (CDR1) amino acid sequence
source                  1..10
                        mol_type = protein
                        organism = synthetic construct
SEQUENCE: 274
SASSSVSYMH                                                   10

SEQ ID NO: 275          moltype = AA  length = 10
FEATURE                 Location/Qualifiers
REGION                  1..10
                        note = MIN-F2-1 light chain variable complementarity
                         determining region 1 (CDR1) amino acid sequence
source                  1..10
                        mol_type = protein
                        organism = synthetic construct
SEQUENCE: 275
SASSSISYIH                                                   10

SEQ ID NO: 276          moltype = AA  length = 10
FEATURE                 Location/Qualifiers
REGION                  1..10
                        note = MIN-F2-2 light chain variable complementarity
                         determining region 1 (CDR1) amino acid sequence
source                  1..10
                        mol_type = protein
                        organism = synthetic construct
SEQUENCE: 276
SASSSISYIH                                                   10

SEQ ID NO: 277          moltype = AA  length = 7
FEATURE                 Location/Qualifiers
REGION                  1..7
                        note = MIN-A2-1 light chain variable complementarity
                         determining region 2 (CDR2) amino acid sequence
source                  1..7
                        mol_type = protein
                        organism = synthetic construct
SEQUENCE: 277
GTSNLAS                                                      7

SEQ ID NO: 278          moltype = AA  length = 7
FEATURE                 Location/Qualifiers
REGION                  1..7
                        note = MIN-A2-2 light chain variable complementarity
                         determining region 2 (CDR2) amino acid sequence
source                  1..7
                        mol_type = protein
                        organism = synthetic construct
```

```
SEQUENCE: 278
STSNLAS                                                    7

SEQ ID NO: 279          moltype = AA  length = 7
FEATURE                 Location/Qualifiers
REGION                  1..7
                        note = MIN-C9-1 light chain variable complementarity
                         determining region 2 (CDR2) amino acid sequence
source                  1..7
                        mol_type = protein
                        organism = synthetic construct
SEQUENCE: 279
STSNLAS                                                    7

SEQ ID NO: 280          moltype = AA  length = 7
FEATURE                 Location/Qualifiers
REGION                  1..7
                        note = MIN-C9-2 light chain variable complementarity
                         determining region 2 (CDR2) amino acid sequence
source                  1..7
                        mol_type = protein
                        organism = synthetic construct
SEQUENCE: 280
STSNLAS                                                    7

SEQ ID NO: 281          moltype = AA  length = 7
FEATURE                 Location/Qualifiers
REGION                  1..7
                        note = MIN-D7-1 light chain variable complementarity
                         determining region 2 (CDR2) amino acid sequence
source                  1..7
                        mol_type = protein
                        organism = synthetic construct
SEQUENCE: 281
STSNLAS                                                    7

SEQ ID NO: 282          moltype = AA  length = 7
FEATURE                 Location/Qualifiers
REGION                  1..7
                        note = MIN-D7-2 light chain variable complementarity
                         determining region 2 (CDR2) amino acid sequence
source                  1..7
                        mol_type = protein
                        organism = synthetic construct
SEQUENCE: 282
STSNLAS                                                    7

SEQ ID NO: 283          moltype = AA  length = 7
FEATURE                 Location/Qualifiers
REGION                  1..7
                        note = MIN-F2-1 light chain variable complementarity
                         determining region 2 (CDR2) amino acid sequence
source                  1..7
                        mol_type = protein
                        organism = synthetic construct
SEQUENCE: 283
GTSNLAS                                                    7

SEQ ID NO: 284          moltype = AA  length = 7
FEATURE                 Location/Qualifiers
REGION                  1..7
                        note = MIN-F2-2 light chain variable complementarity
                         determining region 2 (CDR2) amino acid sequence
source                  1..7
                        mol_type = protein
                        organism = synthetic construct
SEQUENCE: 284
GTSNLAS                                                    7

SEQ ID NO: 285          moltype = AA  length = 9
FEATURE                 Location/Qualifiers
REGION                  1..9
                        note = MIN-A2-1 light chain variable complementarity
                         determining region 3 (CDR3) amino acid sequence
source                  1..9
                        mol_type = protein
                        organism = synthetic construct
SEQUENCE: 285
QQRSNYPFT                                                  9
```

```
SEQ ID NO: 286          moltype = AA  length = 9
FEATURE                 Location/Qualifiers
REGION                  1..9
                        note = MIN-A2-2 light chain variable complementarity
                         determining region 3 (CDR3) amino acid sequence
source                  1..9
                        mol_type = protein
                        organism = synthetic construct
SEQUENCE: 286
QQRSSYPST                                                               9

SEQ ID NO: 287          moltype = AA  length = 9
FEATURE                 Location/Qualifiers
REGION                  1..9
                        note = MIN-C9-1 light chain variable complementarity
                         determining region 3 (CDR3) amino acid sequence
source                  1..9
                        mol_type = protein
                        organism = synthetic construct
SEQUENCE: 287
QQRSSYPST                                                               9

SEQ ID NO: 288          moltype = AA  length = 9
FEATURE                 Location/Qualifiers
REGION                  1..9
                        note = MIN-C9-2 light chain variable complementarity
                         determining region 3 (CDR3) amino acid sequence
source                  1..9
                        mol_type = protein
                        organism = synthetic construct
SEQUENCE: 288
QQRSSYPST                                                               9

SEQ ID NO: 289          moltype = AA  length = 9
FEATURE                 Location/Qualifiers
REGION                  1..9
                        note = MIN-D7-1 light chain variable complementarity
                         determining region 3 (CDR3) amino acid sequence
source                  1..9
                        mol_type = protein
                        organism = synthetic construct
SEQUENCE: 289
QQRSSYPST                                                               9

SEQ ID NO: 290          moltype = AA  length = 9
FEATURE                 Location/Qualifiers
REGION                  1..9
                        note = MIN-D7-2 light chain variable complementarity
                         determining region 3 (CDR3) amino acid sequence
source                  1..9
                        mol_type = protein
                        organism = synthetic construct
SEQUENCE: 290
QQRSSYPST                                                               9

SEQ ID NO: 291          moltype = AA  length = 9
FEATURE                 Location/Qualifiers
REGION                  1..9
                        note = MIN-F2-1 light chain variable complementarity
                         determining region 3 (CDR3) amino acid sequence
source                  1..9
                        mol_type = protein
                        organism = synthetic construct
SEQUENCE: 291
QQRSNYPFT                                                               9

SEQ ID NO: 292          moltype = AA  length = 9
FEATURE                 Location/Qualifiers
REGION                  1..9
                        note = MIN-F2-2 light chain variable complementarity
                         determining region 3 (CDR3) amino acid sequence
source                  1..9
                        mol_type = protein
                        organism = synthetic construct
SEQUENCE: 292
QQRSNYPFT                                                               9

SEQ ID NO: 293          moltype = AA  length = 5
```

-continued

```
FEATURE                Location/Qualifiers
REGION                 1..5
                       note = MIN-A2-1 heavy chain variable complementarity
                        determining region 1 (CDR1) amino acid sequence
source                 1..5
                       mol_type = protein
                       organism = synthetic construct
SEQUENCE: 293
NYGMN                                                                   5

SEQ ID NO: 294         moltype = AA  length = 5
FEATURE                Location/Qualifiers
REGION                 1..5
                       note = MIN-A2-2 heavy chain variable complementarity
                        determining region 1 (CDR1) amino acid sequence
source                 1..5
                       mol_type = protein
                       organism = synthetic construct
SEQUENCE: 294
NYGMN                                                                   5

SEQ ID NO: 295         moltype = AA  length = 5
FEATURE                Location/Qualifiers
REGION                 1..5
                       note = MIN-C9-1 heavy chain variable complementarity
                        determining region 1 (CDR1) amino acid sequence
source                 1..5
                       mol_type = protein
                       organism = synthetic construct
SEQUENCE: 295
NNGMN                                                                   5

SEQ ID NO: 296         moltype = AA  length = 5
FEATURE                Location/Qualifiers
REGION                 1..5
                       note = MIN-C9-2 heavy chain variable complementarity
                        determining region 1 (CDR1) amino acid sequence
source                 1..5
                       mol_type = protein
                       organism = synthetic construct
SEQUENCE: 296
NNGMN                                                                   5

SEQ ID NO: 297         moltype = AA  length = 5
FEATURE                Location/Qualifiers
REGION                 1..5
                       note = MIN-D7-1 heavy chain variable complementarity
                        determining region 1 (CDR1) amino acid sequence
source                 1..5
                       mol_type = protein
                       organism = synthetic construct
SEQUENCE: 297
NYGMN                                                                   5

SEQ ID NO: 298         moltype = AA  length = 5
FEATURE                Location/Qualifiers
REGION                 1..5
                       note = MIN-D7-2 heavy chain variable complementarity
                        determining region 1 (CDR1) amino acid sequence
source                 1..5
                       mol_type = protein
                       organism = synthetic construct
SEQUENCE: 298
NYGMN                                                                   5

SEQ ID NO: 299         moltype = AA  length = 5
FEATURE                Location/Qualifiers
REGION                 1..5
                       note = MIN-F2-1 heavy chain variable complementarity
                        determining region 1 (CDR1) amino acid sequence
source                 1..5
                       mol_type = protein
                       organism = synthetic construct
SEQUENCE: 299
NYGMN                                                                   5

SEQ ID NO: 300         moltype = AA  length = 5
FEATURE                Location/Qualifiers
REGION                 1..5
```

```
                     note = MIN-F2-2 heavy chain variable complementarity
                      determining region 1 (CDR1) amino acid sequence
source               1..5
                     mol_type = protein
                     organism = synthetic construct
SEQUENCE: 300
DYEMH                                                                    5

SEQ ID NO: 301       moltype = AA  length = 5
FEATURE              Location/Qualifiers
REGION               1..5
                     note = MIN-F2-3 heavy chain variable complementarity
                      determining region 1 (CDR1) amino acid sequence
source               1..5
                     mol_type = protein
                     organism = synthetic construct
SEQUENCE: 301
NYGMN                                                                    5

SEQ ID NO: 302       moltype = AA  length = 5
FEATURE              Location/Qualifiers
REGION               1..5
                     note = MIN-F2-4 heavy chain variable complementarity
                      determining region 1 (CDR1) amino acid sequence
source               1..5
                     mol_type = protein
                     organism = synthetic construct
SEQUENCE: 302
NYGMN                                                                    5

SEQ ID NO: 303       moltype = AA  length = 17
FEATURE              Location/Qualifiers
REGION               1..17
                     note = MIN-A2-1 heavy chain variable complementarity
                      determining region 2 (CDR2) amino acid sequence
source               1..17
                     mol_type = protein
                     organism = synthetic construct
SEQUENCE: 303
WINTYTGEPT YAGDFKG                                                       17

SEQ ID NO: 304       moltype = AA  length = 17
FEATURE              Location/Qualifiers
REGION               1..17
                     note = MIN-A2-2 heavy chain variable complementarity
                      determining region 2 (CDR2) amino acid sequence
source               1..17
                     mol_type = protein
                     organism = synthetic construct
SEQUENCE: 304
WINTYTGEPT YAGDFKG                                                       17

SEQ ID NO: 305       moltype = AA  length = 17
FEATURE              Location/Qualifiers
REGION               1..17
                     note = MIN-C9-1 heavy chain variable complementarity
                      determining region 2 (CDR2) amino acid sequence
source               1..17
                     mol_type = protein
                     organism = synthetic construct
SEQUENCE: 305
WINTYTGEPT YADDFKG                                                       17

SEQ ID NO: 306       moltype = AA  length = 17
FEATURE              Location/Qualifiers
REGION               1..17
                     note = MIN-C9-2 heavy chain variable complementarity
                      determining region 2 (CDR2) amino acid sequence
source               1..17
                     mol_type = protein
                     organism = synthetic construct
SEQUENCE: 306
WINTYTGEPT YADDFKG                                                       17

SEQ ID NO: 307       moltype = AA  length = 17
FEATURE              Location/Qualifiers
REGION               1..17
                     note = MIN-D7-1 heavy chain variable complementarity
                      determining region 2 (CDR2) amino acid sequence
```

```
source                1..17
                      mol_type = protein
                      organism = synthetic construct
SEQUENCE: 307
WINTYTGEPT YVDDFKG                                                17

SEQ ID NO: 308        moltype = AA  length = 17
FEATURE               Location/Qualifiers
REGION                1..17
                      note = MIN-D7-2 heavy chain variable complementarity
                       determining region 2 (CDR2) amino acid sequence
source                1..17
                      mol_type = protein
                      organism = synthetic construct
SEQUENCE: 308
WINTYTGEPT YAGDFKG                                                17

SEQ ID NO: 309        moltype = AA  length = 17
FEATURE               Location/Qualifiers
REGION                1..17
                      note = MIN-F2-1 heavy chain variable complementarity
                       determining region 2 (CDR2) amino acid sequence
source                1..17
                      mol_type = protein
                      organism = synthetic construct
SEQUENCE: 309
WINTYTGEPT YVDDFKG                                                17

SEQ ID NO: 310        moltype = AA  length = 17
FEATURE               Location/Qualifiers
REGION                1..17
                      note = MIN-F2-2 heavy chain variable complementarity
                       determining region 2 (CDR2) amino acid sequence
source                1..17
                      mol_type = protein
                      organism = synthetic construct
SEQUENCE: 310
AIHPGSGGTA YNQKFKG                                                17

SEQ ID NO: 311        moltype = AA  length = 17
FEATURE               Location/Qualifiers
REGION                1..17
                      note = MIN-F2-3 heavy chain variable complementarity
                       determining region 2 (CDR2) amino acid sequence
source                1..17
                      mol_type = protein
                      organism = synthetic construct
SEQUENCE: 311
WINTYTGEPT YVDDFKG                                                17

SEQ ID NO: 312        moltype = AA  length = 17
FEATURE               Location/Qualifiers
REGION                1..17
                      note = MIN-F2-4 heavy chain variable complementarity
                       determining region 2 (CDR2) amino acid sequence
source                1..17
                      mol_type = protein
                      organism = synthetic construct
SEQUENCE: 312
WINTYTGEPT YVDDFKG                                                17

SEQ ID NO: 313        moltype = AA  length = 9
FEATURE               Location/Qualifiers
REGION                1..9
                      note = MIN-A2-1 heavy chain variable complementarity
                       determining region 3 (CDR3) amino acid sequence
source                1..9
                      mol_type = protein
                      organism = synthetic construct
SEQUENCE: 313
SGDGYWYYA                                                         9

SEQ ID NO: 314        moltype = AA  length = 9
FEATURE               Location/Qualifiers
REGION                1..9
                      note = MIN-A2-2 heavy chain variable complementarity
                       determining region 3 (CDR3) amino acid sequence
source                1..9
                      mol_type = protein
```

```
                         organism = synthetic construct
SEQUENCE: 314
SGDGYWYYA                                                                   9

SEQ ID NO: 315           moltype = AA  length = 9
FEATURE                  Location/Qualifiers
REGION                   1..9
                         note = MIN-C9-1 heavy chain variable complementarity
                          determining region 3 (CDR3) amino acid sequence
source                   1..9
                         mol_type = protein
                         organism = synthetic construct
SEQUENCE: 315
TGTARAFYA                                                                   9

SEQ ID NO: 316           moltype = AA  length = 9
FEATURE                  Location/Qualifiers
REGION                   1..9
                         note = MIN-C9-2 heavy chain variable complementarity
                          determining region 3 (CDR3) amino acid sequence
source                   1..9
                         mol_type = protein
                         organism = synthetic construct
SEQUENCE: 316
TGTARAFYA                                                                   9

SEQ ID NO: 317           moltype = AA  length = 9
FEATURE                  Location/Qualifiers
REGION                   1..9
                         note = MIN-D7-1 heavy chain variable complementarity
                          determining region 3(CDR3) amino acid sequence
source                   1..9
                         mol_type = protein
                         organism = synthetic construct
SEQUENCE: 317
TGTTAILNG                                                                   9

SEQ ID NO: 318           moltype = AA  length = 9
FEATURE                  Location/Qualifiers
REGION                   1..9
                         note = MIN-D7-2 heavy chain variable complementarity
                          determining region3 (CDR3) amino acid sequence
source                   1..9
                         mol_type = protein
                         organism = synthetic construct
SEQUENCE: 318
SGDGYWYYA                                                                   9

SEQ ID NO: 319           moltype = AA  length = 9
FEATURE                  Location/Qualifiers
REGION                   1..9
                         note = MIN-F2-1 heavy chain variable complementarity
                          determining region 3 (CDR3) amino acid sequence
source                   1..9
                         mol_type = protein
                         organism = synthetic construct
SEQUENCE: 319
TGTTAILNG                                                                   9

SEQ ID NO: 320           moltype = AA  length = 5
FEATURE                  Location/Qualifiers
REGION                   1..5
                         note = MIN-F2-2 heavy chain variable complementarity
                          determining region 3(CDR3) amino acid sequence
source                   1..5
                         mol_type = protein
                         organism = synthetic construct
SEQUENCE: 320
YGSFA                                                                       5

SEQ ID NO: 321           moltype = AA  length = 9
FEATURE                  Location/Qualifiers
REGION                   1..9
                         note = MIN-F2-3 heavy chain variable complementarity
                          determining region 3 (CDR3) amino acid sequence
source                   1..9
                         mol_type = protein
                         organism = synthetic construct
SEQUENCE: 321
```

```
TGTTAILNG                                                    9

SEQ ID NO: 322          moltype = AA  length = 9
FEATURE                 Location/Qualifiers
REGION                  1..9
                        note = MIN-F2-4 heavy chain variable complementarity
                         determining region 3(CDR3) amino acid sequence
source                  1..9
                        mol_type = protein
                        organism = synthetic construct
SEQUENCE: 322
TGTTAILNG                                                    9

SEQ ID NO: 323          moltype = AA  length = 11
FEATURE                 Location/Qualifiers
REGION                  1..11
                        note = MIN-14 light chain variable complementarity
                         determining region 1 (CDR1) amino acid sequence
source                  1..11
                        mol_type = protein
                        organism = synthetic construct
SEQUENCE: 323
RASQDIGSSL N                                                 11

SEQ ID NO: 324          moltype = AA  length = 15
FEATURE                 Location/Qualifiers
REGION                  1..15
                        note = MIN-17-1 light chain variable complementarity
                         determining region 1 (CDR1) amino acid sequence
source                  1..15
                        mol_type = protein
                        organism = synthetic construct
SEQUENCE: 324
RASKSVSTSG YSYMH                                             15

SEQ ID NO: 325          moltype = AA  length = 11
FEATURE                 Location/Qualifiers
REGION                  1..11
                        note = MIN-17-2 light chain variable complementarity
                         determining region 1 (CDR1) amino acid sequence
source                  1..11
                        mol_type = protein
                        organism = synthetic construct
SEQUENCE: 325
LASQTIGTWL A                                                 11

SEQ ID NO: 326          moltype = AA  length = 15
FEATURE                 Location/Qualifiers
REGION                  1..15
                        note = MIN-29 light chain variable complementarity
                         determining region 1 (CDR1) amino acid sequence
source                  1..15
                        mol_type = protein
                        organism = synthetic construct
SEQUENCE: 326
RASKSVSTSG YSYMH                                             15

SEQ ID NO: 327          moltype = AA  length = 15
FEATURE                 Location/Qualifiers
REGION                  1..15
                        note = MIN-34 light chain variable complementarity
                         determining region 1 (CDR1) amino acid sequence
source                  1..15
                        mol_type = protein
                        organism = synthetic construct
SEQUENCE: 327
RASKSVSTSG YSYMH                                             15

SEQ ID NO: 328          moltype = AA  length = 11
FEATURE                 Location/Qualifiers
REGION                  1..11
                        note = MIN-42 light chain variable complementarity
                         determining region 1 (CDR1) amino acid sequence
source                  1..11
                        mol_type = protein
                        organism = synthetic construct
SEQUENCE: 328
KASQNVGTNV G                                                 11
```

-continued

```
SEQ ID NO: 329          moltype = AA  length = 11
FEATURE                 Location/Qualifiers
REGION                  1..11
                        note = MIN-45 light chain variable complementarity
                         determining region 1 (CDR1) amino acid sequence
source                  1..11
                        mol_type = protein
                        organism = synthetic construct
SEQUENCE: 329
RASGNIHNFL A                                                    11

SEQ ID NO: 330          moltype = AA  length = 7
FEATURE                 Location/Qualifiers
REGION                  1..7
                        note = MIN-14 light chain variable complementarity
                         determining region 2 (CDR2) amino acid sequence
source                  1..7
                        mol_type = protein
                        organism = synthetic construct
SEQUENCE: 330
ATSSLDS                                                         7

SEQ ID NO: 331          moltype = AA  length = 7
FEATURE                 Location/Qualifiers
REGION                  1..7
                        note = MIN-17-1 light chain variable complementarity
                         determining region 2 (CDR2) amino acid sequence
source                  1..7
                        mol_type = protein
                        organism = synthetic construct
SEQUENCE: 331
LVSNLES                                                         7

SEQ ID NO: 332          moltype = AA  length = 7
FEATURE                 Location/Qualifiers
REGION                  1..7
                        note = MIN-17-2 light chain variable complementarity
                         determining region 2 (CDR2) amino acid sequence
source                  1..7
                        mol_type = protein
                        organism = synthetic construct
SEQUENCE: 332
AATSLAD                                                         7

SEQ ID NO: 333          moltype = AA  length = 7
FEATURE                 Location/Qualifiers
REGION                  1..7
                        note = MIN-29 light chain variable complementarity
                         determining region 2 (CDR2) amino acid sequence
source                  1..7
                        mol_type = protein
                        organism = synthetic construct
SEQUENCE: 333
LVSNLES                                                         7

SEQ ID NO: 334          moltype = AA  length = 7
FEATURE                 Location/Qualifiers
REGION                  1..7
                        note = MIN-34 light chain variable complementarity
                         determining region 2 (CDR2) amino acid sequence
source                  1..7
                        mol_type = protein
                        organism = synthetic construct
SEQUENCE: 334
LVSNLES                                                         7

SEQ ID NO: 335          moltype = AA  length = 7
FEATURE                 Location/Qualifiers
REGION                  1..7
                        note = MIN-42 light chain variable complementarity
                         determining region 2 (CDR2) amino acid sequence
source                  1..7
                        mol_type = protein
                        organism = synthetic construct
SEQUENCE: 335
SASYRYS                                                         7

SEQ ID NO: 336          moltype = AA  length = 7
FEATURE                 Location/Qualifiers
```

-continued

```
REGION                 1..7
                       note = MIN-45 light chain variable complementarity
                        determining region 2 (CDR2) amino acid sequence
source                 1..7
                       mol_type = protein
                       organism = synthetic construct
SEQUENCE: 336
NAKTLAD                                                                   7

SEQ ID NO: 337         moltype = AA  length = 5
FEATURE                Location/Qualifiers
REGION                 1..5
                       note = MIN-14 heavy chain complementarity determining
                        region 1 (CDR1) amino acid sequence
source                 1..5
                       mol_type = protein
                       organism = synthetic construct
SEQUENCE: 337
SYWMH                                                                     5

SEQ ID NO: 338         moltype = AA  length = 5
FEATURE                Location/Qualifiers
REGION                 1..5
                       note = MIN-17-1 heavy chain complementarity determining
                        region 1 (CDR1) amino acid sequence
source                 1..5
                       mol_type = protein
                       organism = synthetic construct
SEQUENCE: 338
SYWMH                                                                     5

SEQ ID NO: 339         moltype = AA  length = 5
FEATURE                Location/Qualifiers
REGION                 1..5
                       note = MIN-17-2 heavy chain complementarity determining
                        region 1 (CDR1) amino acid sequence
source                 1..5
                       mol_type = protein
                       organism = synthetic construct
SEQUENCE: 339
GIGVT                                                                     5

SEQ ID NO: 340         moltype = AA  length = 5
FEATURE                Location/Qualifiers
REGION                 1..5
                       note = MIN-34 heavy chain complementarity determining
                        region 1 (CDR1) amino acid sequence
source                 1..5
                       mol_type = protein
                       organism = synthetic construct
SEQUENCE: 340
SYGVH                                                                     5

SEQ ID NO: 341         moltype = AA  length = 5
FEATURE                Location/Qualifiers
REGION                 1..5
                       note = MIN-42 heavy chain complementarity determining
                        region 1 (CDR1) amino acid sequence
source                 1..5
                       mol_type = protein
                       organism = synthetic construct
SEQUENCE: 341
SFGMS                                                                     5

SEQ ID NO: 342         moltype = AA  length = 5
FEATURE                Location/Qualifiers
REGION                 1..5
                       note = MIN-45 heavy chain complementarity determining
                        region 1 (CDR1) amino acid sequence
source                 1..5
                       mol_type = protein
                       organism = synthetic construct
SEQUENCE: 342
GYFMS                                                                     5

SEQ ID NO: 343         moltype = AA  length = 17
FEATURE                Location/Qualifiers
REGION                 1..17
                       note = MIN-14 heavy chain complementarity determining
```

```
                         region 2 (CDR2) amino acid sequence
source                  1..17
                        mol_type = protein
                        organism = synthetic construct
SEQUENCE: 343
EINPSNGRTN YNEKFKS                                                      17

SEQ ID NO: 344          moltype = AA  length = 17
FEATURE                 Location/Qualifiers
REGION                  1..17
                        note = MIN-17-1 heavy chain complementarity determining
                         region 2 (CDR2) amino acid sequence
source                  1..17
                        mol_type = protein
                        organism = synthetic construct
SEQUENCE: 344
EINPSNGRTN YNEKFKS                                                      17

SEQ ID NO: 345          moltype = AA  length = 16
FEATURE                 Location/Qualifiers
REGION                  1..16
                        note = MIN-17-2 heavy chain complementarity determining
                         region 2 (CDR2) amino acid sequence
source                  1..16
                        mol_type = protein
                        organism = synthetic construct
SEQUENCE: 345
TIWWDDDNRY NPSLKS                                                       16

SEQ ID NO: 346          moltype = AA  length = 18
FEATURE                 Location/Qualifiers
REGION                  1..18
                        note = MIN-29 heavy chain complementarity determining
                         region 2 (CDR2) amino acid sequence
source                  1..18
                        mol_type = protein
                        organism = synthetic construct
SEQUENCE: 346
GIVSGDGESA LHSVWIVG                                                     18

SEQ ID NO: 347          moltype = AA  length = 16
FEATURE                 Location/Qualifiers
REGION                  1..16
                        note = MIN-34 heavy chain complementarity determining
                         region 2 (CDR2) amino acid sequence
source                  1..16
                        mol_type = protein
                        organism = synthetic construct
SEQUENCE: 347
VIWGGGSTDY NAAFIS                                                       16

SEQ ID NO: 348          moltype = AA  length = 17
FEATURE                 Location/Qualifiers
REGION                  1..17
                        note = MIN-42 heavy chain complementarity determining
                         region 2 (CDR2) amino acid sequence
source                  1..17
                        mol_type = protein
                        organism = synthetic construct
SEQUENCE: 348
TISSGGTYTY YPDSVKG                                                      17

SEQ ID NO: 349          moltype = AA  length = 17
FEATURE                 Location/Qualifiers
REGION                  1..17
                        note = MIN-45 heavy chain complementarity determining
                         region 2 (CDR2) amino acid sequence
source                  1..17
                        mol_type = protein
                        organism = synthetic construct
SEQUENCE: 349
RINPYNGDTF YNQKFKG                                                      17

SEQ ID NO: 350          moltype = AA  length = 122
FEATURE                 Location/Qualifiers
REGION                  1..122
                        note = Humanized E6 heavy chain variable region sequence
source                  1..122
                        mol_type = protein
```

-continued

```
                         organism = synthetic construct
SEQUENCE: 350
EVQLVESGGG LVKPGGSLRL SCAASGFTFS RYGMSWVRQA PGKRLEWVST ISGGGTYIYY  60
PDSVKGRFTI SRDNAKNTLY LQMNSLRAED TAVYYCTRDN YGRNYDYGMD YWGQGTLVTV  120
SS                                                                122

SEQ ID NO: 351           moltype = AA  length = 5
FEATURE                  Location/Qualifiers
REGION                   1..5
                         note = Humanized E6 heavy chain variable complementarity
                          determining regions 1 (CDR1) sequence
source                   1..5
                         mol_type = protein
                         organism = synthetic construct
SEQUENCE: 351
RYGMS                                                             5

SEQ ID NO: 352           moltype = AA  length = 17
FEATURE                  Location/Qualifiers
REGION                   1..17
                         note = Humanized E6 heavy chain variable complementarity
                          determining regions 2 (CDR2) sequence
source                   1..17
                         mol_type = protein
                         organism = synthetic construct
SEQUENCE: 352
TISGGGTYIY YPDSVKG                                                17

SEQ ID NO: 353           moltype = AA  length = 13
FEATURE                  Location/Qualifiers
REGION                   1..13
                         note = Humanized E6 heavy chain variable complementarity
                          determining regions 3 (CDR3) sequence
source                   1..13
                         mol_type = protein
                         organism = synthetic construct
SEQUENCE: 353
DNYGRNYDYG MDY                                                    13

SEQ ID NO: 354           moltype = AA  length = 106
FEATURE                  Location/Qualifiers
REGION                   1..106
                         note = Humanized E6 light chain variable region sequence
source                   1..106
                         mol_type = protein
                         organism = synthetic construct
SEQUENCE: 354
EIVLTQSPAT LSLSPGERAT LTCSATSSVS YIHWYQQRPG QSPRLLIYST SNLASGIPAR  60
FSGSGSGSDY TLTISSLEPE DFAVYYCQQR SSSPFTFGSG TKVEIK                106

SEQ ID NO: 355           moltype = AA  length = 10
FEATURE                  Location/Qualifiers
REGION                   1..10
                         note = Humanized E6 light chain variable complementarity
                          determining regions 1 (CDR1) sequence
source                   1..10
                         mol_type = protein
                         organism = synthetic construct
SEQUENCE: 355
SATSSVSYIH                                                        10

SEQ ID NO: 356           moltype = AA  length = 7
FEATURE                  Location/Qualifiers
REGION                   1..7
                         note = Humanized E6 light chain variable complementarity
                          determining regions 2 (CDR2) sequence
source                   1..7
                         mol_type = protein
                         organism = synthetic construct
SEQUENCE: 356
STSNLAS                                                           7

SEQ ID NO: 357           moltype = AA  length = 9
FEATURE                  Location/Qualifiers
REGION                   1..9
                         note = Humanized E6 light chain variable complementarity
                          determining regions 3 (CDR3) sequence
source                   1..9
                         mol_type = protein
```

```
                        organism = synthetic construct
SEQUENCE: 357
QQRSSSPFT                                                         9

SEQ ID NO: 358          moltype = AA  length = 121
FEATURE                 Location/Qualifiers
REGION                  1..121
                        note = Humanized C2 heavy chain variable region sequence
source                  1..121
                        mol_type = protein
                        organism = synthetic construct
SEQUENCE: 358
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
S                                                                 121

SEQ ID NO: 359          moltype = AA  length = 5
FEATURE                 Location/Qualifiers
REGION                  1..5
                        note = Humanized C2 heavy chain variable complementarity
                         determining regions 1 (CDR1) sequence
source                  1..5
                        mol_type = protein
                        organism = synthetic construct
SEQUENCE: 359
GYAMS                                                             5

SEQ ID NO: 360          moltype = AA  length = 17
FEATURE                 Location/Qualifiers
REGION                  1..17
                        note = Humanized C2 heavy chain variable complementarity
                         determining regions 2 (CDR2) sequence
source                  1..17
                        mol_type = protein
                        organism = synthetic construct
SEQUENCE: 360
TISSGGTYIY YPDSVKG                                                17

SEQ ID NO: 361          moltype = AA  length = 12
FEATURE                 Location/Qualifiers
REGION                  1..12
                        note = Humanized C2 heavy chain variable complementarity
                         determining regions 3 (CDR3) sequence
source                  1..12
                        mol_type = protein
                        organism = synthetic construct
SEQUENCE: 361
LGGDNYYEYF DV                                                     12

SEQ ID NO: 362          moltype = AA  length = 113
FEATURE                 Location/Qualifiers
REGION                  1..113
                        note = Humanized C2 light chain variable region sequence
source                  1..113
                        mol_type = protein
                        organism = synthetic construct
SEQUENCE: 362
DIVLTQSPAS LAVSPGQRAT ITCRASKSVS TSGYSYMHWY QQKPGQPPKL LIYLASNLES  60
GVPARFSGSG SGTDFTLTIN PVEANDTANY YCQHSRELPF TFGGGTKVEI KRT         113

SEQ ID NO: 363          moltype = AA  length = 15
FEATURE                 Location/Qualifiers
REGION                  1..15
                        note = Humanized C2 light chain variable complementarity
                         determining regions 1 (CDR1) sequence
source                  1..15
                        mol_type = protein
                        organism = synthetic construct
SEQUENCE: 363
RASKSVSTSG YSYMH                                                  15

SEQ ID NO: 364          moltype = AA  length = 7
FEATURE                 Location/Qualifiers
REGION                  1..7
                        note = Humanized C2 light chain variable complementarity
                         determining regions 2 (CDR2) sequence
source                  1..7
                        mol_type = protein
                        organism = synthetic construct
```

-continued

```
SEQUENCE: 364
LASNLES                                                    7

SEQ ID NO: 365          moltype = AA  length = 9
FEATURE                 Location/Qualifiers
REGION                  1..9
                        note = Humanized C2 light chain variable complementarity
                         determining regions 3 (CDR3) sequence
source                  1..9
                        mol_type = protein
                        organism = synthetic construct
SEQUENCE: 365
QHSRELPFT                                                  9

SEQ ID NO: 366          moltype = AA  length = 9
FEATURE                 Location/Qualifiers
REGION                  1..9
                        note = Humanized C2 light chain variable complementarity
                         determining regions 3 (CDR3) sequence
source                  1..9
                        mol_type = protein
                        organism = synthetic construct
SEQUENCE: 366
LQSKNFPPT                                                  9

SEQ ID NO: 367          moltype = AA  length = 507
FEATURE                 Location/Qualifiers
REGION                  1..507
                        note = pSECTag2 C2 scFV-FC
source                  1..507
                        mol_type = protein
                        organism = synthetic construct
SEQUENCE: 367
METDTLLLWV LLLWVPGSTG DAAQPAEVQL VESGGGLVKP GGSLRLSCAA SGFTFSGYAM  60
SWVRQAPGKG LEWVSTISSG GTYIYYPDSV KGRFTISRDN AKNSLYLQMN SLRAEDTAVY  120
YCARLGGDNY YEYFDVWGKG TTVTVSSGGG GSGGGGSGGG GSDIVLTQSP ASLAVSPGQR  180
ATITCRASKS VSTSGYSYMH WYQQKPGQPP KLLIYLASNL ESGVPARFSG SGSGTDFTLT  240
INPVEANDTA NYYCQHSREL PFTFGGGTKV EIKRTEPKSC DKTHTCPPCP APELLGGPSV  300
FLFPPKPKDT LMISRTPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSREEMTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGK                                      507

SEQ ID NO: 368          moltype = AA  length = 501
FEATURE                 Location/Qualifiers
REGION                  1..501
                        note = pSECTag2 E6 scFV-FC
source                  1..501
                        mol_type = protein
                        organism = synthetic construct
SEQUENCE: 368
METDTLLLWV LLLWVPGSTG DAAQPAEVQL VESGGGLVKP GGSLRLSCAA SGFTFSRYGM  60
SWVRQAPGKR LEWVSTISGG GTYIYYPDSV KGRFTISRDN AKNTLYLQMN SLRAEDTAVY  120
YCTRDNYGRN YDYGMDYWGQ GTLVTVSSGG GGSGGGGSGG GGSEIVLTQS PATLSLSPGE  180
RATLTCSATS SVSYIHWYQQ RPGQSPRLLI YSTSNLASGI PARFSGSGSG SDYTLTISSL  240
EPEDFAVYYC QQRSSSPFTF GSGTKVEIKE PKSCDKTHTC PPCPAPELLG GPSVFLFPPK  300
PKDTLMISRT PEVTCVVVDV SHEDPEVKFN WYVDGVEVHN AKTKPREEQY NSTYRVVSVL  360
TVLHQDWLNG KEYKCKVSNK ALPAPIEKTI SKAKGQPREP QVYTLPPSRE EMTKNQVSLT  420
CLVKGFYPSD IAVEWESNGQ PENNYKTTPP VLDSDGSFFL YSKLTVDKSR WQQGNVFSCS  480
VMHEALHNHY TQKSLSLSPG K                                           501

SEQ ID NO: 369          moltype = AA  length = 249
FEATURE                 Location/Qualifiers
REGION                  1..249
                        note = Humanized C2 scFV (VH-VL) sequence
source                  1..249
                        mol_type = protein
                        organism = synthetic construct
SEQUENCE: 369
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRT                                                          249

SEQ ID NO: 370          moltype = AA  length = 249
FEATURE                 Location/Qualifiers
REGION                  1..249
                        note = Humanized E6 scFV (VL-VH) sequence
```

-continued

```
source                  1..249
                        mol_type = protein
                        organism = synthetic construct
SEQUENCE: 370
DIVLTQSPAS LAVSPGQRAT ITCRASKSVS TSGYSYMHWY QQKPGQPPKL LIYLASNLES  60
GVPARFSGSG SGTDFTLTIN PVEANDTANY YCQHSRELPF TFGGGTKVEI KRTGGGGSGG  120
GGSGGGGSEV QLVESGGGLV KPGGSLRLSC AASGFTFSGY AMSWVRQAPG KGLEWVSTIS  180
SGGTYIYYPD SVKGRFTISR DNAKNSLYLQ MNSLRAEDTA VYYCARLGGD NYYEYFDVWG  240
KGTTVTVSS                                                          249

SEQ ID NO: 371          moltype = AA  length = 119
FEATURE                 Location/Qualifiers
REGION                  1..119
                        note = Humanized C3 heavy chain variable region sequence
source                  1..119
                        mol_type = protein
                        organism = synthetic construct
SEQUENCE: 371
QVQLVQSGAE VKKPGASVKV SCKASGYTFT DYAMNWVRQA PGQGLEWMGV ISTFSGNTNF  60
NQKFKGRVTM TTDTSTSTAY MELRSLRSDD TAVYYCARSD YYGPYFDYWG QGTTLTVSS   119

SEQ ID NO: 372          moltype = AA  length = 5
FEATURE                 Location/Qualifiers
REGION                  1..5
                        note = Humanized C3 heavy chain variable complementarity
                         determining regions 1 (CDR1) sequence
source                  1..5
                        mol_type = protein
                        organism = synthetic construct
SEQUENCE: 372
DYAMN                                                              5

SEQ ID NO: 373          moltype = AA  length = 17
FEATURE                 Location/Qualifiers
REGION                  1..17
                        note = Humanized C3 heavy chain variable complementarity
                         determining regions 2 (CDR2) sequence
source                  1..17
                        mol_type = protein
                        organism = synthetic construct
SEQUENCE: 373
VISTFSGNTN FNQKFKG                                                 17

SEQ ID NO: 374          moltype = AA  length = 10
FEATURE                 Location/Qualifiers
REGION                  1..10
                        note = Humanized C3 heavy chain variable complementarity
                         determining regions 3 (CDR3) sequence
source                  1..10
                        mol_type = protein
                        organism = synthetic construct
SEQUENCE: 374
SDYYGPYFDY                                                         10

SEQ ID NO: 375          moltype = AA  length = 114
FEATURE                 Location/Qualifiers
REGION                  1..114
                        note = Humanized C3 light chain variable region sequence
source                  1..114
                        mol_type = protein
                        organism = synthetic construct
SEQUENCE: 375
DIVMTQTPLS LSVTPGQPAS ISCRSSQTIV HSNGNTYLEW YLQKPGQSPQ LLIYKVSNRF  60
SGVPDRFSGS GSGTDFTLKI SRVEAEDVGV YYCFQGSHVP FTFGGGTKVE IKRT        114

SEQ ID NO: 376          moltype = AA  length = 16
FEATURE                 Location/Qualifiers
REGION                  1..16
                        note = Humanized C3 light chain variable complementarity
                         determining regions 1 (CDR1) sequence
source                  1..16
                        mol_type = protein
                        organism = synthetic construct
SEQUENCE: 376
RSSQTIVHSN GNTYLE                                                  16

SEQ ID NO: 377          moltype = AA  length = 7
FEATURE                 Location/Qualifiers
REGION                  1..7
```

-continued

```
                        note = Humanized C3 light chain variable complementarity
                         determining regions 2 (CDR2) sequence
source                  1..7
                        mol_type = protein
                        organism = synthetic construct
SEQUENCE: 377
KVSNRFS                                                                     7

SEQ ID NO: 378          moltype = AA  length = 9
FEATURE                 Location/Qualifiers
REGION                  1..9
                        note = Humanized C3 light chain variable complementarity
                         determining regions 3 (CDR3) sequence
source                  1..9
                        mol_type = protein
                        organism = synthetic construct
SEQUENCE: 378
FQGSHVPFT                                                                   9

SEQ ID NO: 379          moltype = AA  length = 118
FEATURE                 Location/Qualifiers
REGION                  1..118
                        note = Humanized C8 heavy chain variable region sequence
source                  1..118
                        mol_type = protein
                        organism = synthetic construct
SEQUENCE: 379
EVQLVESGGG LVKPGGSLRL SCAASGFTFS GYAMSWVRQA PGKGLEWVST ISSGGTYIYY  60
PDSVKGRFTI SRDNAKNSLY LQMNSLRAED TAVYYCARLG GDNYYEYWGK GTTVTVSS    118

SEQ ID NO: 380          moltype = AA  length = 5
FEATURE                 Location/Qualifiers
REGION                  1..5
                        note = Humanized C8 heavy chain variable complementarity
                         determining region 1 (CDR1) sequence
source                  1..5
                        mol_type = protein
                        organism = synthetic construct
SEQUENCE: 380
GYAMS                                                                       5

SEQ ID NO: 381          moltype = AA  length = 17
FEATURE                 Location/Qualifiers
REGION                  1..17
                        note = Humanized C8 heavy chain variable complementarity
                         determining region 2 (CDR2) sequence
source                  1..17
                        mol_type = protein
                        organism = synthetic construct
SEQUENCE: 381
TISSGGTYIY YPDSVKG                                                          17

SEQ ID NO: 382          moltype = AA  length = 9
FEATURE                 Location/Qualifiers
REGION                  1..9
                        note = Humanized C8 heavy chain variable complementarity
                         determining region 3 (CDR3) sequence
source                  1..9
                        mol_type = protein
                        organism = synthetic construct
SEQUENCE: 382
LGGDNYYEY                                                                   9

SEQ ID NO: 383          moltype = AA  length = 114
FEATURE                 Location/Qualifiers
REGION                  1..114
                        note = Humanized C8 light chain variable region sequence
source                  1..114
                        mol_type = protein
                        organism = synthetic construct
SEQUENCE: 383
DIVMTQSPDS LAVSLGERAT INCRASKSVS TSGYSYMHWY QQKPGQPPKL LIYLVSNLES  60
GVPDRFSGSG SGTDFTLTIS SLQAEDVAVY YCQHIRELTR SEFGGGTKVE IKRT        114

SEQ ID NO: 384          moltype = AA  length = 14
FEATURE                 Location/Qualifiers
REGION                  1..14
                        note = Humanized C8 light chain variable complementarity
                         determining region 1 (CDR1) sequence
```

-continued

```
source                  1..14
                        mol_type = protein
                        organism = synthetic construct
SEQUENCE: 384
RASKSVSTSG YSYM                                              14

SEQ ID NO: 385          moltype = AA  length = 7
FEATURE                 Location/Qualifiers
REGION                  1..7
                        note = Humanized C8 light chain variable complementarity
                         determining region 2 (CDR2) sequence
source                  1..7
                        mol_type = protein
                        organism = synthetic construct
SEQUENCE: 385
LVSNLES                                                      7

SEQ ID NO: 386          moltype = AA  length = 45
FEATURE                 Location/Qualifiers
REGION                  1..45
                        note = Humanized C8 light chain variable complementarity
                         determining region 3 (CDR3) sequence
source                  1..45
                        mol_type = protein
                        organism = synthetic construct
SEQUENCE: 386
GLNHISILEA RGGLULEUTH RARGSERGLU SEQUENCELI STING            45
```